US012577526B2

(12) United States Patent
Kehe et al.

(10) Patent No.: US 12,577,526 B2
(45) Date of Patent: Mar. 17, 2026

(54) MASSIVELY PARALLEL ON-CHIP CONSTRUCTION OF SYNTHETIC MICROBIAL COMMUNITIES

(71) Applicants: MASSACHUSETTS INSTITUTE OF TECHNOLOGY, Cambridge, MA (US); THE BROAD INSTITUTE, INC., Cambridge, MA (US)

(72) Inventors: Jared Scott Kehe, Cambridge, MA (US); Cheri Ackerman, Cambridge, MA (US); Paul Blainey, Cambridge, MA (US); Anthony Kulesa, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1093 days.

(21) Appl. No.: 17/607,780

(22) PCT Filed: Apr. 30, 2020

(86) PCT No.: PCT/US2020/030747

§ 371 (c)(1),
(2) Date: Oct. 29, 2021

(87) PCT Pub. No.: WO2020/223498

PCT Pub. Date: Nov. 5, 2020

(65) Prior Publication Data

US 2022/0228190 A1 Jul. 21, 2022

Related U.S. Application Data

(60) Provisional application No. 62/841,546, filed on May 1, 2019.

(51) Int. Cl.
*B01L 3/00* (2006.01)
*B01F 33/302* (2022.01)
(Continued)

(52) U.S. Cl.
CPC .......... *C12N 1/14* (2013.01); *B01L 3/502715* (2013.01); *B01L 3/50273* (2013.01);
(Continued)

(58) Field of Classification Search
CPC . C12N 1/14; C12N 1/20; C12N 1/145; C12N 1/205; B01L 3/502715;
(Continued)

(56) References Cited

U.S. PATENT DOCUMENTS

2007/0166770 A1* 7/2007 Hsieh ............... G01N 33/56966 435/7.2
2013/0078163 A1* 3/2013 Chung .................. C12M 21/06 422/502

(Continued)

FOREIGN PATENT DOCUMENTS

EP 3130905 A1 2/2017
WO 2016/149639 A1 9/2016

(Continued)

OTHER PUBLICATIONS

Extended European Search Report in corresponding EP application No. 20799253.8 dated Aug. 14, 2023.

(Continued)

*Primary Examiner* — Jennifer Wecker
*Assistant Examiner* — Oyeleye Alexander Alabi
(74) *Attorney, Agent, or Firm* — Day Pitney LLP; Christopher R Cowles; Erica A Fishel

(57) ABSTRACT

The present disclosure relates to compositions and methods for combinatorial assessment of nanoscale droplets, as specifically exemplified by massively parallel assessment of (Continued)

spatially-directed (while agnostic as to precise droplet content) combinations of droplets harboring distinct and independently identifiable microbial types and/or chemical compounds or mixtures. More particularly, the disclosure relates to a platform and methodologies for identifying advantageous (including synergistic, additive, etc.) microbial interactions and/or chemical compound or mixture interactions with microbes in a manner that allows for binary, trinary, etc. combinatorial assessments to be performed across a range of many discrete input types of microbes (e.g., 6-16 or more discrete input microbial types), to an extent capable of approaching comprehensive sampling and measurement of microbial community combinations from a selected panel of microbial inputs, optionally also in the presence of chemical compounds or mixtures (e.g., test compounds or mixtures for antimicrobial effect).

23 Claims, 81 Drawing Sheets

Specification includes a Sequence Listing.

(51) Int. Cl.

| | |
|---|---|
| ***B01F 33/3033*** | (2022.01) |
| ***B01L 7/00*** | (2006.01) |
| ***B01L 9/00*** | (2006.01) |
| ***B65G 47/80*** | (2006.01) |
| ***B82Y 20/00*** | (2011.01) |
| ***B82Y 30/00*** | (2011.01) |
| ***B82Y 40/00*** | (2011.01) |
| ***C12M 1/34*** | (2006.01) |
| ***C12M 3/06*** | (2006.01) |
| ***C12N 1/14*** | (2006.01) |
| ***C12N 1/20*** | (2006.01) |
| ***C12Q 1/02*** | (2006.01) |
| ***C12Q 1/6848*** | (2018.01) |
| ***C12Q 1/686*** | (2018.01) |
| ***G01N 15/10*** | (2024.01) |
| ***G01N 15/14*** | (2024.01) |
| ***G01N 15/1433*** | (2024.01) |
| ***G01N 21/29*** | (2006.01) |
| ***G01N 21/65*** | (2006.01) |
| ***G01N 33/543*** | (2006.01) |
| ***G01N 33/574*** | (2006.01) |
| ***G01N 33/58*** | (2006.01) |

(52) U.S. Cl.

CPC ............ *C12M 23/16* (2013.01); *C12M 41/46* (2013.01); *C12N 1/20* (2013.01); *C12Q 1/02* (2013.01); *G01N 15/1433* (2024.01); *G01N 15/1484* (2013.01); *B01L 2300/0654* (2013.01); *B01L 2300/0681* (2013.01); *B01L 2300/0829* (2013.01); *B01L 2300/0893* (2013.01); *B01L 2400/0496* (2013.01); *G01N 2015/1006* (2013.01); *G01N 2015/1481* (2013.01)

(58) Field of Classification Search

CPC ......... B01L 3/50273; B01L 2300/0654; B01L 2300/0681; B01L 2300/0829; B01L 2300/0893; B01L 2400/0496; B01L 2200/0673; B01L 3/502761; B01L 2200/0668; B01L 2300/0864; B01L 2400/086; B01L 3/5085; C12M 23/16; C12M 41/46; C12Q 1/02; G01N 15/1433; G01N 15/1484; G01N 2015/1006; G01N 2015/1481; G01N 15/147; G01N 2015/1493; C12R 2001/645; C12R 2001/01

See application file for complete search history.

(56) References Cited

U.S. PATENT DOCUMENTS

| | | | | |
|---|---|---|---|---|
| 2018/0071738 | A1* | 3/2018 | Blainey | B01L 3/502761 |
| 2018/0085755 | A1 | 3/2018 | Azpiroz | |
| 2018/0203005 | A1* | 7/2018 | Konry | G01N 33/54346 |
| 2019/0118177 | A1* | 4/2019 | Ismagilov | C12Q 1/6855 |
| 2021/0102954 | A1* | 4/2021 | Ha | G01N 33/6851 |

FOREIGN PATENT DOCUMENTS

| | | | | |
|---|---|---|---|---|
| WO | 2016/172362 A1 | 10/2016 | | |
| WO | 2017/048975 A1 | 3/2017 | | |
| WO | WO-2017218202 A1 * | 12/2017 | | C12Q 1/18 |
| WO | 2018/183126 A1 | 10/2018 | | |
| WO | WO-2018183744 A1 * | 10/2018 | | B01L 3/502715 |

OTHER PUBLICATIONS

International Search Report and Written Opinion in corresponding PCT Application No. PCT/US2020/030747 dated Aug. 4, 2020.

Partial Supplementary European Search Report in corresponding EP application No. 20799253.8-1101 dated May 12, 2023.

* cited by examiner

| *k* | 1 | 2 | 3 | 4 | 5 | 6 | 7 | 19 |
|---|---|---|---|---|---|---|---|---|
| **Density (/cm$^2$)** | 2,000 | 1,200 | 800 | 700 | 530 | 470 | 430 | 200 |
| **Full kChip** | 60,000 | 35,000 | 24,000 | 21,000 | 16,000 | 14,000 | 13,000 | 6,000 |
| ***k* = {1:7;19} Chip** | 3,500 | 2,000 | 2,900 | 2,400 | 1,900 | 2,600 | 2,400 | 650 |

| k | Total assay points |
|---|---|
| 1 | 19,000 |
| 2 | 14,000 |
| 3 | 19,000 |
| 4 | 13,000 |
| 5 | 11,000 |
| 6 | 12,000 |
| 7 | 10,000 |
| 10 | 1,500 |
| Total | 100,000 |

Fig. 3C $n$ = size of library $k$ = number of droplets in microwell ("community")

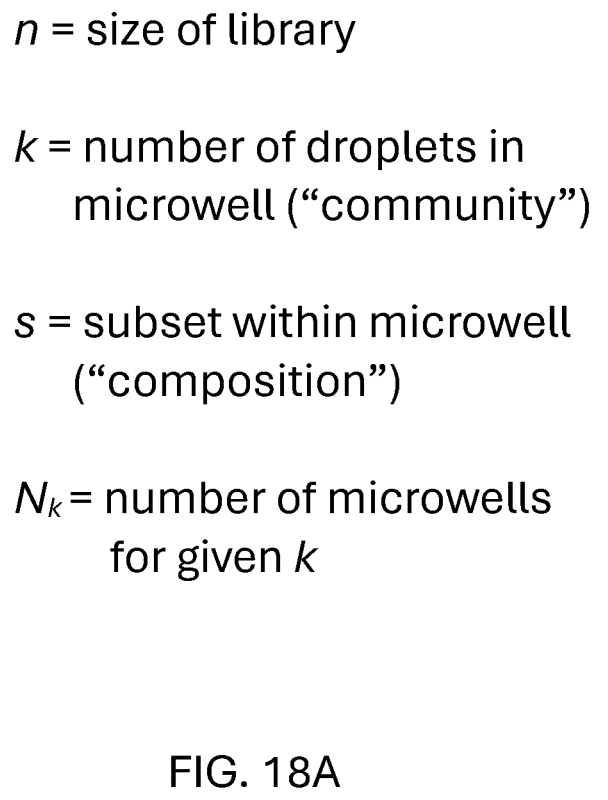

$s$ = subset within microwell ("composition")

$N_k$ = number of microwells for given $k$

FIG. 18A

| | $s \neq k$ (considering compositions within communities) | $s = k$ |
|---|---|---|
| $P_1$(all unique inputs) | $\frac{\frac{n!}{(n-k)!}}{n^k}$ | $\frac{\frac{n!}{(n-k)!}}{n^k}$ |
| $P_2$(desired subset present \| all unique inputs) | $\frac{\binom{n-s}{k-s}}{\binom{n}{k}} = \frac{k!(n-s)!}{n!(k-s)!}$ | $\frac{1}{\binom{n}{k}} = \frac{(n-k)!\,k!}{n!}$ |
| $p$(desired subset present and all inputs unique) = $p_1 p_2$ | $\frac{k!}{n^k}\binom{n-s}{k-s} = \frac{k!(n-s)!}{n^k(k-s)!(n-k)!}$ | $\frac{k!}{n^k}$ |
| number of replicates $R = N_k p$ | $N_k \frac{k!}{n^k}\binom{n-s}{k-s}$ | $N_k \frac{k!}{n^k}$ |

FIG. 18B

A given $s = K = 3$ combination (i.e microwell contains 3 droplets total and all are unique) is replicated 5 times on average for a library of $n$ = 16 inputs (current screen)

Hf-GFP monoculture 72 hr — Max in 127 hr

Hf-GFP yield (a.f.u.)

Hf-GFP+BuC

Hf-GFP yield (a.f.u.)

Hf-GFP + [BaL + Ra]  Hf-GFP + BaL  Hf-GFP + Ra

Hf-GFP yield (a.f.u.)

| Abbreviation | Genus | Species | Strain | Fluorescent protein | Integration/Plasmid | Original source |
|---|---|---|---|---|---|---|
| Ec | *Escherichia* | *coli* | K-12 MG1655 | GFP | Plasmid (pZE21, Kan resistant) | Jim Collins |
| Pae | *Pseudomonas* | *aeruginosa* | PAO1 | GFP | Plasmid | Katharina Ribbeck |
| Pf | *Pseudomonas* | *fluorescens* | A506 | YFP | Integration | Nadav Kashtan |
| Pci | *Pseudomonas* | *citronellolis* | ATCC#13674 | YFP | Integration | ATCC |
| Pch | *Pseudomonas* | *chlororaphis* | ATCC#9446 | YFP | Integration | ATCC |
| Pv | *Pseudomonas* | *veronii* | ATCC#700474 | YFP | Integration | ATCC |
| Pau | *Pseudomonas* | *aurantiaca* | ATCC#33663 | YFP | Integration | ATCC |
| Pp | *Pseudomonas* | *putida* | ATCC#12633 | GFP | Integration | ATCC |
| Ps | *Pseudomonas* | *syringae* | B728a | GFP | Plasmid | Steve E. Lindow |
| Hf | *Herbaspirillum* | *frisingense* | GSF30(T) | GFP | Plasmid (pJBA28, Kan resistant) | Mike Rothballer |

FIG. 32

| | Compound | Type | Chemical formula | Carbon atoms | Total weight | Component weight | 4X concentration (%w/v) |
|---|---|---|---|---|---|---|---|
| 1 | D-Ribose | monosaccharide | C5H10O5 | 5 | 150.13 | 150.13 | 2 |
| 2 | D-Fructose | monosaccharide | C6H12O6 | 6 | 180.16 | 180.16 | 2 |
| 3 | D-Galactose | monosaccharide | C6H12O6 | 6 | 180.16 | 180.16 | 2 |
| 4 | D-Glucose (Dextrose) | monosaccharide | C6H12O6 | 6 | 180.16 | 180.16 | 2 |
| 5 | N-Acetyl-D-glucosamine | monosaccharide | C8H15NO6 | 8 | 221.21 | 221.21 | 2 |
| 6 | Sodium citrate dihydrate | carboxylate ion | Na3C6H5O7+2H2O | 6 | 294.1 | 189.1 | 2 |
| 7 | Sodium fumarate dibasic | carboxylate ion | C4H2Na2O4 | 4 | 160.04 | 114.06 | 2 |
| 8 | D-Mannitol | sugar alcohol | C6H14O6 | 6 | 182.17 | 182.17 | 2 |
| 9 | D-Sorbitol | sugar alcohol | C6H14O6 | 6 | 182.17 | 182.17 | 2 |
| 10 | L-Alanine (Ala, A) | amino acid (hydrophobic) | C3H7NO2 | 3 | 89.09 | 89.09 | 2 |
| 11 | L-Serine (Ser, S) | amino acid (polar) | C3H7NO3 | 3 | 105.09 | 105.09 | 2 |
| 12 | D-Cellobiose | oligosaccharide(glucose + glucose) | C12H22O11 | 12 | 342.3 | 342.3 | 2 |
| 13 | D-Sucrose | oligosaccharide(glucose + fructose) | C12H22O11 | 12 | 342.3 | 342.3 | 2 |
| 14 | D-Lactose monohydrate | oligosaccharide(glucose + galactose) | C12H22O11+H2O | 12 | 360.31 | 342.3 | 2 |
| 15 | D-Raffinose pentahydrate | oligosaccharide(glucose + galactose + fructose) | C18H32O16+5H2O | 18 | 594.5 | 504.42 | 2 |
| 16 | Arabinogalactan | polysaccharide chain (arabinose + galactose) | | | | | 2 |

FIG. 33

| Plate location | Orientation | S_ab score | Unique common oligomers | Name (used herein) | Abbreviation | Best SeqMatch hit | Domain | Phylum | Class | Order | Family | Genus | 16S SEQ ID NO |
|---|---|---|---|---|---|---|---|---|---|---|---|---|---|
| A10 | Fwd | 0.994 | 1244 | *Bacillus* sp. I | BaT | Bacillus sp. TA_AM; HG942094 | Bacteria | Firmicutes | Bacilli | Bacillales | Bacillaceae 1 | Bacillus | 1 |
| A3 | Fwd | 0.99 | 1415 | *Collimonas* sp. | Co | Collimonas sp. III- 35; AB531414 | Bacteria | Proteobacteria | Betaproteobacteria | Burkholderiales | Oxalobacteraceae | Collimonas | 2 |
| A7 | Fwd | 0.97 | 1407 | *Chryseobacterium* sp. | Ch | bacterium H20; AY345551 | Bacteria | Bacteroidetes | Flavobacteria | Flavobacteriales | Flavobacteriaceae | Chryseobacterium | 3 |
| B5 | Fwd | 0.998 | 1293 | *Burkholderia* sp. I | BuC | Burkholderia sp. CC9F; KM187366 | Bacteria | Proteobacteria | Betaproteobacteria | Burkholderiales | Burkholderiaceae | Burkholderia | 4 |
| B9 | Fwd | 0.986 | 1148 | *Burkholderia* sp. II | BuH | Burkholderia sp. HC128; HG794281 | Bacteria | Proteobacteria | Betaportebacteria | Burkholderiales | Burkholderiaceae | Burkholderia | 5 |
| C11 | Fwd | 1 | 1152 | *Bacillus* sp. II | BaL | Bacillus sp. LRM1; JN367448 | Bacteria | Firmicutes | Bacilli | Bacillales | Bacillaceae 1 | Bacillus | 6 |
| C4 | Fwd | 0.885 | 1570 | *Enterobacter mori* | En | Enterobacter mori; M84; LN890170 | Bacteria | Proteobacteria | Gammaproteobacteria | Enterobacteriales | Enterobacteriaceae | unclassified_Enterobacteriaceae | 7 |

FIG. 34

| Plate location | Orientation | S_ab score | Unique common oligomers | Name (used herein) | Abbreviation | Best SeqMatch hit | Domain | Phylum | Class | Order | Family | Genus | 16S SEQ ID NO |
|---|---|---|---|---|---|---|---|---|---|---|---|---|---|
| C6 | Fwd | 0.975 | 1435 | *Stenotrophomonas maltophilia* | St | Stenotrophomonas maltophilia D457; HE798556 | Bacteria | Proteobacteria | Gammaproteobacteria | Xanthomonadales | Xanthomonadaceae | Stenotrophomonas | 8 |
| D11 | Fwd | 0.996 | 1435 | *Dyella* sp. | Dy | uncultured Dyella; DYB11; EU982450 | Bacteria | Proteobacteria | Gammaproteobacteria | Xanthomonadales | Xanthomonadaceae | Dyella | 9 |
| E10 | Fwd | 0.995 | 1308 | *Ewingella americana* | Ew | Ewingella americana; CH4 ; EU678360 | Bacteria | Proteobacteria | Gammaproteobacteria | Enterobacteriales | Enterobacteriaceae | Ewingella | 10 |
| F10 | Fwd | 0.99 | 1445 | *Rahnella* sp. | Ra | Rahnella sp. 'CDC 21234'; U88435 | Bacteria | Proteobacteria | Gammaproteobacteria | Enterobacteriales | Enterobacteriaceae | unclassified_Enterobacteriaceae | 11 |
| F5 | Fwd | 0.985 | 1448 | *Pseudomonas fluorescens* | Ps | Pseudomonas fluorescens NCIMB11764; CP010945 | Bacteria | Proteobacteria | Gammaproteobacteria | Pseudomonadales | Pseudomonadaceae | Pseudomonas | 12 |
| G4 | Fwd | 0.996 | 1289 | *Burkholderia* sp. III | Bul | Burkholderi sp. IMER-B1-51; FJ796440 | Bacteria | Proteobacteria | Betaporteobacteria | Burkholderiales | Burkholderiaceae | Burkholderia | 13 |
| H7 | Fwd | 0.955 | 1279 | *Averyella delhousiensis* | AV | Averyella dalhousiensis; 9501-97; DQ158206 | Bacteria | Proteobacteria | Gammaproteobacteria | Enterobacteriales | Enterobacteriaceae | Enterrobacter | 14 |

FIG. 34 (Continued)

| Carbon (each chip received one carbon source) | *k* | Total number of microwells | **Total communities constructed passing all data quality filters** (note instances of droplet underfilling were included, e.g. one droplet in a *k* = 2 microwell was instead included in the *k* = 1 dataset) | **Total communites where all inputs unique** (e.g. [A + B + C], but not [A + B + B] or [A + B + C +C]) | Total compo-sitions where all inputs unique | Mean number of replicates per unique combi-nation | Total possible combinations where all inputs uniuqe (calculated as 16-choose-k) |
|---|---|---|---|---|---|---|---|
| Average for *k* = {1:7;19} Chip used in screen | 1 | 3528 | 3149.7 | 3149.7 | 16.0 | 196.9 | 16 |
| | 2 | 2016 | 2352.3 | 2198.2 | 120.0 | 18.3 | 120 |
| | 3 | 2856 | 3096.3 | 2525.2 | 546.5 | 4.6 | 560 |
| | 4 | 2380 | 2195.3 | 1464.3 | 945.0 | 1.5 | 1820 |
| | 5 | 1904 | 1868.0 | 919.7 | 771.8 | 1.2 | 4368 |
| | 6 | 2550 | 1961.8 | 666.2 | 597.2 | 1.1 | 8008 |
| | 7 | 2380 | 1747.2 | 364.0 | 340.2 | 1.1 | 11440 |
| | 19 | 648 | 252.5 | 0.0 | 0.0 | N/A | 0 |
| Galactose chip | 1 | 3528 | 3862 | 3862 | 16 | 241.4 | 16 |
| | 2 | 2016 | 1796 | 1680 | 120 | 14.0 | 120 |
| | 3 | 2856 | 3073 | 2525 | 548 | 4.6 | 560 |
| | 4 | 2380 | 1841 | 1201 | 813 | 1.5 | 1820 |
| | 5 | 1904 | 1104 | 545 | 486 | 1.1 | 4368 |
| | 6 | 2550 | 756 | 276 | 255 | 1.1 | 8008 |
| | 7 | 2380 | 1176 | 251 | 237 | 1.1 | 11440 |
| | 19 | 648 | 88 | 0 | 0 | N/A | 0 |

| | | | | | | | |
|---|---|---|---|---|---|---|---|
| Glucose chip | 1 | 3528 | 2790 | 2790 | 16 | 174.4 | 16 |
| | 2 | 2016 | 2257 | 2111 | 120 | 17.6 | 120 |
| | 3 | 2856 | 2693 | 2184 | 539 | 4.1 | 560 |
| | 4 | 2380 | 2174 | 1483 | 966 | 1.5 | 1820 |
| | 5 | 1904 | 2154 | 1033 | 847 | 1.2 | 4368 |
| | 6 | 2550 | 2254 | 747 | 654 | 1.1 | 8008 |
| | 7 | 2380 | 2122 | 457 | 420 | 1.1 | 11440 |
| | 19 | 648 | 379 | 0 | 0 | N/A | 0 |
| Fructose chip | 1 | 3528 | 3316 | 3316 | 16 | 207.3 | 16 |
| | 2 | 2016 | 2509 | 2343 | 120 | 19.5 | 120 |
| | 3 | 2856 | 3016 | 2499 | 549 | 4.6 | 560 |
| | 4 | 2380 | 2169 | 1423 | 932 | 1.5 | 1820 |
| | 5 | 1904 | 1963 | 969 | 847 | 1.1 | 4368 |
| | 6 | 2550 | 1816 | 620 | 570 | 1.1 | 8008 |
| | 7 | 2380 | 1607 | 344 | 324 | 1.1 | 11440 |
| | 19 | 648 | 209 | 0 | 0 | N/A | 0 |
| Raffinose chip | 1 | 3528 | 2905 | 2905 | 16 | 181.6 | 16 |
| | 2 | 2016 | 2449 | 2279 | 120 | 19.0 | 120 |
| | 3 | 2856 | 3041 | 2469 | 540 | 4.6 | 560 |
| | 4 | 2380 | 1983 | 1293 | 871 | 1.5 | 1820 |
| | 5 | 1904 | 1957 | 983 | 833 | 1.2 | 4368 |
| | 6 | 2550 | 2315 | 769 | 700 | 1.1 | 8008 |
| | 7 | 2380 | 1743 | 353 | 335 | 1.1 | 11440 |
| | 19 | 648 | 147 | 0 | 0 | N/A | 0 |
| Lactose chip | 1 | 3528 | 3112 | 3112 | 16 | 194.5 | 16 |
| | 2 | 2016 | 2659 | 2505 | 120 | 20.9 | 120 |
| | 3 | 2856 | 3543 | 2826 | 551 | 5.1 | 560 |
| | 4 | 2380 | 2543 | 1729 | 1065 | 1.6 | 1820 |
| | 5 | 1904 | 1754 | 805 | 672 | 1.2 | 4368 |
| | 6 | 2550 | 1896 | 646 | 595 | 1.1 | 8008 |
| | 7 | 2380 | 1771 | 361 | 349 | 1.0 | 11440 |
| | 19 | 648 | 300 | 0 | 0 | N/A | 0 |

FIG. 35 (Continued)

| Carbon (each chip received one carbon source) | *k* | Total number of microwells | Total communities constructed passing all data quality filters (note instances of droplet underfilling were included, e.g. one droplet in a *k* = 2 microwell was instead included in the *k* = 1 dataset) | Total communities where all inputs unique (e.g. {A + B + C}, but not {A + B + B} or {A + B + C + C}) | Total compositions where all inputs unique | Mean number of replicates per unique combination | Total possible combinations where all inputs unique (calculated as 16-choose-*k*) |
|---|---|---|---|---|---|---|---|
| | 1 | 3835 | 2913 | 2913 | 16 | 182.1 | 16 |
| | 2 | 2016 | 2444 | 2271 | 120 | 18.9 | 120 |
| | 3 | 2856 | 3212 | 2545 | 552 | 4.6 | 560 |
| | 4 | 2306 | 2482 | 1557 | 1023 | 1.5 | 1820 |
| | 5 | 1804 | 2276 | 1183 | 945 | 1.3 | 4368 |
| | 6 | 2856 | 2734 | 839 | 699 | 1.2 | 8008 |
| | 7 | 2380 | 2054 | 418 | 376 | 1.1 | 11440 |
| Sucrose chip | 16 | 848 | 392 | 0 | 0 | N/A | 0 |

Fig. 35 (Continued)

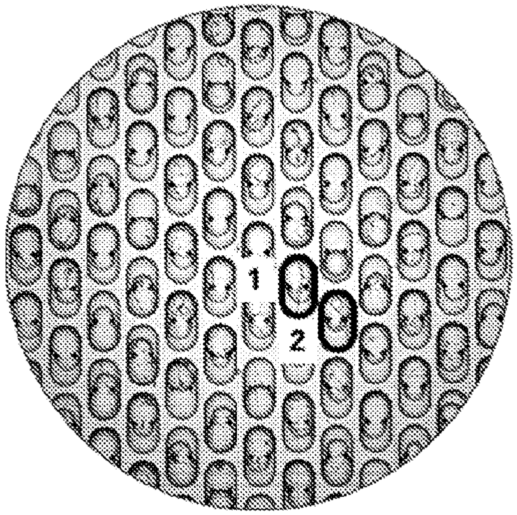

Fig. 36A

SEQUENCE LISTING

```
<160> NUMBER OF SEQ ID NOS: 14

<210> SEQ ID NO 1
<211> LENGTH: 1680
<212> TYPE: DNA
```

<213> ORGANISM: Bacillus subtilis
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(18)
<223> OTHER INFORMATION: n is a, c, g, or t
<220> FEATURE:
<221> NAME/KEY: misc_feature
<222> LOCATION: (22)..(26)
<223> OTHER INFORMATION: n is a, c, g, or t
<220> FEATURE:
<221> NAME/KEY: misc_feature
<222> LOCATION: (29)..(35)
<223> OTHER INFORMATION: n is a, c, g, or t
<220> FEATURE:
<221> NAME/KEY: misc_feature
<222> LOCATION: (37)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (75)..(78)
<223> OTHER INFORMATION: n is a, c, g, or t
<220> FEATURE:
<221> NAME/KEY: misc_feature
<222> LOCATION: (81)..(88)
<223> OTHER INFORMATION: n is a, c, g, or t
<220> FEATURE:
<221> NAME/KEY: misc_feature
<222> LOCATION: (93)..(97)
<223> OTHER INFORMATION: n is a, c, g, or t
<220> FEATURE:
<221> NAME/KEY: misc_feature
<222> LOCATION: (126)..(128)
<223> OTHER INFORMATION: n is a, c, g, or t
<220> FEATURE:
<221> NAME/KEY: misc_feature
<222> LOCATION: (525)..(526)
<223> OTHER INFORMATION: n is a, c, g, or t
<220> FEATURE:
<221> NAME/KEY: misc_feature
<222> LOCATION: (1476)..(1476)
<223> OTHER INFORMATION: n is a, c, g, or t
<220> FEATURE:
<221> NAME/KEY: misc_feature
<222> LOCATION: (1559)..(1559)
<223> OTHER INFORMATION: n is a, c, g, or t
<220> FEATURE:
<221> NAME/KEY: misc_feature
<222> LOCATION: (1561)..(1561)
<223> OTHER INFORMATION: n is a, c, g, or t
<220> FEATURE:
<221> NAME/KEY: misc_feature
<222> LOCATION: (1563)..(1563)
<223> OTHER INFORMATION: n is a, c, g, or t
<220> FEATURE:
<221> NAME/KEY: misc_feature
<222> LOCATION: (1576)..(1576)
<223> OTHER INFORMATION: n is a, c, g, or t
<220> FEATURE:
<221> NAME/KEY: misc_feature
<222> LOCATION: (1587)..(1589)
<223> OTHER INFORMATION: n is a, c, g, or t
<220> FEATURE:
<221> NAME/KEY: misc_feature
<222> LOCATION: (1593)..(1594)
<223> OTHER INFORMATION: n is a, c, g, or t
<220> FEATURE:
<221> NAME/KEY: misc_feature
<222> LOCATION: (1602)..(1602)
<223> OTHER INFORMATION: n is a, c, g, or t
<220> FEATURE:
<221> NAME/KEY: misc_feature
<222> LOCATION: (1604)..(1607)
<223> OTHER INFORMATION: n is a, c, g, or t
<220> FEATURE:
<221> NAME/KEY: misc_feature
<222> LOCATION: (1609)..(1609)
<223> OTHER INFORMATION: n is a, c, g, or t
<220> FEATURE:
<221> NAME/KEY: misc_feature
<222> LOCATION: (1611)..(1611)
<223> OTHER INFORMATION: n is a, c, g, or t
<220> FEATURE:
<221> NAME/KEY: misc_feature
<222> LOCATION: (1614)..(1614)
<223> OTHER INFORMATION: n is a, c, g, or t
<220> FEATURE:
<221> NAME/KEY: misc_feature
<222> LOCATION: (1616)..(1618)
<223> OTHER INFORMATION: n is a, c, g, or t
<220> FEATURE:
<221> NAME/KEY: misc_feature
<222> LOCATION: (1620)..(1620)
<223> OTHER INFORMATION: n is a, c, g, or t
<220> FEATURE:
<221> NAME/KEY: misc_feature
<222> LOCATION: (1622)..(1628)
<223> OTHER INFORMATION: n is a, c, g, or t
<220> FEATURE:
<221> NAME/KEY: misc_feature
<222> LOCATION: (1630)..(1634)
<223> OTHER INFORMATION: n is a, c, g, or t
<220> FEATURE:
<221> NAME/KEY: misc_feature
<222> LOCATION: (1636)..(1636)
<223> OTHER INFORMATION: n is a, c, g, or t
<220> FEATURE:
<221> NAME/KEY: misc_feature
<222> LOCATION: (1638)..(1652)
<223> OTHER INFORMATION: n is a, c, g, or t
<220> FEATURE:
<221> NAME/KEY: misc_feature
<222> LOCATION: (1655)..(1655)
<223> OTHER INFORMATION: n is a, c, g, or t
<220> FEATURE:
<221> NAME/KEY: misc_feature
<222> LOCATION: (1657)..(1659)
<223> OTHER INFORMATION: n is a, c, g, or t
<220> FEATURE:
<221> NAME/KEY: misc_feature
<222> LOCATION: (1664)..(1667)
<223> OTHER INFORMATION: n is a, c, g, or t
<220> FEATURE:
<221> NAME/KEY: misc_feature
<222> LOCATION: (1669)..(1669)
<223> OTHER INFORMATION: n is a, c, g, or t
<220> FEATURE:

```
<221> NAME/KEY: misc_feature
<222> LOCATION: (1671)..(1673)
<223> OTHER INFORMATION: n is a, c, g, or t
<220> FEATURE:
<221> NAME/KEY: misc_feature
<222> LOCATION: (1675)..(1680)
<223> OTHER INFORMATION: n is a, c, g, or t

<400> SEQUENCE: 1

nnnnnncgnt gtnnnnnnaa gnnnnntann nnnnntnnnn nnnncnntaa ntcgtaacaa     60

ngnaacccnn agncnnnncc nnnnnnnnag ttnnnnnttc tgctcaggat gaacgctggc    120

ggcgtnnnaa tacatgcaag tcgagcgaat ggattgagag cttgctctca tgaagttagc    180

ggcggacggg tgagtaacac gtgggtaacc tgcccataag actgggataa ctccgggaaa    240

ccggggctaa taccggataa tattttgaac tgcatggttc gaaattgaaa ggcggcttcg    300

gctgtcactt atggatggac ccgcgtcgca ttagctagtt ggtgaggtaa cggctcacca    360

aggcaacgat gcgtagccga cctgagaggg tgatcggcca cactgggact gagacacggc    420

ccagactcct acgggaggca gcagtaggga atcttccgca atggacgaaa gtctgacgga    480

gcaacgccgc gtgagtgatg aaggctttcg ggtcgtaaaa ctctnntgtt agggaagaac    540

aagtgctagt tgaataagct ggcaccttga cggtacctaa ccagaaagcc acggctaact    600

acgtgccagc agccgcggta atacgtaggt ggcaagcgtt atccggaatt attgggcgta    660

aagcgcgcgc aggtggtttc ttaagtctga tgtgaaagcc cacggctcaa ccgtggaggg    720

tcattggaaa ctgggagact tgagtgcaga agaggaaagt ggaattccat gtgtagcggt    780

gaaatgcgta gagatatgga ggaacaccag tggcgaaggc gactttctgg tctgtaactg    840

acactgaggc gcgaaagcgt ggggagcaaa caggattaga taccctggta gtccacgccg    900

taaacgatga gtgctaagtg ttagagggtt tccgcccttt agtgctgaag ttaacgcatt    960

aagcactccg cctggggagt acggccgcaa ggctgaaact caaaggaatt gacgggggcc   1020

cgcacaagcg gtggagcatg tggtttaatt cgaagcaacg cgaagaacct taccaggtct   1080

tgacatcctc tgaaaaccct agagataggg cttctccttc gggagcagag tgacaggtgg   1140

tgcatggttg tcgtcagctc gtgtcgtgag atgttgggtt aagtcccgca acgagcgcaa   1200

cccttgatct tagttgccat cattaagttg ggcactctaa ggtgactgcc ggtgacaaac   1260

cggaggaagg tggggatgac gtcaaatcat catgcccctt atgacctggg ctacacacgt   1320

gctacaatgg acggtacaaa gagctgcaag accgcgaggt ggagctaatc tcataaaacc   1380

gttctcagtt cggattgtag gctgcaactc gcctacatga agctggaatc gctagtaatc   1440

gcggatcagc atgccgcggt gaatacgttc ccgggncttg tacacaccgc ccgtcacacc   1500

acgagagttt gtaacacccg aagtcggtgg ggtaaccttt atggagccag ccgcctaang   1560

ngnacagatg atgggntgag tcgtacnnng ggnnaccgta angnnnnanc nggnannngn   1620

tnnnnnnngn nnnncncnnn nnnnnnnnnn nnatntnnnt gagnnnntnt nnntnnnnnn   1680


<210> SEQ ID NO 2
<211> LENGTH: 1860
<212> TYPE: DNA
<213> ORGANISM: Collimonas arenae
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(11)
<223> OTHER INFORMATION: n is a, c, g, or t
```

<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(26)
<223> OTHER INFORMATION: n is a, c, g, or t
<220> FEATURE:
<221> NAME/KEY: misc_feature
<222> LOCATION: (28)..(39)
<223> OTHER INFORMATION: n is a, c, g, or t
<220> FEATURE:
<221> NAME/KEY: misc_feature
<222> LOCATION: (41)..(54)
<223> OTHER INFORMATION: n is a, c, g, or t
<220> FEATURE:
<221> NAME/KEY: misc_feature
<222> LOCATION: (56)..(58)
<223> OTHER INFORMATION: n is a, c, g, or t
<220> FEATURE:
<221> NAME/KEY: misc_feature
<222> LOCATION: (60)..(65)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (75)..(78)
<223> OTHER INFORMATION: n is a, c, g, or t
<220> FEATURE:
<221> NAME/KEY: misc_feature
<222> LOCATION: (81)..(82)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (90)..(91)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (96)..(97)
<223> OTHER INFORMATION: n is a, c, g, or t
<220> FEATURE:
<221> NAME/KEY: misc_feature
<222> LOCATION: (100)..(103)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (109)..(116)
<223> OTHER INFORMATION: n is a, c, g, or t
<220> FEATURE:
<221> NAME/KEY: misc_feature
<222> LOCATION: (118)..(118)

<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (133)..(137)
<223> OTHER INFORMATION: n is a, c, g, or t
<220> FEATURE:
<221> NAME/KEY: misc_feature
<222> LOCATION: (139)..(142)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t
<220> FEATURE:
<221> NAME/KEY: misc_feature
<222> LOCATION: (151)..(154)
<223> OTHER INFORMATION: n is a, c, g, or t
<220> FEATURE:
<221> NAME/KEY: misc_feature
<222> LOCATION: (156)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (171)..(172)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(182)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(197)
<223> OTHER INFORMATION: n is a, c, g, or t
<220> FEATURE:
<221> NAME/KEY: misc_feature
<222> LOCATION: (199)..(200)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (212)..(212)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (217)..(219)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (252)..(253)
<223> OTHER INFORMATION: n is a, c, g, or t
<220> FEATURE:
<221> NAME/KEY: misc_feature
<222> LOCATION: (256)..(259)
<223> OTHER INFORMATION: n is a, c, g, or t
<220> FEATURE:
<221> NAME/KEY: misc_feature
<222> LOCATION: (261)..(267)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:

-continued

<221> NAME/KEY: misc_feature
<222> LOCATION: (304)..(306)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (1739)..(1770)
<223> OTHER INFORMATION: n is a, c, g, or t
<220> FEATURE:
<221> NAME/KEY: misc_feature
<222> LOCATION: (1772)..(1773)
<223> OTHER INFORMATION: n is a, c, g, or t
<220> FEATURE:
<221> NAME/KEY: misc_feature
<222> LOCATION: (1788)..(1789)
<223> OTHER INFORMATION: n is a, c, g, or t
<220> FEATURE:
<221> NAME/KEY: misc_feature
<222> LOCATION: (1793)..(1801)
<223> OTHER INFORMATION: n is a, c, g, or t
<220> FEATURE:
<221> NAME/KEY: misc_feature
<222> LOCATION: (1803)..(1804)
<223> OTHER INFORMATION: n is a, c, g, or t
<220> FEATURE:
<221> NAME/KEY: misc_feature
<222> LOCATION: (1806)..(1806)
<223> OTHER INFORMATION: n is a, c, g, or t
<220> FEATURE:
<221> NAME/KEY: misc_feature
<222> LOCATION: (1809)..(1814)
<223> OTHER INFORMATION: n is a, c, g, or t
<220> FEATURE:
<221> NAME/KEY: misc_feature
<222> LOCATION: (1816)..(1818)
<223> OTHER INFORMATION: n is a, c, g, or t
<220> FEATURE:
<221> NAME/KEY: misc_feature
<222> LOCATION: (1820)..(1826)
<223> OTHER INFORMATION: n is a, c, g, or t
<220> FEATURE:
<221> NAME/KEY: misc_feature
<222> LOCATION: (1829)..(1833)
<223> OTHER INFORMATION: n is a, c, g, or t
<220> FEATURE:
<221> NAME/KEY: misc_feature
<222> LOCATION: (1835)..(1838)
<223> OTHER INFORMATION: n is a, c, g, or t
<220> FEATURE:
<221> NAME/KEY: misc_feature
<222> LOCATION: (1840)..(1846)
<223> OTHER INFORMATION: n is a, c, g, or t
<220> FEATURE:
<221> NAME/KEY: misc_feature
<222> LOCATION: (1848)..(1848)
<223> OTHER INFORMATION: n is a, c, g, or t
<220> FEATURE:
<221> NAME/KEY: misc_feature
<222> LOCATION: (1850)..(1860)
<223> OTHER INFORMATION: n is a, c, g, or t

<400> SEQUENCE: 2
nnnngnnnnn ngcnaatngg gggnnncnnn nnnnnnnnna nnnnnnnnnn nnnnannnan 60
nnnnnttnng nnttnnnncc nnttnttntn nagncnngan nnngggnann nnnnnntncc 120
anccncnnta nannnnngnn nnctgtanna nnnnannnnn nnacnangtt nnccctnacn 180
nncncanccn gngtnnngnn tngagccctg gntnccnnna nantccngan ccaagngana 240
ncccaaancc cnnccnnnnt nnnnnnntnt tttttntntg ntcagattga acgctggcgg 300

```
catnnntnac acatgcaagt cgaacggtaa cagggagctt gctccgctga cgagtggcga    360
acgggtgagt aatatatcgg aacgtacctt tgagtggggg ataactagtc gaaagattag    420
ctaataccgc atacgatcta cggatgaaag tgggggatcg caagacntca tgctcataga    480
gcggccgata tctgattagc tagttggtga ggtaaaggct caccaaggct tcgatcagta    540
gctggtctga gaggacgacc agccacactg ggactgagac acggcccaga ctcctacggg    600
aggcagcagt ggggaatttt ggacaatggg ggcaaccctg atccagcaat gccgcgtgag    660
tgaagaaggc cttcgggttg taaagctctt ttgtcaggga agaaacggga tgtcctaata    720
cggtgtccta atgacggtac ctgaagaata agcaccggct aactacgtgc cagcagccgc    780
ggtaatacgt agggtgcaag cgttaatcgg aattactggg cgtaaagcgt gcgcaggcgg    840
ttatgtaaga caggtgtgaa atccccgggc ttaacctggg aatggcattt gtgactgcat    900
agctagagtg tgtcagaggg gggtagaatt ccacgtgtag cagtgaaatg cgtagagatg    960
tggaggaata ccgatggcga aggcagcccc ctgggataac actgacgctc atgcacgaaa   1020
gcgtggggag caaacaggat tagataccct ggtagtccac gccctaaacg atgtctacta   1080
gttgtcgggt cttaattgac ttggtaacgc agctaacgcg tgaagtagac cgcctgggga   1140
gtacggtcgc aagattaaaa ctcaaaggaa ttgacgggga cccgcacaag cggtggatga   1200
tgtggattaa ttcgatgcaa cgcgaaaaac cttacctacc cttgacatgt acggaatgct   1260
gaagagattt ggcagtgctc gaaagagaac cgtaacacag gtgctgcatg gctgtcgtca   1320
gctcgtgtcg tgagatgttg ggttaagtcc cgcaacgagc gcaacccttg tcattagttg   1380
ctacgaaagg gcactctaat gagactgccg gtgacaaacc ggaggaaggt ggggatgacg   1440
tcaagtcctc atggccctta tgggtagggc ttcacacgtc atacaatggt acatacagag   1500
ggccgccaac ccgcgagggg gagctaatcc cagaaagtgt atcgtagtcc ggattgtagt   1560
ctgcaactcg actacatgaa gttggaatcg ctagtaatcg cggatcagca tgtcgcggtg   1620
aatacgttcc cgggtcttgt acacaccgcc cgtcacacca tgggagcggg ttttaccaga   1680
agtaggtagc ctaaccgcaa gggggcgctt accacggtag gattcgtgac tggggtgann   1740
nnnnnnnnnn nnnnnnnnnn nnnnnnnnnn anngggtagg ggtttttnnt ctnnnnnnnn   1800
nannanctnn nnnnannngn nnnnnngtnn nnncnnnncn nnnnnntncn nnnnnnnnnn   1860
```

<210> SEQ ID NO 3
<211> LENGTH: 1543
<212> TYPE: DNA
<213> ORGANISM: Chryseobacterium indologenes
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (1337)..(1338)
<223> OTHER INFORMATION: n is a, c, g, or t
<220> FEATURE:

<221> NAME/KEY: misc_feature
<222> LOCATION: (1365)..(1365)
<223> OTHER INFORMATION: n is a, c, g, or t
<220> FEATURE:
<221> NAME/KEY: misc_feature
<222> LOCATION: (1394)..(1394)
<223> OTHER INFORMATION: n is a, c, g, or t
<220> FEATURE:
<221> NAME/KEY: misc_feature
<222> LOCATION: (1455)..(1455)
<223> OTHER INFORMATION: n is a, c, g, or t
<220> FEATURE:
<221> NAME/KEY: misc_feature
<222> LOCATION: (1469)..(1472)
<223> OTHER INFORMATION: n is a, c, g, or t
<220> FEATURE:
<221> NAME/KEY: misc_feature
<222> LOCATION: (1475)..(1475)
<223> OTHER INFORMATION: n is a, c, g, or t
<220> FEATURE:
<221> NAME/KEY: misc_feature
<222> LOCATION: (1477)..(1477)
<223> OTHER INFORMATION: n is a, c, g, or t
<220> FEATURE:
<221> NAME/KEY: misc_feature
<222> LOCATION: (1480)..(1480)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1490)..(1490)
<223> OTHER INFORMATION: n is a, c, g, or t
<220> FEATURE:
<221> NAME/KEY: misc_feature
<222> LOCATION: (1492)..(1495)
<223> OTHER INFORMATION: n is a, c, g, or t
<220> FEATURE:
<221> NAME/KEY: misc_feature
<222> LOCATION: (1499)..(1520)
<223> OTHER INFORMATION: n is a, c, g, or t
<220> FEATURE:
<221> NAME/KEY: misc_feature
<222> LOCATION: (1522)..(1531)
<223> OTHER INFORMATION: n is a, c, g, or t
<220> FEATURE:
<221> NAME/KEY: misc_feature
<222> LOCATION: (1536)..(1543)
<223> OTHER INFORMATION: n is a, c, g, or t

<400> SEQUENCE: 3
nnnnagttnn ntnnnggctc aggatgaacg ctagcgggag gcntaacaca tgcaagccga 60
gcggtagagt ttcttcggaa acttgagagc ggcgtacggg tgcggaacac gtgtgcaacc 120
tgcctttatc tgggggatag cctttcgaaa ggaagattaa taccccataa tatattgaat 180
ggcatcattc gatattgaaa actccggtgg atagagatgg gcacgcgcaa gattagatag 240
ttggtgaggt aacggctcac caagtctacg atctttaggg ggcctgagag ggtgatcccc 300
cacactggta ctgagacacg gaccagactc ctacgggagg cagcagtgag gaatattgga 360
caatgggtga gagcctgatc cagccatccc gcgtgaagga cgacggccct atgggttgta 420
aacttctttt gtatagggat aaacctactc tcgtgagagt agctgaaggt actatacgaa 480
taagcaccgg ctaactccgt gccagcagcc gcggtaatac ggagggtgca agcgttatcc 540
ggatttattg ggtttaaagg gtccgtaggc ggatctgtaa gtcagtggtg aaatctcaca 600
gcttaactgt gaaactgcca ttgatactgc aggtcttgag tgttgttgaa gtagctggaa 660
taagtagtgt agcggtgaaa tgcatagata ttacttagaa caccaattgc gaaggcaggt 720
tactaagcaa caactgacgc tgatggacga aagcgtgggg agcgaacagg attagatacc 780

```
ctggtagtcc acgccgtaaa cgatgctaac tcgtttttgg tttttcggaa tcagagacta    840

agcgaaagtg ataagttagc cacctgggga gtacgttcgc aagaatgaaa ctcaaaggaa    900

ttgacggggg cccgcacaag cggtggatta tgtggtttaa ttcgatgata cgcgaggaac    960

cttaccaagg cttaaatggg aaatgacagg tttagaaata gacttttctt cggacatttt   1020

tcaaggtgct gcatggttgt cgtcagctcg tgccgtgagg tgttaggtta agtcctgcaa   1080

cgagcgcaac ccctgtcact agttgccatc attaagttgg ggactctagt gagactgcct   1140

acgcaagtag agaggaaggt ggggatgacg tcaaatcatc acggccctta cgccttgggc   1200

cacacacgta atacaatggc cagtacagag ggcagctaca cagcgatgtg atgcaaatct   1260

cgaaagctgg tctcagttcg gattggagtc tgcaactcga ctctatgaag ctggaatcgc   1320

tagtaatcgc gcatcannca tggcgcggtg aatacgttcc cgggncttgt acacaccgcc   1380

cgtcaagcca tggnagtctg ggtacctga agtcggtgac cgtaatagga gctgcctagg   1440

gtaaaacagg tactngggct aagtcgtann nnggnanccn gnaagcaggn annnngtann   1500

nnnnnnnnnn nnnnnnnnnn tnnnnnnnnn ncatcnnnnn nnn                     1543
```

<210> SEQ ID NO 4
<211> LENGTH: 1591
<212> TYPE: DNA
<213> ORGANISM: Burkholderia cepacia
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(46)
<223> OTHER INFORMATION: n is a, c, g, or t
<220> FEATURE:
<221> NAME/KEY: misc_feature
<222> LOCATION: (50)..(50)

<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (75)..(77)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (93)..(94)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (100)..(119)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (143)..(145)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (1584)..(1591)
<223> OTHER INFORMATION: n is a, c, g, or t

<400> SEQUENCE: 4
nttnnntnnn cnccccnccn ttnnnnnngn atnctacnnc nnnnnnatgn gnngnngnng 60
ccccttaaac nngannncaa ngaaacccaa aanncncccn nnnnnnnnnn nnnnnnnnng 120
ntnagatgaa cgctggcggc atnnntnaca catgcaagtc gaacggcagc acgggtgctt 180
gcacctggtg gcgagtggcg aacgggtgag taatacatcg gaacatgtcc tgtagtgggg 240
gatagcccgg cgaaagccgg attaataccg catacgatct acggatgaaa gcgggggacc 300
ttcgggcctc gcgctatagg gttggccgat ggctgattag ctagttggtg gggtaaaggc 360
ctaccaaggc gacgatcagt agctggtctg agaggacgac cagccacact gggactgaga 420
cacggcccag actcctacgg gaggcagcag tggggaattt tggacaatgg gcgaaagcct 480
gatccagcaa tgccgcgtgt gtgaagaagg ccttcgggtt gtaaagcact tttgtccgga 540
aagaaatcct tggctctaat acagtcgggg gatgacggta ccggaagaat aagcaccggc 600

```
taactacgtg ccagcagccg cggtaatacg tagggtgcga gcgttaatcg gaattactgg    660

gcgtaaagcg tgcgcaggcg gtttgttaag accgatgtga aatccccggg ctcaacctgg    720

gaactgcatt ggtgactggc aagctagagt atggcagagg ggggtagaat tccacgtgta    780

gcagtgaaat gcgtagagat gtggaggaat accgatggcg aaggcagccc cctgggccaa    840

tactgacgct catgcacgaa agcgtgggga gcaaacagga ttagataccc tggtagtcca    900

cgccctaaac gatgtcaact agttgttggg gattcatttc cttagtaacg tagctaacgc    960

gtgaagttga ccgcctgggg agtacggtcg caagattaaa actcaaagga attgacgggg   1020

acccgcacaa gcggtggatg atgtggatta attcgatgca acgcgaaaaa ccttacctac   1080

ccttgacatg gtcggaatcc tgctgagagg tgggagtgct cgaaagagaa ccgatacaca   1140

ggtgctgcat ggctgtcgtc agctcgtgtc gtgagatgtt gggttaagtc ccgcaacgag   1200

cgcaaccctt gtccttagtt gctacgcaag agcactctaa ggagactgcc ggtgacaaac   1260

cggaggaagg tggggatgac gtcaagtcct catggccctt atgggtaggg cttcacacgt   1320

catacaatgg tcggaacaga gggttgccaa cccgcgaggg ggagctaatc ccagaaaacc   1380

gatcgtagtc cggattgcac tctgcaactc gagtgcatga agctggaatc gctagtaatc   1440

gcggatcagc atgccgcggt gaatacgttc ccgggtcttg tacacaccgc ccgtcacacc   1500

atgggagtgg gttttaccag aagtggctag tctaaccgca aggaggacgg tcaccacggt   1560

aggattcatg actggggtga agtnnnnnnn n                                  1591
```

<210> SEQ ID NO 5
<211> LENGTH: 1613
<212> TYPE: DNA
<213> ORGANISM: Burkholderia mallei
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (36)..(40)

-continued

<223> OTHER INFORMATION: n is a, c, g, or t
<220> FEATURE:
<221> NAME/KEY: misc_feature
<222> LOCATION: (44)..(47)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (66)..(68)
<223> OTHER INFORMATION: n is a, c, g, or t
<220> FEATURE:
<221> NAME/KEY: misc_feature
<222> LOCATION: (71)..(73)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (101)..(103)
<223> OTHER INFORMATION: n is a, c, g, or t
<220> FEATURE:
<221> NAME/KEY: misc_feature
<222> LOCATION: (106)..(108)
<223> OTHER INFORMATION: n is a, c, g, or t
<220> FEATURE:
<221> NAME/KEY: misc_feature
<222> LOCATION: (110)..(117)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (124)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (153)..(155)
<223> OTHER INFORMATION: n is a, c, g, or t
<220> FEATURE:
<221> NAME/KEY: misc_feature
<222> LOCATION: (157)..(158)
<223> OTHER INFORMATION: n is a, c, g, or t
<220> FEATURE:
<221> NAME/KEY: misc_feature
<222> LOCATION: (1318)..(1318)
<223> OTHER INFORMATION: n is a, c, g, or t
<220> FEATURE:
<221> NAME/KEY: misc_feature
<222> LOCATION: (1536)..(1536)
<223> OTHER INFORMATION: n is a, c, g, or t
<220> FEATURE:
<221> NAME/KEY: misc_feature
<222> LOCATION: (1553)..(1555)
<223> OTHER INFORMATION: n is a, c, g, or t
<220> FEATURE:
<221> NAME/KEY: misc_feature
<222> LOCATION: (1562)..(1562)
<223> OTHER INFORMATION: n is a, c, g, or t
<220> FEATURE:
<221> NAME/KEY: misc_feature
<222> LOCATION: (1590)..(1591)
<223> OTHER INFORMATION: n is a, c, g, or t
<220> FEATURE:
<221> NAME/KEY: misc_feature
<222> LOCATION: (1593)..(1597)
<223> OTHER INFORMATION: n is a, c, g, or t
<220> FEATURE:
<221> NAME/KEY: misc_feature
<222> LOCATION: (1599)..(1613)
<223> OTHER INFORMATION: n is a, c, g, or t

<400> SEQUENCE: 5
ntntntnnnn annncgccnc cccnntcnnn cngatnnnnn cccnnnntna agagtgnann 60
ccgngnnncc nnnaaancgg ancaanggaa nccccaaacc nnnccnnntn nnnnnnnttt 120
tntnnntcng ntcagatgaa cgctggcggc atnnntnnca catgcaagtc gaacggcagc 180
acgggtgctt gcacctggtg gcgagtggcg aacgggtgag taatacatcg gaacatgtcc 240
tgtagtgggg gatagcccgg cgaaagccgg attaataccg catacgatct acggatgaaa 300
gcgggggacc ttcgggcctc gcgctatagg gttggccgat ggctgattag ctagttggtg 360
gggtaaaggc ctaccaaggc gacgatcagt agctggtctg agaggacgac cagccacact 420
gggactgaga cacggcccag actcctacgg gaggcagcag tggggaattt tggacaatgg 480
gcgaaagcct gatccagcaa tgccgcgtgt gtgaagaagg ccttcgggtt gtaaagcact 540
tttgtccgga aagaaatcct tggctctaat acagtcgggg gatgacggta ccggaagaat 600
aagcaccggc taactacgtg ccagcagccg cggtaatacg tagggtgcga gcgttaatcg 660
gaattactgg gcgtaaagcg tgcgcaggcg gtttgttaag accgatgtga aatccccggg 720
ctcaacctgg gaactgcatt ggtgactggc aagctagagt atggcagagg ggggtagaat 780
tccacgtgta gcagtgaaat gcgtagagat gtggaggaat accgatggcg aaggcagccc 840
cctgggccaa tactgacgct catgcacgaa agcgtgggga gcaaacagga ttagataccc 900
tggtagtcca cgccctaaac gatgtcaact agttgttggg gattcatttc cttagtaacg 960
tagctaacgc gtgaagttga ccgcctgggg agtacggtcg caagattaaa actcaaagga 1020
attgacgggg acccgcacaa gcggtggatg atgtggatta attcgatgca acgcgaaaaa 1080
ccttacctac ccttgacatg gtcggaatcc tgctgagagg tgggagtgct cgaaagagaa 1140
ccgatacaca ggtgctgcat ggctgtcgtc agctcgtgtc gtgagatgtt gggttaagtc 1200
ccgcaacgag cgcaaccctt gtccttagtt gctacgcaag agcactctaa ggagactgcc 1260
ggtgacaaac cggaggaagg tggggatgac gtcaagtcct catggccctt atgggtangg 1320
cttcacacgt catacaatgg tcggaacaga gggttgccaa cccgcgaggg ggagctaatc 1380
ccagaaaacc gatcgtagtc cggattgcac tctgcaactc gagtgcatga agctggaatc 1440
gctagtaatc gcggatcagc atgccgcggt gaatacgttc ccgggtcttg tacacaccgc 1500
ccgtcacacc atgggagtgg gttttaccag aagtgntagt ctaaccgcag gannnggtca 1560
cncggtagat tcatgactgg ggtgaagtcn nannnnngnn nnnnnnnnnn nnn 1613

<210> SEQ ID NO 6
<211> LENGTH: 1526
<212> TYPE: DNA
<213> ORGANISM: Bacillus sphaericus
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (90)..(91)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (1481)..(1482)
<223> OTHER INFORMATION: n is a, c, g, or t
<220> FEATURE:
<221> NAME/KEY: misc_feature
<222> LOCATION: (1512)..(1513)
<223> OTHER INFORMATION: n is a, c, g, or t
<220> FEATURE:
<221> NAME/KEY: misc_feature
<222> LOCATION: (1516)..(1517)
<223> OTHER INFORMATION: n is a, c, g, or t
<220> FEATURE:
<221> NAME/KEY: misc_feature
<222> LOCATION: (1519)..(1519)
<223> OTHER INFORMATION: n is a, c, g, or t
<220> FEATURE:
<221> NAME/KEY: misc_feature
<222> LOCATION: (1526)..(1526)
<223> OTHER INFORMATION: n is a, c, g, or t

<400> SEQUENCE: 6
nnnnnnnnnn tnnnnnnncn nntcaggatg aacgctggcg gcgtgcntaa tacatgcaag 60
tcgagcgaat ggattnanga gcttgctctn nangaagtta gcggcggacg ggtgagtaac 120
acgtgggtaa cctgcccata agactgggat aactccggga aaccggggct aataccggat 180
aatattttga actgcatggt tcgaaattga aaggcggctt cggctgtcac ttatggatgg 240
acccgcgtcg cattagctag ttggtgaggt aacggctcac caaggcaacg atgcgtagcc 300
gacctgagag ggtgatcggc cacactggga ctgagacacg gcccagactc ctacgggagg 360

```
cagcagtagg gaatcttccg caatggacga aagtctgacg gagcaacgcc gcgtgagtga    420

tgaaggcttt cgggtcgtaa aactctgttg ttagggaaga acaagtgcta gttgaataag    480

ctggcacctt gacggtacct aaccagaaag ccacggctaa ctacgtgcca gcagccgcgg    540

taatacgtag gtggcaagcg ttatccggaa ttattgggcg taaagcgcgc gcaggtggtt    600

tcttaagtct gatgtgaaag cccacggctc aaccgtggag ggtcattgga aactgggaga    660

cttgagtgca gaagaggaaa gtggaattcc atgtgtagcg gtgaaatgcg tagagatatg    720

gaggaacacc agtggcgaag gcgactttct ggtctgtaac tgacactgag gcgcgaaagc    780

gtggggagca aacaggatta gataccctgg tagtccacgc cgtaaacgat gagtgctaag    840

tgttagaggg tttccgccct ttagtgctga agttaacgca ttaagcactc cgcctgggga    900

gtacggccgc aaggctgaaa ctcaaaggaa ttgacggggg cccgcacaag cggtggagca    960

tgtggtttaa ttcgaagcaa cgcgaagaac cttaccaggt cttgacatcc tctgaaaacc   1020

ctagagatag ggcttctcct tcgggagcag agtgacaggt ggtgcatggt tgtcgtcagc   1080

tcgtgtcgtg agatgttggg ttaagtcccg caacgagcgc aacccttgat cttagttgcc   1140

atcattaagt tgggcactct aaggtgactg ccggtgacaa accggaggaa ggtggggatg   1200

acgtcaaatc atcatgcccc ttatgacctg ggctacacac gtgctacaat ggacggtaca   1260

aagagctgca agaccgcgag gtggagctaa tctcataaaa ccgttctcag ttcggattgt   1320

aggctgcaac tcgcctacat gaagctggaa tcgctagtaa tcgcggatca gcatgccgcg   1380

gtgaatacgt tcccgggcct tgtacacacc gcccgtcaca ccacgagagt ttgtaacacc   1440

cgaagtcggt ggggtaacct ttatggagcc agccgcctaa nngggacaga tgattggggt   1500

gaagtcgtac annggnnanc cgtaan                                        1526
```

<210> SEQ ID NO 7
<211> LENGTH: 1740
<212> TYPE: DNA
<213> ORGANISM: Enterobacter mori
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (86)..(88)
<223> OTHER INFORMATION: n is a, c, g, or t
<220> FEATURE:

<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (1499)..(1499)
<223> OTHER INFORMATION: n is a, c, g, or t
<220> FEATURE:
<221> NAME/KEY: misc_feature
<222> LOCATION: (1501)..(1506)
<223> OTHER INFORMATION: n is a, c, g, or t
<220> FEATURE:
<221> NAME/KEY: misc_feature
<222> LOCATION: (1512)..(1512)
<223> OTHER INFORMATION: n is a, c, g, or t
<220> FEATURE:
<221> NAME/KEY: misc_feature
<222> LOCATION: (1516)..(1516)
<223> OTHER INFORMATION: n is a, c, g, or t
<220> FEATURE:
<221> NAME/KEY: misc_feature
<222> LOCATION: (1518)..(1524)
<223> OTHER INFORMATION: n is a, c, g, or t
<220> FEATURE:
<221> NAME/KEY: misc_feature
<222> LOCATION: (1527)..(1527)
<223> OTHER INFORMATION: n is a, c, g, or t
<220> FEATURE:
<221> NAME/KEY: misc_feature
<222> LOCATION: (1529)..(1531)
<223> OTHER INFORMATION: n is a, c, g, or t
<220> FEATURE:
<221> NAME/KEY: misc_feature
<222> LOCATION: (1537)..(1537)
<223> OTHER INFORMATION: n is a, c, g, or t
<220> FEATURE:
<221> NAME/KEY: misc_feature
<222> LOCATION: (1539)..(1539)
<223> OTHER INFORMATION: n is a, c, g, or t
<220> FEATURE:
<221> NAME/KEY: misc_feature
<222> LOCATION: (1541)..(1543)
<223> OTHER INFORMATION: n is a, c, g, or t
<220> FEATURE:
<221> NAME/KEY: misc_feature
<222> LOCATION: (1546)..(1549)
<223> OTHER INFORMATION: n is a, c, g, or t
<220> FEATURE:
<221> NAME/KEY: misc_feature
<222> LOCATION: (1555)..(1557)
<223> OTHER INFORMATION: n is a, c, g, or t
<220> FEATURE:
<221> NAME/KEY: misc_feature
<222> LOCATION: (1559)..(1562)
<223> OTHER INFORMATION: n is a, c, g, or t
<220> FEATURE:
<221> NAME/KEY: misc_feature
<222> LOCATION: (1564)..(1567)
<223> OTHER INFORMATION: n is a, c, g, or t
<220> FEATURE:
<221> NAME/KEY: misc_feature
<222> LOCATION: (1569)..(1595)
<223> OTHER INFORMATION: n is a, c, g, or t
<220> FEATURE:
<221> NAME/KEY: misc_feature
<222> LOCATION: (1597)..(1597)
<223> OTHER INFORMATION: n is a, c, g, or t
<220> FEATURE:
<221> NAME/KEY: misc_feature
<222> LOCATION: (1600)..(1609)
<223> OTHER INFORMATION: n is a, c, g, or t
<220> FEATURE:
<221> NAME/KEY: misc_feature
<222> LOCATION: (1611)..(1616)
<223> OTHER INFORMATION: n is a, c, g, or t
<220> FEATURE:
<221> NAME/KEY: misc_feature
<222> LOCATION: (1618)..(1623)
<223> OTHER INFORMATION: n is a, c, g, or t
<220> FEATURE:
<221> NAME/KEY: misc_feature
<222> LOCATION: (1625)..(1654)
<223> OTHER INFORMATION: n is a, c, g, or t
<220> FEATURE:
<221> NAME/KEY: misc_feature
<222> LOCATION: (1656)..(1657)
<223> OTHER INFORMATION: n is a, c, g, or t
<220> FEATURE:
<221> NAME/KEY: misc_feature
<222> LOCATION: (1659)..(1666)
<223> OTHER INFORMATION: n is a, c, g, or t
<220> FEATURE:
<221> NAME/KEY: misc_feature
<222> LOCATION: (1668)..(1674)
<223> OTHER INFORMATION: n is a, c, g, or t
<220> FEATURE:
<221> NAME/KEY: misc_feature
<222> LOCATION: (1676)..(1676)
<223> OTHER INFORMATION: n is a, c, g, or t
<220> FEATURE:
<221> NAME/KEY: misc_feature
<222> LOCATION: (1678)..(1682)
<223> OTHER INFORMATION: n is a, c, g, or t
<220> FEATURE:
<221> NAME/KEY: misc_feature
<222> LOCATION: (1684)..(1686)
<223> OTHER INFORMATION: n is a, c, g, or t
<220> FEATURE:
<221> NAME/KEY: misc_feature
<222> LOCATION: (1689)..(1709)
<223> OTHER INFORMATION: n is a, c, g, or t
<220> FEATURE:
<221> NAME/KEY: misc_feature
<222> LOCATION: (1711)..(1720)
<223> OTHER INFORMATION: n is a, c, g, or t
<220> FEATURE:
<221> NAME/KEY: misc_feature
<222> LOCATION: (1722)..(1724)
<223> OTHER INFORMATION: n is a, c, g, or t
<220> FEATURE:
<221> NAME/KEY: misc_feature
<222> LOCATION: (1726)..(1727)
<223> OTHER INFORMATION: n is a, c, g, or t
<220> FEATURE:
<221> NAME/KEY: misc_feature
<222> LOCATION: (1729)..(1739)
<223> OTHER INFORMATION: n is a, c, g, or t

<400> SEQUENCE: 7
nnnnnnngtt tgantcntgn tcaggatgac gctggcggcg tncttaatac atgcaantcg 60
ancgaatgga ttaagagctt gctctnnnga agntagcggc ggacgggtga gtaacacgtg 120
ggtaacctgc ccataagact gggataantc cgggaaaccg gggctaatnc cggataacat 180
tttgaactgc atggttcgaa attgaaaggc ggcttcggct gtcacttatg gatggacccg 240
cgtcgcatta gctagttggt gaggtaacgg ctcaccaagg caacgatgcg tagccgacct 300
gagagggtga tcggccacac tgggactgag acacggccca gactcctacg ggaggcagca 360
gtagggaatc ttccgcaatg gacgaaagtc tgacggagca acgccgcgtg agtgatgaag 420
gctttcgggt cgtaaaactc tgttgttagg gaagaacaag tgctagttga ataagctggc 480
accttgacgg tacctaacca gaaagccacg gctaactacg tgccagcagc cgcggtaata 540
cgtaggtggc aagcgttatc cggaattatt gggcgtaaag cgcacgcagg cggtttgtta 600

-continued agtcagatgt gaaatccccg agcttaactt gggaactgca tttgaaactg gcaagctaga 660
gtcttgtaga ggggggtaga attccaggtg tagcggtgaa atgcgtagag atctggagga 720
ataccggtgg cgaaggcggc cccctggaca aagactgacg ctcaggtgcg aaagcgtggg 780
gagcaaacag gattagatac cctggtagtc cacgctgtaa acgatgtcga cttggaggtt 840
gtgcccttga ggcgtggctt ccggagctaa cgcgttaagt cgaccgcctg gggagtacgg 900
ccgcaaggtt aaaactcaaa tgaattgacg ggggcccgca caagcggtgg agcatgtggt 960
ttaattcgat gcaacgcgaa gaaccttacc tactcttgac atccagagaa ttcgctagag 1020
atagcttagt gccttcggga actctgagac aggtgctgca tggctgtcgt cagctcgtgt 1080
tgtgaaatgt tgggttaagt cccgcaacga gcgcaaccct tatcctttgt tgccagcgag 1140
taatgtcggg aactcaaagg agactgccgg tgataaaccg gaggaaggtg gggatgacgt 1200
caagtcatca tggcccttac gagtagggct acacacgtgc tacaatggcg catacaaaga 1260
gaagcgaact cgcgagagca agcggacctc ataaagtgcg tcgtagtccg gattggagtc 1320
tgcaactcga ctccatgaag tcggaatcgc tagtaatcgt agatcagaat gctacggtga 1380
atacgttccc gggccttgta cacaccgccc gtcacaccat gggagtgggt tgcaaaagaa 1440
gtaggtagct taaccttcgg gagggcgctt accactttgt gattcatgac tggggtgant 1500
nnnnnnggga anaccncnnn nnnnggngnn ngggggngng nnnttnnnnc ggggnnngnn 1560
nnannnnann nnnnnnnnnn nnnnnnnnnn nnnnncnccn nnnnnnnnna nnnnnnannn 1620
nnncnnnnnn nnnnnnnnnn nnnnnnnnnn nnnnanngnn nnnnnnannn nnnnantnnn 1680
nncnnncgnn nnnnnnnnnn nnnnnnnnng nnnnnnnnnn tnnntnntnn nnnnnnnnnc 1740

<210> SEQ ID NO 8
<211> LENGTH: 1515
<212> TYPE: DNA
<213> ORGANISM: Stenotrophomonas maltophilia
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(18)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1253)..(1253)
<223> OTHER INFORMATION: n is a, c, g, or t
<220> FEATURE:
<221> NAME/KEY: misc_feature
<222> LOCATION: (1271)..(1271)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1319)..(1319)
<223> OTHER INFORMATION: n is a, c, g, or t
<220> FEATURE:
<221> NAME/KEY: misc_feature
<222> LOCATION: (1348)..(1348)
<223> OTHER INFORMATION: n is a, c, g, or t
<220> FEATURE:
<221> NAME/KEY: misc_feature
<222> LOCATION: (1361)..(1361)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1394)..(1394)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1409)..(1411)
<223> OTHER INFORMATION: n is a, c, g, or t
<220> FEATURE:
<221> NAME/KEY: misc_feature
<222> LOCATION: (1429)..(1429)
<223> OTHER INFORMATION: n is a, c, g, or t
<220> FEATURE:
<221> NAME/KEY: misc_feature
<222> LOCATION: (1431)..(1432)
<223> OTHER INFORMATION: n is a, c, g, or t
<220> FEATURE:
<221> NAME/KEY: misc_feature
<222> LOCATION: (1435)..(1435)
<223> OTHER INFORMATION: n is a, c, g, or t
<220> FEATURE:
<221> NAME/KEY: misc_feature
<222> LOCATION: (1437)..(1437)
<223> OTHER INFORMATION: n is a, c, g, or t
<220> FEATURE:
<221> NAME/KEY: misc_feature
<222> LOCATION: (1447)..(1447)
<223> OTHER INFORMATION: n is a, c, g, or t
<220> FEATURE:
<221> NAME/KEY: misc_feature
<222> LOCATION: (1477)..(1478)
<223> OTHER INFORMATION: n is a, c, g, or t
<220> FEATURE:
<221> NAME/KEY: misc_feature
<222> LOCATION: (1480)..(1483)
<223> OTHER INFORMATION: n is a, c, g, or t
<220> FEATURE:
<221> NAME/KEY: misc_feature
<222> LOCATION: (1489)..(1489)
<223> OTHER INFORMATION: n is a, c, g, or t
<220> FEATURE:
<221> NAME/KEY: misc_feature
<222> LOCATION: (1493)..(1494)
<223> OTHER INFORMATION: n is a, c, g, or t
<220> FEATURE:
<221> NAME/KEY: misc_feature
<222> LOCATION: (1511)..(1511)
<223> OTHER INFORMATION: n is a, c, g, or t
<220> FEATURE:
<221> NAME/KEY: misc_feature
<222> LOCATION: (1513)..(1513)
<223> OTHER INFORMATION: n is a, c, g, or t
<220> FEATURE:
<221> NAME/KEY: misc_feature
<222> LOCATION: (1515)..(1515)
<223> OTHER INFORMATION: n is a, c, g, or t

<400> SEQUENCE: 8

-continued nntnnnagtt tngnnnnngg ctcagagtga acgctggcgn taggcctaac acatgcaagt 60
cgaacggcag cacaggagag cttgctctct gggtggcgag tggcggacgg gtgaggaata 120
catcggaatc tactctgtcg tgggggataa cgtagggaaa cttacgctaa taccgcatac 180
gacctacggg tgaaagcagg ggatcttcgg accttgcgcg attgaatgag ccgatgtcgg 240
attagctagt tggcggggta aaggcccacc aaggcgacga tccgtagctg gtctgagagg 300
atgatcagcc acactggaac tgagacacgg tccagactcc tacgggaggc agcagtgggg 360
aatattggac aatgggcgca agcctgatcc agccataccg cgtgggtgaa gaaggccttc 420
gggttgtaaa gcccttttgt tgggaaagaa atccagccgg ctaatacccg gttgggatga 480
cggtacccaa agaataagca ccggctaact tcgtgccagc agccgcggta atacgaaggg 540
tgcaagcgtt actcggaatt actgggcgta aagcgtgcgt aggtggtcgt ttaagtccgt 600
tgtgaaagcc ctgggctcaa cctgggaact gcagtggata ctgggcgact agagtgtggt 660
agagggtagc ggaattcctg gtgtagcagt gaaatgcgta gagatcagga ggaacatcca 720
tggcgaaggc agctacctgg accaacactg acactgaggc acgaaagcgt ggggagcaaa 780
caggattaga taccctggta gtccacgccc taaacgatgc gaactggatg ttgggtgcaa 840
tttggcacgc agtatcgaag ctaacgcgtt aagttcgccg cctggggagt acggtcgcaa 900
gactgaaact caaaggaatt gacgggggcc cgcacaagcg gtggagtatg tggtttaatt 960
cgatgcaacg cgaagaacct tacctggcct tgacatgtcg agaaccttcc agagatggat 1020
gggtgccttc gggaactcga acacaggtgc tgcatggctg tcgtcagctc gtgtcgtgag 1080
atgttgggtt aagtcccgca acgagcgcaa cccttgtcct tagttgccag cacgtaatgg 1140
tgggaactct aaggagaccg ccggtgacaa accggaggaa ggtggggatg acgtcaagtc 1200
atcatggccc ttacggccag ggctacacac gtactacaat ggtanggaca ganggctgca 1260
agccggcgac ngnaagccaa tcccagaaac cctatctcag tccggattgg agtctgcanc 1320
tcgactccat gaagtcggaa tcgctagnaa tcgcagatca ncattgctgc ggtgaatacg 1380
ttcccgggnc ttgnacacag cgcccgncnn nccatgggag tttgttgcnc nnaancnggt 1440
agcttancct tcgggagggc gcttgccacg tgtggcnnan nnntggggng aanncgtaac 1500
cagggtaacc ngnan 1515

<210> SEQ ID NO 9
<211> LENGTH: 1554
<212> TYPE: DNA
<213> ORGANISM: Dyella terrae
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t
<220> FEATURE:
<221> NAME/KEY: misc_feature
<222> LOCATION: (1477)..(1477)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1500)..(1502)
<223> OTHER INFORMATION: n is a, c, g, or t
<220> FEATURE:
<221> NAME/KEY: misc_feature
<222> LOCATION: (1506)..(1511)
<223> OTHER INFORMATION: n is a, c, g, or t
<220> FEATURE:
<221> NAME/KEY: misc_feature
<222> LOCATION: (1513)..(1516)
<223> OTHER INFORMATION: n is a, c, g, or t
<220> FEATURE:
<221> NAME/KEY: misc_feature
<222> LOCATION: (1518)..(1528)
<223> OTHER INFORMATION: n is a, c, g, or t
<220> FEATURE:
<221> NAME/KEY: misc_feature
<222> LOCATION: (1531)..(1545)
<223> OTHER INFORMATION: n is a, c, g, or t
<220> FEATURE:
<221> NAME/KEY: misc_feature
<222> LOCATION: (1547)..(1547)
<223> OTHER INFORMATION: n is a, c, g, or t
<220> FEATURE:
<221> NAME/KEY: misc_feature
<222> LOCATION: (1549)..(1554)
<223> OTHER INFORMATION: n is a, c, g, or t

<400> SEQUENCE: 9

```
nnnnnnnttn nnnnnnnnnc tcagattgaa cgctggcggc atgcctaaca catgcaagtc     60

gaacggcagc acagtagagc ttgctctatg ggtggcgagt ggcggacggg tgagtaatgc    120

atcgggatct acccaaacgt gggggataac gtagggaaac ttacgctaat accgcatacg    180

tcttacgaga gaaagcaggg gaccttcggg ccttgcgcgg ttggacgaac cgatgtgcga    240

ttagctagtt ggtagggtaa tggcctacca aggcgacgat cgctagctgg tctgagagga    300

tgatcagcca cactggaact gagacacggt ccagactcct acgggaggca gcagtgggga    360

atattggaca atgggcgcaa gcctgatcca gcaatgccgc gtgtgtgaag aaggccttcg    420

ggttgtaaag cacttttatc aggagcgaaa tactaccggc taatatccgg tggggctgac    480

ggtacctgag gaataagcac cggctaactt cgtgccagca gccgcggtaa tacgaagggt    540

gcaagcgtta atcggaatta ctgggcgtaa agcgtgcgta ggcggttatt taagtctgtt    600

gtgaaatccc cgggctcaac ctgggaatgg caatggatac tggatagcta gagtgtgata    660

gaggatggtg gaattcccgg tgtagcggtg aaatgcgtag agatcgggag gaacatcagt    720

ggcgaaggcg gccatctgga tcaacactga cgctgaggca cgaaagcgtg gggagcaaac    780

aggattagat accctggtag tccacgccct aaacgatgcg aactggatgt tggtctcaac    840

tcggagatca gtgtcgaagc taacgcgtta agttcgccgc ctggggagta cggtcgcaag    900

actgaaactc aaaggaattg acgggggccc gcacaagcgg tggagtatgt ggtttaattc    960

gatgcaacgc gaagaacctt acctggcctt gacatgtctg gaatcctgca gagatgcggg   1020

agtgccttcg ggaatcagaa cacaggtgct gcatggctgt cgtcagctcg tgtcgtgaga   1080

tgttgggtta agtcccgcaa cgagcgcaac ccttgtcctt agttgccagc acgtaatggt   1140

gggaactcta aggagactgc cggtgacaaa ccggaggaag gtggggatga cgtcaagtca   1200

tcatggccct tacggccagg gctacacacg tactacaatg gtcggtacag agggttgcaa   1260

taccgcgagg tggagccaat cccagaaagc cgatcccagt ccggattgga gtctgcaact   1320

cgactccatg aagtcggaat cgctagtaat cgcagatcag ctatgctgcg gtgaatacgt   1380

tcccgggcct tgtacacacc gcccgtcaca ccatgggagt gagttgctcc agaagccgtt   1440

agtctaaccg caagggggac gacgaccacg gagtggntca tgactggggt gaagtcntan   1500

nngggnnnnn ncnnnnannn nnnnnnnngg nnnnnnnnnn nnnnncncnn nnnn         1554
```

<210> SEQ ID NO 10

-continued

<211> LENGTH: 1726
<212> TYPE: DNA
<213> ORGANISM: Ewingella americana
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (15)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (53)..(55)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t -continued
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (108)..(109)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (126)..(127)
<223> OTHER INFORMATION: n is a, c, g, or t
<220> FEATURE:
<221> NAME/KEY: misc_feature
<222> LOCATION: (129)..(131)
<223> OTHER INFORMATION: n is a, c, g, or t
<220> FEATURE:
<221> NAME/KEY: misc_feature
<222> LOCATION: (134)..(144)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (148)..(150)
<223> OTHER INFORMATION: n is a, c, g, or t
<220> FEATURE:
<221> NAME/KEY: misc_feature
<222> LOCATION: (152)..(154)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1629)..(1659)
<223> OTHER INFORMATION: n is a, c, g, or t
<220> FEATURE:
<221> NAME/KEY: misc_feature
<222> LOCATION: (1666)..(1668)

```
<223> OTHER INFORMATION: n is a, c, g, or t
<220> FEATURE:
<221> NAME/KEY: misc_feature
<222> LOCATION: (1672)..(1672)
<223> OTHER INFORMATION: n is a, c, g, or t
<220> FEATURE:
<221> NAME/KEY: misc_feature
<222> LOCATION: (1676)..(1676)
<223> OTHER INFORMATION: n is a, c, g, or t
<220> FEATURE:
<221> NAME/KEY: misc_feature
<222> LOCATION: (1680)..(1687)
<223> OTHER INFORMATION: n is a, c, g, or t
<220> FEATURE:
<221> NAME/KEY: misc_feature
<222> LOCATION: (1689)..(1694)
<223> OTHER INFORMATION: n is a, c, g, or t
<220> FEATURE:
<221> NAME/KEY: misc_feature
<222> LOCATION: (1696)..(1698)
<223> OTHER INFORMATION: n is a, c, g, or t
<220> FEATURE:
<221> NAME/KEY: misc_feature
<222> LOCATION: (1700)..(1702)
<223> OTHER INFORMATION: n is a, c, g, or t
<220> FEATURE:
<221> NAME/KEY: misc_feature
<222> LOCATION: (1704)..(1704)
<223> OTHER INFORMATION: n is a, c, g, or t
<220> FEATURE:
<221> NAME/KEY: misc_feature
<222> LOCATION: (1706)..(1717)
<223> OTHER INFORMATION: n is a, c, g, or t
<220> FEATURE:
<221> NAME/KEY: misc_feature
<222> LOCATION: (1719)..(1726)
<223> OTHER INFORMATION: n is a, c, g, or t

<400> SEQUENCE: 10

nnannnnngn tatannnnng ntngnnnnnn tnttnncccn gnnantngnn acnnngnnac     60

cntaatcntn ncncgntnga gntgtgatcc ctggcncncn gtaantcnna acnaagnaac    120

ccgaanncnn nccnnnnnnn nnnntntnnn tnnnctgctc agattgaacg ctggcggcag    180

gcctaacaca tgcaagtcga gcggcagcgg gaagtagctt gctactttgc cggcgagcgg    240

cggacgggtg agtaatgtct gggaaactgc ctgatggagg gggataacta ctggaaacgg    300

tagctaatac cgcatgacct cgaaagagca aagtggggga ccttcgggcc tcacgccatc    360

ggatgtgccc agatgggatt agctagtagg tgaggtaatg gctcacctag gcgacgatcc    420

ctagctggtc tgagaggatg accagccaca ctggaactga gacacggtcc agactcctac    480

gggaggcagc agtggggaat attgcacaat gggcgcaagc ctgatgcagc catgccgcgt    540

gtgtgaagaa ggccttcggg ttgtaaagca ctttcagcga ggaggaaggc gttaaggtta    600

ataaccttag cgattgacgt tactcgcaga agaagcaccg gctaactccg tgccagcagc    660

cgcggtaata cggagggtgc aagcgttaat cggaattact gggcgtaaag cgcacgcagg    720

cggtttgtta agtcagatgt gaaatccccg agcttaactt gggaactgca tttgaaactg    780

gcaagctaga gtcttgtaga ggggggtaga attccaggtg tagcggtgaa atgcgtagag    840

atctggagga ataccggtgg cgaaggcggc cccctggaca aagactgacg ctcaggtgcg    900

aaagcgtggg gagcaaacag gattagatac cctggtagtc cacgctgtaa acgatgtcga    960

tttggaggtt gtgggcttga cccgtggctt ccggagctaa cgcgttaaat cgaccgcctg   1020

gggagtacgg ccgcaaggtt aaaactcaaa tgaattgacg ggggcccgca caagcggtgg   1080

agcatgtggt ttaattcgat gcaacgcgaa gaaccttacc tactcttgac atccagagaa   1140

ttcgctagag atagcttagt gccttcggga actctgagac aggtgctgca tggctgtcgt   1200
```

-continued

```
cagctcgtgt tgtgaaatgt tgggttaagt cccgcaacga gcgcaaccct tatcctttgt   1260

tgccagcgcg taatggcggg aactcaaagg agactgccgg tgataaaccg gaggaaggtg   1320

gggatgacgt caagtcatca tggcccttac gagtagggct acacacgtgc tacaatggca   1380

tatacaaaga gaagcgaact cgcgagagca agcggacctc ataaagtatg tcgtagtccg   1440

gattggagtc tgcaactcga ctccatgaag tcggaatcgc tagtaatcgt agatcanaat   1500

gctacggtga atacgttccc gggccttgta cacaccgccc gtcacaccat gggagtgggt   1560

tgcaaaagaa gtaggtagct taaccttcgg gagggcgctt accactttgt gattcatgac   1620

tggggtgann nnnnnnnnnn nnnnnnnnnn nnnnnnnnng gggggnnngt gntttntttn   1680

nnnnnnnann nnnnannnan nngnannnnn nnnnnnncnn nnnnnn                  1726


<210> SEQ ID NO 11
<211> LENGTH: 1568
<212> TYPE: DNA
<213> ORGANISM: Rahnella aquatilis
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (1391)..(1391)
<223> OTHER INFORMATION: n is a, c, g, or t
<220> FEATURE:
<221> NAME/KEY: misc_feature
<222> LOCATION: (1419)..(1420)
<223> OTHER INFORMATION: n is a, c, g, or t
<220> FEATURE:
<221> NAME/KEY: misc_feature
<222> LOCATION: (1440)..(1442)
<223> OTHER INFORMATION: n is a, c, g, or t
<220> FEATURE:
<221> NAME/KEY: misc_feature
<222> LOCATION: (1468)..(1469)
<223> OTHER INFORMATION: n is a, c, g, or t
<220> FEATURE:
<221> NAME/KEY: misc_feature
<222> LOCATION: (1491)..(1491)
<223> OTHER INFORMATION: n is a, c, g, or t
<220> FEATURE:
<221> NAME/KEY: misc_feature
<222> LOCATION: (1497)..(1527)
<223> OTHER INFORMATION: n is a, c, g, or t
<220> FEATURE:
<221> NAME/KEY: misc_feature
<222> LOCATION: (1529)..(1530)
```

-continued

<223> OTHER INFORMATION: n is a, c, g, or t
<220> FEATURE:
<221> NAME/KEY: misc_feature
<222> LOCATION: (1533)..(1533)
<223> OTHER INFORMATION: n is a, c, g, or t
<220> FEATURE:
<221> NAME/KEY: misc_feature
<222> LOCATION: (1535)..(1544)
<223> OTHER INFORMATION: n is a, c, g, or t
<220> FEATURE:
<221> NAME/KEY: misc_feature
<222> LOCATION: (1546)..(1548)
<223> OTHER INFORMATION: n is a, c, g, or t
<220> FEATURE:
<221> NAME/KEY: misc_feature
<222> LOCATION: (1550)..(1568)
<223> OTHER INFORMATION: n is a, c, g, or t

<400> SEQUENCE: 11
nntnnnnnnn ntntnnntnn ntctgntcag attgaacgct ggcggcaggn naacacatgc 60
aagtcgagcg gcagcgggaa gtagcttgct actttgccgg cgagcggcgg acgggtgagt 120
aatgtctggg aaactgcctg atggaggggg ataactactg gaaacggtag ctaataccgc 180
atgacctcgc aagagcaaag tgggggacct tcgggcctca cgccatcgga tgtgcccaga 240
tgggattagc tagtaggtga ggtaatggct cacctaggcg acgatcccta gctggtctga 300
gaggatgacc agccacactg gaactgagac acggtccaga ctcctacggg aggcagcagt 360
ggggaatatt gcacaatggg cgcaagcctg atgcagccat gccgcgtgtg tgaagaaggc 420
cttagggttg taaagcactt tcagcgagga ggaagggttc agtgttaata gcactgttca 480
ttgacgttac tcgcagaaga agcaccggct aactccgtgc cagcagccgc ggtaatacgg 540
agggtgcaag cgttaatcgg aattactggg cgtaaagcgc acgcaggcgg tttgttaagt 600
cagatgtgaa atccccgagc ttaacttggg aactgcattt gaaactggca agctagagtc 660
ttgtagaggg gggtagaatt ccaggtgtag cggtgaaatg cgtagagatc tggaggaata 720
ccggtggcga aggcggcccc ctggacaaag actgacgctc aggtgcgaaa gcgtggggag 780
caaacaggat tagataccct ggtagtccac gctgtaaacg atgtcgactt ggaggttgtg 840
cccttgaggc gtggcttccg gagctaacgc gttaagtcga ccgcctgggg agtacggccg 900
caaggttaaa actcaaatga attgacgggg gcccgcacaa gcggtggagc atgtggttta 960
attcgatgca acgcgaagaa ccttacctac tcttgacatc cagagaattc gctagagata 1020
gcttagtgcc ttcgggaact ctgagacagg tgctgcatgg ctgtcgtcag ctcgtgttgt 1080
gaaatgttgg gttaagtccc gcaacgagcg caacccttat cctttgttgc cagcacgtaa 1140
tggtgggaac tcaaaggaga ctgccggtga taaaccggag gaaggtgggg atgacgtcaa 1200
gtcatcatgg cccttacgag tagggctaca cacgtgctac aatggcatat acaaagagaa 1260
gcaaactcgc gagagcaagc ggacctcata aagtatgtcg tagtccggat tggagtctgc 1320
aactcgactc catgaagtcg gaatcgctag taatcgtaga tcagaatgct acggtgaata 1380
cgttcccggg ncttgtacac accgcccgtc acaccatgnn agtgggttgc aaaagaagtn 1440
nnagcttaac cttcgggagg gcgcttanna ctttgtgatt catgactggg ngagtcnnnn 1500
nnnnnnnnnn nnnnnnnnnn nnnnnnnann cgngnnnnnn nnnnannngn nnnnnnnnnn 1560 nnnnnnnn 1568

<210> SEQ ID NO 12
<211> LENGTH: 1634
<212> TYPE: DNA
<213> ORGANISM: Pseudomonas fluorescens
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(76)
<223> OTHER INFORMATION: n is a, c, g, or t
<220> FEATURE:
<221> NAME/KEY: misc_feature
<222> LOCATION: (79)..(84)
<223> OTHER INFORMATION: n is a, c, g, or t
<220> FEATURE:
<221> NAME/KEY: misc_feature
<222> LOCATION: (86)..(100)
<223> OTHER INFORMATION: n is a, c, g, or t
<220> FEATURE:
<221> NAME/KEY: misc_feature
<222> LOCATION: (126)..(127)
<223> OTHER INFORMATION: n is a, c, g, or t
<220> FEATURE:
<221> NAME/KEY: misc_feature
<222> LOCATION: (1364)..(1364)
<223> OTHER INFORMATION: n is a, c, g, or t
<220> FEATURE:
<221> NAME/KEY: misc_feature
<222> LOCATION: (1567)..(1567)
<223> OTHER INFORMATION: n is a, c, g, or t
<220> FEATURE:
<221> NAME/KEY: misc_feature
<222> LOCATION: (1570)..(1597)
<223> OTHER INFORMATION: n is a, c, g, or t
<220> FEATURE:
<221> NAME/KEY: misc_feature
<222> LOCATION: (1599)..(1604)

<223> OTHER INFORMATION: n is a, c, g, or t
<220> FEATURE:
<221> NAME/KEY: misc_feature
<222> LOCATION: (1606)..(1608)
<223> OTHER INFORMATION: n is a, c, g, or t
<220> FEATURE:
<221> NAME/KEY: misc_feature
<222> LOCATION: (1610)..(1610)
<223> OTHER INFORMATION: n is a, c, g, or t
<220> FEATURE:
<221> NAME/KEY: misc_feature
<222> LOCATION: (1612)..(1613)
<223> OTHER INFORMATION: n is a, c, g, or t
<220> FEATURE:
<221> NAME/KEY: misc_feature
<222> LOCATION: (1616)..(1617)
<223> OTHER INFORMATION: n is a, c, g, or t
<220> FEATURE:
<221> NAME/KEY: misc_feature
<222> LOCATION: (1619)..(1625)
<223> OTHER INFORMATION: n is a, c, g, or t
<220> FEATURE:
<221> NAME/KEY: misc_feature
<222> LOCATION: (1630)..(1634)
<223> OTHER INFORMATION: n is a, c, g, or t

<400> SEQUENCE: 12
nnnnnnnncn nnnnnnnnnt nnnagnnnnn nnnccnggnn cccgnnagnc cgnacnnnnn 60
tanacccgaa nncnnnccnn nnnnannnnn nnnnnnnnnn gctcagattg aacgctggcg 120
gcaggnnaac acatgcaagt cgagcggtag agagaagctt gcttctcttg agagcggcgg 180
acgggtgagt aatgcctagg aatctgcctg gtagtggggg ataacgctcg gaaacggacg 240
ctaataccgc atacgtccta cgggagaaag caggggacct tcgggccttg cgctatcaga 300
tgagcctagg tcggattagc tagttggtga ggtaatggct caccaaggcg acgatccgta 360
actggtctga gaggatgatc agtcacactg gaactgagac acggtccaga ctcctacggg 420
aggcagcagt ggggaatatt ggacaatggg cgaaagcctg atccagccat gccgcgtgtg 480
tgaagaaggt cttcggattg taaagcactt taagttggga ggaagggcat taacctaata 540
cgttggtgtc ttgacgttac cgacagaata agcaccggct aactctgtgc cagcagccgc 600
ggtaatacag agggtgcaag cgttaatcgg aattactggg cgtaaagcgc gcgtaggtgg 660
ttcgttaagt tggatgtgaa atccccgggc tcaacctggg aactgcattc aaaactgtcg 720
agctagagta tggtagaggg tggtggaatt tcctgtgtag cggtgaaatg cgtagatata 780
ggaaggaaca ccagtggcga aggcgaccac ctggactgat actgacactg aggtgcgaaa 840
gcgtggggag caaacaggat tagataccct ggtagtccac gccgtaaacg atgtcaacta 900
gccgttggga gccttgagct cttagtggcg cagctaacgc attaagttga ccgcctgggg 960
agtacggccg caaggttaaa actcaaatga attgacgggg gcccgcacaa gcggtggagc 1020
atgtggttta attcgaagca acgcgaagaa ccttaccagg ccttgacatc caatgaactt 1080
tccagagatg gattggtgcc ttcgggaaca ttgagacagg tgctgcatgg ctgtcgtcag 1140
ctcgtgtcgt gagatgttgg gttaagtccc gtaacgagcg caacccttgt ccttagttac 1200
cagcacgtca tggtgggcac tctaaggaga ctgccggtga caaaccggag gaaggtgggg 1260
atgacgtcaa gtcatcatgg cccttacggc ctgggctaca cacgtgctac aatggtcggt 1320
acaaagggtt gccaagccgc gaggtggagc taatcccata aaanccgatc gtagtccgga 1380
tcgcagtctg caactcgact gcgtgaagtc ggaatcgcta gtaatcgcga atcagaatgt 1440
cgcggtgaat acgttcccgg gccttgtaca caccgcccgt cacaccatgg gagtgggttg 1500
caccagaagt agctagtcta accttcggga ggacggttac cacggtgtga ttcatgactg 1560
gggtgantcn nnnnnnnnnn nnnnnnnnnn nnnnnnngnn nnnngnnntn cnntgnngnn 1620
nnnnnaaaan nnnn 1634

<210> SEQ ID NO 13
<211> LENGTH: 1728
<212> TYPE: DNA
<213> ORGANISM: Burkholderia pseudomallei
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (21)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (57)..(61)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (80)..(85)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (99)..(102)
<223> OTHER INFORMATION: n is a, c, g, or t
<220> FEATURE:

<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (134)..(136)
<223> OTHER INFORMATION: n is a, c, g, or t
<220> FEATURE:
<221> NAME/KEY: misc_feature
<222> LOCATION: (139)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (155)..(165)
<223> OTHER INFORMATION: n is a, c, g, or t
<220> FEATURE:
<221> NAME/KEY: misc_feature
<222> LOCATION: (1608)..(1608)
<223> OTHER INFORMATION: n is a, c, g, or t
<220> FEATURE:
<221> NAME/KEY: misc_feature
<222> LOCATION: (1626)..(1626)
<223> OTHER INFORMATION: n is a, c, g, or t
<220> FEATURE:
<221> NAME/KEY: misc_feature
<222> LOCATION: (1632)..(1636)
<223> OTHER INFORMATION: n is a, c, g, or t
<220> FEATURE:
<221> NAME/KEY: misc_feature
<222> LOCATION: (1639)..(1643)
<223> OTHER INFORMATION: n is a, c, g, or t
<220> FEATURE:
<221> NAME/KEY: misc_feature
<222> LOCATION: (1645)..(1646)
<223> OTHER INFORMATION: n is a, c, g, or t
<220> FEATURE:
<221> NAME/KEY: misc_feature
<222> LOCATION: (1648)..(1650)
<223> OTHER INFORMATION: n is a, c, g, or t
<220> FEATURE:
<221> NAME/KEY: misc_feature
<222> LOCATION: (1652)..(1652)
<223> OTHER INFORMATION: n is a, c, g, or t
<220> FEATURE:
<221> NAME/KEY: misc_feature
<222> LOCATION: (1654)..(1659)
<223> OTHER INFORMATION: n is a, c, g, or t
<220> FEATURE:
<221> NAME/KEY: misc_feature
<222> LOCATION: (1661)..(1661)
<223> OTHER INFORMATION: n is a, c, g, or t
<220> FEATURE:
<221> NAME/KEY: misc_feature
<222> LOCATION: (1664)..(1664)
<223> OTHER INFORMATION: n is a, c, g, or t
<220> FEATURE:
<221> NAME/KEY: misc_feature
<222> LOCATION: (1666)..(1666)
<223> OTHER INFORMATION: n is a, c, g, or t
<220> FEATURE:
<221> NAME/KEY: misc_feature
<222> LOCATION: (1668)..(1668)
<223> OTHER INFORMATION: n is a, c, g, or t
<220> FEATURE:
<221> NAME/KEY: misc_feature
<222> LOCATION: (1670)..(1670)
<223> OTHER INFORMATION: n is a, c, g, or t
<220> FEATURE:
<221> NAME/KEY: misc_feature
<222> LOCATION: (1672)..(1672)
<223> OTHER INFORMATION: n is a, c, g, or t
<220> FEATURE:
<221> NAME/KEY: misc_feature
<222> LOCATION: (1674)..(1674)
<223> OTHER INFORMATION: n is a, c, g, or t
<220> FEATURE:
<221> NAME/KEY: misc_feature
<222> LOCATION: (1680)..(1687)
<223> OTHER INFORMATION: n is a, c, g, or t
<220> FEATURE:
<221> NAME/KEY: misc_feature
<222> LOCATION: (1689)..(1691)
<223> OTHER INFORMATION: n is a, c, g, or t
<220> FEATURE:
<221> NAME/KEY: misc_feature
<222> LOCATION: (1697)..(1698)
<223> OTHER INFORMATION: n is a, c, g, or t
<220> FEATURE:
<221> NAME/KEY: misc_feature
<222> LOCATION: (1700)..(1700)
<223> OTHER INFORMATION: n is a, c, g, or t
<220> FEATURE:
<221> NAME/KEY: misc_feature
<222> LOCATION: (1702)..(1707)
<223> OTHER INFORMATION: n is a, c, g, or t
<220> FEATURE:
<221> NAME/KEY: misc_feature
<222> LOCATION: (1709)..(1718)
<223> OTHER INFORMATION: n is a, c, g, or t
<220> FEATURE:
<221> NAME/KEY: misc_feature
<222> LOCATION: (1720)..(1720)
<223> OTHER INFORMATION: n is a, c, g, or t
<220> FEATURE:
<221> NAME/KEY: misc_feature
<222> LOCATION: (1722)..(1723)
<223> OTHER INFORMATION: n is a, c, g, or t
<220> FEATURE:
<221> NAME/KEY: misc_feature
<222> LOCATION: (1727)..(1728)
<223> OTHER INFORMATION: n is a, c, g, or t

<400> SEQUENCE: 13
nannnnatct annncgggta nnnnnngntg ntnntnnagn aaagcgttac cnnagtnnnn 60
ntaaatggta nnanggtaan nnnnngagcn cngactccnn nnaatnctta ancnaagggn 120
aacccgnaag tcgnnnccnn nnnnnnnnnn ttntnnnnnn nnnnnctcag attgaacgct 180
ggcggcatgc cttacacatg caagtcgaac ggcagcacgg gtgcttgcac ctggtggcga 240
gtggcgaacg ggtgagtaat acatcggaac atgtcctgta gtgggggata gcccggcgaa 300
agccggatta ataccgcata cgatctacgg atgaaagcgg gggaccttcg ggcctcgcgc 360
tatagggttg gccgatggct gattagctag ttggtggggt aaaggcctac caaggcgacg 420
atcagtagct ggtctgagag gacgaccagc cacactggga ctgagacacg gcccagactc 480
ctacgggagg cagcagtggg gaattttgga caatgggcga aagcctgatc cagcaatgcc 540
gcgtgtgtga agaaggcctt cgggttgtaa agcacttttg tccggaaaga aatccttgac 600
cctaatacgg tcgggggatg acggtaccgg aagaataagc accggctaac tacgtgccag 660
cagccgcggt aatacgtagg gtgcgagcgt taatcggaat tactgggcgt aaagcgtgcg 720

-continued

```
caggcggttt gctaagaccg atgtgaaatc cccgggctca acctgggaac tgcattggtg    780

actggcaggc tagagtatgg cagagggggg tagaattcca cgtgtagcag tgaaatgcgt    840

agagatgtgg aggaataccg atggcgaagg cagccccctg ggccaatact gacgctcatg    900

cacgaaagcg tggggagcaa acaggattag ataccctggt agtccacgcc ctaaacgatg    960

tcaactagtt gttggggatt catttcctta gtaacgtagc taacgcgtga agttgaccgc   1020

ctggggagta cggtcgcaag attaaaactc aaaggaattg acggggaccc gcacaagcgg   1080

tggatgatgt ggattaattc gatgcaacgc gaaaaacctt acctaccctt gacatggtcg   1140

gaatcccgct gagaggtggg ggtgctcgaa agagaaccga tacacaggtg ctgcatggct   1200

gtcgtcagct cgtgtcgtga gatgttgggt taagtcccgc aacgagcgca acccttgtcc   1260

ttagttgcta cgcaagagca ctctaaggag actgccggtg acaaaccgga ggaaggtggg   1320

gatgacgtca agtcctcatg gcccttatgg gtagggcttc acacgtcata caatggtcgg   1380

aacagagggt tgccaacccg cgagggggag ctaatcccag aaaaccgatc gtagtccgga   1440

ttgcactctg caactcgagt gcatgaagct ggaatcgcta gtaatcgcgg atcagcatgc   1500

cgcggtgaat acgttcccgg gtcttgtaca caccgcccgt cacaccatgg gagtgggttt   1560

taccagaagt ggctagtcta accgcaagga ggacggtcac cacggtanat tcatgactgg   1620

ggtgantcgt annnnnggnn nnncnncnnn anannnnnnc nggntngngn tntnttcttn   1680

nnnnnnnann ncctcanncn cnnnnnncnn nnnnnnnnan anntgtnn                1728


<210> SEQ ID NO 14
<211> LENGTH: 1555
<212> TYPE: DNA
<213> ORGANISM: Averyella dalhousiensis
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(24)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t
<220> FEATURE:
<221> NAME/KEY: misc_feature
<222> LOCATION: (47)..(49)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
```

<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (83)..(85)
<223> OTHER INFORMATION: n is a, c, g, or t
<220> FEATURE:
<221> NAME/KEY: misc_feature
<222> LOCATION: (87)..(89)
<223> OTHER INFORMATION: n is a, c, g, or t
<220> FEATURE:
<221> NAME/KEY: misc_feature
<222> LOCATION: (91)..(94)
<223> OTHER INFORMATION: n is a, c, g, or t
<220> FEATURE:
<221> NAME/KEY: misc_feature
<222> LOCATION: (96)..(99)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (1451)..(1451)
<223> OTHER INFORMATION: n is a, c, g, or t

<400> SEQUENCE: 14

```
nnnnnnnnnn nnnanncnnn nnnncctcan nccgntnnaa nnngatnnng gcnnccgtan     60

ntcgtaacnc angnaaccnn aannncnnnc nnnntnnnnt tttttttntc tgctcagatt    120

gaacgctggc ggcaggccta acacatgcaa gtcgaacggt aacaggaagc agcttgctgc    180

tttgctgacg agtggcggac gggtgagtaa tgtctgggaa actgcccgat ggagggggat    240

aactactgga aacggtagct aataccgcat aacgtcttcg gaccaaagag ggggaccttc    300

gggcctcttg ccatcggatg tgcccagatg ggattagcta gtaggtgggg taacggctca    360

cctaggcgac gatccctagc tggtctgaga ggatgaccag ccacactgga actgagacac    420

ggtccagact cctacgggag gcagcagtgg ggaatattgc acaatgggcg caagcctgat    480

gcagccatgc cgcgtgtatg aagaaggcct tcgggttgta aagtactttc agcgaggagg    540

aaggcattgt ggttaataac cacagtgatt gacgttactc gcagaagaag caccggctaa    600

ctccgtgcca gcagccgcgg taatacggag ggtgcaagcg ttaatcggaa ttactgggcg    660

taaagcgcac gcaggcggtc tgtcaagtcg gatgtgaaat ccccgggctc aacctgggaa    720

ctgcattcga aactggcaga ctagagtctt gtagaggggg gtagaattcc aggtgtagcg    780

gtgaaatgcg tagagatctg gaggaatacc ggtggcgaag gcggccccct ggacaaagac    840

tgacgctcag gtgcgaaagc gtggggagca aacaggatta gataccctgg tagtccacgc    900

cgtaaacgat gtcgacttgg aggttgtgcc cttgaggcgt ggcttccgga gctaacgcgt    960

taagtcgacc gcctggggag tacggccgca aggttaaaac tcaaatgaat tgacgggggc   1020

ccgcacaagc ggtggagcat gtggtttaat tcgatgcaac gcgaagaacc ttacctactc   1080
```

-continued

```
ttgacatcca gagaacttag cagagatgct ttggtgcctt cgggaactct gagacaggtg   1140

ctgcatggct gtcgtcagct cgtgttgtga aatgttgggt taagtcccgc aacgagcgca   1200

acccttatcc tttgttgcca gcggttcggc cgggaactca aaggagactg ccagtgataa   1260

actggaggaa ggtggggatg acgtcaagtc atcatggccc ttacgagtag ggctacacac   1320

gtgctacaat ggcgcataca aagagaagcg acctcgcgag agcaagcgga cctcataaag   1380

tgcgtcgtag tccggattgg agtctgcaac tcgactccat gaagtcggaa tcgctagtaa   1440

tcgtagatca naatgctacg gtgaatacgt tcccgggcct tgtacacacc gcccgtcaca   1500

ccatgggagt gggttgcaaa agaagtaggt agcttaacct tcgggagggc gctta        1555
```

MASSIVELY PARALLEL ON-CHIP CONSTRUCTION OF SYNTHETIC MICROBIAL COMMUNITIES

CROSS REFERENCE TO RELATED APPLICATIONS

This application is a national stage application, filed under 35 U.S.C. § 371, of international application No. PCT/US2020/030747, filed Apr. 30, 2020, which claims the benefit of U.S. Provisional Application No. 62/841,546, filed May 1, 2019, entitled "Massively Parallel On-Chip Construction of Synthetic Microbial Communities," the entire contents of which are incorporated herein by reference.

FIELD OF THE DISCLOSURE

The disclosure relates to compositions and methods for combinatorial assessment of nanoscale droplets, as specifically exemplified by massively parallel assessment of spatially-directed (though agnostic as to precise content) combinations of droplets harboring distinct and independently identifiable microbial types. More particularly, the disclosure relates to a platform and methodologies for identifying advantageous (including synergistic, additive, etc.) microbial interactions in a manner that allows for binary, trinary, etc. combinatorial assessments to be performed across a range of many discrete input types of microbes (e.g., 6-16 or more discrete input microbial types), to an extent that approaches comprehensive sampling of microbial community combinations from a selected panel of microbial inputs.

SEQUENCE LISTING

The instant application contains a Sequence Listing which has been filed electronically in ASCII format and is hereby incorporated by reference in its entirety. Said ASCII copy, created on Oct. 29, 2021, is named BN00007_0962_BI_10514_SL.txt and is 66 KB in size.

BACKGROUND OF THE DISCLOSURE

Microbial communities have numerous potential applications in biotechnology, agriculture, and medicine. Yet the limited accuracy with which interspecies interactions and environmental dependencies can be predicted has heretofore hindered efforts to rationally engineer beneficial consortia. Empirical screening is a complementary approach wherein synthetic communities are combinatorially constructed and assayed in high throughput. However, assembling many combinations of microbes is logistically complex and difficult to achieve on a timescale commensurate with microbial growth. Extant experimental strategies to investigate microbial community behavior have therefore been limited by the challenges posed by the combinatorial complexity of interactions between species. Accordingly, there is an urgent need for compositions and methods for identifying microbial communities possessing preferred attributes, where input microbes are selected from among even a modest panel of discrete types of microbes (e.g., 6-16 or more), in a scalable and cost-efficient manner that allows for microbial community assessment coverage to occur across a significant portion of the probability-defined complexity space (specifically, where complex microbial populations are assembled to include precisely k inputs (e.g. strains or media) selected from a larger library of n (e.g. strains or media), comprehensive assessment of such complex microbial combinations would require sampling of n-multichoose-k combinations).

SUMMARY OF THE DISCLOSURE

The instant disclosure is based, at least in part, upon the discovery of a platform and associated methodology that enables parallel screening of distinct combinations of input liquid samples (encapsulated in droplets, which in certain aspects encapsulate distinct microbe and/or chemical compound inputs) in a manner that both maximizes tested combinations of input samples while minimizing the number of liquid handling processes required to achieve such combinations and measure properties associated with such combinations. In certain aspects, the instant disclosure specifically provides a platform to automatically construct and test synthetic communities of microbes—optionally together with chemical compounds (e.g., test compounds) —from a set of input species, at a scale of ~100,000 (~$10^5$) to ~$10^8$ or more communities per day.

In one aspect, the instant disclosure provides a microfluidic screening platform that includes at least one droplet input for receiving one or more sets of droplets, each set of droplets including individual droplets each individual droplet having a single type of microbe and/or chemical compound or mixture; and an array of microwells, where each microwell is capable of receiving an individual droplet.

In one embodiment, a plurality (optionally a majority) of the microwells of the array of microwells includes one and only one droplet.

In another embodiment, individual droplets of the array of microwells are optically screened, and optionally optical screening of individual droplets identifies the single type of microbe and/or chemical compound or mixture present in the individual droplet. In a related embodiment, the optical screening includes measurement of luminescence and/or fluorescence, optionally where the fluorescence of one or more agents such as Alexa Fluor 488, Alexa Fluor 555, Alexa Fluor 594 and/or Alexa Fluor 647 is measured, optionally where a ratio or ratios of Alexa Fluor 488, Alexa Fluor 555, Alexa Fluor 594 and/or Alexa Fluor 647 identifies the single type of microbe present in the individual droplet.

In an additional embodiment, individual droplets in user-selected adjacent microwells are merged into a single merged assay, optionally by electrocoalescence, thermal coalescence or acoustic coalescence.

In a further embodiment, across the array, individual droplets in k=2-50 adjoining microwells, optionally in k=2, 3, 4, 5, 6, 7 and/or 19 adjoining microwells, are merged into single merged assays.

In another embodiment, one or more attributes of the microbes and/or chemical compounds or mixtures present in each merged assay are measured via optical screening. Optionally, the optical screening includes measurement of luminescence and/or fluorescence, optionally autofluorescence, optionally in a label-free optical assay, optionally where the optical screening includes measurement of GFP, YFP and/or resorufin fluorescence.

In one embodiment, the droplets including microbes and/or chemical compounds or mixtures self-assemble randomly into microwells.

In another embodiment, the one or more attributes of the microbes present in each merged assay measured via optical screening include growth of the microbes, optionally growth of the microbes on a carbon source of Table 1.

In an additional embodiment, each single merged assay includes two or more types of microbes and optionally three or more types of microbes, optionally where the two or more types of microbes are *Achromobacter* spp. (e.g., *Achromobacter denitrificans, Achromobacter xylosoxidans, Achromobacter ruhlandii*); *Actinomadura* spp. (e.g., *Actinomadura luteofluorescens, Actinomadura madurae, Actinomadura pelletieri, Actinomadura viridis*); *Agrobacterium* spp. (e.g., *Agrobacterium radiobacter, Agrobacterium luteum, Agrobacterium agile, Agrobacterium rubi*); *Arthrobacter* spp. (e.g., *Arthrobacter arilaitensis, Arthrobacter chlorophenolicus, Arthrobacter aurescens*); *Bacillus* spp. (e.g., *Bacillus cereus, Bacillus subtilis, Bacillus coagulans, Bacillus psychrosaccharolyticus, Bacillus amyloliquefaciens, Bacillus lentus, Bacillus circulans, Bacillus firmus*); *Burkholderia* spp. (e.g., *Burkholderia gladioli, Burkholderia plantarii, Burkholderia cepacia*); *Clostridium* spp. (e.g., *Clostridium orbiscindens, Clostridium formicaceticum*); *Escherichia coli; Ewingella* spp. (e.g., *Ewingella* americana); *Flavobacterium* spp. (e.g., *Flavobacterium flevense, Flavobacterium aquatile, Flavobacterium saccharophilum, Flavobacterium hydatis, Flavobacterium johnsoniae*); *Flexibacter* spp. (e.g., *Flexibacter flexilis, Flexibacter columnare*); *Herbaspirillum frisingense; Hyphomicrobium* spp. (e.g., *Hyphomicrobium aestuarii*); *Micromonospora* spp. (e.g., *Micromonospora rosaria, Micromonospora facile, Micromonospora zavarzinii, Micromonospora denitrificans*); *Mycobacterium* spp. (e.g., *Mycobacterium neoaurum*); *Nocardia* spp. (e.g., *Nocardia jiangxiensis, Nocardia miyunensis*); *Paenibacillus* spp. (e.g., *Paenibacillus macquariensis, Paenibacillus macerans, Paenibacillus alvei, Paenibacillus polymyxa, Paenibacillus chibensis*); *Pseudomonas* spp. (e.g., *Pseudomonas aeruginosa, Pseudomonas putida, Pseudomonas fluorescens, Pseudomonas citronellolis, Pseudomonas chlororaphis, Pseudomonas aurantiaca, Pseudomonas pseudopalustris, Pseudomonas palustris, Pseudomonas syringae, Pseudomonas veronii, Pseudomonas aurantiaca*); *Ralstonia* spp. (e.g., *Ralstonia solanacearum, Ralstonia pickettii, Ralstonia syzygii*); *Rhodococcus* spp. (e.g., *Rhodococcus erythropolis, Rhodococcus rhodochrous*); *Serratia* spp. (e.g., *Serratia marcescens, Serratia liquefaciens*); *Sphingomonas* spp. (e.g., *Sphingomonas echinoides, Sphingomonas leidyi, Sphingomonas wittichii*); *Streptomyces* spp. (e.g., *Streptomyces lividans, Streptomyces coelicolor, Streptomyces tanashiensis, Streptomyces clavuligerus, Streptomyces griseus*); *Venturia, Aspergillus, Podosphaera, Erysiphe, Monilinia, Uncinula, Aureobasidium, Sclerophoma, Acremonium, Actinoplanes, Agaricus, Chrysosporium, Colletotrichum, Coprinus, Cryptococcus, Filibasidum, Humicola, Magnaporthe, Myceliophthora, Neocallimastix, Neurospora, Paecilomyces, Phytophthora, Piromyces, Panerochaete, Pleurotus, Pythium, Schizophyllum, Talaromyces, Thermoascus, Thielavia, Tolypocladium, Trichoderma, Hemileia, Rhizoctonia, Puccinia, Coniophora, Serpula, Poria, Uromyces, Gloeophyllum, Lentinus, Coriolus, Irpex, Mucor, Botrytis, Helminthosporium, Rhynchosporium, Fusarium, Septoria, Cercospora, Alternaria, Pyricularia, Penicillium, Geotrichum*, and/or *Zymoseptoria*. In certain embodiments, it is contemplated that pairwise combinations of microbe types, or even single species of microbes, can be assessed using the compositions and methods disclosed herein.

In one embodiment, each single merged assay harbors two or more types of microbes and/or chemical compounds or mixtures, where at least one of the two or more types of microbes and/or chemical compounds or mixtures is a microbe. Optionally, at least one of the two or more types of microbes is a fungus. Optionally, the fungus is *Venturia, Aspergillus, Podosphaera, Erysiphe, Monilinia, Uncinula, Aureobasidium, Sclerophoma, Acremonium, Actinoplanes, Agaricus, Chrysosporium, Colletotrichum, Coprinus, Cryptococcus, Filibasidum, Humicola, Magnaporthe, Myceliophthora, Neocallimastix, Neurospora, Paecilomyces, Phytophthora, Piromyces, Panerochaete, Pleurotus, Pythium, Schizophyllum, Talaromyces, Thermoascus, Thielavia, Tolypocladium, Trichoderma, Hemileia, Rhizoctonia, Puccinia, Coniophora, Serpula, Poria, Uromyces, Gloeophyllum, Lentinus, Coriolus, Irpex, Mucor, Botrytis, Helminthosporium, Rhynchosporium, Fusarium, Septoria, Cercospora, Alternaria, Pyricularia, Penicillium, Geotrichum*, and/or *Zymoseptoria*, In certain embodiments, the fungus is a filamentous fungus, e.g., *Acremonium, Agaricus, Aspergillus* (e.g., *Aspergillus niger* (i.e., *A. niger* van Tieghem ATCC® 10535™); *Aspergillus fumigatus* (i.e., *A. fumigatus* Fresenius ATCC® 969187™); *Aspergillus penicillioides* (i.e., *A. penicillioides* Spegazzini, anamorph ATCC® 42692™)), *Aureobasidium, Chrysosporium, Coprinus, Cryptococcus, Filibasidium, Fusarium* (e.g., *Fusarium oxysporum* (i.e., *F. oxysporum* Schlechtendahl ATCC® MYA-1198™)), *Humicola, Magnaporthe, Mucor* (e.g., *Mucor circinelloides* (i.e., *M. circinelloides* van Tieghem ATCC® 38592™)), *Myceliophthora, Neocallimastix, Neurospora, Paecilomyces, Penicillium* (e.g., *Penicillium glabrum* (i.e., *P. glabrum* (Wehmer) Westling ATCC® 10103™)), *Piromyces, Panerochaete, Pleurotus, Schizophyllum, Talaromyces, Thermoascus, Thielavia, Tolypocladium, Trichoderma*, and/or *Zymoseptoria*.

In some embodiments, at least one of the two or more types of microbes and/or chemical compounds or mixtures is a chemical compound. Optionally, the chemical compound is a small molecule.

In certain embodiments, at least one of the two or more types of microbes and/or chemical compounds or mixtures is a bacterium. Optionally, the bacterium is *Achromobacter* spp. (e.g., *Achromobacter denitrificans, Achromobacter xylosoxidans, Achromobacter ruhlandii*); *Actinomadura* spp. (e.g., *Actinomadura luteofluorescens, Actinomadura madurae, Actinomadura pelletieri, Actinomadura viridis*); *Agrobacterium* spp. (e.g., *Agrobacterium radiobacter, Agrobacterium luteum, Agrobacterium agile, Agrobacterium rubi*); *Arthrobacter* spp. (e.g., *Arthrobacter arilaitensis, Arthrobacter chlorophenolicus, Arthrobacter aurescens*); *Bacillus* spp. (e.g., *Bacillus cereus, Bacillus subtilis, Bacillus coagulans, Bacillus psychrosaccharolyticus, Bacillus amyloliquefaciens, Bacillus lentus, Bacillus circulans, Bacillus firmus*); *Burkholderia* spp. (e.g., *Burkholderia gladioli, Burkholderia plantarii, Burkholderia cepacia*); *Clostridium* spp. (e.g., *Clostridium orbiscindens, Clostridium formicaceticum*); *Escherichia coli; Ewingella* spp. (e.g., *Ewingella americana*); *Flavobacterium* spp. (e.g., *Flavobacterium flevense, Flavobacterium aquatile, Flavobacterium saccharophilum, Flavobacterium hydatis, Flavobacterium johnsoniae*); *Flexibacter* spp. (e.g., *Flexibacter flexilis, Flexibacter columnare*); *Herbaspirillum frisingense; Hyphomicrobium* spp. (e.g., *Hyphomicrobium aestuarii*); *Micromonospora* spp. (e.g., *Micromonospora rosaria, Micromonospora facile, Micromonospora zavarzinii, Micromonospora denitrificans*); *Mycobacterium* spp. (e.g., *Mycobacterium neoaurum*); *Nocardia* spp. (e.g., *Nocardia jiangxiensis, Nocardia miyunensis*); *Paenibacillus* spp. (*e.g., Paenibacillus macquariensis, Paenibacillus macerans, Paenibacillus alvei, Paenibacillus polymyxa, Paenibacillus chibensis*); *Pseudomonas* spp. (*e.g., Pseudomonas aeruginosa, Pseudomonas putida, Pseudomonas fluorescens, Pseudomo-*

*nas citronellolis, Pseudomonas chlororaphis, Pseudomonas aurantiaca, Pseudomonas pseudopalustris, Pseudomonas palustris, Pseudomonas syringae, Pseudomonas veronii, Pseudomonas aurantiaca*); *Ralstonia* spp. (*e.g., Ralstonia solanacearum, Ralstonia pickettii, Ralstonia syzygii*); *Rhodococcus* spp. (*e.g., Rhodococcus erythropolis, Rhodococcus rhodochrous*); *Serratia* spp. (*e.g., Serratia marcescens, Serratia liquefaciens*); *Sphingomonas* spp. (*e.g., Sphingomonas echinoides, Sphingomonas leidyi, Sphingomonas wittichii*); and/or *Streptomyces* spp. (*e.g., Streptomyces lividans, Streptomyces coelicolor, Streptomyces tanashiensis, Streptomyces clavuligerus, Streptomyces griseus*).

In an embodiment, each single merged assay harbors two or more types of fungi. Optionally, the two or more types of fungi are *Venturia, Aspergillus, Podosphaera, Erysiphe, Monilinia, Uncinula, Aureobasidium, Sclerophoma, Acremonium, Actinoplanes, Agaricus, Chrysosporium, Colletotrichum, Coprinus, Cryptococcus, Filibasidum, Humicola, Magnaporthe, Myceliophthora, Neocallimastix, Neurospora, Paecilomyces, Phytophthora, Piromyces, Panerochaete, Pleurotus, Pythium, Schizophyllum, Talaromyces, Thermoascus, Thielavia, Tolypocladium, Trichoderma, Hemileia, Rhizoctonia, Puccinia, Coniophora, Serpula, Poria, Uromyces, Gloeophyllum, Lentinus, Coriolus, Irpex, Mucor, Botrytis, Helminthosporium, Rhynchosporium, Fusarium, Septoria, Cercospora, Alternaria, Pyricularia, Penicillium, Geotrichum*, and/or *Zymoseptoria.*

In one embodiment, at least one of the single merged assays harbors a combination of at least one fungus and at least one bacteria. Optionally, a plurality of the single merged assays harbor a combination of at least one fungus and at least one bacteria. Optionally, a majority of the single merged assays harbor a combination of at least one fungus and at least one bacteria.

In an embodiment, at least one of the single merged assays harbors a combination of at least one fungus and at least one chemical compound or mixture. Optionally, a plurality of the single merged assays harbor a combination of at least one fungus and at least one chemical compound or mixture. Optionally, a majority of the single merged assays harbor a combination of at least one fungus and at least one chemical compound or mixture.

In one embodiment, at least one of the single merged assays harbors a combination of at least one bacteria and at least one chemical compound or mixture. Optionally, a plurality of the single merged assays harbor a combination of at least one bacteria and at least one chemical compound or mixture. Optionally, a majority of the single merged assays harbor a combination of at least one bacteria and at least one chemical compound or mixture.

In an embodiment, at least one of the single merged assays harbors a combination of at least one bacteria, at least one fungus and at least one chemical compound or mixture. Optionally, a plurality of the single merged assays harbor a combination of at least one bacteria, at least one fungus and at least one chemical compound or mixture. Optionally, a majority of the single merged assays harbor a combination of at least one bacteria, at least one fungus and at least one chemical compound or mixture.

Optionally, the array of microwells includes droplets constituting at least four different types of microbe, at least five different types of microbe, optionally at least six different types of microbe, optionally at least seven different types of microbe, optionally at least eight different types of microbe, optionally at least nine different types of microbe, optionally at least ten different types of microbe, optionally at least eleven different types of microbe, optionally at least twelve different types of microbe, optionally at least thirteen different types of microbe, optionally at least fourteen different types of microbe, optionally at least fifteen different types of microbe, optionally at least sixteen different types of microbe, optionally at least seventeen different types of microbe, optionally at least eighteen different types of microbe, or optionally at least nineteen different types of microbe.

In certain embodiments, each microwell of the array of microwells is approximately 80 μm to approximately 180 μm or more in diameter, approximately 80 μm to approximately 170 μm or more in diameter, approximately 125 μm to 165 μm in diameter, optionally approximately 130 μm to 160 μm in diameter, optionally approximately 135 μm to 155 μm in diameter, optionally approximately 140 μm to 150 μm in diameter, optionally approximately 145 μm to 150 μm in diameter, optionally approximately 148 μm in diameter, optionally precisely 148.2 μm in diameter.

In additional embodiments, each microwell of the array of microwells is approximately 110 μm to 120 μm deep.

In some embodiments, a majority of the individual droplets are of size approximately 120 μm to 150 μm in diameter, optionally 125 μm to 145 μm in diameter, optionally 130 μm to 140 μm in diameter.

In certain embodiments, three or more posts encircle each microwell of the array, optionally six posts encircle each microwell of the array, optionally the posts are triangular, square, round, oval, rectangular, cylindrical or hemispherical, optionally each post is approximately 10 μm to 100 μm wide, optionally approximately 40 μm wide. Optionally, the posts are of a sufficient size to enhance loading of each of the majority of the microwells with one and only one droplet, as compared to a microfluidic screening platform lacking said posts.

Another aspect of the instant disclosure provides a microfluidic screening platform that includes at least one droplet input for receiving one or more sets of droplets; and an array of microwells for receiving the droplets, where a majority of the microwells receives one and only one droplet.

In one embodiment, the platform further includes a series of channels designed to trap droplets of less than a predefined diameter, where the series of channels is positioned upstream of the microarray.

Optionally, the platform includes a series of 10 or more channels, optionally 15 or more channels, optionally 30 or more channels, optionally where each of the series of channels is approximately 90 μm wide.

Another aspect of the instant disclosure provides a microfluidic screening platform that includes at least one droplet input for receiving one or more sets of droplets, where the one or more sets of droplets are administered to a high-pass size filter including a series of channels designed to trap droplets of less than a predefined diameter; and an array of microwells for receiving the droplets (e.g., those that transit the high-pass size filter).

In one embodiment, the high-pass size filter includes a series of 10 or more channels, optionally a series of 15 or more channels, optionally a series of 30 or more channels.

In certain embodiments, the high-pass size filter channels are of approximately 80 μm to 134 μm in width, optionally approximately 90 μm in width.

An additional aspect of the instant disclosure provides a method of comparing pairwise or higher order complexes of droplet-encapsulated fluids in parallel, the method involving administering a variety of droplet-encapsulated fluidic compositions to a microfluidic screening platform including an array of microwells, where the microwells possess an arrangement and size that allow for a plurality of the microwells of the array of microwells to receive one and only one droplet; applying electrocoalescence, thermal coalescence or acoustic coalescence to merge droplets in user-selected adjacent microwells into a single merged assay, across the array of microwells, thereby forming an array of at least 500 independent merged assays; and comparing merged assays selected from among the at least 500 independent merged assays with one another to identify attributes of the merged assays, thereby comparing pairwise or higher order complexes of droplet-encapsulated fluidic compositions in parallel.

In one embodiment, the number of independent merged assays on the platform is at least 1000, optionally at least 5000, optionally at least 10000, optionally at least 100000, optionally approximately 1,000,000 or more.

In certain embodiments, the droplet-encapsulated fluids include microbes and/or chemical compounds or mixtures, optionally where the identity of the microbes and/or chemical compounds or mixtures encapsulated in an individual droplet is determined by detection of luminescent and/or fluorescent agents present in the droplet, optionally where the luminescent and/or fluorescent agents are present in a ratio that defines the identity of the microbe and/or chemical compound(s) or mixture(s) in the droplet, optionally where measurement of the luminescent and/or fluorescent agents in the droplet is performed before applying the electrocoalescence, thermal coalescence or acoustic coalescence to merge droplets in user-selected adjacent microwells into a single merged assay.

Another aspect of the disclosure provides a method of performing pairwise or higher order comparisons between droplet-encapsulated fluidic compositions in parallel, the method involving administering a variety of droplet-encapsulated fluidic compositions to a microfluidic screening platform of the instant disclosure; applying electrocoalescence, thermal coalescence or acoustic coalescence to merge droplets in user-selected adjacent microwells into a single merged assay, across the array of microwells, thereby forming an array of at least 500 independent merged assays; and comparing merged assays selected from among the at least 500 independent merged assays with one another to identify attributes of the merged assays.

In another aspect, the disclosure provides a microfluidic screening platform that includes: a top plate having an upper portion including a plurality of top plate through holes, a lower portion, and an inlet, wherein the inlet extends through both the upper portion and the lower portion; a bottom plate having an upper portion including a plurality of bottom plate through holes and a lower portion, wherein the lower portion includes an internal cut out; a glass substrate configured to seat on the upper portion of the bottom plate and cover the internal cut out; and a plurality of shafts corresponding to the plurality of top plate through holes and bottom plate through holes configured to mate the top plate to the bottom plate, wherein a droplet flow channel is defined by an upper surface of the glass substrate and a lower surface of the lower portion of the top plate when the top plate is mated to the bottom plate.

In embodiments, a surface that includes a plurality of microwells, each of which is configured to hold at least one droplet (optionally a single droplet), contacts the lower surface of the lower portion of the top plate. Optionally, the surface that includes the plurality of microwells comprises PDMS (polydimethylsiloxane).

In embodiments, each of the plurality of microwells is surrounded by one or more posts.

In embodiments, a surface that includes a plurality of microwells, each of which is configured to hold at least one droplet (optionally a single droplet), includes a filter positioned between the inlet and the plurality of microwells.

Another aspect of the instant disclosure provides a microfluidic screening platform including: at least one droplet input for receiving one or more sets of droplets, each set of droplets including individual droplets each individual droplet harboring a single type of bacteria and/or chemical compound (and/or a single type of combination thereof) or mixture, where the bacteria is *Achromobacter* spp. (e.g., *Achromobacter denitrificans, Achromobacter xylosoxidans, Achromobacter ruhlandii*); *Actinomadura* spp. (e.g., *Actinomadura luteofluorescens, Actinomadura madurae, Actinomadura pelletieri, Actinomadura viridis*); *Agrobacterium* spp. (e.g., *Agrobacterium radiobacter, Agrobacterium luteum, Agrobacterium agile, Agrobacterium rubi*); *Arthrobacter* spp. (e.g., *Arthrobacter arilaitensis, Arthrobacter chlorophenolicus, Arthrobacter aurescens*); *Bacillus* spp. (e.g., *Bacillus cereus, Bacillus subtilis, Bacillus coagulans, Bacillus psychrosaccharolyticus, Bacillus amyloliquefaciens, Bacillus lentus, Bacillus circulans, Bacillus firmus*); *Burkholderia* spp. (e.g., *Burkholderia gladioli, Burkholderia plantarii, Burkholderia cepacia*); *Clostridium* spp. (e.g., *Clostridium orbiscindens, Clostridium formicaceticum*); *Escherichia coli; Ewingella* spp. (e.g., *Ewingella americana*); *Flavobacterium* spp. (e.g., *Flavobacterium flevense, Flavobacterium aquatile, Flavobacterium saccharophilum, Flavobacterium hydatis, Flavobacterium johnsoniae*); *Flexibacter* spp. (e.g., *Flexibacter flexilis, Flexibacter columnare*); *Herbaspirillum frisingense; Hyphomicrobium* spp. (e.g., *Hyphomicrobium aestuarii*); *Micromonospora* spp. (e.g., *Micromonospora rosaria, Micromonospora facile, Micromonospora zavarzinii, Micromonospora denitrificans*); *Mycobacterium* spp. (e.g., *Mycobacterium neoaurum*); *Nocardia* spp. (e.g., *Nocardia jiangxiensis, Nocardia miyunensis*); *Paenibacillus* spp. (e.g., *Paenibacillus macquariensis, Paenibacillus macerans, Paenibacillus alvei, Paenibacillus polymyxa, Paenibacillus chibensis*); *Pseudomonas* spp. (e.g., *Pseudomonas aeruginosa, Pseudomonas putida, Pseudomonas fluorescens, Pseudomonas citronellolis, Pseudomonas chlororaphis, Pseudomonas aurantiaca, Pseudomonas pseudopalustris, Pseudomonas palustris, Pseudomonas syringae, Pseudomonas veronii, Pseudomonas aurantiaca*); *Ralstonia* spp. (e.g., *Ralstonia solanacearum, Ralstonia pickettii, Ralstonia syzygii*); *Rhodococcus* spp. (e.g., *Rhodococcus erythropolis, Rhodococcus rhodochrous*); *Serratia* spp. (e.g., *Serratia marcescens, Serratia liquefaciens*); *Sphingomonas* spp. (e.g., *Sphingomonas echinoides, Sphingomonas leidyi, Sphingomonas wittichii*); *Streptomyces* spp. (e.g., *Streptomyces lividans, Streptomyces coelicolor, Streptomyces tanashiensis, Streptomyces clavuligerus, Streptomyces griseus*); and an array of microwells, where each microwell is capable of receiving an individual droplet.

An additional aspect of the instant disclosure provides a microfluidic screening platform including: at least one droplet input for receiving one or more sets of droplets, each set of droplets including individual droplets each individual droplet harboring a single type of fungi and/or a chemical compound (and/or a single type of combination thereof) or mixture, where the fungi is *Venturia, Aspergillus, Podosphaera, Erysiphe, Monilinia, Uncinula, Aureobasidium, Sclerophoma, Acremonium, Actinoplanes, Agaricus, Chrysosporium, Colletotrichum, Coprinus, Cryptococcus, Filibasidum, Humicola, Magnaporthe, Myceliophthora, Neocallimastix, Neurospora, Paecilomyces, Phytophthora,*

*Piromyces, Panerochaete, Pleurotus, Pythium, Schizophyllum, Talaromyces, Thermoascus, Thielavia, Tolypocladium, Trichoderma, Hemileia, Rhizoctonia, Puccinia, Coniophora, Serpula, Poria, Uromyces, Gloeophyllum, Lentinus, Coriolus, Irpex, Mucor, Botrytis, Helminthosporium, Rhynchosporium, Fusarium, Septoria, Cercospora, Alternaria, Pyricularia, Penicillium, Geotrichum*, and/or *Zymoseptoria*; and an array of microwells, where each microwell is capable of receiving an individual droplet.

Another aspect of the instant disclosure provides a microfluidic screening platform including: at least one droplet input for receiving one or more sets of droplets, each set of droplets including individual droplets each individual droplet harboring a single type of bacteria, fungi and/or chemical compound (and/or a single type of combination thereof) or mixture, where the bacteria is *Achromobacter* spp. (e.g., *Achromobacter denitrificans, Achromobacter xylosoxidans, Achromobacter ruhlandii*); *Actinomadura* spp. (e.g., *Actinomadura luteofluorescens, Actinomadura madurae, Actinomadura pelletieri, Actinomadura viridis*); *Agrobacterium* spp. (e.g., *Agrobacterium radiobacter, Agrobacterium luteum, Agrobacterium agile, Agrobacterium rubi*); *Arthrobacter* spp. (e.g., *Arthrobacter arilaitensis, Arthrobacter chlorophenolicus, Arthrobacter aurescens*); *Bacillus* spp. (e.g., *Bacillus cereus, Bacillus subtilis, Bacillus coagulans, Bacillus psychrosaccharolyticus, Bacillus amyloliquefaciens, Bacillus lentus, Bacillus circulans, Bacillus firmus*); *Burkholderia* spp. (e.g., *Burkholderia gladioli, Burkholderia plantarii, Burkholderia cepacia*); *Clostridium* spp. (e.g., *Clostridium orbiscindens, Clostridium formicaceticum*); *Escherichia coli; Ewingella* spp. (e.g., *Ewingella americana*); *Flavobacterium* spp. (e.g., *Flavobacterium flevense, Flavobacterium aquatile, Flavobacterium saccharophilum, Flavobacterium hydatis, Flavobacterium johnsoniae*); *Flexibacter* spp. (e.g., *Flexibacter flexilis, Flexibacter columnare*); *Herbaspirillum frisingense; Hyphomicrobium* spp. (e.g., *Hyphomicrobium aestuarii*); *Micromonospora* spp. (e.g., *Micromonospora rosaria, Micromonospora facile, Micromonospora zavarzinii, Micromonospora denitrificans*); *Mycobacterium* spp. (e.g., *Mycobacterium neoaurum*); *Nocardia* spp. (e.g., *Nocardia jiangxiensis, Nocardia miyunensis*); *Paenibacillus* spp. (e.g., *Paenibacillus macquariensis, Paenibacillus macerans, Paenibacillus alvei, Paenibacillus polymyxa, Paenibacillus chibensis*); *Pseudomonas* spp. (e.g., *Pseudomonas aeruginosa, Pseudomonas putida, Pseudomonas fluorescens, Pseudomonas citronellolis, Pseudomonas chlororaphis, Pseudomonas aurantiaca, Pseudomonas pseudopalustris, Pseudomonas palustris, Pseudomonas syringae, Pseudomonas veronii, Pseudomonas aurantiaca*); *Ralstonia* spp. (e.g., *Ralstonia solanacearum, Ralstonia pickettii, Ralstonia syzygii*); *Rhodococcus* spp. (e.g., *Rhodococcus erythropolis, Rhodococcus rhodochrous*); *Serratia* spp. (e.g., *Serratia marcescens, Serratia liquefaciens*); *Sphingomonas* spp. (e.g., *Sphingomonas echinoides, Sphingomonas leidyi, Sphingomonas wittichii*); and/or *Streptomyces* spp. (e.g., *Streptomyces lividans, Streptomyces coelicolor, Streptomyces tanashiensis, Streptomyces clavuligerus, Streptomyces griseus*); where the fungi is *Venturia, Aspergillus, Podosphaera, Erysiphe, Monilinia, Uncinula, Aureobasidium, Sclerophoma, Acremonium, Actinoplanes, Agaricus, Chrysosporiun, Colletotrichum, Coprinus, Cryptococcus, Filibasidum, Humicola, Magnaporthe, Myceliophthora, Neocallimastix, Neurospora, Paecilomyces, Phytophthora, Piromyces, Panerochaete, Pleurotus, Pythium, Schizophyllum, Talaromyces, Thermoascus, Thielavia, Tolypocladium, Trichoderma, Hemileia, Rhizoctonia, Puccinia, Coniophora, Serpula, Poria, Uromyces, Gloeophyllum, Lentinus, Coriolus, Irpex, Mucor, Botrytis, Helminthosporium, Rhynchosporium, Fusarium, Septoria, Cercospora, Alternaria, Pyricularia, Penicillium, Geotrichum*, and/or *Zymoseptoria*, optionally wherein the fungi is a filamentous fungi, e.g., *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium, Trichoderma*, and/or *Zymoseptoria*; and an array of microwells, where each microwell is capable of receiving an individual droplet.

In certain embodiments, a fungal biology/activity is evaluated. Optionally, the fungal biology/activity is a fungal growth cycle or behavior attribute. Optionally, the growth cycle or behavior attribute is sporulation, germination and/or formation of mycelium, and/or is expression of a gene associated with such growth cycle or behavior attribute. Optionally, a bacteria and/or chemical compound or mixture that suppresses germination and/or suppresses expression of gene relevant to germination is evaluated and/or identified.

In some embodiments, image analysis is performed to quantify aspects of the shape, morphology and/or growth of microbes. Optionally, image analysis is performed to identify the shape and/or morphology of fungal spores, fungal filaments and/or other fungal characteristics.

In certain aspects, it is further provided that individual droplets can be made and used in which each individual droplet harbors a discrete form of microbial and/or chemical compound combination or mixture, and such individual droplets and/or sets of individual droplets harboring a discrete form of microbial and/or chemical compound combination or mixture can be used as if they were a single set of droplets as provided for elsewhere herein.

DEFINITIONS

The term "microbe" refers to a member of a community of microorganisms that occur (sustainably or transiently) in and on, but not limited to, animals, plants, and soil. The term "microbe" comprises, but is not limited to, a eukaryote, archaea, a bacterium, and a virus (including bacterial viruses, i.e., phage). In particular, the term "microbe" described herein may be used for different strains of bacteria and algae.

The term "combination of two or more microbes" refers to the presence of two or more microbes in physical proximity to one another (e.g., within the same well, merged droplet, etc.). Physical co-existence of the two (or more) microbes can be either in the same material or product or in physically connected products and/or can refer to the temporal co-administration or co-localization of the two (or more) microbes.

As used herein, the term "microfluidic screening platform" may define a high-density array of microwells for cultivating at least one biological entity. The term "high density" may refer to a capability of a system or method to distribute a number of experiments within a constant area. A "microfluidic screening platform" may include a substrate with a series of functional layers. The series of functional layers may include a first functional layer defining a first array of experimental units (e.g., wells) and at least one subsequent functional layer defining a subsequent array of experimental units (e.g., microwells) in each experimental unit of the preceding functional layer. Each of the experimental units may be configured to receive and cultivate and/or screen biological entities and/or nutrients. In particular, systems, kits, apparatus, and methods described herein may be used for automated and/or high throughput combinatorial screening of different microbes.

The term "high throughput" may refer to a capability of a system or method to enable quick performance of a very large number of experiments in parallel or in series. An example of a "high throughput" system may include automation equipment with cell biology techniques to prepare, incubate, and/or conduct a large number of chemical, genetic, pharmacological, optical, and/or imaging analyses to screen one or more biological entities for at least one of a metabolite, an enzyme, a protein, a nucleic acid, a phenotype, a mutation, a metabolic pathway, a gene, an adaptation, and a capability, as discussed herein. According to some embodiments, "high throughput" may refer to simultaneous or near simultaneous experiments on a scale ranging from at least about 96 experiments to at least about 10,000,000 experiments.

The term "low-pass filter," as used herein, refers to a physical enmity capable of disrupting or preventing the passage of droplets of a size that exceeds a predefined size. In particular embodiments, the term "low-pass filter" as exemplified herein refers to internal posts arranged around the periphery of a microwell and that are capable of disrupting or preventing the entry of large droplets into individual microwells.

The term "high-pass filter," as used herein, refers to a physical entity that disrupts or prevents the passage of droplets below a predefined size. In particular embodiments, the term "high-pass filter" as exemplified herein (as a pre-filter) refers to a series of channels/moat-like engravings of a defined size designed to trap small droplets during fluid flow.

The term "chemical compound", as used herein refers to any non-microbe agent (alternatively referred to as a "test agent") optionally a non-living agent—capable of being included in droplets of the instant disclosure. Exemplary chemical compounds for use with the instant disclosure include, but are not limited to, macromolecules (e.g., proteins, oligonucleotides, antibodies and/or fragments thereof, etc.) and small molecules. In certain embodiments, libraries of test chemicals can be used in the present disclosure, optionally from which candidate molecule(s) can be selected during use of the microfluidic platform of the instant disclosure. In some embodiments, test compounds are small molecules, in other embodiments they are members of randomer or combinatorial sequence or shape libraries, optionally comprising sequenceable oligomers and/or other macromolecules. In some embodiments, the candidate chemicals are conjugates, chimera and/or modular constructs. In certain embodiments, exemplary chemical compounds or mixtures can also include complex mixtures of chemicals and/or microbes, for example natural products and/or spent or conditioned media libraries from other microbes, including extracts from natural sources (e.g., extracts from bodily fluids, plants, soil) —including fractionated extracts (i.e., eluents from chemical fractionation of extracts from natural sources), filtered natural fluids (e.g. urine, saliva, blood, etc.), and other such natural products. In some specifically contemplated embodiments, washing of soil in media to separate microbes and solids can be performed, with the wash then directly added to droplets (with such wash containing a complex mixture of microbes and chemicals, not a single type of microbe or a single chemical compound), or such a wash could even be fractionated using, e.g., HPLC or other separation method, with droplets made from individual fractions and introduced to the instant kChip. Thus, mixtures of compounds, not only pure compounds, are expressly contemplated for use as chemical compounds or mixtures in certain embodiments of the instant disclosure.

The term "small molecule" refers to compounds, optionally organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. Small molecules typically have a molecular weight of 100, 200, or 300 Daltons or more. Small molecules include, but are not limited to, inorganic molecules, organic molecules, organic molecules containing an inorganic component, molecules comprising a radioactive atom and/or fluor, synthetic molecules, peptide mimetics, and antibody mimetics.

As used herein, "changed as compared to a control" sample or subject is understood as having a level of the analytic or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analytic substance can be a naturally occurring substance that is characteristically expressed or produced by the cell or organism (e.g., pathogenic bacteria, antibodies, pathogenic peptides or particles, and the like) or a substance produced by a reporter construct (e.g., β-galactosidase or luciferase). Depending on the method used for detection the amount and measurement of the change can vary. Determination of statistical significance is within the ability of those skilled in the art.

As used herein, the terms "comprises," "comprising," "containing" and "having" and the like are open-ended as defined by U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, "detecting," "detection," and the like are understood to mean that an assay is performed to determine one or more characteristics of a sample, e.g. identifying the presence, absence or amount of the analyte to be detected. For example, detection can include identification of a specific analyte in a sample or an activity of an agent in a sample. Detection can include the determination of the presence of nucleic acid, protein (e.g., antibody, cytokine, and the like) by PCR, immunoassay (e.g., ELISA), microscopy, pathogen challenge, and the like. The amount of analyte or activity detected in the sample can be none or below the level of detection of the assay or method.

By "enhances" is meant a positive alteration of at least 10%, 25%, 50%, 75%, 100%, or any number therebetween.

"Obtaining" is understood herein as manufacturing, purchasing, synthesizing, isolating, purifying, or otherwise coming into possession of.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, 100%, or any number therebetween. By "reference" is meant a standard or control condition.

A "sample" as used herein refers to a biological material that is isolated from its environment (e.g., microbes obtained and isolated from soil, blood or tissue from an animal, cells, or conditioned media from tissue culture).

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of an embodiment for a variable or aspect herein includes that embodiment as any single embodiment or in combination with any other embodiments or portions thereof.

Other definitions appear in context throughout this disclosure.

Any therapeutic agents, compositions, or methods provided herein can be combined with one or more of any of the other therapeutic agents, compositions, and methods provided herein.

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following Detailed Description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows how 1 nL droplets were first produced. Each droplet contained a color code (a specific ratio of three fluorescent dyes) that maps to a corresponding input. After they were pooled, droplets were loaded onto the kChip, where they randomly grouped into microwells. The microwells were designed to group precisely k droplets. The kChip was imaged to identify the contents of each microwell from the droplet color codes. Droplets were then merged within their respective microwells via exposure to an alternating-current electric field, which generated parallel synthetic communities. Community phenotypes could be tracked via optical assays, including fluorescent protein expression and respiration-driven reduction of resazurin to the fluorescent product resorufin. Solid microwell borders=conceptual microwell outlines. Dotted microwell borders=microscopy images where borders were not visible. FIG. 1B shows how microwell types were produced by encircling sets of internals posts (see FIGS. 6A-6D below). Examples of micrographs show grouping and merging of droplets for these microwell types. FIG. 1C depicts a general schematic of kChip. Pooled droplets were dispensed into a kChip-loading apparatus (see FIGS. 5A-5D below). Any small droplets were first filtered out via moat-like traps ("Small droplet size filter", 90 μm wide) prior to droplet grouping. Specific microwell arrangements can be determined by the user and can include ≥1 microwell type per kChip. Dotted lines=user-determined borders between different microwell types. FIG. 1D shows how microwells were densely packed on the kChip (FIGS. 6A-6D), with k dictating microwell density. A single microwell type can be arrayed across a kChip ("Full kChip"). For the screening application reported in FIG. 3 and FIG. 4, "k={1:7;19} Chip" was generated and it included different microwell types arranged in parallel.

FIG. 2A summarizes how droplet libraries could be made from a library of fluorescently labeled strains (see FIG. 28 below) and a library of carbon sources (see FIG. 33 below). The ability of each strain to grow on each carbon source could be measured by monitoring microwells that received one microbe-containing droplet and one carbon source-containing droplet. FIG. 2B is a micrograph of grouped droplets containing color codes and assay result. FIG. 2C shows how fluorescence was measured for a panel of 10 fluorescent strains (starting $OD_{600}$=0.02) across 15 conditions (13 carbon sources at 0.5 w/v+1 glucose replicate control+1 no-carbon condition) in k=2 Chip microwells (21° C., no shaking) as well 200-μL cultures in 96-well plates (21° C., 220 RPM). Heatmaps show the relative signal at 50 hours, with interleaved columns corresponding to the kChip and 96-well plates (Pearson r=0.868) (full time course in FIG. 10B below). FIG. 2D shows how the dye resazurin was added to carbon source media prior to droplet production (post-merge concentration 40 μM) to measure growth of unlabeled strains. Resazurin gets reduced to the fluorescent product resorufin in the presence of metabolically active cells (growth is therefore monitored via resazurin's respiration-driven reduction to resorufin). FIG. 2E is a micrograph of grouped droplets containing color codes and resazurin assay result. FIG. 2F summarizes the resazurin signal (fluorescence due to resorufin accumulation) obtained for three strains (starting $OD_{600}$=0.005) across four carbon source conditions in k=2 Chip microwells (21° C., no shaking) and compared to $OD_{600}$ measurements from 200-μL cultures in 96-well plates (21° C., 220 RPM). Heatmaps show signal at 22 hours (Pearson r=0.969) (full time course in FIG. 12B below). In FIG. 2C and FIG. 2F, relative signal for each row was obtained by normalizing to the maximum across all carbon sources and timepoints after background subtraction.

FIGS. 3A-3G show how high-throughput kChip screening identified Hf-promoting compositions that were robust to carbon source and additional bacterial isolates. FIG. 3A shows a screen schematic to identify Hf-promoting compositions. Communities were constructed whereby Hf-GFP represents half of the starting biomass (starting Hf-GFP $OD_{600}$=0.02) and the other half was divided evenly among 1 to 7 or 19 soil isolate inputs (starting total isolate $OD_{600}$=0.02 if no control droplets present). Each of these communities was constructed in one of six media that each contained a single carbon source. These carbon sources enabled Hf-GFP monoculture growth to varying extents (bars=Hf-GFP yield at 72 hrs in k=1 microwells where droplet received no isolate; error bars=standard deviation). FIG. 3B summarizes the screening strategy. Each droplet received Hf-GFP, a single isolate or control, and a single carbon source. Droplets containing the same carbon source were pooled and loaded onto the same kChip (six kChips in total, at 21° C., no shaking). After droplet merging, Hf-GFP yield was measured (at 24, 48, 72 hr) in each community/carbon source environment. This analysis differentiated between a "composition" as a subset of size s embedded in larger "communities" of size k that contained the composition+(k−s) additional isolates. FIG. 3C shows the total number of assay points collected for different values of 19 k (about evenly divided among the six kChips, see FIG. 35 below). FIG. 3D shows the ranked Hf-GFP yield at 72 hr for all communities (s=k) constructed. Median calculated when community replicated >1 time; error bar=standard error of the mean; dotted line=Hf-GFP yield in monoculture. FIG. 3E is an example s=k=2 pair of isolates with a facilitative effect on Hf-GFP that was not robust to carbon source. FIG. 3F is an example s=2 composition with a facilitative effect on Hf-GFP in galactose that was not robust to community context. FIG. 3G is a graph of Hf-GFP robustness against Hf-GFP yield. For compositions represented ≥30 times across all carbon sources (only k=1, 2, 3 compositions met this criteria), median Hf-GFP yield (x-axis) quantifies the effect of the composition on Hf-GFP across carbon sources. The 10th percentile of Hf-GFP for all communities containing a given composition (y-axis) quantifies a robustness to community context across all carbon sources. (Insets) Each data point represents Hf-GFP yield in a single microwell where the color indicates carbon source (corresponding to FIG. 3A). The left distribution shows Hf-GFP yield when the given composition was present (used to calculate x-axis yield metric). The right distribution shows Hf-GFP yield for all communities containing the composition (used to calculate y-axis robustness metric). Blue points=composition contains at least BuC. Brown points=composition contains at least [BaL+Ra]. Dotted line=1500 GFP counts, a minimal viable and detectable signal from Hf-GFP (one standard deviation above Hf-GFP yield in sucrose).

FIG. 4A shows that in a medium containing sucrose, lactose, or raffinose, Hf-GFP yield increased with community richness. Colored distributions=median Hf-GFP yields for all unique compositions at given k (i.e. all droplets in a given combination contain different strains). Gray data point=median of distribution. Outlined distributions=medians of 100 bootstrap-resampled datasets at each k, whereby the Hf-GFP yield dataset for each k was resampled with replacement (with resampling sample size equal to the actual sampling size), and a median of the resampled data was calculated each time. FIG. 4B shows how primary facilitators (outlined in orange) were classified as the isolates increasing Hf-GFP yield by ≥100 GFP counts (a.f.u.). FIG. 4C presents graphs that ascertained that the presence of 21 primary facilitator was necessary and typically sufficient to enable Hf-GFP growth and drive a facilitative effect when additional isolates were present. Colored distributions=Hf-GFP growth in communities possessing ≥1 primary facilitators. Gray distributions=Hf-GFP yield in communities with no primary facilitators. FIG. 4D presents graphs and data from a resazurin assay which was conducted on a separate k=2 Chip in parallel with the screen to measure growth rate of each isolate (see FIG. 24 below). The subset of isolates that grew on a given carbon source (defined at ≥1 doubling of resorufin fluorescence by 36 hr) corresponded with the subsets of isolates identified as primary facilitators.

FIG. 5A shows how kChip microwells are loaded with droplets by suspending the kChip within a loading apparatus. This apparatus consists of an acrylic housing and hydrophobic glass substrate. The kChip naturally forms a seal with the top piece of acrylic. In its unclamped state, a flow space (~500-700 μm) is maintained between by a repulsive magnetic force such that droplets can flow under the kChip. Tilting the apparatus moves droplets through the flow space, and random sets of droplets spontaneously group within microwells. FIG. 5B is a photograph of the kChip loading apparatus. FIG. 5C is a diagram of the side-view of loading apparatus and droplet loading procedure (not to scale). FIG. 5D shows a cross-sectional side view of a microfluidic screening platform according to an exemplary embodiment of the disclosure. FIG. 5E shows a bottom view of a lower surface of a top plate of a microfluidic screening platform including a plurality of microwells according to an exemplary embodiment of the disclosure. FIG. 5F and FIG. 5G show a top view and a side view, respectively, of a top plate of a microfluidic screening platform according to an exemplary embodiment of the disclosure. FIG. 5H and FIG. 5I show a top view and a side view, respectively, of a bottom plate of a microfluidic screening platform according to an exemplary embodiment of the disclosure.

FIG. 6A shows how triangular posts were arrayed such that each hexagonal arrangement enclosed a space optimized for a single droplet. The diameter of the enclosed space used in all kChip microwell types was set to 148.2 μm, which was optimized for 135-μm droplets, the mean droplet size of minimal medium (MM) droplets made with 0.05% BSA added to the medium and 2% stabilizing fluorosurfactant (see FIGS. 28A-28C below). FIG. 6B shows that microwell shapes were carved by encircling internal posts to achieve the desired k. These microwell designs are modular and generalizable: increasing the size of the boundary around posts produces microwells that group more droplets. FIG. 6C shows that each microwell design was arrayed with ~50 μm inter-microwell spacing. FIG. 6D shows that specific microwell arrangements on a kChip are determined by the user and can include 21 microwell type per kChip. A given kChip can have entirely one type ("Full kChip"), e.g. all k=2 microwells (e.g. experiments discussed in FIGS. 2A-2F above) or an assortment of different types, e.g. subsets of k={1:7;19} microwells (e.g. the Hf-GFP facilitation screen discussed in FIGS. 3A-3G above). All exemplified kChips also included a series of 30 90-μm wide moat-like engravings ("slots") designed to make up a small droplet size filter. In exemplified kChips, hese slots are spaced 50 μm apart from each other and 400 μm from the onset of the microwells. The slots are inset 3 mm from the edge of the kChip.

FIG. 7A is a fluorescence micrograph (10× magnification) highlighting how internal posts produce correct droplet grouping. Presumably, internal posts enable low-pass size filtering and spatial confinement of droplets within microwells.

FIG. 7B shows a graph that depicts the percentage of correct grouping observed for kChips with and without internal posts. Four kChips were loaded that included internal posts (Chips #1-4) and two that did not (Chips #5-6). Over 90%, of microwells filled correctly for all values of k={1:7} if posts were included. If microwells did not contain internal posts, grouping performance decreased drastically as k increased. Dotted gray line=90% grouping correctly. Droplets were merged in three kChips containing internal posts (Chips #1, 2, and 4). Droplets in microwells that have filled correctly will typically merge correctly. Dotted gray line=90% merging correctly. (Merging data for k=19 was not measured due to limitations in the image data analysis.) FIG. 7C shows the results of an assay in which in order to assess the biological effects of larger microwell geometries and the concomitant increase in internal posts, the yield of Hf-GFP in monoculture ("alone") was measured at 24, 48, and 72 hrs (taken from the no-isolate control droplets in Hf-GFP facilitation screen dataset, which is described in FIGS. 3A-3G above). No adverse effects on growth rate or 72-hr yield were observed. FIG. 7D shows the results of the assay of FIG. 7C with results grouped and plotted by k on the x-axis.

FIG. 9A is a micrograph of droplets containing color codes and assay result (constitutive GFP or YFP expression). FIG. 9B shows example droplets showing the increase in signal for a panel of 11 inputs (10 fluorescently labeled strains+1 "empty" medium-only control) over the course of the experiment (first 6 time points between 0 and ~40 hr shown corresponding to data points in FIG. 9C). FIG. 9C presents graphs of fluorescence against time for the different strains. Growth curves between 200-μL cultures in 96-well plates and k=1 Chip cultures were compared against each other for each strain. It was deduced that the growth dynamics broadly matched between the two platforms. Data has been linearly rescaled from plates to the kChip data by computing a linear fit for each strain. Full names of labeled strains are listed in FIG. 32 below.

FIG. 10A shows an exemplary micrograph of fluorescent protein expression on a kChip. FIG. 10B shows that on a k=2 Chip and in 200-μL cultures in 96-well plates, strain-carbon source combinations were generated to assess between-platform agreement of growth dynamics. The t=50 hr measurements are represented in FIG. 2C above. Data has been normalized in this manner: First, a second no-carbon control (not shown here) was subtracted from the growth curves. Second, all data for a given strain was divided by the maximum signal value across all carbon sources and time points. Error bars represent the standard deviation of signal across replicate microwells. Plate measurements were taken with two replicates, shown as a solid and dotted line. Based on the broad agreement, it was concluded that kChip screening recapitulates 96-well plate experimentation. Full names of labeled strains are listed in FIG. 32 below.

FIG. 12A shows an example micrograph of resazurin assay on a kChip. FIG. 12B shows that on a k=2 Chip and in 200-μL cultures in 96-well plates, strain-carbon source combinations were generated to assess agreement between the resazurin assay in droplets and conventional $OD_{600}$ measurements in plates. Endpoint measurements are represented in FIG. 2D above. Data have been normalized in this manner: First, a no-carbon control (not shown here) was subtracted from the growth curves. Second, all data for a given strain was divided by the maximum signal value across all carbon sources and time points. Error bars represent standard deviation of droplets. Plate measurements were taken with two replicates, shown as solid and dotted lines. Based on the broad agreement, it was conclude that kChip screening with the resazurin assay recapitulates 96-well plate experimentation. Full names of strains used are listed in FIG. 32 below.

FIG. 15A shows an example s=k=2 pair of isolates that exhibited a facilitative effect on Hf-GFP that was not robust to carbon source. FIG. 15B shows an example s=2 composition that exhibited a facilitative effect on Hf-GFP in galactose that was not robust to community context.

FIGS. 18A-18D summarize that the experimental setup determines the combinatorial space sampled. FIG. 18A is a table of definitions of variables used. FIG. 18B shows a list of expressions describing sampling probabilities when the desired subsets ("compositions") under consideration are either less than total number of droplet inputs ("communities") (in which case s<k) or equal (in which case s=k). FIG. 17C shows graphs of probability of sampling a given composition for different desired subsets s for different input library sizes (left panel), and also shows graphs of expected representation of a given composition with current k={1:7; 19} Chips used in the Hf-GFP facilitation screen (right panel). Red line=library sized used presently (n=16). For k=1-3 in the Hf-GFP facilitation screen, the mean number of replicates for k=1, 2, and 3 was ~200, ~20, and ~5, respectively. 5 replicates were set as a threshold to measure the effect of a composition (s=k), which excluded ~half of k=3 compositions represented <5 times (FIG. 16 and FIG. 17 above, FIG. 35 below). Robustness of these compositions to additional isolates (s<k) could be measured due to high replicability, which increased with k. Dotted red line=In the Hf-GFP facilitation screen, the cutoff at s=k=3 to produce a mean of 5 replicates per composition was a library of n=16 inputs. FIG. 18D elucidates that the maximum allowable library depends on the desired mean number of replicates per composition, first showing graphs of allowable library size with current k={1:7;19} Chips (left panel), then showing graphs of allowable library size if using kChip consisting only of single microwell type ("Full kChip") (right panel). While the Hf-GFP facilitation screen used six kChips, it has also been previously demonstrated that screens can be feasibly completed with ~100s of chips (Kulesa et al. *Proc Natl Acad Sci USA* 115(26):6685-6690).

FIG. 20A shows Hf-GFP monoculture yields at 72 hours for 200-μL cultures in 96-well plates (21° C., 220 RPM). FIG. 20B shows Hf-GFP yields at 72 hr for 200-μL co-cultures with *Burkholderia* sp. I in 96-well plates (21° C., 220 RPM). FIG. 20C shows Hf-GFP yields at 72 hr and 127 hr for 200-μL co-cultures in 96-well plates (21° C., 220 RPM), with co-culture conditions indicated in plot titles. Each carbon source was added to MM at 0.5% w/v. Mix=Each carbon source at 0.083% w/v such that total carbon content was 0.5% w/v. FIG. 20D shows the comparison of raw yield values in 96-well plate bulk cultures and kChip screen, with results corresponding to FIG. 20A. FIG. 20E shows the comparison of raw yield values in 96-well plate bulk co-cultures and kChip screen, with results corresponding to FIG. 20B. FIG. 20F shows the comparison of raw yield values in 96-well plate bulk co-cultures as indicated and kChip screen, with results corresponding to FIG. 20C. Dotted line="Minimal viable yield" of Hf-GFP in screen. Hf-GFP yield in bulk co-culture recapitulated the result from the screen.

FIG. 27A shows that the BuC alone and the pair [BaL+Ra] could utilize all carbon sources tested, as indicated by the resazurin assay (see FIG. 24 above). FIG. 27B shows that compositions that contain at least BuC consistently imparted relatively strong Hf-GFP yield and the strongest robustness (explanation of these scores described in the "Identification of highly facilitative and robust compositions" section below). FIG. 27C shows that the compositions that contained [BaL+Ra] consistently imparted high yield and robustness to Hf-GFP (top panel). Compositions were identified that contained [BaL+Ra] (i.e. [BaL+Ra+isolate X]) and imparted a facilitative effect size and robustness to Hf-GFP that was greater than that imparted by the composition [BaL+Ra] alone, e.g. the composition [BaL+Ra+Ps] (labeled). FIG. 27C also shows that the composition BaL and the composition Ra did not impart high robustness to Hf-GFP, and compositions containing BaL or Ra often did not impart robustness. Gray distribution=All compositions (represented ≥30 times). Red distribution=Compositions that contain at least isolate given in plot title. Black-encircled point=Composition given in title.

FIG. 28A shows measurement of the growth of a panel of fluorescently labeled strains on different carbon sources with BSA. Almost no difference was observed in growth dynamics for 0.05% w/v BSA (1×, the working concentration for droplet generation) or 0.5% BSA (10×), as compared to the MM-only control. Full names of labeled strains are listed in FIG. 32 below. FIG. 28B shows that different medium formulations and fluorosurfactant (FS) concentrations produced droplets of different sizes, which affected the optimal microwell geometries (see FIGS. 6A-6D above). An 8-channel 300-μL flow cell, into which droplets of fluorescently dyed media (Alexa Fluor 647) could be loaded and image was constructed to measure droplet size via the circular Hough transform (implemented in a Matlab script). FIG. 28C shows that mean and distribution of droplet size were affected by the medium, the inclusion of BSA (which is included to improve the retention of hydrophobic small molecules within the droplets), and FS concentration. Droplets of MM+0.05% w/v BSA made with 2% w/v FS (to promote droplet stability and inhibit surface wetting) were prepared and examined. These droplets (distribution highlighted in yellow) had a mean diameter of ~135 μm (~1.3 nL). For this medium formulation, droplets became larger as FS concentration increased. Droplet size was notably larger when BSA was not added, irrespective of FS concentration.

FIG. 29A shows that for each kChip used in the Hf-GFP facilitation screen (as described in FIGS. 3A-3G above), the area of the merged droplet was measured at each time point (24, 48, and 72 hr). The distributions represent all droplets passing quality filters (with the total number of droplets per distribution listed in FIG. 35 below). Because the height of each droplet is assumed to be flat (in contact with the kChip microwell on one side and glass on the other), and this height is approximately uniform for all microwells, it was assumed that volume scales linearly with area for this analysis. Lines in each plot connect the mean values of the distributions. Distributions for each kChip at a given time point have been offset to aid in visualization. FIG. 29B demonstrates that the area at 72 hr (final time point) relative to 24 hr (first time point) indicated <10% evaporation for k≥2, and slightly more for k=1, in the timespan of the time points.

FIG. 30A shows the experimental setup whereby droplets containing either *E. coli* ($OD_{600}$=0.01, or ~10 cells/droplet) or the phototrophic alga *Chlamydomonas reinhardtii* CC-503 ($OD_{600}$=0.125, or ~1-2 cells/droplet) were randomly grouped on a k=7 Chip. Each microwell contained a random fraction of each droplet type, such that a wide range of relative starting densities of the two organisms was achieved upon droplet merging. FIG. 30B shows how the kChip was incubated at 30° C. with slow shaking (25 RPM) beneath Arduino-controlled LED strips. An array of neutral density filters was constructed to fit on the surface of the loading apparatus (see FIG. 5 above), dividing the kChip into sections exposed to different amounts of illumination (100%, 52%, 25%, and 0%). FIG. 30C shows how co-cultures were monitored (2× imaging) for 50 hours, enabling the tracking of the abundance of each organism in each microwell. FIG. 30D presents 10× images of microwells (stars corresponding to microwells in panel c) which showed that the spatial arrangement of two co-cultured organisms could also be tracked. FIG. 30E shows the yield of each organism, which was measured for each initial starting fraction and light condition at 50 hours. For each organism in each microwell, a mean fluorescence intensity over the microwell area was measured. Data points represent a median of all replicates, and error bars represent standard error. Noise in the curves may be attributable to stochasticity in initial cell count per droplet.

FIG. 31A shows that while an assay like constitutive GFP expression requires labeling microbes of interest, phase contrast microscopy allows for the visualization of unlabeled microbes by converting changes in light paths caused by the presence of cellular components to brightness changes in the image. Microbial growth in droplets can be inferred through scale-dependent contrast changes over time. FIG. 31B displays micrographs of *E. coli* cultures in the same k=2 microwell (post-merge, 2× magnification) at two timepoints used for the GFP assay (top) and phase contrast assay (bottom). FIG. 31C shows results where *E. coli* cultures constitutively expressing GFP were cultured on a k=2 Chip (and monitored using GFP expression and phase contrast) and 200 μL cultures in 96-well plates (and monitored using GFP expression and optical density (OD600)) in MM containing different single carbon sources (0.5% w/v). The growth metric in phase ("Phase contrast score") is estimated by measuring local variation in contrast: (1) For each pixel in a given droplet, the range of pixel intensities in a local 10×10 pixel neighborhood centered on each pixel is measured (via the rangefit function implemented in a Matlab script); (2) the mean of these values is taken to measure the contrast of a single droplet; (3) a Phase contrast score is calculated as the median of all replicate measurements (reported here). Based on broad between-assay agreement (GFP signal on kChip and phase contrast score on kChip) and between-platform agreement (phase contrast score on kChip $OD_{600}$ in well plates), it was concluded that phase contrast is a suitable assay for measuring the growth of a microbe on the kChip. Cultures on plates were conducted in triplicate; the number of replicates on the kChip for each carbon source was {82, 77, 66, 69, 88, 75, 79} (left to right). Error bars represent 95% confidence interval.

FIG. 32 lists the fluorescently labeled strains. Labeling strains via constitutive fluorescent protein expression, e.g. GFP or YFP, can be used to monitor growth a microbial culture in a droplet. The growth of this panel of labeled strains was used to assess how growth in droplets compared to growth in 96-well plates as well as to compare growth across different carbon sources (see FIGS. 2, 9, 10A and 10B)

FIG. 33 lists the carbon compounds used on kChip. These carbon compounds have been tested for solubility and compatibility with fluorescent dyes used to make up the color codes. They appear in experiments associated with assay validation (see FIGS. 2A-2F above) and/or the Hf-GFP facilitation screen (see FIGS. 3A-3G and FIGS. 4A-4D above).

FIG. 34 presents a summary of soil isolates used in the Hf-GFP facilitation screen of the instant disclosure.

FIG. 35 presents a per-kChip breakdown of the number of individual assays in the Hf-GFP facilitation screen of the instant disclosure (see FIGS. 3A-3G and FIGS. 4A-4D above) and the number of instances where constructed communities were composed of all unique strains. An "average" kChip was also calculated and is shown as the first entry in the summary. N/A indicates that the number cannot be calculated, e.g. because no combinations of 19 unique inputs can be constructed with a library <19 inputs in size. In support of data in FIGS. 4A-4D above, where the two control droplets (not containing a bacterial isolate) are not included in the construction of distributions, a breakdown of the numbers for the relevant 14 (non-control) inputs has been included.

FIGS. 36A and 36B show that bright field microscopy enabled label-less and reagent-free growth readout images for various unlabeled filamentous fungi assessed on the kChip. FIG. 36A shows microscope images of multiple microwells of the kChip with filamentous fungi (*Aspergillus, Penicillium*, and *Mucor*) cultured in the wells. The image specifically demonstrates that growth readout imaging was successfully obtained for four different fungal combinations (as the wells shown in #1 and #2 of the image are different from one another), as well as for pairwise interactions of the four species of fungi (for which a subset of such pairwise interactions are displayed in the current image). FIG. 36B shows zoomed-in images of wells harboring fungi (of at least two different species), over a period of 48 hours.

DETAILED DESCRIPTION OF THE DISCLOSURE

Figure 1A:
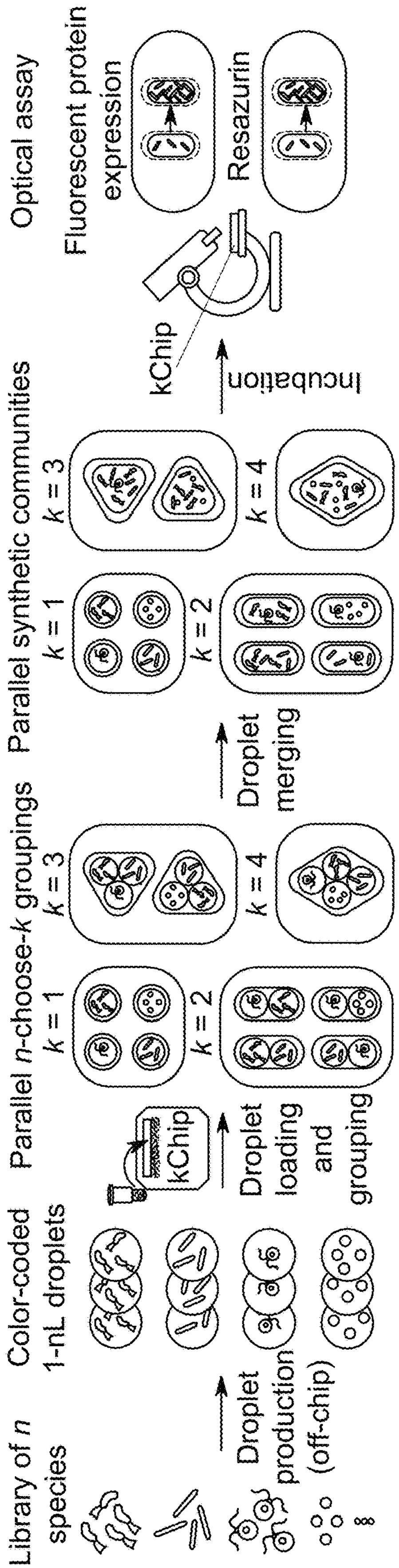
FIGS. 1A-1D depict how the kChip of the instant disclosure enables massively parallel construction of microbial communities.

The present disclosure is based, at least in part, on the discovery of a platform and methodology for massively parallel assessment of combinatorial assemblages of droplet-encapsulated fluid volumes, in a precise and efficient manner that requires only minimal fluid transfer steps. In certain aspects, such droplet-encapsulated fluid volumes include specific microbes, chemical compounds and/or mixtures, optionally further including fluorescent agents in defined ratios within each type of droplet that can be measured to identify the source and/or microbial, chemical compound and/or mixture composition of a specific droplet. In some aspects, the platform of the instant disclosure provides a microwell-presenting solid surface that promotes self-assembly of individual droplets into individual microwells. Once assembled into an array, individual droplets within individual microwells can be precisely fused with other droplets contained in other microwells, via application, e.g., of an electrical and/or magnetic field, to form precisely merged wells, which can be assessed for effects imparted by having merged a selected number of input droplets into a single larger well/assay.

In certain aspects, the instant disclosure provides a platform termed "kChip," that addresses experimental scale and setup time requirements to assay microbial community (optionally including chemical compound(s) and/or mixture(s)) function in high throughput. The kChip system enables parallel construction and quantitative screening of ~$10^5$ synthetic microbial communities per day and requires no robotic liquid handling. The platform screens n-multi-choose-k combinations, meaning each parallel community is composed of precisely k inputs (e.g. strains or media) randomly selected (with replacement) from a larger library of n, where both n and k are selected by the user (in certain embodiments, n can be defined as, e.g., 2 to 50 or more, including, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more inputs). Drawing on advances in micro-compartmentalization (30, 31), the kChip platform generalizes a high-density microwell array approach that groups and merges sets of nanoliter droplets that each carry input components, an approach previously demonstrated for pair-wise combinatorial compound screening (32). The instant disclosure has demonstrated that droplets can self-assemble randomly into groupings of k=(1, 2, . . . , 7, 19) dictated by microwell geometries (in certain embodiments, k can be defined as, e.g., 2 to 50 or more, including, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more groupings dictated by microwell geometry), and that these self-assembled droplets can be merged, greatly reducing the time and logistical complexity of combination assembly. As with other droplet microfluidic systems, the kChip platform is amenable to fluorescent and label-free optical assays and uses small assay volumes that conserve valuable or hard-to-produce inputs. Furthermore, the length scale of kChip microwells (~100-1000 μm) is a natural ecological scale for interaction-driven microbial community assembly (33).

Certain aspects of the instant disclosure therefore solve the problem of discovery of functional microbial communities via the direct construction and screening of combinations of microbial types. Previous methods for identifying functional combinations of microbes include forward engineering (which relies on theory and a deep mechanistic understanding of microbial interactions) and reverse engineering (which uses computational analyses to infer functional communities). Approaches involving direct discovery have heretofore been limited by the throughput of existing liquid handling methods and the complex logistics of constructing combinations. The instant platform overcomes these issues to generate $10^5$-$10^7$ microbial communities per screen.

A library of inputs, e.g. individual microbial types (e.g., individual microbial species), can be loaded into droplets; these droplets are then loaded onto a microwell array whereby the design of each microwell dictates how many droplets are randomly sampled by the microwell. In certain aspects, distinguishing features of the instant disclosure include: the design of the microwells and microwell chips; the process whereby the chips are loaded with droplets; and the adoption of specific assays to track microbial growth. Prior innovations have included: the color-coding strategy, the process of fabricating the chips, and the strategy for merging droplets within microwells (see, e.g., PCT/US2016/023245, the contents of which are incorporated by reference in their entirety).

As presently exemplified, the device can be used to screen different combinations of microbes toward the discovery of living therapeutics, i.e. a specific collection of microbes used in combination to treat disease. More generally, it can be used to screen for any function, e.g. the degradation or production of a compound of interest. More broadly, the data collected through screening on the platform can inform and accelerate rational approaches for microbial community design.

The platform can be deployed to screen, in massively parallel fashion (e.g., $10^5$-$10^7$ independently combined microbial communities per screen), for microbe combinations for which a functional assay is available in the art (or is developed). For example, combinations that exert an effect on a microbe of interest (e.g. promote a beneficial microbe or suppress a pathogenic microbe) can be screened for (as exemplified herein) by labeling this microbe and screening its growth across all constructed communities. The ability of a microbe to grow can also be rapidly profiled across a multitude of biotic (microbes) and abiotic (e.g. compounds or growth substrates) conditions.

Overview

The instant disclosure provides a platform that enables combinatorial assessment of independently resolvable microbial, chemical compound and/or mixture inputs, in a manner that is massively parallel, efficient, and that minimizes the number of fluid manipulations. Termed the "kChip" herein, the instant disclosure describes development and implementation of a droplets-based platform that performs rapid, massively parallel, bottom-up construction and screening of synthetic microbial, chemical compound and/or mixture communities. As initially exemplified below, the kChip has been demonstrated herein to enable phenotypic characterization of both fluorescently labeled and non-labeled microbial strains across a panel of environmental conditions. The utility of high-throughput screening achieved via use of the kChip has also been demonstrated herein by measuring the yield of a GFP-expressing model plant symbiont *Herbaspirillum frisingense* (Hf) in co-culture with ~100,000 communities comprising up to 19 soil isolates. Specific compositions that promoted Hf growth on different carbon sources and in the presence of additional strains were identified. Broadly, kChip screening has been demonstrated to be capable of identifying multistrain consortia possessing any optically assayable function, including facilitation of biocontrol agents, suppression of pathogens, degradation of recalcitrant substrates (optionally for use in biofuel production or environmental remediation), and robustness of these functions to perturbation. Moreover, large datasets collected through kChip screening can be leveraged to characterize how a given species responds across a large array of biotic and abiotic environments, elucidate how these factors drive microbial interactions, and uncover design principles for functional consortia. Altogether, the kChip platform is provided to advance basic and applied microbial ecology.

Microbial communities exhibit emergent consortia-level functions that are vital to all ecosystems on Earth. These functions include photosynthetic and chemosynthetic primary production (1), regulation of greenhouse gas levels (2), recycling of recalcitrant organic compounds (3), and protection of plant and animal hosts against infectious agents (4, 5). The diversity, complexity, and robustness of functions performed by natural microbial communities indicate that synthetic consortia can someday be leveraged broadly as biotechnological tools (6). Indeed, such consortia have already been deployed for bioproduction (7), bioremediation (8), and probiotic-mediated therapies for a wide range of hosts and diseases (9-12).

The complexity of microbial interactions and environmental dependencies (13-16) can lead to unpredictable behaviors even in apparently simple communities, posing a challenge to consortia design. Addressing this challenge is expected to require the integration of multiple approaches—including the reverse-engineering of natural communities (e.g. via inference-based co-occurrence analyses) (17) and further development of forward-engineering strategies (e.g. metabolic flux-balance analyses) (18, 19). An additional complementary approach is screening of experimentally constructed synthetic combinations of strains in order to identify consortia with desired properties and functions or validate designs based on rational approaches (20-22).

High-throughput phenotypic screening has found widespread use as a discovery strategy for novel gene targets (23) and drugs (24), but its adoption in microbial consortia discovery has been hindered by the logistical complexity of constructing strain combinations. Conventional liquid handling techniques and platforms, e.g. pipette-based construction of combinations in multiwell plates, may not be sufficient to adequately sample combinatorial space in a single experiment (25). For example, from a library of just n=16 strains, generating all subsets of size k={1, 2, . . . 7} in a single medium would require ~160,000 liquid handling steps and 275 96-well plates (without replicates). As these combinations could not be prepared in advance and would have to be assembled on the timescale of cell division (~1 hour), generating even 10% of these combinations would likely be logistically impractical. Because constructing each community requires a unique set of liquid transfers, these experiments are also difficult to automate robotically. Indeed, combinatorial studies conducted in liquid media typically construct $<10^3$ unique synthetic communities (20, 26-28). Some of the largest combinatorial studies (29) instead use the Burkholder agar assay, whereby an array of n microbial colonies is introduced to an agar gel inoculated with a second species, generating n×1 combinations per agar plate. Single studies using this assay can generate $\sim10^3$-$10^4$ interactions but are typically restricted to binary compositions. Diffusion between colonies further places an upper bound on the density of the colony array and throughput of the screen.

Microfluidic Device/kChip Design

Figure 5A:
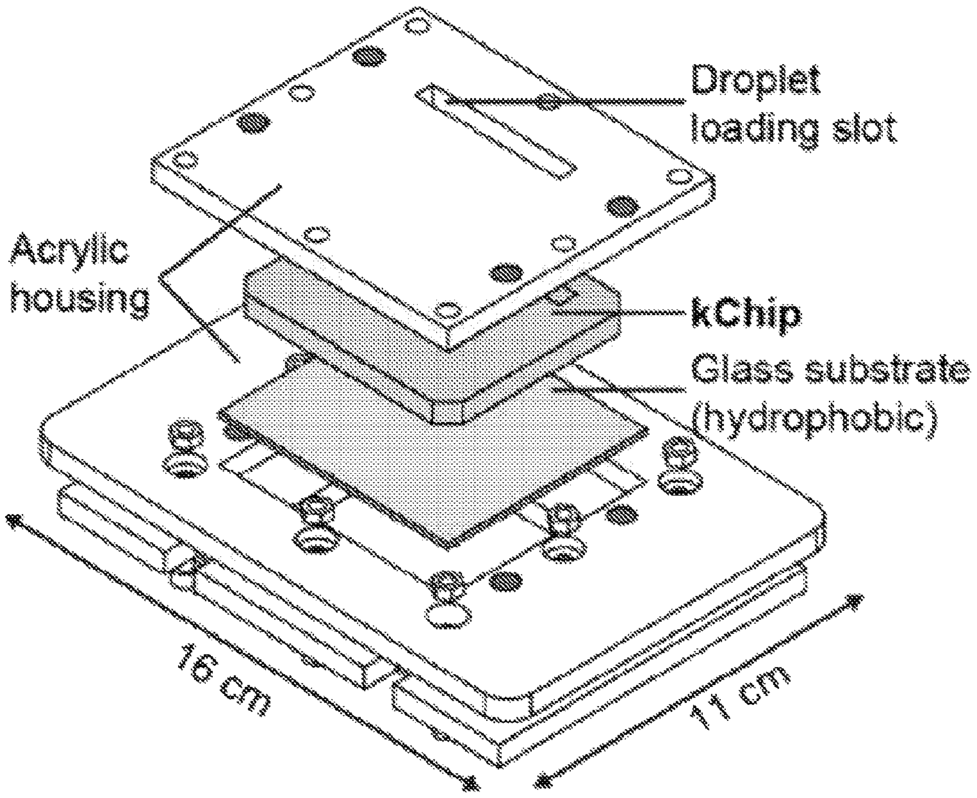
FIGS. 5A-5I show how a loading apparatus assists droplet loading onto kChip.
Figure 5B:
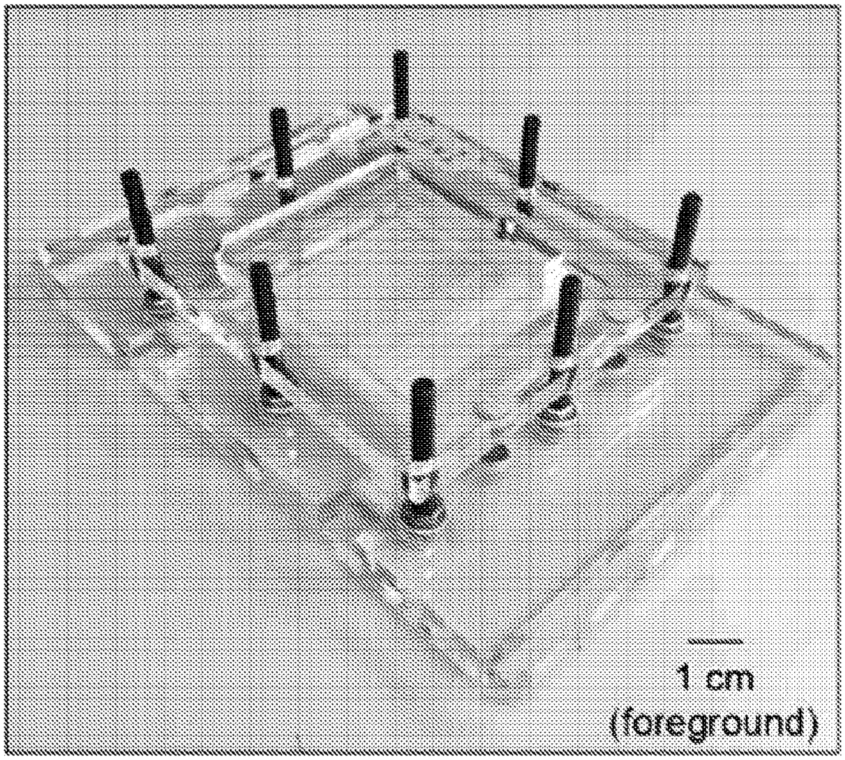
Figure 5C:
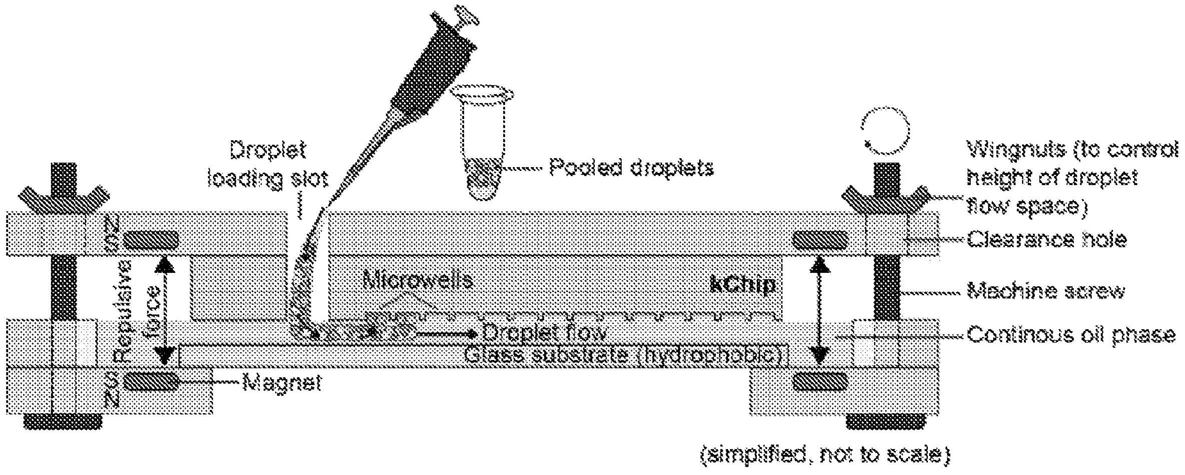

Referring to FIG. 5C, in one aspect, the embodiments disclosed herein are directed to microfluidic devices with at least one droplet input, at least one flow channel, and an array of microwells. Droplets comprising different molecular species are generated and loaded onto the device. The droplets may be formed off chip and then loaded via a droplet input onto the microfluidic device comprising the array of microwells. Alternatively, the microfluidic device may be connected directly to a second microfluidic device for forming droplets, which then feeds the formed droplets onto the microfluidic devices comprising the array of microwells via a droplet input. In certain example embodiments the microfluidic devices disclosed herein may form a module that is combined with other modules on a single chip. For example, a chip may comprise a droplet formation module and the devices disclosed herein may form a droplet merge module. In one embodiment, the droplets are formed in the droplet formation module and then input into the one or more flow channels of the droplet merge module. The formed droplets are then distributed across one or more flow channels of the microfluidic device for delivery to the microwells.

In certain example embodiments, the device comprises a single flow channel.

In certain other example embodiments, the device comprises two or more flow channels. In one embodiment, the one or more flow channels are defined on a bottom layer or a top layer of the device. The flow channel may be an integral part of a device that is formed from the same mold used to define the array of microarrays. Alternatively, the flow channel may be formed by mounting the array of microwells to a solid substrate, such as a glass substrate. In certain example embodiments, a thin space may be inserted between the microfluidic device and the solid substrate to define the one or more flow channels. In certain embodiments, the width of the flow channel(s) is adjustable via loosening or tightening of machine screw-attached wingnuts positioned at the periphery of the device that control the height of the droplet flow space. After loading droplets into the microwells, the spacers may be removed to completely seal the microfluidic device to the solid substrate. Droplets rise or sink via buoyancy from the one or more flow channels into empty microwell spaces.

Each flow channel may have a width of approximately 5 mm to approximately 75 mm; approximately 5 mm to approximately 50 mm; approximately 5 mm to approximately 25 mm; approximately 5 mm to approximately 15 mm; approximately 10 mm to approximately 20 mm; approximately 20 mm to approximately 30 mm; approximately 30 mm to approximately 40 mm; approximately 40 mm to approximately 50 mm; approximately 50 mm to approximately 60 mm; and approximately 60 mm to approximately 70 mm.

Each flow channel may have a length of approximately 10 mm to approximately 100 mm in length; approximately 20 mm to approximately 100 mm; approximately 30 mm to approximately 100 mm in length; approximately 40 mm to approximately 100 mm in length; approximately 50 mm to approximately 100 mm in length; approximately 60 mm to approximately 100 mm; approximately 70 mm to approximately 100 mm; approximately 80 mm to approximately 100 mm; approximately 90 mm to approximately 100 mm; approximately 10 mm to approximately 50 mm; approximately 10 mm to approximately 40 mm; approximately 10 mm to approximately 30 mm; approximately 10 mm to approximately 20 mm; approximately 50 mm to approximately 100 mm; approximately 50 mm to approximately 90 mm; approximately 50 mm to approximately 80 mm; approximately 50 mm to approximately 70 mm; approximately 50 mm to approximately 60 mm.

Each flow channel may have a depth or height of approximately 100μιη to approximately 500 μm; approximately 100 μm to 400 μm; approximately 100 μm to approximately 300 μm; approximately 100 μm to approximately 200 μm; approximately 200 μm to approximately 300 μm; approximately 300 μm to approximately 400 μm; approximately 400 μm to approximately 500 μm.

In various embodiments, the length, depth or height of the flow channels may be optimized for the type of material being assayed. For example, larger dimensions may be used when analyzing whole cells or cell populations, whereas smaller dimensions may be used when analyzing acellular fractions or chemical libraries and the like.

The flow channels allow flow beneath a top layer of the microfluidic device comprising an array of microwells. In alternative embodiments the flow channels may allow flow of a carrier fluid above a bottom layer of the microfluidic device comprising an array of microwells. Such an embodiment would be an inverted version of the embodiment shown in FIG. 5C. The microwells are sized to hold a single individual drop which will then be merged with individual droplets in other adjoined microwells, allowing the contents of the individual drops to combine into a merged droplet assay area. FIGS. 6A-6D shows an exemplified embodiment in which each microwell of the microarray is sized to hold an individual droplet, where a majority of the individual droplets are of size 135 μm t 5 μm in diameter and the size of the microwell is 148.2 μm in diameter. In certain embodiments, it is contemplated that a plurality (optionally a majority, optionally >80% of all droplets, optionally >90% of all droplets, optionally >95% of all droplets) of input droplets range from 120 μm to 150 μm in diameter, optionally 125 μm to 145 μm in diameter, and optionally 130 μm to 140 μm in diameter. Similarly, in related embodiments, each individual microwell of the array is of about 125 μm to 165 μm in diameter, optionally of about 130 μm to 160 μm in diameter, optionally of about 135 μm to 155 μm in diameter, optionally of about 140 μm to 150 μm in diameter, optionally of about 145 μm to 150 μm in diameter, optionally of about 148 μm in diameter, optionally precisely 148.2 μm in diameter. In additional related embodiments, the microwells are of 90-140 μm feature height, optionally 100-130 μm feature height, optionally 105-125 μm feature height, optionally 110-120 μm feature height.

In various embodiments, the pooled droplets are dispensed into the droplet loading slot. In certain embodiments, droplet flow then traverses a small droplet size filter, which is exemplified herein as a series of moat-like channels capable of filtering out/trapping small droplets prior to droplet flow reaching the array of microwells. In select embodiments, each of the channels of the small droplet size filter has a width of approximately 75 μm to approximately 134 μm. Optionally, each of the channels of the small droplet size filter has a width of approximately 80 μm to approximately 120 μm; optionally approximately 85 μm to approximately 105 μm in width; optionally approximately 90 μm to approximately 95 μm in width; optionally the channels of the small droplet size filter are approximately 90 μm wide. In related embodiments, the small droplet size filter includes 5-25 or more channels, optionally 10-20 or more channels, optionally 11, 12, 13, 14, 15, 16, 17, 18, 19 or 20 or more channels.

In certain embodiments, the device includes internal posts arranged around the periphery of each microwell, where such internal posts are capable of functioning as a low pass filter (by disrupting or preventing the entry of large droplets into individual microwells). In specific exemplified embodiments, six triangular internal posts are equally spaced around the circumference of each microwell of the device, with these six triangular internal posts capable of controlling the number of droplets entering a microwell by reducing overfilling that would otherwise be caused by oversized droplets squeezing into a microwell. In addition, the internal posts are also capable of reducing underfilling that would otherwise be caused by droplets exiting microwells due to the fluid flow (e.g., oil flow) associated with device loading. Based on the desired k, a subset of internal posts can be drawn to enclose the boundary of a merged well (including k microwells). In certain embodiments, each incorporation of two additional internal posts increases the well grouping capacity by one droplet. In certain embodiments, the internal posts have a width of approximately 5 μm to approximately 100 μm; optionally a width of approximately 10 μm to approximately 70 μm; optionally a width of approximately 20 μm to approximately 60 μm; optionally a width of approximately 30 μm to approximately 50 μm; optionally a width of approximately 40 μm. While for the exemplified kChips of the instant disclosure six internal posts encircle each individual well, functional kChips of the instant disclosure may be constructed with any number of internal posts encircling each individual well. Thus, in certain embodiments, 1 to 36 internal posts encircle each individual well of the kChip; optionally 2 to 18 internal posts encircle each individual well of the kChip; optionally 3 to 12 internal posts encircle each individual well of the kChip; optionally 4 to 10 individual posts encircle each individual well of the kChip; optionally 5 to 8 internal posts encircle each individual well of the kChip; optionally 6 or 7 internal posts encircle each individual well of the kChip; optionally precisely 6 internal posts encircle each individual well of the kChip.

The array of microwells is located in a layer above or below the flow channel and is situated such that each microwell in the array is accessible via the flow channel. In certain example embodiments, there is a single array of microwells located above a single flow channel. In certain other example embodiments, there may be two or more arrays of microwells, each situated above a separate flow channel. In certain example embodiments, the number of microwells may range from 1,000 to 1,000,000.

In certain example embodiments, the microfluidic device may further comprise one or more droplet outputs for collecting the merged droplets off the device for further downstream processing. In certain example embodiments, to elute the merged droplets, the device is inverted, and the merged droplets are allowed to enter the flow channel which then directs flows of the released merged droplets to the one or more droplet outputs.

In certain example embodiments, the microfluidic device may further comprise a clamping mechanism for loading the device. Referring to FIG. 5B, and in accordance with certain example embodiments, the clamping mechanism may comprise a bottom clamp and a top clamp. The bottom clamp may further comprise a glass slide (not shown) onto which the microfluidic device is placed. The bottom clamp may also further comprise one or more spacers (not shown) that define the flow channel beneath the array of microwells when inserted between the glass slide and the microfluidic device. When removed the spacers allow the top and bottom clamps to seal the microfluidic device against the glass slide of the bottom clamp. The top clamp may comprise an opening sized to fit the microfluidic device such that a portion of the microfluidic device sits above the opening in the top clamp. The top clamp and bottom clamp are clamped together by one or more connectors. In certain example embodiments, the connections may be one or more magnets, such as but not limited to, rare earth magnets. In certain example embodiments the top and bottom clamps are made from acrylic or other similar material.

Figure 5D:
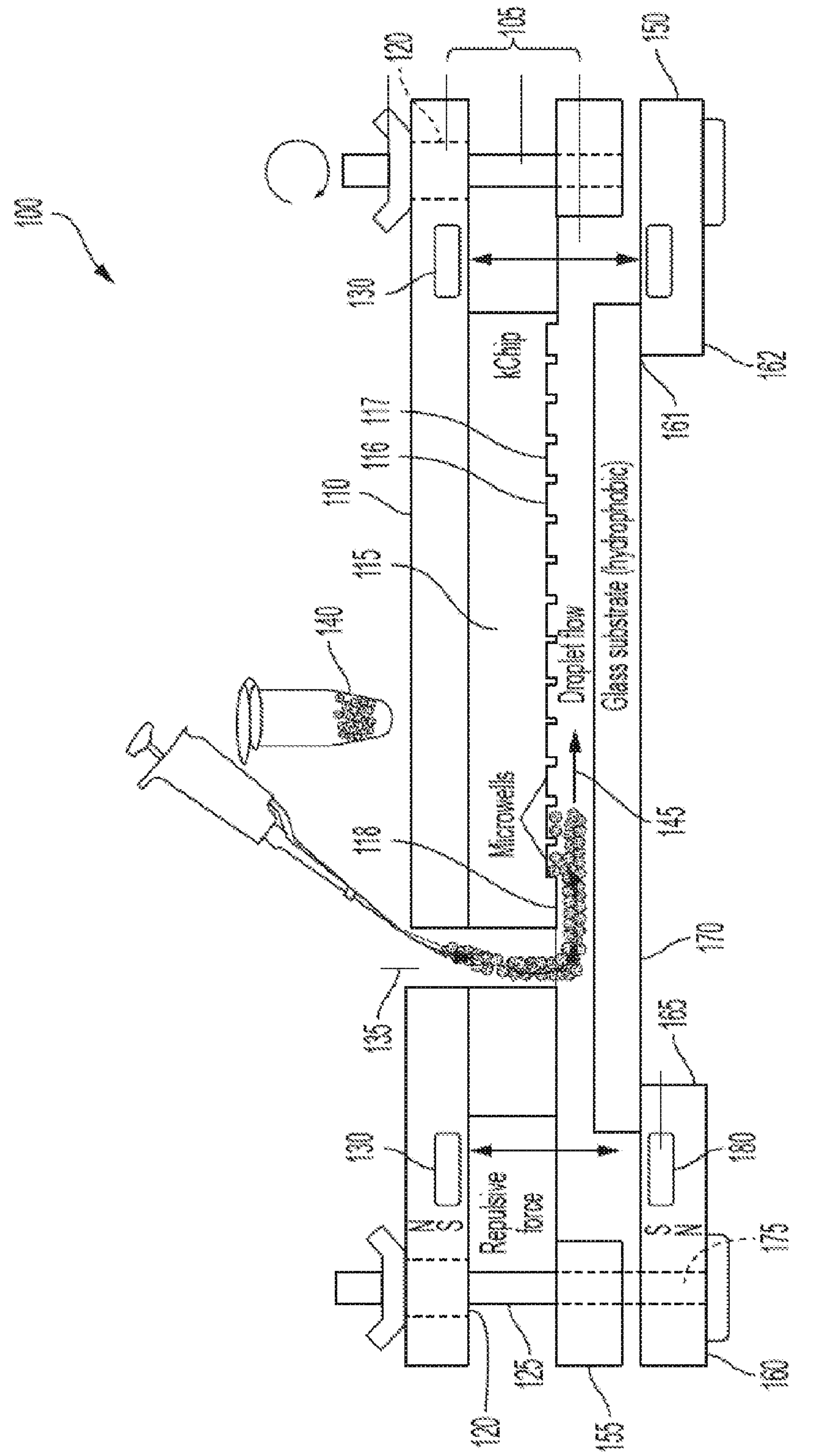
Figure 5E:
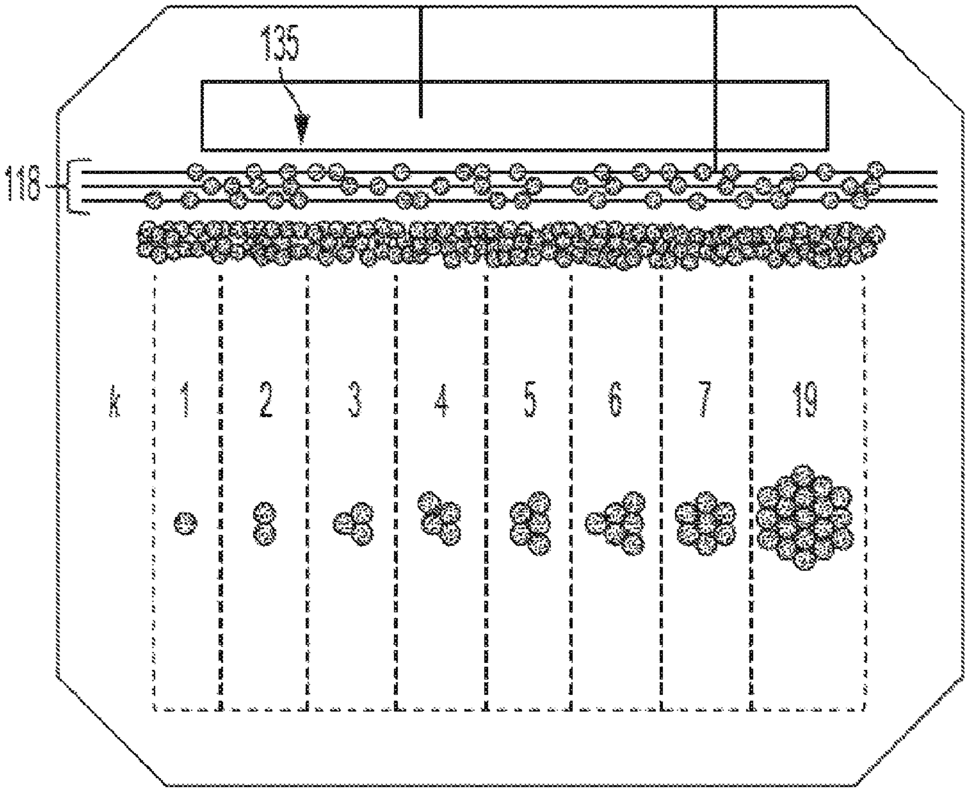

As shown in FIG. 5D and FIG. 5E, microfluidic screening platform 100 includes a top plate 105 and a bottom plate 150. Top plate 105 includes an upper portion 110 and a lower portion 115. Upper portion 110 includes a plurality of through holes 120, each of which is configured to receive a connecting shaft 125. Upper portion 110 also includes a plurality of magnets 130. Top plate 105 includes an inlet 135 that extends through both upper portion 110 and lower portion 115. Inlet 135 is configured to receive a plurality of droplets 140, and allowing them to pass through upper portion 110 and lower portion 115, and enter droplet flow channel 145. Bottom plate 150 includes an upper portion 155, a lower portion 160, and an internal cut out 165, which forms an internal through passage in lower portion 160 of the bottom plate 150. Lower portion 160 includes a top side 161 and a bottom side 162. The internal cut out 165 is covered by a glass substrate 170 that rests on, and partially overlaps, topside 161 of the lower portion 160 of the bottom plate 150. Like top plate 105, bottom plate 150 also includes a plurality of through holes 130, which generally line up with through holes 120 located in top plate 105. In this way, shaft 125 is seated in through hole 175, which is positioned within bottom plate 150 in a manner that corresponds with an analogous through hole 120 located in top plate 105, thereby allowing top plate 105 to seat on shaft 125 and be positioned proximate to bottom plate 150. Like top plate 105, bottom plate 150 includes a plurality of magnets 180, each of which is positioned opposite to a corresponding magnet 130 located in top plate 105. In concert, the juxtaposition of magnets 130 and 180 creates a repulsive force that helps to position top plate 105 relative to bottom plate 150 and maintain an appropriate spacing to create droplet flow channel 145. A lower side 116 of lower portion 115 includes a plurality of microwells 117, each of which is configured to hold at least one droplet (in certain embodiments, configured to hold a single droplet). Additionally, lower side 116 of lower portion 115 also includes a high-pass filter 118, which is configured to function as a pre-filter to limit the size of droplets 140 capable of entering droplet flow channel.

Figure 5F:
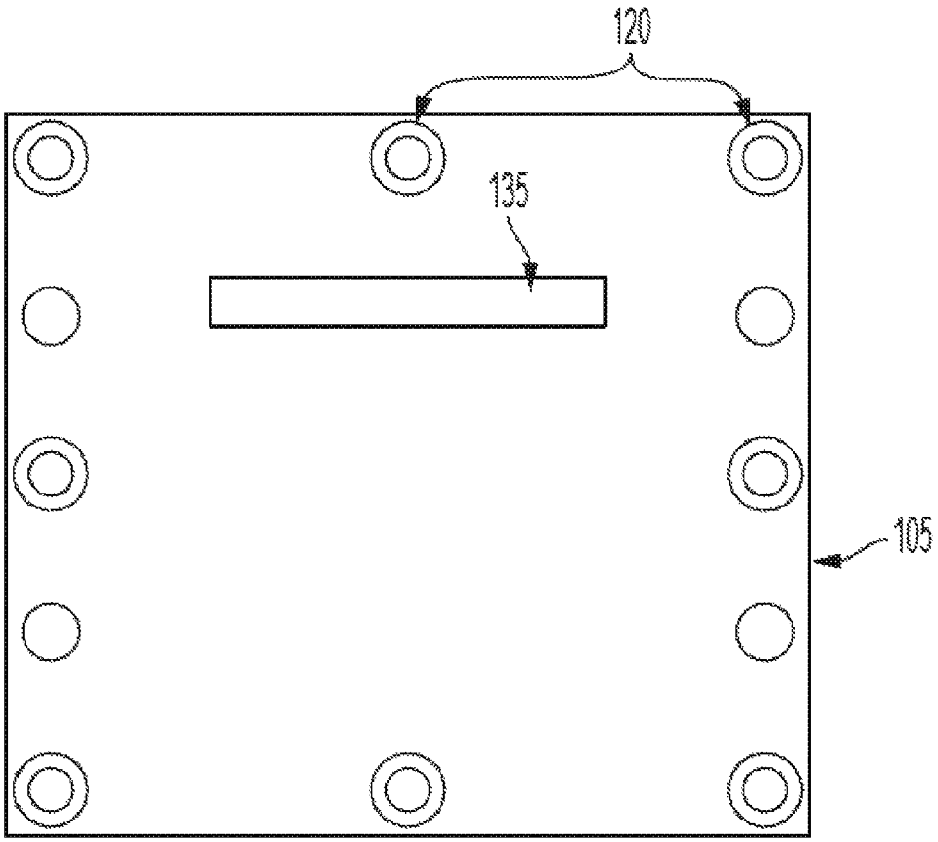
Figure 5G:
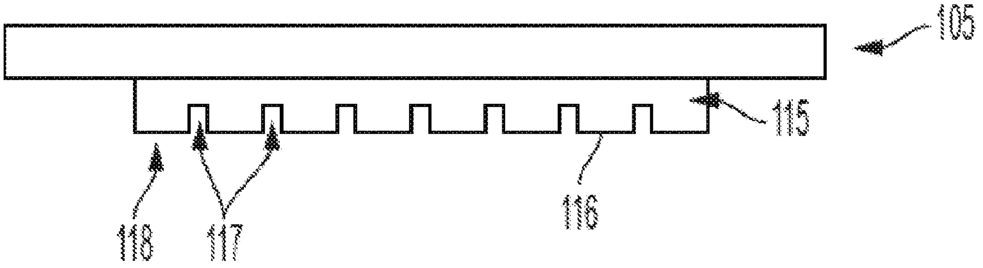

FIG. 5F and FIG. 5G show a top view and a side view, respectively, of top plate 105 of a microfluidic screening platform according to an exemplary embodiment of the disclosure, and show exemplary positioning of inlet 135 and through holes 120. Additionally, FIG. 5G shows a side view of top plate 105 including lower portion 115, which further includes high pass filter 118 and a plurality of microwells 117 positioned on lower surface 116 of lower portion 115.

Figure 5H:
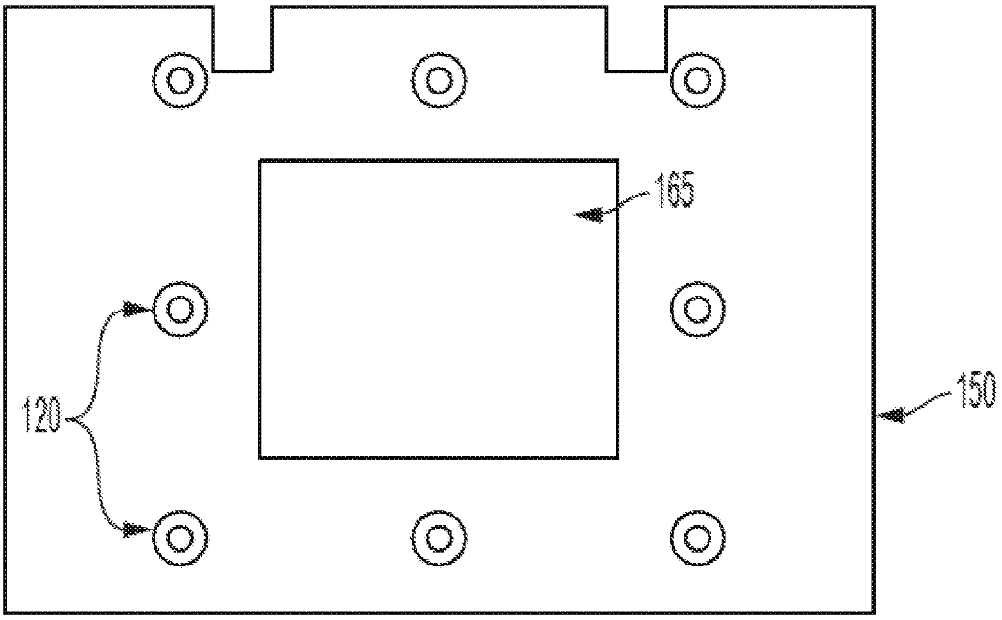
Figure 5I:

FIG. 5H and FIG. 5I show a top view and a side view, respectively, of bottom plate 150 of a microfluidic screening platform according to an exemplary embodiment of the disclosure, and show an exemplary positioning of inlet 165 and through holes 120.

In certain embodiments, the microfluidic device may be loaded using a loading system as described in PCT/US2016/023245.

Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. Suitable materials for fabricating the microfluidic devices include, but are not limited to, cyclic olefin copolymer (COC), polycarbonate, poly (dimethyl siloxane) (PDMS), and poly(methylacrylate) (PMMA). In one embodiment, soft lithography in PDMS may be used to prepare the microfluidic devices. For example, a mold may be made using photolithography which defines the location of the one or more flow channels and the array of microwells. The substrate material is poured into a mold and allowed to set to create a stamp. The stamp is then sealed to a solid support such as, but not limited to, glass.

Due to the hydrophobic nature of some polymers, such as PDMS, which absorbs some proteins and may inhibit certain biological processes, a passivating agent may be necessary (Schoffner et al. Nucleic Acids Research, 1996, 24:375-379). Suitable passivating agents are known in the art and include, but are not limited to, silanes, parylene, n-Dodecyl-b-D-matoside (DDM), pluronic, Tween-20, other similar surfactants, polyethylene glycol (PEG), albumin, collagen, and other similar proteins and peptides.

The microfluidic devices may further comprise inlet and outlet ports, or openings, which in turn may be connected to valves, tubes, channels, chambers, and syringes and/or pumps for the introduction and extraction of fluids into and from the microfluidic device. The microfluidic devices may be connected to fluid flow actuators that allow directional movement of fluids within the microfluidic device. Example actuators include, but are not limited to, e.g., syringe pumps, mechanically actuated recirculating pumps, electroosmotic pumps, bulbs, bellows, diaphragms, or bubbles intended to force movement of fluids.

Droplet Production and Filtering

Droplets can be prepared and/or tagged for identification by any method known in the art. In exemplified embodiments, droplets containing discrete microbes are prepared as described in Example 1 below and are loaded onto a kChip, e.g., using a pipette, as shown in FIG. 5C, kChip microwells are designed to harbor a single droplet per microwell (self-assembly into an array of microwells/droplets), as described elsewhere herein. In certain aspects, the identity and position of the kChip-loaded droplets within microwells is determined, e.g., by measurement of two or more fluorescent agents, proportions of which can be varied depending upon the contents (e.g., microbe identity) of the particular droplet, and determination of the ratio of such agents within a selected droplet. In certain embodiments, droplets can be distinguished on the basis of luminescent and/or fluorescent dye content, with exemplified droplet identity fluorescent dyes including, but not limited to, Alexa Fluor 488, Alexa Fluor 555, Alexa Fluor 594, and/or Alexa Fluor 647. These particular dyes can be employed in some embodiments to avoid wavelength overlap with optical assay fluorescent dyes. In particular exemplified embodiments, luminescence and/or fluorescence-based assay signals employed for optical assays (optionally on chip/in well optical assays) include, but are not limited to, green fluorescent protein (GFP), yellow fluorescent protein (YFP), and resorufin, though it is expressly contemplated that a wide range of art-recognized luminescent and/or fluorescent agents or other signal-emitting agents (e.g., radioactive agents, etc.) can be employed for droplet identification or for performing optical assays.

After the droplets have been loaded into the microwells and the identity and position of initial droplets within microwells is determined, the droplets are merged in parallel. The droplets may be merged by any mechanism sufficient to coalesce two or more droplets into a single droplet, such as but not limited to, electrocoalescence, thermal coalescence, acoustic coalescence, vortexing, or changes in surfactant concentration. In certain example embodiments, the droplets are merged using electrocoalescence. For example, a suitable electric field may be applied to the microfluidic device using a corona treater wand. In certain other example embodiments, coalescence can be triggered by surfactant depletion. For example, the inside of the microwells may be modified with surface treatment chemistry that binds surfactant thereby depleting surfactant available to the droplets. Alternatively, a solution may be flushed through the system that washes surfactant out of the microwells. Standard droplet coalescence methods that may be used with the embodiments described herein are described in Niu et al. "Electro-Coalescence of Digitally Controlled Droplets," Analytical Techniques. (2009) 81(17), 7321-7325; Niu et al. "Pillar-induced droplet merging in microfluidic circuits," Lab On A Chip (2008), 8(11), 1837-1841; and Mazutis et al. "Selective droplet coalescence using microfluidic systems," (2012), Lab on a Chip, 12, 1800-1806.

Microbes

In certain embodiments, microwell-directed droplets encapsulate discrete microbes. The instant disclosure contemplates droplet encapsulation of any art-recognized form of microbe, and exemplified embodiments feature droplets that respectively include distinct bacterial strains (e.g., *Escherichia Coli*) and an auto-fluorescent algae strain (e.g., *Chlamydomonas reinhardtii*), for loading onto a kChip of the instant disclosure. Exemplary microbes for use with the platform and methods of the instant disclosure include, but are not limited to, the following.

Bacterial Strains

*Escherichia* is a genus of Gram-negative, non-spore-forming, facultatively anaerobic, rod-shaped bacteria from the family Enterobacteriaceae. A number of the species of *Escherichia* are pathogenic. The *Escherichia* genus includes, but is not limited to, *Escherichia coli* (*E. coli*). *E. coli* is one of the most commonly used bacteria in microbiology experiments. *E. coli* is a rod-shaped, Gram-negative bacteria. Gram-negative bacteria contain an outer membrane surrounding the cell wall that provides a barrier to certain antibiotics. Most strains of *E. coli* are harmless, but some serotypes cause illnesses such as food poisoning. Cells are able to survive outside the body for a limited amount of time, which makes them ideal indicator organisms to test environmental samples for fecal contamination. The bacterium can also be grown easily and inexpensively in a laboratory setting.

*Pseudomonas* is a genus of Gram-negative, Gammaproteobacteria, belonging to the family Pseudomonadaceae and containing 191 validly described species. The members of the genus demonstrate a great deal of metabolic diversity and consequently are able to colonize a wide range of niches. Their ease of culture in vitro and availability of an increasing number of *Pseudomonas* strain genome sequences has made the genus favorable for scientific research. A number of the species of *Escherichia* are pathogenic to plants and animals, including humans. The *Pseudomonas* genus includes, but is not limited to, the strains commonly used in a lab setting: *Pseudomonas aeruginosa, Pseudomonas fluorescens, Pseudomonas citronellolis, Pseudomonas chlororaphis, veronii, Pseudomonas aurantiaca, Pseudomonas putida*, and *Pseudomonas syringae*.

*Herbaspirillum* is a genus of bacteria, including the nitrogen-fixing *Herbaspirillum lusitanum*. The genus of bacteria is generally found in soil environments. The *Herbaspirillum* genus includes, but is not limited to, the strain *Herbaspirillum frisingense. Herbaspirillum frisingense* is a nitrogen-fixing bacterium which was found in C4-fibre plants like prairie cordgrass (*Spartina pectinata*), Chinese silver grass (*Miscanthus sinensis*), Amur silvergrass (*Miscanthus sacchariflorus*), and Napier grass (*Pennisetum purpureum*).

An exemplary but not comprehensive list of bacteria for use with the platform and methods of the instant disclosure includes *Achromobacter* spp, *Acidaminococcus fermentans, Acinetobacter calcoaceticus, Actinomyces* spp, *Actinomyces viscosus, Actinomyces naeslundii, Aeromonas* spp, *Aggregatibacter actinomycetemcomitans, Anaerobiospirillum* spp, *Alcaligenes faecalis, Arachnia propionica, Bacillus* spp, *Bacteroides* spp, *Bacteroides gingivalis, Bacteroides fragilis, Bacteroides intermedius, Bacteroides melaninogenicus, Bacteroides pneumosintes, Bacterionema matruchotii, Bifidobacterium* spp, *Buchnera aphidicola, Butyriviberio fibrosolvens, Campylobacter* spp, *Campylobacter coli, Campylobacter sputorum, Campylobacter upsaliensis, Capnocytophaga* spp, *Clostridium* spp, *Citrobacter freundii, Clostridium difficile, Clostridium sordellii, Corynebacterium* spp, *Eikenella corrodens, Enterobacter cloacae, Enterococcus* spp, *Enterococcus faecalis, Enterococcus faecium, Escherichia coli, Eubacterium* spp, *Flavobacterium* spp, *Fusobacterium* spp, *Fusobacterium nucleatum, Gordonia Bacterium* spp, *Haemophilus parainfluenzae, Haemophilus paraphrophilus, Lactobacillus* spp, *Leptotrichia buccalis, Methanobrevibacter smithii, Morganella morganii, Mycobacteria* spp, *Mycoplasma* spp, *Micrococcus* spp. *Mycoplasma* spp. *Mycobacterium chelonae, Neisseria* spp. *Neisseria sicca, Peptococcus* spp, *Peptostreptococcus* spp. *Plesiomonas shigelloides, Porphyromonas gingivalis, Propionibacterium* spp, *Propionibacterium acnes, Providencia* spp, *Pseudomonas aeruginosa, Ruminococcus bromii, Rothia dentocariosa, Ruminococcus* spp, *Sarcina* spp, *Staphylococcus aureus, Staphylococcus epidermidis, Streptococcus anginosus, Streptococcus mutans, Streptococcus oralis, Streptococcus pneumoniae, Streptococcus sobrinus, Streptococcus viridans, Torulopsis glabrata, Treponema denticola, Treponema refringens, Veillonella* spp. *Vibrio* spp. *Vibrio sputorum, Wolinella succinogenes* and *Yersinia enterocolitica*. In certain embodiments, exemplary bacteria include *Achromobacter* spp. (e.g., *Achromobacter denitrificans, Achromobacter xylosoxidans, Achromobacter ruhlandii*); *Actinomadura* spp. (e.g., *Actinomadura luteofluorescens, Actinomadura madurae, Actinomadura pelletieri, Actinomadura viridis*); *Agrobacterium* spp. (e.g., *Agrobacterium radiobacter, Agrobacterium luteum, Agrobacterium agile, Agrobacterium rubi*); *Arthrobacter* spp. (e.g., *Arthrobacter arilaitensis, Arthrobacter chlorophenolicus, Arthrobacter aurescens*); *Bacillus* spp. (e.g., *Bacillus cereus, Bacillus subtilis, Bacillus coagulans, Bacillus psychrosaccharolyticus, Bacillus amyloliquefaciens, Bacillus lentus, Bacillus circulans, Bacillus firmus*); *Burkholderia* spp. (e.g., *Burkholderia gladioli, Burkholderia plantarii, Burkholderia cepacia*); *Clostridium* spp. (e.g., *Clostridium orbiscindens, Clostridium formicaceticum*); *Escherichia coli; Ewingella* spp. (e.g., *Ewingella americana*); *Flavobacterium* spp. (e.g., *Flavobacterium flevense, Flavobacterium aquatile, Flavobacterium saccharophilum, Flavobacterium hydatis, Flavobacterium johnsoniae*); *Flexibacter* spp. (e.g., *Flexibacter flexilis, Flexibacter columnare*); *Herbaspirillum frisingense; Hyphomicrobium* spp. (e.g., *Hyphomicrobium aestuarii*); *Micromonospora* spp. (e.g., *Micromonospora rosaria, Micromonospora facile, Micromonospora zavarzinii, Micromonospora denitrificans*); *Mycobacterium* spp. (e.g., *Mycobacterium neoaurum*); *Nocardia* spp. (e.g., *Nocardia jiangxiensis, Nocardia miyunensis*); *Paenibacillus* spp. (e.g., *Paenibacillus macquariensis, Paenibacillus macerans, Paenibacillus alvei, Paenibacillus polymyxa, Paenibacillus chibensis*); *Pseudomonas* spp. (e.g., *Pseudomonas aeruginosa, Pseudomonas putida, Pseudomonas fluorescens, Pseudomonas citronellolis, Pseudomonas chlororaphis, Pseudomonas aurantiaca, Pseudomonas pseudopalustris, Pseudomonas palustris, Pseudomonas syringae, Pseudomonas veronii, Pseudomonas aurantiaca*); *Ralstonia* spp. (e.g., *Ralstonia solanacearum, Ralstonia pickettii, Ralstonia syzygii*); *Rhodococcus* spp. (e.g., *Rhodococcus erythropolis, Rhodococcus rhodochrous*); *Serratia* spp. (e.g., *Serratia marcescens, Serratia liquefaciens*); *Sphingomonas* spp. (e.g., *Sphingomonas echinoides, Sphingomonas leidyi, Sphingomonas wittichii*); and/or *Streptomyces* spp. (e.g., *Streptomyces lividans, Streptomyces coelicolor, Streptomyces tanashiensis, Streptomyces clavuligerus, Streptomyces griseus*).

Algae

*Chlamydomonas* is a genus of green algae consisting of about 325 species, all unicellular flagellates, found in stagnant water, damp soil, freshwater, seawater, and snow. *Chlamydomonas* is used as a model organism for molecular biology, especially studies of flagellar motility and chloroplast dynamics, biogeneses, and genetics. *Chlamydomonas* contain ion channels that are directly activated by light. The *Chlamydomonas* genus includes, but is not limited to, the strain *Chlamydomonas reinhardtii. Chlamydomonas reinhardtii* is an especially well studied biological model organism, partly due to its ease of culturing and the ability to manipulate its genetics (e.g., *Chlamydomonas reinhardtii* CC-503 auto-fluorescent strain).

Fungi

Fungi are a group of eukaryotic, non-phototrophic organisms possessing rigid cell walls. Examples of the group include mushrooms, molds and yeasts, among others. The cell walls of fungi contain a large amount of chitin, which makes the cell wall rigid. An exemplary but not comprehensive list of fungi, obtained from nature or genetically modified, for use with the platform and methods of the instant disclosure includes Ascomycetes (e.g., *Venturia, Aspergillus, Podosphaera, Erysiphe, Monilinia, Uncinula, Aureobasidium, Sclerophoma*); Basidiomycetes (e.g., *Hemileia, Rhizoctonia, Puccinia, Coniophora, Serpula, Poria, Uromyces, Gloeophyllum, Lentinus, Coriolus, Irpex*); zygomycetes (e.g., *Mucor*) and fungi imperfecti (e.g., *Botrytis, Helminthosporium, Rhynchosporium, Fusarium, Septoria, Cercospoa, Alternaria, Pyricularia, Penicillium, Geotrichum*, and *Zymoseptoria*). In certain embodiments, representative but not comprehensive examples of fungi are *Venturia, Aspergillus, Podosphaera, Erysiphe, Monilinia, Uncinula, Aureobasidium, Sclerophoma, Acremonium, Actinoplanes, Agaricus, Chrysosporium, Colletotrichum, Coprinus, Cryptococcus, Filibasidum, Humicola, Magnaporthe, Myceliophthora, Neocallimastix, Neurospora, Paecilomyces, Phytophthora, Piromyces, Panerochaete, Pleurotus, Pythium, Schizophyllum, Talaromyces, Thermoascus, Thielavia, Tolypocladium, Trichoderma, Hemileia, Rhizoctonia, Puccinia, Coniophora, Serpula, Poria, Uromyces, Gloeophyllum, Lentinus, Coriolus, Irpex, Mucor, Botrytis, Helminthosporium, Rhynchosporium, Fusarium, Septoria, Cercospora, Alternaria, Pyricularia, Penicillium, Geotrichum*, and/or *Zymoseptoria.*

Filamentous fungi are a sub-class of fungi that have hyphae, which are a long branching filamentous structure. Filamentous fungi are typically saprophytic microorganisms which secrete a wide array of enzymes involved in the decomposition and recycling of complex biopolymers from both plant and animal tissues. The filamentous fungi are characterized by a mycelial wall composed of chitin, cellulose, glucan, chitosan, mannan, and other complex polysaccharides. Vegetative growth is by hyphal elongation and carbon catabolism is obligately aerobic. An exemplary but not comprehensive list of filamentous fungi for use with the platform and methods of the instant disclosure includes strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium, Trichoderma*, and *Zymoseptoria.*

Yeast

Yeasts are unicellular organisms belonging to one of three classes: Ascomycetes, Basidiomycetes and fungi imperfecti. Pathogenic yeast strains and nonpathogenic yeast strains, including mutants thereof (whether pathogenic or nonpathogenic) are expressly contemplated for use in the instant disclosure. Explicitly contemplated yeast strains include *Saccharomyces, Candida, Cryptococcus, Hansenula, Kluyveromyces, Pichia, Rhodotorula, Schizosaccharomyces* and *Yarrowia*. Exemplary species include *Saccharomyces cerevisiae, Saccharomyces pastorianus, Candida albicans, Candida tropicalis, Candida stellatoidea, Candida glabrata, Candida krusei, Candida parapsilosis, Candida guilliermondii, Candida viswanathii, Candida lusitaniae, Candida kefyr, Candida laurentii, Cryptococcus neoformans, Hansenula anomala, Hansenula polymorpha, Kluyveromyces fragilis, Kluyveromyces lactis, Kluyveromyces marxianus* var. *Lactis, Pichia pastoris, Rhodotorula rubra, Schizosaccharomyces pombe, Leucosporidium frigidum, Saccharomyces telluris, Candida slooffi, Torulopsis, Trichosporon cutaneum, Dekkera intermedia, Candida blankii, Cryptococcus gattii, Rhodotorula mucilaginosa, Brettanomyces bruxellensis, Candida stellata, Torulaspora delbrueckii, Zygosaccharomyces bailii, Brettanomyces anomalus, Brettanomyces custersianus, Brettanomyces naardenensis, Brettanomyces nanus, Dekkera bruxellensis, Dekkera anomala* and *Yarrowia lipolytica*. As will be understood to one of ordinary skill in the art, a number of these species include a variety of subspecies, types and subtypes, etc. that are to be understood as included within the aforementioned species.

Carbon Sources

Exemplary carbon sources are presented in Table 1 below (derived from Ebenhöh, Oliver & Handorf, Thomas. (2009). Full List of Carbon Sources):

TABLE 1

| Carbon Sources | | | |
|---|---|---|---|
| $CO_2$ | S-Malate | beta-D-Glucose | D-Xylulose |
| Pyruvate | 4-Hydroxybenzoate | 3-Oxopropanoate | Isocitrate |
| 2-Oxoglutarate | Citrate | 3,4-Dihydroxybenzoate | L-Xylulose |
| D-Glucose | D-Mannose | Succinatesemialdehyde | 2-Oxoadipate |
| Acetate | Glycolate | 4-Methyl-2-oxopentanoate | D-Galacturonate |
| Oxaloacetate | Propanoate | CO | 2-Methyl-3-oxopropanoate |
| Succinate | Acetoacetate | Lactose | Sterol |
| Glyoxylate | Phenylpyruvate | Butanoicacid | Retinal |
| Formate | Hydroxypyruvate | L-Sorbose | Xylitol |
| Formaldehyde | Benzoate | Hexadecanoicacid | Quercetin |
| Ascorbate | D-Xylose | Chorismate | Mannitol |
| Acetaldehyde | Glycerone | Isomaltose | Progesterone |
| Sucrose | Cellobiose | Prephenate | Cyclohexanone |
| Catechol | S-Lactate | R-Lactate | cis-Aconitate |
| D-Fructose | Cholesterol | D-Gluconicacid | R-Mevalonate |
| 2-Oxobutanoate | D-Glucuronate | D-Glycerate | trans-Cinnamate |
| Glycerol | 2,3-Dihydroxybenzoate | L-Arabinose | S-Lactaldehyde |

TABLE 1-continued

| Carbon Sources | | | |
|---|---|---|---|
| D-Ribose | D-Glucono-1,5-lactone | Benzaldehyde | Dehydroascorbate |
| Fumarate | 2-Dehydro-3-deoxy-D-gluconate | Glycolaldehyde | ProstaglandinH2 |
| D-Galactose | Acetone | alpha-D-Glucose | 2 5-Dioxopentanoate |
| Methanol | Maltose | Androst-4-ene-3,17-dione | Acetoin |
| myo-Inositol | Oxalate | HCO3- | Estrone |
| 3-Methyl-2-oxobutanoicacid | D-Arabinose | Quinate | Ethanol |
| Phenol | 5Z,8Z,11Z,14Z-Icosatetraenoicacid | D-Ribulose | p-Benzoquinone |
| Retinol | Phenylacetate | 5-Dehydro-4-deoxy-D-glucarate | R-Acetoin |
| Ribitol | meso-Tartaricacid | 2-Hydroxymuconatesemialdehyde | 4-Coumarate |
| Propanal | Benzylalcohol | 2,4,6/3,5-Pentahydroxycyclohexanone | D-Altronate |
| Sinapate | Cyclopentanone | 3alpha,7alpha,12alpha-Trihydroxy-5beta-cholanate | D-Glucarate |
| Itaconate | D-Tagaturonate | 5Z,13E-15S-9alpha,15-Dihydroxy-11-oxoprosta-5,13-dienoate | Naphthalene |
| Raffinose | D-Glyceraldehyde | 9Z-Octadecenoicacid | 3-Oxoadipate |
| Shikimate | Propane-1,2-diol | Cortisol | Cyclohexanol |
| R-Malate | ProstaglandinE2 | D-Hexose | GibberellinA1 |
| Erythritol | 2-Deoxy-D-glucose | Diacetyl | L-Rhamnulose |
| L-Rhamnose | 3-Hydroxybenzoate | Squalene | D-Arabinonate |
| L-Ribulose | Coniferylalcohol | 4-Hydroxy-3-methoxy-benzaldehyde | D-Galactarate |
| Naringenin | 2-Hydroxy-2,4-pentadienoate | 1-Octanol | D-Galactonate |
| Propenoate | Cholest-4-en-3-one | Cortisone | Isochorismate |
| D-Mannonate | Phenylacetaldehyde | D-Sorbose | R,R-Tartaricacid |
| Hexadecanal | 3-Dehydro-L-gulonate | Flavanone | 11-cis-Retinol |
| --Limonene | 3-Oxo-delta4-steroid | L-Idonate | 2-Acetolactate |
| R-Pantoate | 2,5-Dihydroxybenzoate | Retinoate | Cinnamaldehyde |
| Androsterone | 2-Dehydro-D-gluconate | Scytalone | D-Fructuronate |
| p-Benzenediol | 4-Hydroxybenzaldehyde | Vestitone | LeukotrieneA4 |
| L-Arabitol | ProstaglandinF2alpha | D-Sorbitol | R-Lactaldehyde |
| Testosterone | 4-Hydroxyphenylacetate | L-Gulonate | 3-Dehydroquinate |
| Homogentisate | D-Arabinono-1,4-lactone | Propynoate | Estradiol-17beta |
| L-Arabinonate | S-3-Methyl-2-oxopentanoicacid | Salicylate | beta-D-Galactose |
| Methylglyoxal | 5alpha-Androstane-3,17-dione | +-Camphor | --trans-Carveol |
| 2-Dehydropantoate | 17alpha-Hydroxyprogesterone | Salicin | Vermelone |
| 3-Hydroxypropanal | 3-4-Hydroxyphenylpyruvate | Toluate | Calcitriol |
| Dihydrokaempferol | 3-Deoxy-D-manno-octulosonate | Toluene | Ergosterol |
| 4-Hydroxybutanoicacid | 3-Hydroxy-2-methylpropanoate | 3-Cresol | Galactitol |
| 3-Hydroxypropanoate | 5alpha-Cholest-7-en-3beta-ol | 4-Cresol | GibberellinA3 |
| 6-Deoxy-L-galactose | 3,4-Dihydroxy-trans-cinnamate | Apigenin | L-Fuculose |
| 3-Oxo-delta5-steroid | 2-Dehydro-3-deoxy-D-galactonate | D-Allose | Lanosterol |
| 4-Maleylacetoacetate | 15Z-12-Oxophyto-10,15-dienoate | D-Iditol | Mesaconate |
| L-Gulono-1,4-lactone | 3beta-Hydroxyandrost-5-en-17-one | Ferulate | Resorcinol |
| Monodehydroascorbate | 1-alpha-D-Galactosyl-myo-inositol | Flavonol | --Carvone |
| S-2,3-Epoxysqualene | 2-Hydroxybutane-1,2,4-tricarboxylate | o-Methoxyphenol | Aldosterone |
| 4-Fumarylacetoacetate | 2-Hydroxy-6-oxo-6-phenylhexa-2,4-dienoate | Indanone | Benzenediol |
| 5-Dehydro-D-gluconate | 2-Carboxy-2,5-dihydro-5-oxofuran-2-acetate | L-Iditol | Deoxyribose |
| alpha,alpha-Trehalose | ProstaglandinI2 | L-Lyxose | Pentalenene |
| R-3-Hydroxybutanoate | Carbonicacid | Luteolin | Secologanin |
| L-Galactono-1,4-lactone | Ethyleneglycol | o-Cresol | 3-Oxosteroid |
| 18-Hydroxycorticosterone | Maleicacid | Acetylene | 6-Hexanolide |

TABLE 1-continued

| Carbon Sources | | | |
|---|---|---|---|
| 4-Hydroxy-2-oxoglutarate | Octane | Calcidiol | Cycloartenol |
| 2-Hydroxy-3-oxopropanoate | Phytol | Galactose | D-Arabitol |
| 2-Hydroxycyclo-hexan-1-one | Xylose | Linoleate | Obtusifoliol |
| 3,4-Dihydroxyphenyl-acetate | Benzene | Phthalate | Pregnenolone |
| 3-Carboxy-cis,cis-muconate | Butanal | Phytanate | Ubiquinone-9 |
| Cholesta-5,7-dien-3beta-ol | Gallate | Stachyose | Undecaprenol |
| 1,3,8-Naphthalenertriol | Methane | Taxifolin | R-Mandelate |
| S-Mandelate | Sinapylalcohol | 4-Coumarylalcohol | 2-Carboxybenzaldehyde |
| Cellotetraose | beta-D-Fructose | 5-Dehydroshikimate | 2-Oxohept-3-enedioate |
| Cyclopentanol | trans-Aconitate | 6-Carboxyhexanoate | Phenanthrene-3,4-diol |
| GibberellinA19 | 4-Methylpentanal | 6-Methylsalicylate | S-2-Hydroxyglutarate |
| GibberellinA20 | Benzosemiquinone | Coniferylaldehyde | S-4-Hydroxymandelate |
| Phylloquinone | Cinnamylalcohol | D-Glucuronolactone | 1-Hydroxy-2-naphthoate |
| beta-Carotene | Perillylalcohol | 2-Succinylbenzoate | 11-Deoxycorticosterone |
| 11-cis-Retinal | Propane-1,3-diol | alpha-Pinene-oxide | 3-Demethylubiquinone-9 |
| Acetyl-maltose | Sabinenehydrate | enol-Phenylpyruvate | 4,5-Dihydroxyphthalate |
| alpha-Oxo-benzeneaceticacid | alpha-Tocopherol | 2-Dehydro-D-glucose | 6-DeoxyerythronolideB |
| Corticosterone | cis,cis-Muconate | 2,5-Didehydro-D-gluconate | D-galacto-Hexodialdose |
| Cycloeucalenol | gamma-Tocopherol | 2-Deoxy-D-gluconate | L-xylo-Hexulonolactone |
| LeukotrieneB4 | 2-Hydroxybiphenyl | 3-Oxo-5beta-steroid | D-Galactono-1,4-lactone |
| Maleylpyruvate | 2-Hydroxymuconate | Benzene-1,2,4-triol | +-exo-5-Hydroxycamphor |
| Methylmalonate | 2S-2-Isopropylmalate | Dihydromyricetin | Z-5-Oxohex-2-enedioate |
| ThromboxaneA2 | 3-Fumarylpyruvate | 2-Naphthylmethanol | 2-Hydroxy-3-oxosuccinate |
| E-Glutaconate | Biphenyl-2,3-diol | R-Propane-1,2-diol | 3-Methyl-2-oxopentanoate |
| 2-Maleylacetate | Chenodeoxycholate | S-Propane-1,2-diol | 3-Oxo-4-methylpentanoicacid |
| 2-Methylcitrate | Perillylaldehyde | 2'-Hydroxyformononetin | 2,2',3-Trihydroxybiphenyl |
| 2-Methylmaleate | R-2-Methylmalate | 2,3-Dihydroxytoluene | 2beta-Hydroxygibberellin1 |
| D-Xylonolactone | 2-Hydroxyglutarate | 3-Oxo-5alpha-steroid | 3,4',5-Trihydroxystilbene |
| Digalacturonate | 2-Isopropylmaleate | 3-Oxo-delta1-steroid | 2-Oxo-2,3-dihydrofuran-5-acetate |
| Dihydrocoumarin | 2-Methylpropanoate | Naphthalene-1,2-diol | 4-Hydroxy-2-oxopentanoate |
| Salicylalcohol | 3-Dehydroshikimate | R,R-Butane-2,3-diol | 4-Hydroxyphenylglyoxylate |
| 7alpha-Hydroxycholesterol | 3,4-Dihydroxyphenyl-acetaldehyde | E-3,7-Dimethylocta-1,6-diene-3,8-diol | 1,6-Dihydroxycyclohexa-2,4-diene-1-carboxylate |
| Sterol3-beta-D-glucoside | 3-2,3-Dihydroxyphenyl-propanoate | Z-2-Methyl-5-isopropylhexa-2,5-dienal | 2-Hydroxy-5-carboxymethylmuconate-semialdehyde |
| cis-3,4-Leucopelargonidin | 5-Carboxy-2-oxohept-3-enedioate | 3',4',5,7-Tetrahydroxy-3-methoxyflavone | 3alpha,12alpha-Dihydroxy-7-oxo-5beta-cholanate |
| 1,4-Dihydroxy-2-naphthoate | 5-Dehydro-4-deoxy-D-glucuronate | 4-Carboxy-2-hydroxyhexa-2,4-dienedioate | 13E-11alpha-Hydroxy-9,15-dioxoprost-13-enoate |
| 2-Pyrone-4,6-dicarboxylate | cis-1,2-Dihydrobenzene-1,2-diol | 4alpha-Methyl- 5alpha-cholest-7-en-3-one | 5Z,13E-11alpha-Hydroxy-9,15-dioxoprost-13-enoate |
| 3-Hydroxy-cis,cis-muconate | 2,5-Dihydro-5-oxofuran-2-acetate | alpha,alpha'-Trehalose6,6'-bismycolate | 9Z,11E-13S-13-Hydroperoxyoctadeca-9,11-dienoicacid |
| 4-Hydroxyphenyl-acetaldehyde | 3-Methyl-cis,cis-hexadienedioate | +-cis-3,4-Dihydrophenanthrene-3,4-diol | 3alpha,7alpha,12alpha-Trihydroxy-5beta-cholestanoate |
| 5beta-Androstane-3,17-dione | 4-Carboxy-4-hydroxy-2-oxoadipate | 2-Hydroxy-6-oxonona-2,4-diene-1,9-dioate | 4-4-Deoxy-beta-D-gluc-4-enuronosyl-D-galacturonate |
| 2-Dehydro-3-deoxy-D-xylonate | 2,3-Dihydro-2,3-dihydroxybenzoate | 3-Carboxy-2-hydroxymuconatesemialdehyde | Alprostadil |
| 3beta-Hydroxy-delta5-steroid | 3-Hydroxy-3-methyl-2-oxobutanoicacid | 3alpha,12alpha-Dihydroxy-5beta-cholanate | 15S-15-Hydroxy-5,8,11-cis-13-trans-eicosatetraenoate |
| 5alpha-Cholest-8-en-3beta-ol | 4-Hydroxy-4-methyl-2-oxoglutarate | 4-Carboxy-2-hydroxymuconatesemialdehyde | 8-1R,2R-3-Oxo-2-Z-pent-2-enylcyclopentyloctanoate |
| Androstan-3alpha,17beta-diol | 5-Carboxymethyl-2-hydroxymuconate | 1S,2S-1,2-Dihydronaphthalene-1,2-diol | cis-4,5-Dihydroxycyclohexa-16,2-diene-1,2-dicarboxylate |
| 17beta-Hydroxyandrostan-3-one | alpha,alpha'-Trehalose6-mycolate | 17alpha,20alpha-Dihydroxypregn-4-en-3-one | 9Z,11E,14Z-13S-13-Hydroperoxyoctadeca-9,11,14-trienoicacid |

TABLE 1-continued

| Carbon Sources | | | |
|---|---|---|---|
| 2-Dehydro-3-deoxy-D-glucarate | trans-1,2-Dihydrobenzene-1,2-diol | 2-Protocatechoylphloro-glucinolcarboxylate | 5S-HETE |
| 3-Dehydro-2-deoxy-D-gluconate | Z-But-2-ene-1,2,3-tricarboxylate | Fecosterol | 4beta-Hydroxymethyl-4alpha-methyl-5alpha-cholest-7-en-3beta-ol |
| 5-Dehydro-2-deoxy-D-gluconate | 2S-2-Isopropyl-3-oxosuccinate | 4,4-Dimethyl-5alpha-cholest-7-en-3beta-ol | 3beta-Hydroxy-4beta-methyl-5alpha-cholest-7-ene-4alpha-carboxylate |
| Flavonol3-O-beta-D-glucoside | R-2,3-Dihydroxy-3-methylbutanoate | R-3-R-3-Hydroxybutanoyloxy-butanoate | 20-OH-LeukotrieneB4 |
| 1F-alpha-D-Galactosylraffinose | Androst-5-ene-3beta,17beta-diol | 1,2-Bis4-hydroxy-3-methoxyphenylethylene | 14-Demethyllanosterol |
| 2-Hydroxyethylene-dicarboxylate | cis-1,2-Dihydronaphthalene-1,2-diol | 3-Carboxy-2,5-dihydro-5-oxofuran-2-acetate | 4alpha-Methylcholesta-8-en-3beta-ol |
| 3,7-Dimethylocta-1,6-dien-3-ol | 4-Carboxy-2-hydroxy-cis,cis-muconate | 3alpha,7alpha-Dihydroxy-5beta-cholestanate | Methostenol |
| But-1-ene-1,2,4-tricarboxylate | 4S-4,6-Dihydroxy-2,5-dioxohexanoate | 4-Carboxymethyl-4-methylbut-2-en-1,4-olide | 17alpha-Hydroxypregnenolone |
| 1,3,6,8-Naphthalenetetrol | 3alpha-Hydroxy-5beta-androstan-17-one | 4R,5S-4,5,6-Trihydroxy-2,3-dioxohexanoate | 16alpha-Hydroxydehydroepi-androsterone |
| 2,3-Dihydroxy-3-methylbutanoate | 2R,3S-3-Isopropylmalate | 2S,3R-3-Hydroxybutane-1,2,3-tricarboxylate | 16alpha-Hydroxyandrost-4-ene-3,17-dione |
| 20alpha-Hydroxy-4-pregnen-3-one | cis-4-Carboxymethylenebut-2-en-4-olide | 9Z-13S-12,13-Epoxyoctadeca-9,11-dienoicacid | Estriol |
| trans-beta-D-Glucosyl-2-hydroxycinnamate | 3-beta-D-Galactosyl-sn-glycerol | 3alpha,7alpha,26-Trihydroxy-5beta-cholestane | 3 alpha,20alpha,21-Trihydroxy-5beta-pregnane-11-one |
| 3-Hexaprenyl-4,5-dihydroxybenzoate | Melibiose | 3alpha,7alpha-Dihydroxy-5beta-cholestan-26-al | Pregnanediol |
| Hydroxyacetone | 3-Ketolactose | 3alpha,7alpha,12alpha,26-Tetrahydroxy-5beta-cholestane | 21-Hydroxypregnenolone |
| 11beta-Hydroxyandrost-4-ene-3,17-dione | D-Galalpha1->6D-Galalpha1->6D-Glucose | 7alpha-Hydroxy-5beta-cholestan-3-one | 17alpha,21-Dihydroxypregnenolone |
| Adrenosterone | L-Arabinono-1,5-lactone | 3alpha,7alpha-Dihydroxy-5beta-cholestane | 11-Deoxycortisol |
| 19-Hydroxyandrost-4-ene-3,17-dione | L-Xylonate | 7alpha,12alpha-Dihydroxy-5beta-cholestan-3-one | 11beta,17alpha,21-Trihydroxypregnenolone |
| 5beta-Dihydrotestosterone | L-Lyxonate | 3alpha,7alpha,12alpha-Trihydroxy-5beta-cholestane | 11-Dehydrocorticosterone |
| 19-Hydroxytestosterone | Phytoene | 7alpha-Hydroxycholest-4-en-3-one | 21-Deoxycortisol |
| 19-Oxoandrost-4-ene-3,17-dione | Phytofluene | 7alpha,12alpha-Dihydroxycholest-4-en-3-one | 11beta-Hydroxyprogesterone |
| 2-Hydroxyestrone | Cholesterol-5beta,6beta-epoxide | 7alpha,12alpha-Dihydroxy-5alpha-cholestan-3-one | 17alpha,20alpha-Dihydroxycholesterol |
| 2-Methoxyestrone | Cholesterol-5alpha,6beta-epoxide | 17alpha,21-Dihydroxy-5beta-pregnane-3,11,20-trione | 20alpha-Hydroxycholesterol |
| 16alpha-Hydroxyestrone | cis-Phytoene | Urocortisone | 20alpha,22beta-Dihydroxycholesterol |
| 2-Hydroxyestradiol-17beta | L-Dehydroascorbate | 11beta,17alpha,21-Trihydroxy-5beta-pregnane-3,20-dione | 22beta-Hydroxycholesterol |
| 2-Methoxyestradiol-17beta | 3beta,5alpha,6beta-Cholestanetriol | Urocortisol | Estradiol-17beta3-glucuronide |
| 3-Hexaprenyl-4-hydroxy-5-methoxybenzoate | zeta-Carotene | 11beta,21-Dihydroxy-3,20-oxo-5beta-pregnan-18-al | 16-Glucuronide-estriol |
| R-4-Hydroxymandelate | Neurosporene | 3alpha,11beta,21-Trihydroxy-20-oxo-5beta-pregnan-18-al | Oxaloglutarate |
| 2-Hydroxy-3-4-hydroxyphenyl-propenoate | Lycopene | 11beta,21-Dihydroxy-5beta-pregnane-3,20-dione | 3,4-Dihydroxyphenylethylene-glycol |
| 5S-HPETE | alpha-Carotene | Tetrahydrocorticosterone | 3,4-Dihydroxymandelaldehyde |

TABLE 1-continued

| Carbon Sources | | | |
|---|---|---|---|
| 4-Carboxy-2-oxo-3-hexenedioate | beta-Zeacarotene | 21-Hydroxy-5beta-pregnane-3,11,20-trione | 3,4-Dihydroxymandelate |
| 2-Hydroxy-2-hydropyrone-4,6-dicarboxylate | gamma-Carotene | 3alpha,21-Dihydroxy-5 beta-pregnane-11,20-dione | 3-Methoxy-4-hydroxyphenylacetaldehyde |
| Oxalosuccinate | Zymosterol | 5beta-Pregnane-3,20-dione | Homovanillate |
| 3-Keto-beta-D-galactose | 5alpha-Cholesta-7,24-dien-3beta-ol | 3alpha-Hydroxy-5beta-pregnane-20-one | 3-Methoxy-4-hydroxyphenylglycolaldehyde |
| Melibiitol | Ergosta-5,7,22,2428-tetraen-3beta-ol | Cortolone | 3-Methoxy-4-hydroxymandelate |
| Epimelibiose | VitaminD3 | Cortol | Gentisatealdehyde |
| 3-Hydroxyphenylacetate | 2-Octaprenyl-3-methyl-5-hydroxy-6-methoxy-1,4-benzoquinone | Propane-1-ol | 4-4-Deoxy-alpha-D-gluc-4-enuronosyl-D-galacturonate |
| 3-Methoxy-4-hydroxyphenylethylene-glycol | 2-Succinyl-6-hydroxy-2,4-cyclohexadiene-1-carboxylate | 2-Hydroxybutanoicacid | 1-Butanol |
| 2-Hydroxyhepta-2,4-dienedioate | cis-2-Hydroxycinnamate | 2-Propyn-1-al | 3-Butynoate |
| 4-Hydroxy-2-oxo-heptanedioate | cis-beta-D-Glucosyl-2-hydroxycinnamate | 2-Propyn-1-ol | 3-Butyn-1-al |
| 4-Hydroxycinnamyl-aldehyde | VitaminKepoxide | 2-Propylmalate | 3-Butyn-1-ol |
| Sinapoylaldehyde | Coumarin | Lactaldehyde | Arbutin |
| 3-O-Methylgallate | 2-Hydroxyphenylacetate | S-3-Hydroxyisobutyrate | 2,4-Dihydroxyhept-2-enedioate |
| 5-Hydroxyferulate | Phenylethylalcohol | S-Methylmalonatesemi-aldehyde | Salicylaldehyde |
| Quercetin3-O-glucoside | 4-Carboxy-2-oxo-4-pentanoate | S-2-Aceto-2-hydroxybutanoate | 1,2-Dihydronaphthalene-1,2-diol |
| 4-Hydroxystyrene | 3,3',4'5-Tetrahydroxystilbene | R-2,3-Dihydroxy-3-methylpentanoate | 2,6-Dihydroxyphenylacetate |
| Phenylpropanoate | 3-Methoxyapigenin | S-2-Acetolactate | 2-Hydroxy-6-keto-2,4-heptadienoate |
| Eriodictyol | Kaempferol | D-erythro-3-Methylmalate | Celloheptaose |
| Homoisocitrate | Pelargonidin | 4-Hydroxyphenylethanol | Cellohexaose |
| 3-Ketosucrose | Cyanidin | ent-Kaurene | Cellopentaose |
| 2-Hexaprenyl-6-methoxyphenol | Leucocyanidin | GibberellinA12aldehyde | Cellotriose |
| 2-Hexaprenyl-6-methoxy-1,4-benzoquinone | Luteoforol | GibberellinA53 | 3,4-Dihydroxystyrene |
| 2-Hexaprenyl-3-methyl-6-methoxy-1,4-benzoquinone | Delphinidin | GibberellinA44diacid | 2-Oxopentanoicacid |
| 2-Hexaprenyl-3-methyl-5-hydroxy-6-methoxy-1,4-benzoquinone | Leucodelphinidin | GibberellinA29 | --beta-Pinene |
| 3-Octaprenyl-4-hydroxybenzoate | Pentahydroxyflavanone | Zeaxanthin | --alpha-Pinene |
| 2-Octaprenylphenol | D-4-Hydroxy-2-oxoglutarate | +-Limonene | Diplopterol |
| 2-Octaprenyl-6-hydroxyphenol | ProstaglandinG2 | Adipatesemialdehyde | Diploptene |
| 2-Octaprenyl-6-methoxyphenol | 11-epi-ProstaglandinF2alpha | 6-Hydroxyhexanoicacid | D-erythro-Ascorbate |
| 2-Octaprenyl-6-methoxy-1,4-benzoquinone | 12S-HPETE | Adipate | 4-Hydroxy-3-methoxy-benzenemethanol |
| 2-Octaprenyl-3-methyl-6-methoxy-1,4-benzoquinone | 15S-HPETE | Cyclohexan-1,2-dione | 3S,4R-3,4-Dihydroxycyclohexa-1,5-diene-1,4-dicarboxylate |
| 1,6-Dihydroxy-cis-2,4-cyclohexadiene-1-carboxylicacid | Styrenecis-glycol | Benzpyrene | Liquiritigenin |
| Terephthalate | 3-Vinylcatechol | Fluorene | Benzylsuccinate |
| 6Z,9Z,12Z-Octadecatrienoicacid | Phenylaceticacid | 3,4-Dihydroxyfluorene | Cyclohexane-1-carboxylate |
| 2-Dehydro-D-glucono-1,5-lactone | 2-Hydroxy-6-oxoocta-2,4,7-trienoate | 2-Hydroxy-4-1-oxo-1,3-dihydro-2H-inden-2-ylidene-but-2-enoicacid | alpha-Pinene |
| Ethylene | Protoanemonin | 3-Hydroxy-1-indanone | Pinocarvone |

TABLE 1-continued

Carbon Sources

| | | | |
|---|---|---|---|
| Ethyleneoxide | cis-Acetylacrylate | +-3S,4R-cis-3,4-Dihydroxy-3,4-dihydrofluorene | Myricetin |
| Isosalipurpol | 2-Hydroxy-1,4-benzoquinone | 3,4-Dihydroxy-3,4-dihydro-9-fluorenone | Ferreirin |
| p-Cumicalcohol | Ethylbenzene | 1,2-Dihydroxyfluorene | 4'-Hydroxyacetophenone |
| p-Cumicaldehyde | 1-Phenylethanol | 2-Hydroxy-4-2-oxo-1,3-dihydro-2H-inden-1-ylidenebut-2-enoicacid | D-Fructose |
| Biphenyl | Acetophenone | 2-Indanone | Caffeicaldehyde |
| cis-2,3-Dihydro-2,3-dihydroxybiphenyl | Benzoylacetate | 3-Isochromanone | all-trans-Retinoyl-beta-glucuronide |
| Vanillate | 2-Hydroxyacetophenone | Dibenzofuran | 2-Methoxy-estradiol-17beta3-glucuronide |
| 4-Hydroxyphthalate | 3-Methylbenzaldehyde | 2-Hydroxy-6-oxo-6-2-hydroxyphenyl-hexa-2,4-dienoate | 2-Methoxyestrone3-glucuronide |
| Fluoren-9-ol | m-Methylbenzoate | Dibenzo-p-dioxin | Estroneglucuronide |
| Fluoren-9-one | 2-Methylbenzylalcohol | 2,2',3-Trihydroxydiphenylether | Testosteroneglucuronide |
| 4-Methylcatechol | 2-Methylbenzaldehyde | 2-Hydroxy-6-oxo-6-2-hydroxyphenoxy-hexa-2,4-dienoate | Androsteroneglucuronide |
| 4-Methylbenzylalcohol | o-Toluate | --Jasmonicacid | Etiocholan-3alpha-ol-17-one3-glucuronide |
| p-Tolualdehyde | 3-Methylbenzylalcohol | delta-Carotene | Cyclohexane |
| 2-Hydroxy-5-methyl-cis,cis-muconicsemialdehyde | Limonene-1,2-epoxide | Echinenone | 2-Hydroxy-cis-hex-2,4-dienoate |
| 4E-2-Oxohexenoicacid | Limonene-1,2-diol | Cyanidin3-O-glucoside | +-S-Carvone |
| 4-Hydroxy-2-oxohexanoicacid | Crepenynate | Isoliquiritigenin | 1R,4R-Dihydrocarvone |
| D-2,3-Diketo4-deoxy-epi-inositol | 3-Methylbut-2-enal | Lophenol | 3R-3-Isopropenyl-6-oxoheptanoate |
| 2-Deoxy-5-keto-D-gluconicacid | 2-Hydroxy-5-methyl-cis,cis-muconate | 2'-Hydroxychalcone | +-trans-Carveol |
| Styrene | 2-Oxo-5-methyl-cis-muconate | --Epicatechin | 1R,4S-Iso-dihydrocarvone |
| Phenanthracene | GibberellinA29-catabolite | trans-2-Methyl-5-isopropylhexa-2,5-dienal | 3-Hexaprenyl-4-hydroxybenzoate |
| 2-Hydroxy-2H-benzohchromene-2-carboxylate | GibberellinA12 | trans-2-Methyl-5-isopropylhexa-2,5-dienoicacid | 24-Hydroxycholesterol |
| cis-4-1'-Hydroxynaphth-2'-yl-2-oxobut-3-enoate | GibberellinA15open-lactone | cis-2-Methyl-5-isopropylhexa-2,5-dienoicacid | Bisphenol A |
| 1-Hydroxy-2-naphthaldehyde | GibberellinA24 | 3-Isopropylbut-3-enoicacid | 1,2-Bis4-hydroxyphenyl-2-propanol |
| trans-9S,10S-Dihydrodiol-phenanthrene | GibberellinA9 | Apiforol | 2,2-Bis4-hydroxyphenyl-1-propanol |
| Phenanthrene-9,10-oxide | GibberellinA4 | --Epiafzelechin | 4,4'-Dihydroxy-alpha-methylstilbene |
| Phenanthrene-1,2-oxide | GibberellinA51 | 2'-HydroxybiochaninA | 2,2-Bis4-hydroxyphenyl-propanoicacid |
| 1-Phenanthrol | 2,3-Dehydro-gibberellinA9 | --Epigallocatechin | 2,3-Bis4-hydroxyphenyl-1,2-propanediol |
| 1-Methoxyphen-anthrene | GibberellinA7 | Pelargonidin3-O-glucoside | 4-Hydroxyphenacylalcohol |
| 4,4-Dimethyl-5alpha-cholesta-8,14,24-trien-3beta-ol | GibberellinA34 | Delphinidin3-O-glucoside | 4-Hydroxyphenylacetate |
| 3-3-Hydroxy-phenyl-propanoicacid | GibberellinA34-catabolite | 5-Hydroxyconiferaldehyde | 4-Ethylphenol |
| L-Arabinose | GibberellinA8-catabolite | 5-Hydroxyconiferylalcohol | 1-4'-Hydroxyphenylethanol |
| 4alpha-Methyl-5alpha-ergosta-8,14,2428-trien-3beta-ol | GibberellinA5 | Caffeylalcohol | 1-Methylnaphthalene |
| 3beta-Hydroxy-4beta-methyl-5alpha-cholest-7-ene-4alpha-carbaldehyde | Kaur-16-en-18-ol | Kaempferol3-O-glucoside | cis-1,2-Dihydroxy-1,2-dihydro-8-methylnaphthalene |

TABLE 1-continued

| Carbon Sources | | | |
|---|---|---|---|
| Methyljasmonate | Kaur-16-en-18-al | GibberellinA44 | 1,2-Dihydroxy-8-methylnaphthalene |
| E-3-Methoxycarbonylpent-2-enedioate | Kaur-16-en-18-oicacid | 1-Oxa-2-oxo-3-hydroxycycloheptane | 2-Hydroxy-8-methylchromene-2-carboxylate |
| 24-Methylenelophenol | ent-7alpha-Hydroxykaur-16-en-19-oicacid | cis-Dihydroquercetin | 2-Hydroxy-3-methylbenzalpyruvate |
| 24-Ethylidenelophenol | 6beta,7beta-Dihydroxykaurenoicacid | 5alpha-Androstan-3beta,17beta-diol | 3-Methylsalicylaldehyde |
| 2alpha-D-Mannosyl-D-glycerate | Perillicacid | trans-3-Hydroxycinnamate | 3-Methylsalicylate |
| 2-beta-D-Glucosyl-sn-glycerol | 1S,4R-1-Hydroxy-2-oxolimonene | cis-3-3-Carboxyethenyl-3,5-cyclohexadiene-1,2-diol | 1-Hydroxymethylnaphthalene |
| cis-3-Carboxy-ethyl-3,5-cyclo-hexadiene-1,2-diol | Myrtenol | trans-2,3-Dihydroxycinnamate | 1-Naphthaldehyde |
| beta-Naphthol | Myrtenal | 2-Hydroxy-6-ketononatrienedioate | 1-Naphthoicacid |
| alpha-Naphthol | Myrtenicacid | trans-4-Carboxymethylenebut-2-en-4-olide | cis-1,2-Dihydroxy-1,2-dihydro-8-carboxynaphthalene |
| GibberellinA51-catabolite | Pinocarveol | 2-Phytyl-1,4-naphthoquinone | 1,2-Dihydroxy-8-carboxynaphthalene |
| 2-Carboxy-2-hydroxy-8-carboxychromene | R-3-Hydroxy-3-methyl-2-oxopentanoate | 1,2-Dihydroxy-3,4-epoxy-1,2,3,4-tetrahydronaphthalene | all-trans-13,14-Dihydroretinol |
| 2-Hydroxy-3-carboxybenzalpyruvate | 9-Hydroxybenzoapyrene | 1R,2S-Naphthalene1,2-oxide | Pentane-2,4-dione |
| 3-Formylsalicylicacid | S-5-Oxo-2,5-dihydrofuran-2-acetate | 1S,2R-Naphthalene1,2-oxide | 24S-Cholest-5-ene-3beta,7alpha,24-triol |
| 2-Hydroxyisophthalicacid | 20-HETE | 12R-HPETE | Cholest-5-ene-3beta,25-diol |
| 2-Methylnaphthalene | 19S-HETE | 11H-14,15-EETA | Cholest-5-ene-3beta,7alpha,25-triol |
| 2-Naphthaldehyde | 13S-HODE | 11,14,15-THETA | 2-alpha-D-Glucosyl-D-glucose |
| 2-Naphthoicacid | 13-OxoODE | 8S-HPETE | 7alpha,12alpha-Dihydroxy-3-oxochol-4-enoate |
| cis-1,2-Dihydroxy-1,2-dihydro-7-methylnaphthalene | 5,6-EET | 910-EpOME | 12alpha-Hydroxy-3-oxochola-4,6-dienoate |
| 4-Methylsalicylate | 8,9-EET | 1213-EpOME | Dihydroflavonol |
| cis-1,2-Dihydroxy-1,2-dihydro-7-hydroxymethyl-naphthalene | 11,12-EET | 9S-HPODE | Catechol |
| 1,2-Dihydroxy-7-hydroxymethyl-naphthalene | 14,15-EET | 9,10-DHOME | Guaiacol |
| 2-Hydroxy-7-hydroxymethyl-chromene-2-carboxylate | 5,6-DHET | 12,13-DHOME | Phenylacetate |
| 2-Hydroxy-4-hydroxymethyl-benzalpyruvate | 8,9-DHET | Benzoapyrene-9,10-oxide | Phenol |
| 4-Hydroxymethyl-salicylaldehyde | 11,12-DHET | Benzoapyrene-7,8-oxide | Chalcone |
| 4-Hydroxymethyl-salicylate | 14,15-DHET | Benzoapyrene-4,5-oxide | Prenal |
| 4-Hydroxymethyl-catechol | 16R-HETE | Benzoapyrene-7,8-diol | Cholest-5-ene-3beta,26-diol |
| Naphthyl-2-methyl-succinicacid | 15H-11,12-EETA | Benzoapyrene-7,8-dihydrodiol-9,10-oxide | Cholest-5-ene-3beta,7alpha,26-triol |
| alpha-Zeacarotene | 11,12,15-THETA | 9-Hydroxybenzoapyrene-4,5-oxide | |

Screening Methodology

Figure 8:
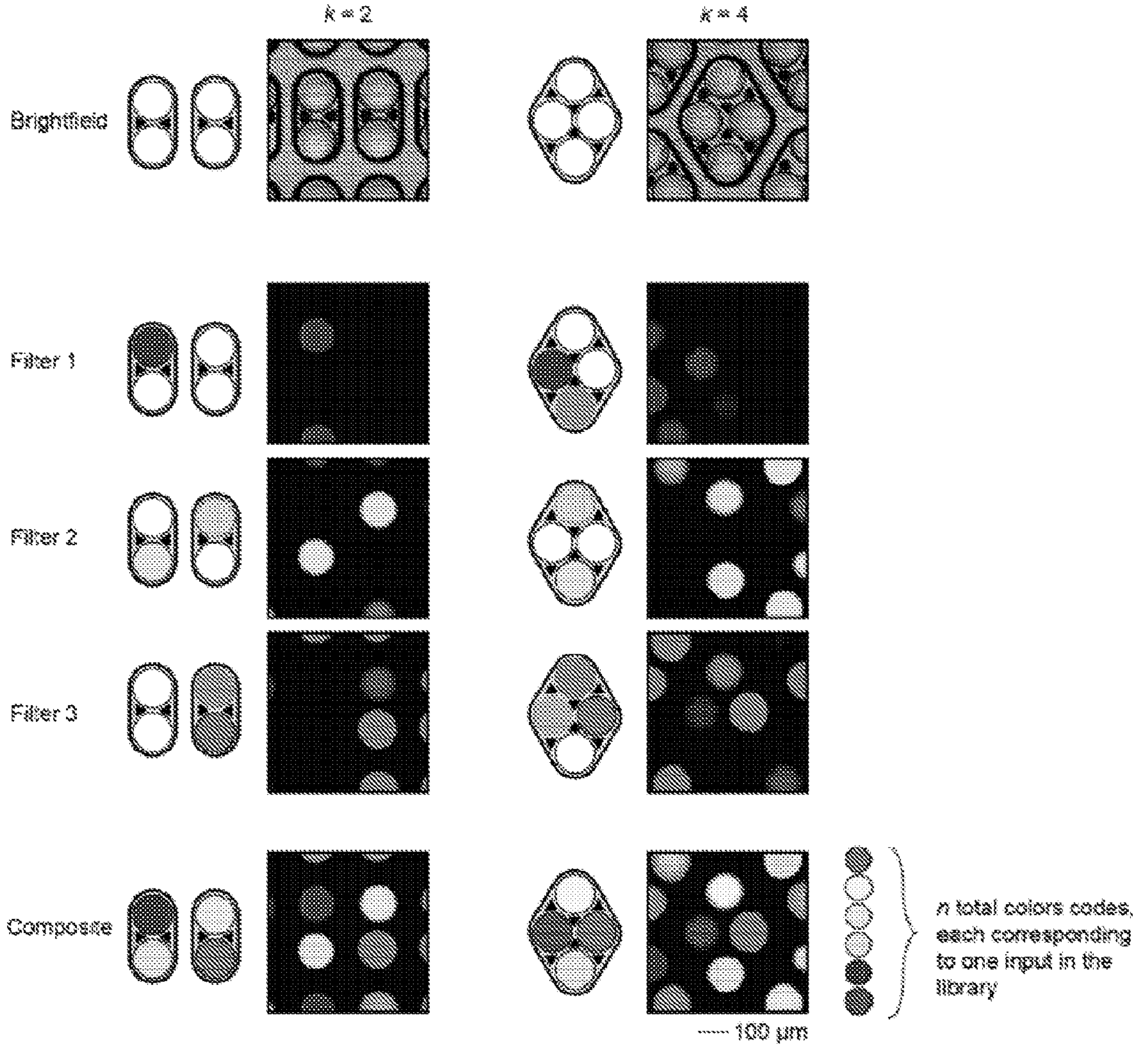
FIG. 8 shows how color coding of droplets is used to identify the contents of each microwell. To identify the contents of the droplets that group within a given microwell, the kChip is scanned at 2× magnification after grouping and before merging droplets. Each fluorescent dye is excited sequentially, producing a corresponding image (dyes are chosen to avoid overlap with any fluorescence-based assays used concomitantly). Each droplet contains a unique ratio of the three fluorescent dyes such that the composite emission profile provides the droplet's unique color code. In the left panel is an example for k=2 microwells, and in the right panel is an example for a k=4 microwell. At bottom-right, the full set of colors produced maps to the n different inputs and is used to identify the combination of inputs that have grouped within each microwell.
Figure 9A:
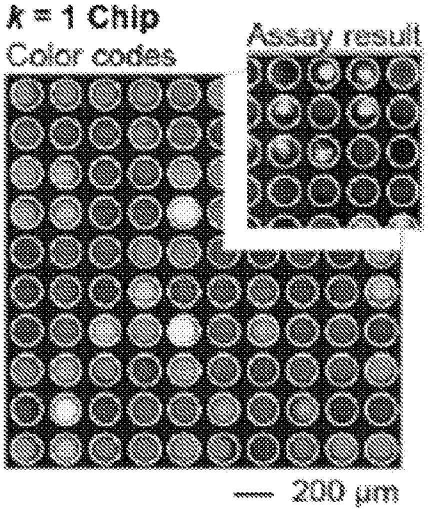
FIGS. 9A-9C depict how growth on glucose was similar between a k=1 Chip and a 96-well plate for 10 labeled strains.
Figure 9B:
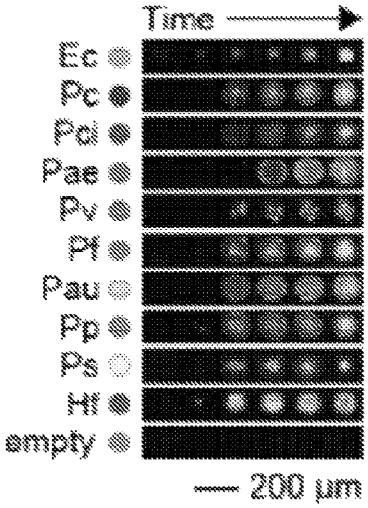
Figure 9C:
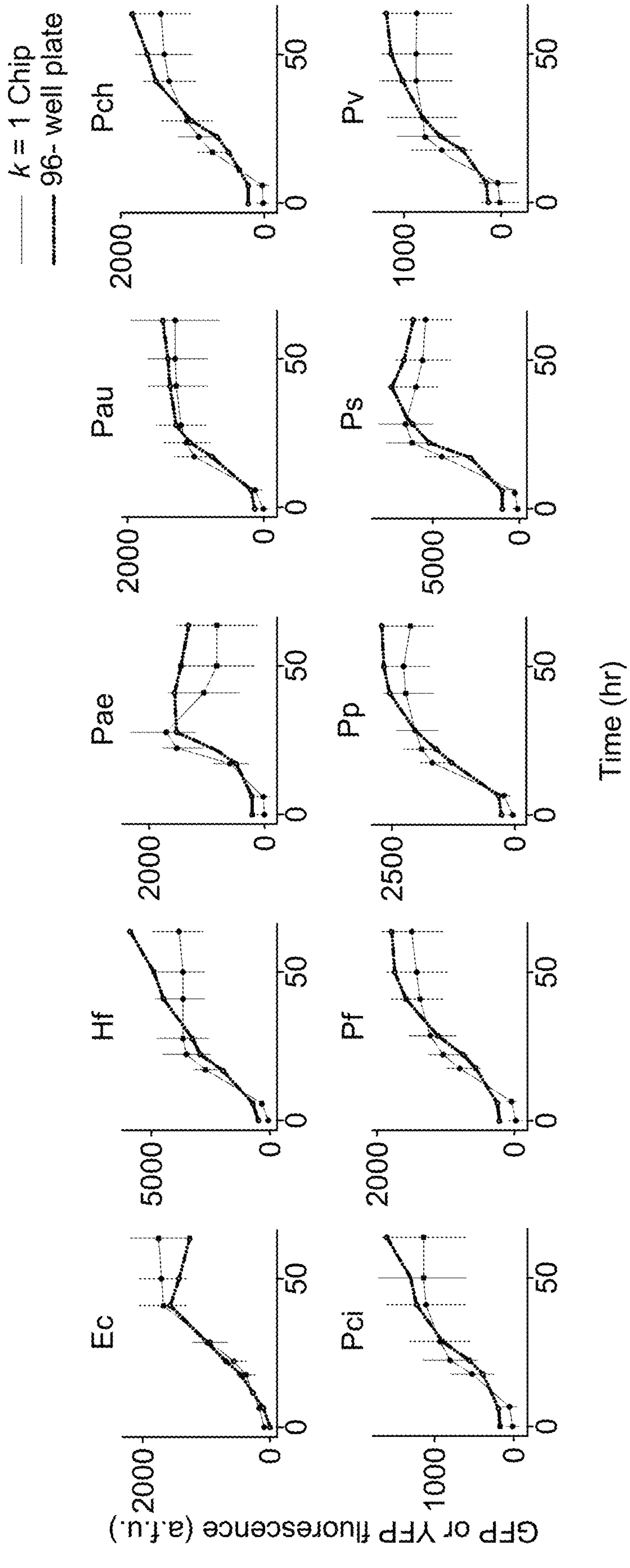

Certain aspects of the instant disclosure feature use of fluorescence microscopy for the screening of merged droplets in microwells. Both label and label-free approaches have been exemplified herein and are contemplated for further application. In exemplified embodiments, fluorescence microscopy was performed using a Nikon Ti-E inverted fluorescence microscope with fluorescence excitation by a Lumencor Sola light emitting diode illuminator (100% power setting). Images were taken across up to four fluorescence channels-three for the color codes and one additional channel for fluorescence-based assays. Each dye (or assay signal) was detected with a different excitation wavelength generated by a collection of filter cubes. The following dyes can readily used for fluorescence-reliant optical screening: Alexa Fluor 488 (e.g., GFP/YFP expression, Semrock GFP-1828A, blue excitation), Alexa Fluor 555, resazurin/resorufin (Semrock SpGold-B, green excitation), Alexa Fluor 594 (Semrock 3FF03-575/25-25+FF01-615/24-25, yellow excitation), and Alexa Fluor 647 (Semrock LF635-B, red excitation). As shown in FIGS. 30A-30E, red excitation can also be utilized, optionally when the autofluorescent *C. reinhardtii* is used. At the image analysis stage, the emission signals corresponding to each dye channel can be used to identify the contents of a given droplet within each droplet grouping prior to droplet merging (FIG. 8). The final channel can be used post-merge and at subsequent time points to quantify the assay signal. Images found in the instant figures were collected by a Hamamatsu ORCA-Flash 4.0 CMOS camera (exposure times range 50 ms-500 ms) and 2× optical magnification (with 2× pixel binning resulting in 6.5 μm/pixel resolution). The total scanning time for a single kChip was 12-15 minutes.

In exemplified embodiments, the fluorescent dyes Alexa Fluor 555, 594, and 647 have been used to avoid overlap with the GFP or YFP excitation channel (i.e. Alexa Fluor 488 has been excluded from the encoding set) (see "Fluorescently labeled microbe assay in droplets" section below). For experiments involving the *C. reinhardtii* CC-503, which was autofluorescent for red excitation, the fluorescent dyes Alexa Fluor 488, 555, and 594 have been used (i.e. Alexa Fluor 647 has been excluded from the encoding set). Multiple fluorescent organisms can be monitored simultaneously. As shown in FIGS. 30A-30E, *C. reinhardtii* monitored in co-culture with GFP-labeled *E. coli* was monitored simultaneously (for which both Alexa Fluor 488 and Alexa Flour 647 has been excluded from the encoding set). It is expressly contemplated that growth of a fluorescent strain or set of fluorescent strains can be readily screened against biotic backgrounds (i.e. microbial communities), abiotic backgrounds (e.g. drug combinations, carbon source combinations) or a combination thereof.

In certain aspects, growth of complex microbial communities can be measured in massively parallel fashion across varying carbon sources. It is further contemplated that growth or other fluorescent readouts from the instant platform could be monitored in the presence or absence of other agents, including probiotics, antibiotics and/or a wide range of small molecule drugs, peptides or other biologics, optionally in the presence or absence of varying other environmental conditions (e.g., temperature or other conditions).

In certain embodiments, e.g., as exemplified herein, community phenotypes that can be tracked via optical assays performed upon the kChip include fluorescent protein expression and respiration-driven reduction of resazurin to the fluorescent product resorufin (see "Resazurin assay in droplets" section below for additional details), among others. In some embodiments, kChip community phenotypes can be tracked via use of phase contrast microscopy as a readout, among other contemplated readouts.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

EXAMPLES

The present disclosure is further illustrated by the following examples, which should not be construed as limiting. The contents of all references, published patents and patent applications cited throughout the application are hereby incorporated by reference. Those skilled in the art will recognize that the disclosure may be practiced with variations on the disclosed structures, materials, compositions and methods, and such variations are regarded as within the scope of the disclosure.

Example 1: Materials and Methods kChip Design and Fabrication

All kChips possessed the following features: (1) An array of microwell geometries of one or more predetermined values of k, the number of droplets each microwell was designed to receive, e.g. a full set of identical microwells like k=2 ("Full kChip") (as described in the experiments of FIGS. 2A-2F) or varied microwells containing k={1:7;19} (as described in the screen of FIGS. 3A-3G); (2) internal posts within these microwells (FIGS. 6A-6D, 7A and 7B) designed to (a) control the number of droplets entering a microwell by reducing overfilling (via droplets squeezing into a microwell) and underfilling (via droplets exiting microwells due to the oil flow associated with kChip loading), and (b) inhibit the entry of large droplets inherent to the droplet pool (i.e. a low-pass size filter); (3) a series of 30 90-μm deep moat-like engravings designed to trap small droplets (i.e. a high-pass size filter) (FIG. 6D); and (4) a loading slot into which droplets are injected via micropipette (FIGS. 5A-5C, 6D and "Droplet making and kChip loading" section below).

Figure 6A:
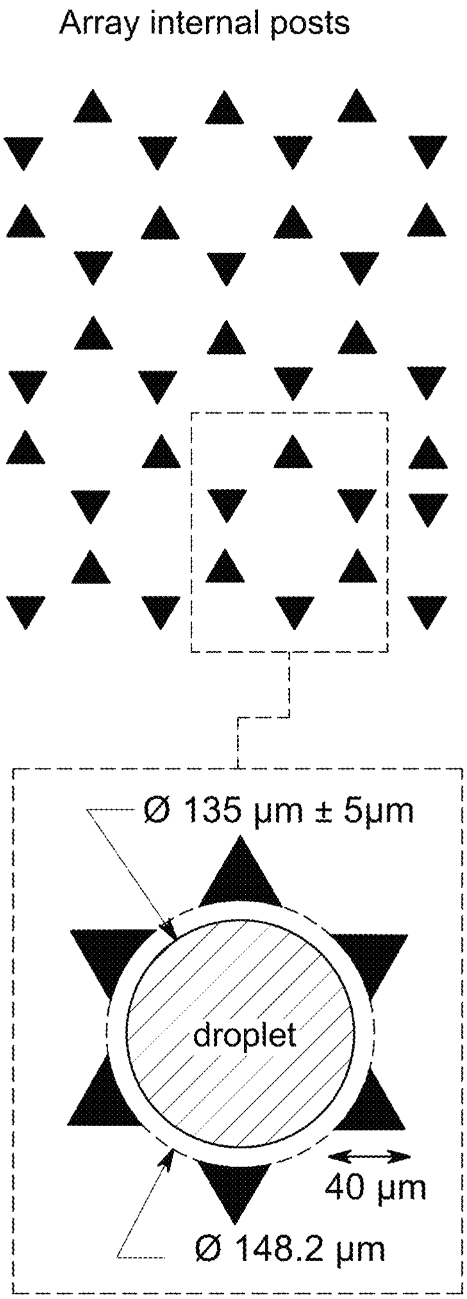
FIGS. 6A-6D show an exemplary kChip design strategy.
Figure 7A:
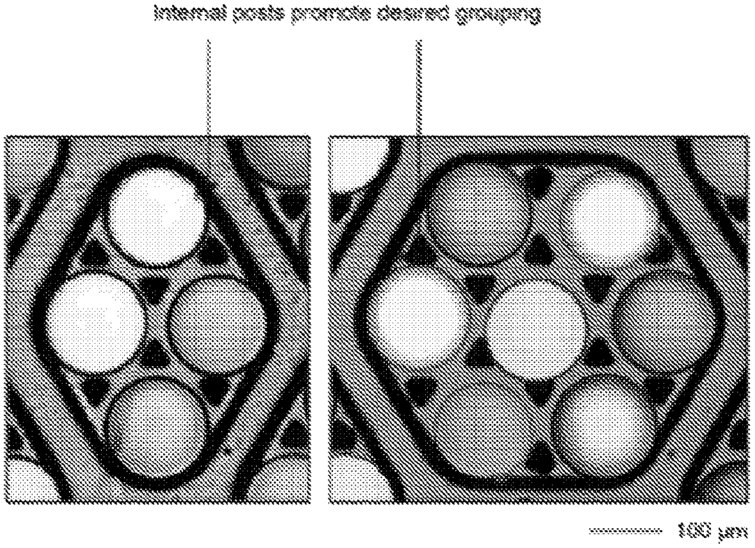
FIGS. 7A to 7D show that microwell geometry and internal posts promoted precise droplet grouping without affecting microbial growth.

All kChips were designed in AutoCAD (Autodesk). Designs began with a hexagonal array of triangles that would ultimately become internal posts (FIGS. 6A and 7A). The optimal spacing between posts (i.e. the diameter of the space encircled by posts) was determined based on the choice of medium and concentration of fluorosurfactant (RAN Biotech 008 FluoroSurfactant), which were shown to affect the size of droplets produced by a droplet generator (Bio-Rad QX200) ("Microbial culture input preparation" section below), and by extension, droplet grouping and merging performance. For droplets of minimal medium (MM) made with 2% w/w fluorosurfactant, which produced droplets of 135±5 μm diameter, this spacing parameter was determined to be 148.2 μm (FIG. 6A).

Figure 6B:
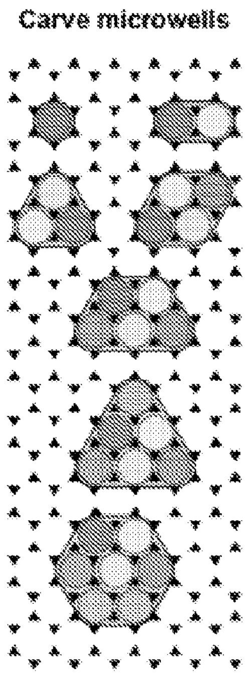
Figure 6C:
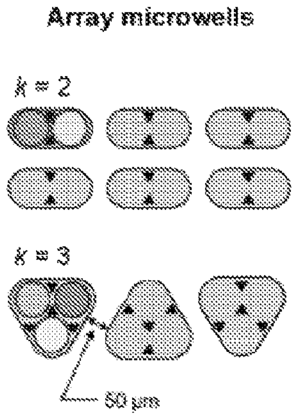
Figure 7B:
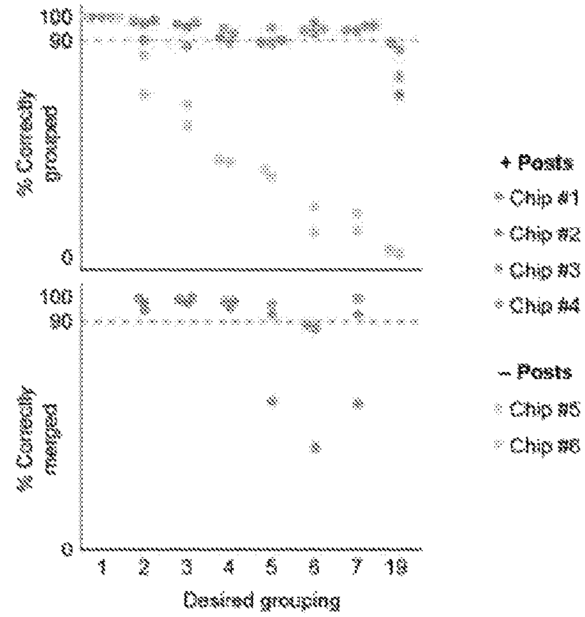

A microwell boundary was then drawn to enclose a subset of posts in accordance with the desired k (FIG. 6B). These geometries were modular in their expansion: With each incorporation of two additional posts via enlargement of this enclosure, the grouping capacity increased by one droplet. With internal posts included, microwell droplet grouping appeared agnostic to k for k={1:7} (>90% grouping as desired) (FIG. 7B). The generalizability of the approach was maintained for k=19 microwells, with only a small decrease in grouping performance. It was deemed likely that a geometry to capture k droplets could be inductively generated for any value of k by enclosing posts in this manner. By comparison, a strong drop-off in grouping performance with k was observed if no internal posts were included (<50% grouping correctly for k≥4 with a strong dependence on k) (FIG. 7B).

Figure 1B:
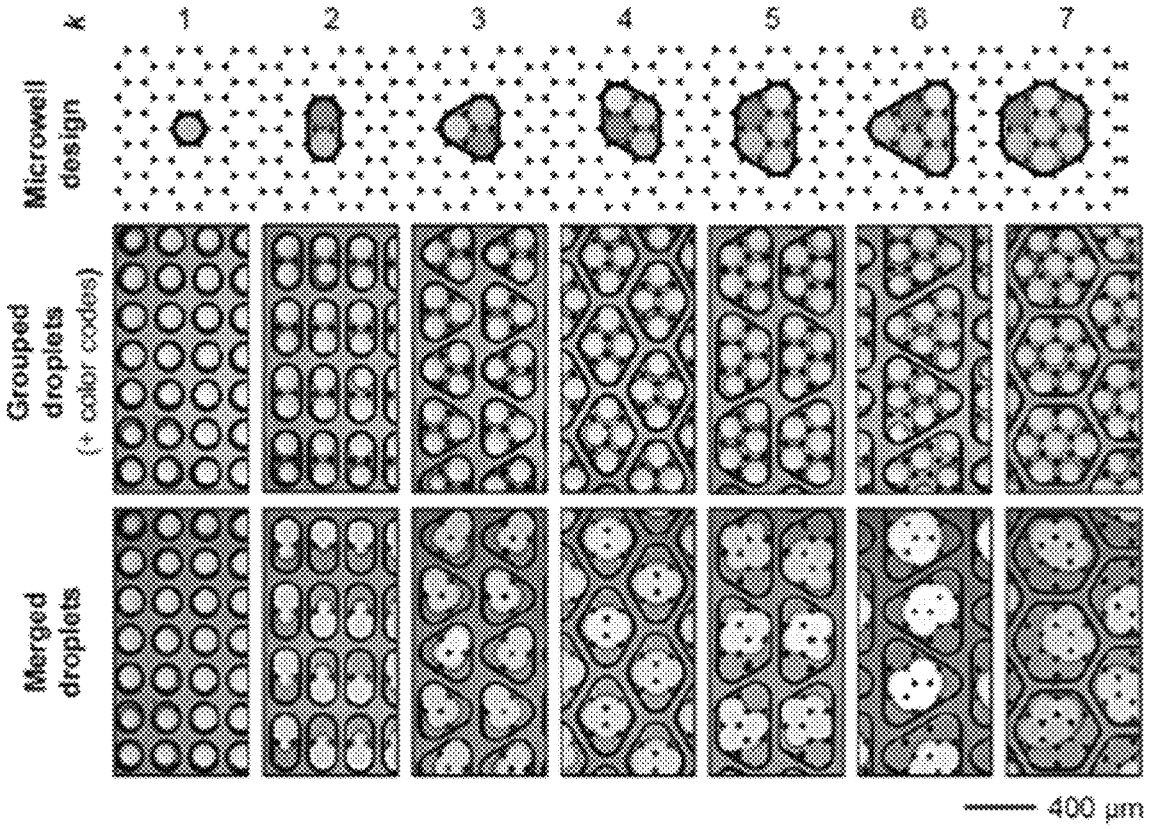
Figure 6D:
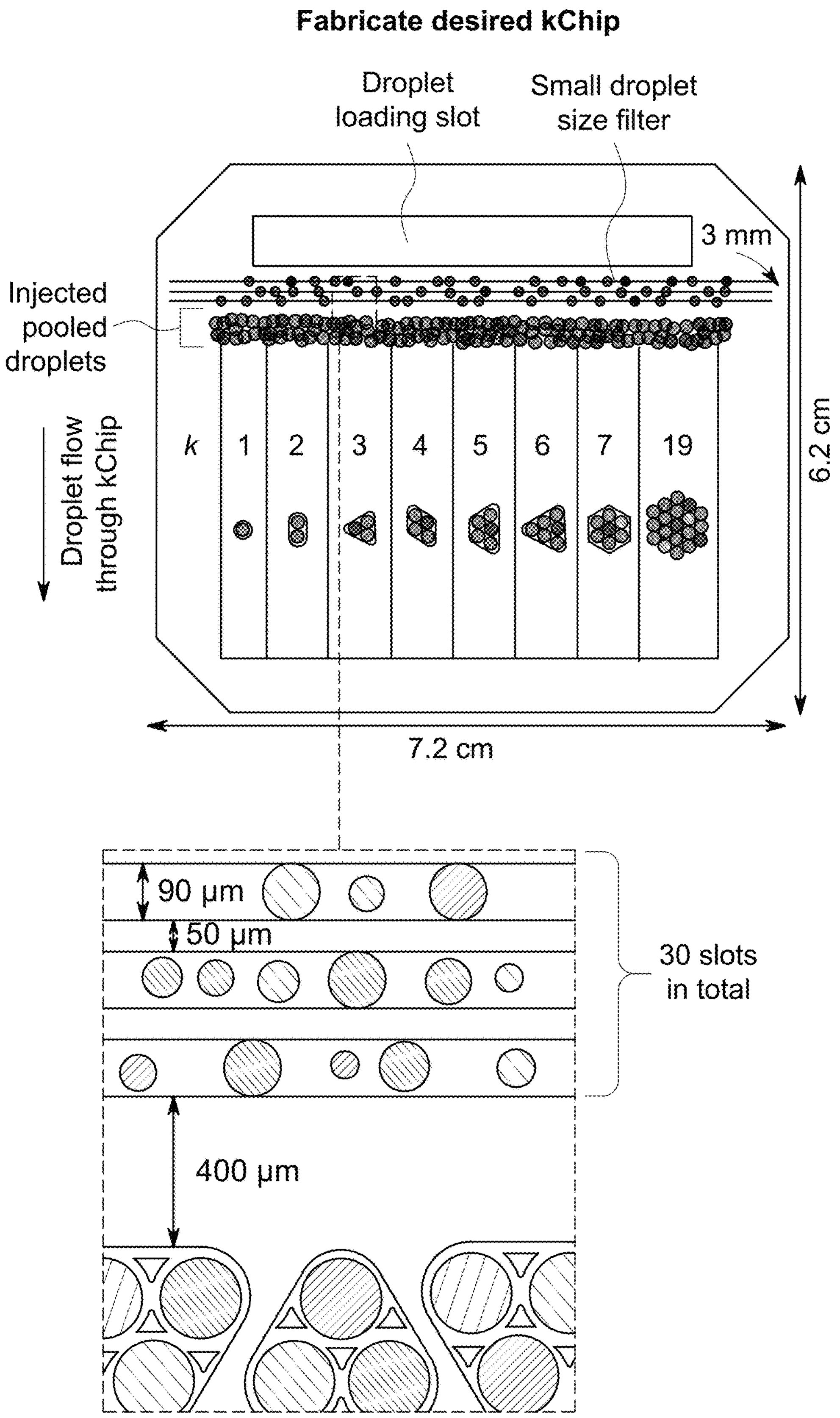

Microwells were arrayed with 50-μm inter-microwell spacing (FIG. 5C). Because different k microwells have different sizes, the density of the arrays also depended on k (FIG. 1B). A user-defined organization of different microwells within the kChip boundaries (6.2 cm×7.2 cm) defined the final kChip structure (FIG. 6D). All kChips were also equipped with a series of 30 90-μm wide moat-like engravings ("slots"). The slots served as a high-pass size filter by trapping small droplets. Droplets around the desired size (~135 μm, FIGS. 6A and 28A-28C) remained unaffected. Given the deformability of droplets, the conservative cutoff of 90 μm was chosen for the filtering size to ensure that no droplets of desired size were trapped. The slots were spaced 50 μm apart from each other and 400 μm from the onset of the microfluidic field. The slots were inset 3 mm from the edge of the kChip due to the observation that air bubbles can enter slots that extend to the edge of the kChip.

Photomasks were generated from AutoCAD designs (FineLine Imaging). kChip designs were then fabricated to 110-120 μm feature height using photolithography on silicon wafers (Microchem SU8-2050). Microwells produced from this feature height were found to best trap droplets in a monolayer, as deeper features can allow droplets to stack causing loading of an undesired number of droplets. These wafers were then embedded into custom molds to create PDMS (Dow Corning Sylgard) kChips by soft lithography with consistent thickness (0.635 cm) and droplet-loading slot location and size. The side of the kChip that contained microwell features was then coated with 1.5 μm parylene C by vapor deposition (Paratronix) to inhibit water loss from droplets and stiffen the kChip to prevent interior collapse during droplet loading ("Droplet making and kChip loading" section below).

Soil Isolate Microbe 16S rRNA Sequences

Soil isolates used in the *H. frisingense* facilitation screen of the instant disclosure (see FIGS. 3A-3G and FIGS. 4A-4D for results) are tabulated in FIG. 34. DNA sequences corresponding to 16S ribosomal RNA (rRNA) sequences for these isolates are the following:

*Bacillus* sp. I (SEQ ID NO: 1):
NNNNNNCGNTGTNNNNNNAAGNNNNNTANNNNNNNTNNNNNNNNCNNTAANTCGT

AACAANGNAACCCNNAGNCNNNNCCNNNNNNNNNAGTTNNNNNTTCTGCTCAGGAT

GAACGCTGGCGGCGTNNNAATACATGCAAGTCGAGCGAATGGATTGAGAGCTTGCT

CTCATGAAGTTAGCGGCGGACGGGTGAGTAACACGTGGGTAACCTGCCCATAAGAC

TGGGATAACTCCGGGAAACCGGGGCTAATACCGGATAATATTTTGAACTGCATGGTT

CGAAATTGAAAGGCGGCTTCGGCTGTCACTTATGGATGGACCCGCGTCGCATTAGCT

AGTTGGTGAGGTAACGGCTCACCAAGGCAACGATGCGTAGCCGACCTGAGAGGGTG

ATCGGCCACACTGGGACTGAGACACGGCCCAGACTCCTACGGGAGGCAGCAGTAGG

GAATCTTCCGCAATGGACGAAAGTCTGACGGAGCAACGCCGCGTGAGTGATGAAGG

CTTTCGGGTCGTAAAACTCTNNTGTTAGGGAAGAACAAGTGCTAGTTGAATAAGCTG

GCACCTTGACGGTACCTAACCAGAAAGCCACGGCTAACTACGTGCCAGCAGCCGCG

GTAATACGTAGGTGGCAAGCGTTATCCGGAATTATTGGGCGTAAAGCGCGCGCAGG

TGGTTTCTTAAGTCTGATGTGAAAGCCCACGGCTCAACCGTGGAGGGTCATTGGAAA

CTGGGAGACTTGAGTGCAGAAGAGGAAAGTGGAATTCCATGTGTAGCGGTGAAATG

CGTAGAGATATGGAGGAACACCAGTGGCGAAGGCGACTTTCTGGTCTGTAACTGAC

ACTGAGGCGCGAAAGCGTGGGGAGCAAACAGGATTAGATACCCTGGTAGTCCACGC

CGTAAACGATGAGTGCTAAGTGTTAGAGGGTTTCCGCCCTTTAGTGCTGAAGTTAAC

GCATTAAGCACTCCGCCTGGGGAGTACGGCCGCAAGGCTGAAACTCAAAGGAATTG

ACGGGGGCCCGCACAAGCGGTGGAGCATGTGGTTTAATTCGAAGCAACGCGAAGAA

CCTTACCAGGTCTTGACATCCTCTGAAAACCCTAGAGATAGGGCTTCTCCTTCGGGA

GCAGAGTGACAGGTGGTGCATGGTTGTCGTCAGCTCGTGTCGTGAGATGTTGGGTTA

AGTCCCGCAACGAGCGCAACCCTTGATCTTAGTTGCCATCATTAAGTTGGGCACTCT

AAGGTGACTGCCGGTGACAAACCGGAGGAAGGTGGGGATGACGTCAAATCATCATG

CCCCTTATGACCTGGGCTACACACGTGCTACAATGGACGGTACAAAGAGCTGCAAG

ACCGCGAGGTGGAGCTAATCTCATAAAACCGTTCTCAGTTCGGATTGTAGGCTGCAA

CTCGCCTACATGAAGCTGGAATCGCTAGTAATCGCGGATCAGCATGCCGCGGTGAAT

ACGTTCCCGGGNCTTGTACACACCGCCCGTCACACCACGAGAGTTTGTAACACCCGA

-continued

AGTCGGTGGGGTAACCTTTATGGAGCCAGCCGCCTAANGNGNACAGATGATGGGNT

GAGTCGTACNNNGGGNNACCGTAANGNNNNANCNGGNANNNGNTNNNNNNNGNNN

NNCNCNNNNNNNNNNNNNNNNATNTNNNTGAGNNNNTNTNNNTNNNNNN

*Collimonas* sp. (SEQ ID NO: 2):
NNNNGNNNNNNGCNAATNGGGGGNNNCNNNNNNNNNNNNANNNNNNNNNNNNNN

ANNNANNNNNNTTNNGNNTTNNNNCCNNTTNTTNTNNAGNCNNGANNNNGGGNAN

NNNNNNNTNCCANCCNCNNTANANNNNNGNNNNCTGTANNANNNNANNNNNNNAC

NANGTTNNCCCTNACNNNCNCANCCNGNGTNNNGNNTNGAGCCCTGGNTNCCNNNA

NANTCCNGANCCAAGNGANANCCCAAANCCCNNCCNNNNTNNNNNNNTNTTTTTTN

TNTGNTCAGATTGAACGCTGGCGGCATNNNTNACACATGCAAGTCGAACGGTAACA

GGGAGCTTGCTCCGCTGACGAGTGGCGAACGGGTGAGTAATATATCGGAACGTACC

TTTGAGTGGGGGATAACTAGTCGAAAGATTAGCTAATACCGCATACGATCTACGGAT

GAAAGTGGGGGATCGCAAGACNTCATGCTCATAGAGCGGCCGATATCTGATTAGCT

AGTTGGTGAGGTAAAGGCTCACCAAGGCTTCGATCAGTAGCTGGTCTGAGAGGACG

ACCAGCCACACTGGGACTGAGACACGGCCCAGACTCCTACGGGAGGCAGCAGTGGG

GAATTTTGGACAATGGGGGCAACCCTGATCCAGCAATGCCGCGTGAGTGAAGAAGG

CCTTCGGGTTGTAAAGCTCTTTTGTCAGGGAAGAAACGGGATGTCCTAATACGGTGT

CCTAATGACGGTACCTGAAGAATAAGCACCGGCTAACTACGTGCCAGCAGCCGCGG

TAATACGTAGGGTGCAAGCGTTAATCGGAATTACTGGGCGTAAAGCGTGCGCAGGC

GGTTATGTAAGACAGGTGTGAAATCCCCGGGCTTAACCTGGGAATGGCATTTGTGAC

TGCATAGCTAGAGTGTGTCAGAGGGGGGTAGAATTCCACGTGTAGCAGTGAAATGC

GTAGAGATGTGGAGGAATACCGATGGCGAAGGCAGCCCCCTGGGATAACACTGACG

CTCATGCACGAAAGCGTGGGGAGCAAACAGGATTAGATACCCTGGTAGTCCACGCC

CTAAACGATGTCTACTAGTTGTCGGGTCTTAATTGACTTGGTAACGCAGCTAACGCG

TGAAGTAGACCGCCTGGGGAGTACGGTCGCAAGATTAAAACTCAAAGGAATTGACG

GGGACCCGCACAAGCGGTGGATGATGTGGATTAATTCGATGCAACGCGAAAAACCT

TACCTACCCTTGACATGTACGGAATGCTGAAGAGATTTGGCAGTGCTCGAAAGAGA

ACCGTAACACAGGTGCTGCATGGCTGTCGTCAGCTCGTGTCGTGAGATGTTGGGTTA

AGTCCCGCAACGAGCGCAACCCTTGTCATTAGTTGCTACGAAAGGGCACTCTAATGA

GACTGCCGGTGACAAACCGGAGGAAGGTGGGGATGACGTCAAGTCCTCATGGCCCT

TATGGGTAGGGGCTTCACACGTCATACAATGGTACATACAGAGGGCCGCCAACCCGC

GAGGGGGAGCTAATCCCAGAAAGTGTATCGTAGTCCGGATTGTAGTCTGCAACTCG

ACTACATGAAGTTGGAATCGCTAGTAATCGCGGATCAGCATGTCGCGGTGAATACGT

TCCCGGGTCTTGTACACACCGCCCGTCACACCATGGGAGCGGGTTTTACCAGAAGTA

GGTAGCCTAACCGCAAGGGGGCGCTTACCACGGTAGGATTCGTGACTGGGGTGANN

NNNNNNNNNNNNNNNNNNNNNNNNNNNNNNNANNGGGTAGGGGTTTTNNTCTNNN

NNNNNNANNANCTNNNNNNANNNGNNNNNNNGTNNNNNCNNNNCNNNNNNNNTNC

NNNNNNNNNNN

Chryseobacterium sp. (SEQ ID NO: 3):
NNNNAGTTNNNTNNNGGCTCAGGATGAACGCTAGCGGGAGGCNTAACACATGCAA

GCCGAGCGGTAGAGTTTCTTCGGAAACTTGAGAGCGGCGTACGGGTGCGGAACACG

-continued

TGTGCAACCTGCCTTTATCTGGGGGATAGCCTTTCGAAAGGAAGATTAATACCCCAT

AATATATTGAATGGCATCATTCGATATTGAAAACTCCGGTGGATAGAGATGGGCAC

GCGCAAGATTAGATAGTTGGTGAGGTAACGGCTCACCAAGTCTACGATCTTTAGGG

GGCCTGAGAGGGTGATCCCCCACACTGGTACTGAGACACGGACCAGACTCCTACGG

GAGGCAGCAGTGAGGAATATTGGACAATGGGTGAGAGCCTGATCCAGCCATCCCGC

GTGAAGGACGACGGCCCTATGGGTTGTAAACTTCTTTTGTATAGGGATAAACCTACT

CTCGTGAGAGTAGCTGAAGGTACTATACGAATAAGCACCGGCTAACTCCGTGCCAG

CAGCCGCGGTAATACGGAGGGTGCAAGCGTTATCCGGATTTATTGGGTTTAAAGGGT

CCGTAGGCGGATCTGTAAGTCAGTGGTGAAATCTCACAGCTTAACTGTGAAACTGCC

ATTGATACTGCAGGTCTTGAGTGTTGTTGAAGTAGCTGGAATAAGTAGTGTAGCGGT

GAAATGCATAGATATTACTTAGAACACCAATTGCGAAGGCAGGTTACTAAGCAACA

ACTGACGCTGATGGACGAAAGCGTGGGGAGCGAACAGGATTAGATACCCTGGTAGT

CCACGCCGTAAACGATGCTAACTCGTTTTTGGTTTTTCGGAATCAGAGACTAAGCGA

AAGTGATAAGTTAGCCACCTGGGGAGTACGTTCGCAAGAATGAAACTCAAAGGAAT

TGACGGGGGCCCGCACAAGCGGTGGATTATGTGGTTTAATTCGATGATACGCGAGG

AACCTTACCAAGGCTTAAATGGGAAATGACAGGTTTAGAAATAGACTTTTCTTCGGA

CATTTTTCAAGGTGCTGCATGGTTGTCGTCAGCTCGTGCCGTGAGGTGTTAGGTTAA

GTCCTGCAACGAGCGCAACCCGTGTCACTAGTTGCCATCATTAAGTTGGGGACTCTA

GTGAGACTGCCTACGCAAGTAGAGAGGAAGGTGGGGATGACGTCAAATCATCACGG

CCCTTACGCCTTGGGCCACACACGTAATACAATGGCCAGTACAGAGGGCAGCTACA

CAGCGATGTGATGCAAATCTCGAAAGCTGGTCTCAGTTCGGATTGGAGTCTGCAACT

CGACTCTATGAAGCTGGAATCGCTAGTAATCGCGCATCANNCATGGCGCGGTGAAT

ACGTTCCCGGGNCTTGTACACACCGCCCGTCAAGCCATGGNAGTCTGGGGTACCTGA

AGTCGGTGACCGTAATAGGAGCTGCCTAGGGTAAAACAGGTACTNGGGCTAAGTCG

TANNNNGGNANCCNGNAAGCAGGNANNNNGTANNNNNNNNNNNNNNNNNNNNNN

TNNNNNNNNNNCATCNNNNNNNN

*Burkholderia* sp. I (SEQ ID NO: 4):
NTTNNNTNNNCNCCCCNCCNTTNNNNNNGNATNCTACNNCNNNNNNATGNGNNGNN

GNNGCCCCTTAAACNNGANNNCAANGAAACCCAAAANNCNCCCNNNNNNNNNNN

NNNNNNNNGNTNAGATGAACGCTGGCGGCATNNNTNACACATGCAAGTCGAACGG

CAGCACGGGTGCTTGCACCTGGTGGCGAGTGGCGAACGGGTGAGTAATACATCGGA

ACATGTCCTGTAGTGGGGGATAGCCCGGCGAAAGCCGGATTAATACCGCATACGAT

CTACGGATGAAAGCGGGGGACCTTCGGGCCTCGCGCTATAGGGTTGGCCGATGGCT

GATTAGCTAGTTGGTGGGGTAAAGGCCTACCAAGGCGACGATCAGTAGCTGGTCTG

AGAGGACGACCAGCCACACTGGGACTGAGACACGGCCCAGACTCCTACGGGAGGC

AGCAGTGGGGAATTTTGGACAATGGGCGAAAGCCTGATCCAGCAATGCCGCGTGTG

TGAAGAAGGCCTTCGGGTTGTAAAGCACTTTTGTCCGGAAAGAAATCCTTGGCTCTA

ATACAGTCGGGGGATGACGGTACCGGAAGAATAAGCACCGGCTAACTACGTGCCAG

CAGCCGCGGTAATACGTAGGGTGCGAGCGTTAATCGGAATTACTGGGCGTAAAGCG

TGCGCAGGCGGTTTGTTAAGACCGATGTGAAATCCCCGGGCTTTCAACCTGGGAACTGC

ATTGGTGACTGGCAAGCTAGAGTATGGCAGAGGGGGGTAGAATTCCACGTGTAGCA

-continued

GTGAAATGCGTAGAGATGTGGAGGAATACCGATGGCGAAGGCAGCCCCCTGGGCCA

ATACTGACGCTCATGCACGAAAGCGTGGGGAGCAAACAGGATTAGATACCCTGGTA

GTCCACGCCCTAAACGATGTCAACTAGTTGTTGGGGATTCATTTCCTTAGTAACGTA

GCTAACGCGTGAAGTTGACCGCCTGGGGAGTACGGTCGCAAGATTAAAACTCAAAG

GAATTGACGGGGACCCGCACAAGCGGTGGATGATGTGGATTAATTCGATGCAACGC

GAAAAACCTTACCTACCCTTGACATGGTCGGAATCCTGCTGAGAGGTGGGAGTGCTC

GAAAGAGAACCGATACACAGGTGCTGCATGGCTGTCGTCAGCTCGTGTCGTGAGAT

GTTGGGTTAAGTCCCGCAACGAGCGCAACCCTTGTCCTTAGTTGCTACGCAAGAGCA

CTCTAAGGAGACTGCCGGTGACAAACCGGAGGAAGGTGGGGATGACGTCAAGTCCT

CATGGCCCTTATGGGTAGGGCTTCACACGTCATACAATGGTCGGAACAGAGGGTTGC

CAACCCGCGAGGGGGAGCTAATCCCAGAAAACCGATCGTAGTCCGGATTGCACTCT

GCAACTCGAGTGCATGAAGCTGGAATCGCTAGTAATCGCGGATCAGCATGCCGCGG

TGAATACGTTCCCGGGTCTTGTACACACCGCCCGTCACACCATGGGAGTGGGTTTTA

CCAGAAGTGGCTAGTCTAACCGCAAGGAGGACGGTCACCACGGTAGGATTCATGAC

TGGGGTGAAGTNNNNNNNN

*Burkholderia* sp. II (SEQ ID NO: 5):
NTNTNTNNNNANNNCGCCNCCCCNNTCNNNCNGATNNNNNCCCNNNNTNAAGAGTG

NANNCCGNGNNNCCNNNAAANCGGANCAANGGAANCCCCAAACCNNNCCNNNTNN

NNNNNNTTTTNTNNNTCNGNTCAGATGAACGCTGGCGGCATNNNTNNCACATGCAA

GTCGAACGGCAGCACGGGTGCTTGCACCTGGTGGCGAGTGGCGAACGGGTGAGTAA

TACATCGGAACATGTCCTGTAGTGGGGGATAGCCCGGCGAAAGCCGGATTAATACC

GCATACGATCTACGGATGAAAGCGGGGGACCTTCGGGCCTCGCGCTATAGGGTTGG

CCGATGGCTGATTAGCTAGTTGGTGGGGTAAAGGCCTACCAAGGCGACGATCAGTA

GCTGGTCTGAGAGGACGACCAGCCACACTGGGACTGAGACACGGCCCAGACTCCTA

CGGGAGGCAGCAGTGGGGAATTTTGGACAATGGGCGAAAGCCTGATCCAGCAATGC

CGCGTGTGTGAAGAAGGCCTTCGGGTTGTAAACTCACTTTTGTCCGGAAAGAAATCCT

TGGCTCTAATACAGTCGGGGGATGACGGTACCGGAAGAATAAGCACCGGCTAACTA

CGTGCCAGCAGCCGCGGTAATACGTAGGGTGCGAGCGTTAATCGGAATTACTGGGC

GTAAAGCGTGCGCAGGCGGTTTGTTAAGACCGATGTGAAATCCCCGGGCTCAACCT

GGGAACTGCATTGGTGACTGGCAAGCTAGAGTATGGCAGAGGGGGGTAGAATTCCA

CGTGTAGCAGTGAAATGCGTAGAGATGTGGAGGAATACCGATGGCGAAGGCAGCCC

CCTGGGGCAATACTGACGCTCATGCACGAAAGCGTGGGGAGCAAACAGGATTAGAT

ACCCTGGTAGTCCACGCCCTAAACGATGTCAACTAGTTGTTGGGGATTCATTTCCTT

AGTAACGTAGCTAACGCGTGAAGTTGACCGCCTGGGGAGTACGGTCGCAAGATTAA

AACTCAAAGGAATTGACGGGGACCCGCACAAGCGGTGGATGATGTGGATTAATTCG

ATGCAACGCGAAAAACCTTACCTACCCTTGACATGGTCGGAATCCTGCTGAGAGGTG

GGAGTGCTCGAAAGAGAACCGATACACAGGTGCTGCATGGCTGTCGTCAGCTCGTG

TCGTGAGATGTTGGGTTAAGTCCCGCAACGAGCGCAACCCTTGTCCTTAGTTGCTAC

GCAAGAGCACTCTAAGGAGACTGCCGGTGACAAACCGGAGGAAGGTGGGGATGAC

GTCAAGTCCTCATGGCCCTTATGGGTANGGCTTCACACGTCATACAATGGTCGGAAC

AGAGGGTTGCCAACCCGCGAGGGGGAGCTAATCCCAGAAAACCGATCGTAGTCCGG

-continued

ATTGCACTCTGCAACTCGAGTGCATGAAGCTGGAATCGCTAGTAATCGCGGATCAGC

ATGCCGCGGTGAATACGTTCCCGGGTCTTGTACACACCGCCCGTCACACCATGGGAG

TGGGTTTTACCAGAAGTGNTAGTCTAACCGCAGGANNNGGTCACNCGGTAGATTCA

TGACTGGGGTGAAGTCNNANNNNNGNNNNNNNNNNNNNNN

*Bacillus* sp. II (SEQ ID NO: 6):
NNNNNNNNNNTNNNNNNNCNNNTCAGGATGAACGCTGGCGGCGTGCNTAATACAT

GCAAGTCGAGCGAATGGATTNANGAGCTTGCTCTNNANGAAGTTAGCGGCGGACGG

GTGAGTAACACGTGGGTAACCTGCCCATAAGACTGGGATAACTCCGGGAAACCGGG

GCTAATACCGGATAATATTTTGAACTGCATGGTTCGAAATTGAAAGGCGGCTTCGGC

TGTCACTTATGGATGGACCCGCGTCGCATTAGCTAGTTGGTGAGGTAACGGCTCACC

AAGGCAACGATGCGTAGCCGACCTGAGAGGGTGATCGGCCACACTGGGACTGAGAC

ACGGCCCAGACTCCTACGGGAGGCAGCAGTAGGGAATCTTCCGCAATGGACGAAAG

TCTGACGGAGCAACGCCGCGTGAGTGATGAAGGCTTTCGGGTCGTAAAACTCTGTTG

TTAGGGAAGAACAAGTGCTAGTTGAATAAGCTGGCACCTTGACGGTACCTAACCAG

AAAGCCACGGCTAACTACGTGCCAGCAGCCGCGGTAATACGTAGGTGGCAAGCGTT

ATCCGGAATTATTGGGCGTAAAGCGCGCGCAGGTGGTTTCTTAAGTCTGATGTGAAA

GCCCACGGCTCAACCGTGGAGGGTCATTGGAAACTGGGAGACTTGAGTGCAGAAGA

GGAAAGTGGAATTCCATGTGTAGCGGTGAAATGCGTAGAGATATGGAGGAACACCA

GTGGCGAAGGCGACTTTCTGGTCTGTAACTGACACTGAGGCGCGAAAGCGTGGGGA

GCAAACAGGATTAGATACCCTGGTAGTCCACGCCGTAAACGATGAGTGCTAAGTGT

TAGAGGGTTTCCGCCCTTTAGTGCTGAAGTTAACGCATTAAGCACTCCGCCTGGGGA

GTACGGCCGCAAGGCTGAAACTCAAAGGAATTGACGGGGGCCCGCACAAGCGGTG

GAGCATGTGGTTTAATTCGAAGCAACGCGAAGAACCTTACCAGGTCTTGACATCCTC

TGAAAACCCTAGAGATAGGGCTTGTCCTTCGGGAGCAGAGTGACAGGTGGTGCATG

GTTGTCGTCAGCTCGTGTCGTGAGATGTTGGGTTAAGTCCCGCAACGAGCGCAACCC

TTGATCTTAGTTGCCATCATTAAGTTGGGCACTCTAAGGTGACTGCCGGTGACAAAC

CGGAGGAAGGTGGGGATGACGTCAAATCATCATGCCCCTTATGACCTGGGCTACAC

ACGTGCTACAATGGACGGTACAAAGAGCTGCAAGACCGCGAGGTGGAGCTAATCTC

ATAAAACCGTTCTCAGTTCGGATTGTAGGCTGCAACTCGCCTACATGAAGCTGGAAT

CGCTAGTAATCGCGGATCAGCATGCCGCGGTGAATACGTTCCCGGGCCTTGTACACA

CCGCCCGTCACACCACGAGAGTTTGTAACACCCGAAGTCGGTGGGGTAACCTTTATG

GAGCCAGCCGCCTAANNGGGACAGATGATTGGGGTGAAGTCGTACANNGGNNANC

CGTAAN

*Enterobacter mori* SEQ ID NO: 7):
NNNNNNNGTTTGANTCNTGNTCAGGATGACGCTGGCGGCGTNCTTAATACATGCAA

NTCGANCGAATGGATTAAGAGCTTGCTCTNNNGAAGNTAGCGGCGGACGGGTGAGT

AACACGTGGGTAACCTGCCCATAAGACTGGGATAANTCCGGGAAACCGGGGCTAAT

NCCGGATAACATTTTGAACTGCATGGTTCGAAATTGAAAGGCGGCTTCGGCTGTCAC

TTATGGATGGACCCGCGTCGCATTAGCTAGTTGGTGAGGTAACGGCTCACCAAGGCA

ACGATGCGTAGCCGACCTGAGAGGGTGATCGGCCACACTGGGACTGAGACACGGCC

CAGACTCCTACGGGAGGCAGCAGTAGGGAATCTTCCGCAATGGACGAAAGTCTGAC

GGAGCAACGCCGCGTGAGTGATGAAGGCTTTCGGGTCGTAAAACTCTGTTGTTAGG

-continued

GAAGAACAAGTGCTAGTTGAATAAGCTGGCACCTTGACGGTACCTAACCAGAAAGC

CACGGCTAACTACGTGCCAGCAGCCGCGGTAATACGTAGGTGGCAAGCGTTATCCG

GAATTATTGGGCGTAAAGCGCACGCAGGCGGTTTGTTAAGTCAGATGTGAAATCCCC

GAGCTTAACTTGGGAACTGCATTTGAAACTGGCAAGCTAGAGTCTTGTAGAGGGGG

GTAGAATTCCAGGTGTAGCGGTGAAATGCGTAGAGATCTGGAGGAATACCGGTGGC

GAAGGCGGCCCCCTGGACAAAGACTGACGCTCAGGTGCGAAAGCGTGGGGAGCAA

ACAGGATTAGATACCCTGGTAGTCCACGCTGTAAACGATGTCGACTTGGAGGTTGTG

CCCTTGAGGCGTGGCTTCCGGAGCTAACGCGTTAAGTCGACCGCCTGGGGAGTACG

GCCGCAAGGTTAAAACTCAAATGAATTGACGGGGGCCCGCACAAGCGGTGGAGCAT

GTGGTTTAATTCGATGCAACGCGAAGAACCTTACCTACTCTTGACATCCAGAGAATT

CGCTAGAGATAGCTTAGTGCCTTCGGGAACTCTGAGACAGGTGCTGCATGGCTGTCG

TCAGCTCGTGTTGTGAAATGTrGGGTTAAGTCCCGCAACGAGCGCAACCCTTATCCT

TTGTTGCCAGCGAGTAATGTCGGGAACTCAAAGGAGACTGCCGGTGATAAACCGGA

GGAAGGTGGGGATGACGTCAAGTCATCATGGCCCTTACGAGTAGGGCTACACACGT

GCTACAATGGCGCATACAAAGAGAAGCGAACTCGCGAGAGCAAGCGGACCTCATA

AAGTGCGTCGTAGTCCGGATTGGAGTCTGCAACTCGACTCCATGAAGTCGGAATCGC

TAGTAATCGTAGATCAGAATGCTACGGTGAATACGTTCCCGGGCCTTGTACACACCG

CCCGTCACACCATGGGAGTGGGTTGCAAAAGAAGTAGGTAGCTTAACCTTCGGGAG

GGCGCTTACCACTTTGTGATTCATGACTGGGGTGANTNNNNNNGGGAANACCNCNN

NNNNNGGNGNNNGGGGGNGNGNNNTTNNNNCGGGGNNNGNNNNANNNNANNNNN

NNNNNNNNNNNNNNNNNNNNNNCNCCNNNNNNNNNNANNNNNNANNNNNNCNNN

NNNNNNNNNNNNNNNNNNNNNNNNNNNNANNGNNNNNNNNANNNNNNNANTNNNN

NCNNNCGNNNNNNNNNNNNNNNNNNNNNNGNNNNNNNNNNTNNNTNNTNNNNNNN

NNNNC

*Stenotrophomonas maltophilia* (SEQ ID NO: 8):
NNTNNNAGTTTNGNNNNNGGCTCAGAGTGAACGCTGGCGNTAGGCCTAACACATGC

AAGTCGAACGGCAGCACAGGAGAGCTTGCTCTCTGGGTGGCGAGTGGCGGACGGGT

GAGGAATACATCGGAATCTACTCTGTCGTGGGGGATAACGTAGGGAAACTTACGCT

AATACCGCATACGACCTACGGGTGAAAGCAGGGGATCTTCGGACCTTGCGCGATTG

AATGAGCCGATGTCGGATTAGCTAGTTGGCGGGGTAAAGGCCCACCAAGGCGACGA

TCCGTAGCTGGTCTGAGAGGATGATCAGCCACACTGGAACTGAGACACGGTCCAGA

CTCCTACGGGAGGCAGCAGTGGGGAATATrGGACAATGGGCGCAAGCCTGATCCAG

CCATACCGCGTGGGTGAAGAAGGCCTTCGGGTTGTAAAGCCCTTTTGTTGGGAAAGA

AATCCAGCCGGCTAATACCCGGTTGGGATGACGGTACCCAAAGAATAAGCACCGGC

TAACTTCGTGCCAGCAGCCGCGGTAATACGAAGGGTGCAAGCGTTACTCGGAATTA

CTGGGCGTAAAGCGTGCGTAGGTGGTCGTTTAAGTCCGTTGTGAAAGCCCTGGGCTC

AACCTGGGAACTGCAGTGGATACTGGGCGACTAGAGTGTGGTAGAGGGTAGCGGAA

TTCCTGGTGTAGCAGTGAAATGCGTAGAGATCAGGAGGAACATCCATGGCGAAGGC

AGCTACCTGGACCAACACTGACACTGAGGCACGAAAGCGTGGGGAGCAAACAGGA

TTAGATACCCTGGTAGTCCACGCCCTAAACGATGCGAACTGGATGTTGGGTGCAATT

TGGCACGCAGTATCGAAGCTAACGCGTTAAGTTCGCCGCCTGGGGAGTACGGTCGC

-continued

AAGACTGAAACTCAAAGGAATTGACGGGGGCCCGCACAAGCGGTGGAGTATGTGGT

TTAATTCGATGCAACGCGAAGAACCTTACCTGGCCTTGACATGTCGAGAACCTTCCA

GAGATGGATGGGTGCCTTCGGGAACTCGAACACAGGTGCTGCATGGCTGTCGTCAG

CTCGTGTCGTGAGATGTTGGGTTAAGTCCCGCAACGAGCGCAACCCTTGTCCTTAGT

TGCCAGCACGTAATGGTGGGAACTCTAAGGAGACCGCCGGTGACAAACCGGAGGAA

GGTGGGGATGACGTCAAGTCATCATGGCCCTTACGGCCAGGGCTACACACGTACTA

CAATGGTANGGACAGANGGCTGCAAGCCGGCGACNGNAAGCCAATCCCAGAAACC

CTATCTCAGTCCGGATTGGAGTCTGCANCTCGACTCCATGAAGTCGGAATCGCTAGN

AATCGCAGATCANCATTGCTGCGGTGAATACGTTCCCGGGNCTTGNACACAGCGCC

CGNCNNNCCATGGGAGTTTGTTGCNCNNAANCNGGTAGCTTANCCTTCGGGAGGGC

GCTTGCCACGTGTGGCNNANNNNTGGGGNGAANNCGTAACCAGGGTAACCNGNAN

*Dyella* sp. (SEQ ID NO: 9):
NNNNNNNTTNNNNNNNNNNCTCAGATTGAACGCTGGCGGCATGCCTAACACATGCA

AGTCGAACGGCAGCACAGTAGACTCTTGCTCTATGGGTGGCGAGTGGCGGACGGGTG

AGTAATGCATCGGGATCTACCCAAACGTGGGGGATAACGTAGGGAAACTTACGCTA

ATACCGCATACGTCTTACGAGAGAAAGCAGGGGACCTTCGGGCCTTGCGCCTGTTGG

ACGAACCGATGTGCGATTAGCTAGTTGGTAGGGTAATGGCCTACCAAGGCGACGAT

CGCTAGCTGGTCTGAGAGGATGATCAGCCACACTGGAACTGAGACACGGTCCAGAC

TCCTACGGGAGGCAGCAGTGGGGAATATTGGACAATGGGCGCAAGCCTGATCCAGC

AATGCCGCGTGTGTGAAGAAGGCCTTCGGGTTGTAAAGCACTTTTATCAGGAGCGA

AATACTACCGGCTAATATCCGGTGGGGCTGACGGTACCTGAGGAATAAGCACCGGC

TAACTTCGTGCCAGCAGCCGCGGTAATACGAAGGGTGCAAGCGTTAATCGGAATTA

CTGGGCGTAAAGCGTGCGTAGGCGGTTATTTAAGTCTGTTGTGAAATCCCCGGGCTC

AACCTGGGAATGGCAATGGATACTGGATAGCTAGAGTGTGATAGAGGATGGTGGAA

TTCCCGGTGTAGCGGTGAAATGCGTAGAGATCGGGAGGAACATCAGTGGCGAAGGC

GGCCATCTGGATCAACACTGACGCTGAGGCACGAAAGCGTGGGGAGCAAACAGGAT

TAGATACCCTGGTAGTCCACGCCCTAAACGATGCGAACTGGATGTTGGTCTCAACTC

GGAGATCAGTGTCGAAGCTAACGCGTTAAGTTCGCCGCCTGGGGAGTACGGTCGCA

AGACTGAAACTCAAAGGAATTGACGGGGGCCCGCACAAGCGGTGGAGTATGTGGTT

TAATTCGATGCAACGCGAAGAACCTTACCTGGCCTTGACATGTCTGGAATCCTGCAG

AGATGCGGGAGTGCCTTCGGGAATCAGAACACAGGTGCTGCATGGCTGTCGTCAGC

TCGTGTCGTGAGATGTTGGGTTAAGTCCCGCAACGAGCGCAACCCTTGTCCTTAGTT

GCCAGCACGTAATGGTGGGAACTCTAAGGAGACTGCCGGTGACAAACCGGAGGAAG

GTGGGGATGACGTCAAGTCATCATGGCCCTTACGGCCAGGGCTACACACGTACTAC

AATGGTCGGTACAGAGGGTTGCAATACCGCGAGGTGGAGCCAATCCCAGAAAGCCG

ATCCCAGTCCGGATTGGAGTCTGCAACTCGACTCCATGAAGTCGGAATCGCTAGTAA

TCGCAGATCAGCTATGCTGCGGTGAATACGTTCCCGGGCCTTGTACACACCGCCCGT

CACACCATGGGAGTGAGTTGCTCCAGAAGCCGTTAGTCTAACCGCAAGGGGGACGA

CGACCACGGAGTGGNTCATGACTGGGGTGAAGTCNTANNNGGGNNNNNNCNNNNA

NNNNNNNNNNNGGNNNNNNNNNNNNNNNCNCNNNNNN

-continued

*Ewingella americana* (SEQ ID NO: 10):
NNANNNNNGNTATANNNNNGNTNGNNNNNNTNTTNNCCCNGNNANTNGNNACNNN

GNNACCNTAATCNTNNCNCGNTNGAGNTGTGATCCCTGGCNCNCNGTAANTCNNAA

CNAAGNAACCCGAANNCNNNCCNNNNNNNNNNNTNTNNNTNNNCTGCTCAGATTG

AACGCTGGCGGCAGGCCTAACACATGCAAGTCGAGCGGCAGCGGGAAGTAGCTTGC

TACTTTGCCGGCGAGCGGCGGACGGGTGAGTAATGTCTGGGAAACTGCCTGATGGA

GGGGGATAACTACTGGAAACGGTAGCTAATACCGCATGACCTCGAAAGAGCAAAGT

GGGGGACCTTCGGGCCTCACGCCATCGGATGTGCCCAGATGGGATTAGCTAGTAGG

TGAGGTAATGGCTCACCTAGGCGACGATCCCTAGCTGGTCTGAGAGGATGACCAGC

CACACTGGAACTGAGACACGGTCCAGACTCCTACGGGAGGCAGCAGTGGGGAATAT

TGCACAATGGGCGCAAGCCTGATGCAGCCATGCCGCGTGTGTGAAGAAGGCCTTCG

GGTTGTAAAGCACTTTCAGCGAGGAGGAAGGCGTTAAGGTTAATAACCTTAGCGAT

TGACGTTACTCGCAGAAGAAGCACCGGCTAACTCCGTGCCAGCAGCCGCGGTAATA

CGGAGGGTGCAAGCGTTAATCGGAATTACTGGGCGTAAAGCGCACGCAGGCGGTTT

GTTAAGTCAGATGTGAAATCCCCGAGCTTAACTTGGGAACTGCATTTGAAACTGGCA

AGCTAGAGTCTTGTAGAGGGGGGTAGAATTCCAGGTGTAGCGGTGAAATGCGTAGA

GATCTGGAGGAATACCGGTGGCGAAGGCGGCCCCCTGGACAAAGACTGACGCTCAG

GTGCGAAAGCGTGGGGAGCAAACAGGATTAGATACCCTGGTAGTCCACGCTGTAAA

CGATGTCGATTTGGAGGTTGTGGGCTTGACCCGTGGCTTCCGGAGCTAACGCGTTAA

ATCGACCGCCTGGGGAGTACGGCCGCAAGGTTAAAACTCAAATGAATTGACGGGGG

CCCGCACAAGCGGTGGAGCATGTGGTTTAATTCGATGCAACGCGAAGAACCTTACCT

ACTCTTGACATCCAGAGAATTCGCTAGAGATAGCTTAGTGCCTTCGGGAACTCTGAG

ACAGGTGCTGCATGGCTGTCGTCAGCTCGTGTTGTGAAATGTTGGGTTAAGTCCCGC

AACGAGCGCAACCCTTATCCTTTGTTGCCAGCGCGTAATGGCGGGAACTCAAAGGA

GACTGCCGGTGATAAACCGGAGGAAGGTGGGGATGACGTCAAGTCATCATGGCCCT

TACGAGTAGGGCTACACACGTGCTACAATGGCATATACAAAGAGAAGCGAACTCGC

GAGAGCAAGCGGACCTCATAAAGTATGTCGTAGTCCGGATTGGAGTCTGCAACTCG

ACTCCATGAAGTCGGAATCGCTAGTAATCGTAGATCANAATGCTACGGTGAATACGT

TCCCGGGCCTTGTACACACCGCCCGTCACACCATGGGAGTGGGTTGCAAAAGAAGT

AGGTAGCTTAACCTTCCTGGAGGGCGCTTACCACTTTGTGATTCATGACTGGGGTGAN

NNNNNNNNNNNNNNNNNNNNNNNNNNNNNNNNGGGGGGNNNGTGNTTTNTTTNNNNN

NNNANNNNNNANNNANNNGNANNNNNNNNNNNNNCNNNNNNNN

*Rahnella* sp. (SEQ ID NO: 11):
NNTNNNNNNNNTNTNNNTNNNTCTGNTCAGATTGAACGCTGGCGGCAGGNNAACAC

ATGCAAGTCGAGCGGCAGCGGGAAGTAGCTTGCTACTTTGCCGGCGAGCGGCGGAC

GGGTGAGTAATGTCTGGGAAACTGCCTGATGGAGGGGGATAACTACTGGAAACGGT

AGCTAATACCGCATGACCTCGCAAGAGCAAAGTGGGGGACCTTCGGGCCTCACGCC

ATCGGATGTGCCCAGATGGGATTAGCTAGTAGGTGAGGTAATGGCTCACCTAGGCG

ACGATCCCTAGCTGGTCTGAGAGGATGACCAGCCACACTGGAACTGAGACACGGTC

CAGACTCCTACGGGAGGCAGCAGTGGGGAATATTGCACAATGGGCGCAAGCCTGAT

GCAGCCATGCCGCGTGTGTGAAGAAGGCCTTAGGGTTGTAAAGCACTTTCAGCGAG

-continued

GAGGAAGGGTTCAGTGTTAATAGCACTGTTCATTGACGTTACTCGCAGAAGAAGCA

CCGGCTAACTCCGTGCCAGCAGCCGCGGTAATACGGAGGGTGCAAGCGTTAATCGG

AATTACTGGGCGTAAAGCGCACGCAGGCGGTTTGTTAAGTCAGATGTGAAATCCCC

GAGCTTAACTTGGGAACTGCATTTGAAACTGGCAAGCTAGAGTCTTGTAGAGGGGG

GTAGAATTCCAGGTGTAGCGGTGAAATGCGTAGAGATCTGGAGGAATACCGGTGGC

GAAGGCGGCCCCCTGGACAAAGACTGACGCTCAGGTGCGAAAGCGTGGGGAGCAA

ACAGGATTAGATACCCTGGTAGTCCACGCTGTAAACGATGTCGACTTGGAGGTTGTG

CCCTTGAGGCGTGGCTTCCGGAGCTAACGCGTTAAGTCGACCGCCTGGGGAGTACG

GCCGCAAGGTTAAAACTCAAATGAATTGACGGGGGCCCGCACAAGCGGTGGAGCAT

GTGGTTTAATTCGATGCAACGCGAAGAACCTTACCTACTCTTGACATCCAGAGAATT

CGCTAGAGATAGCTTAGTGCCTTCGGGAACTCTGAGACAGGTGCTGCATGGCTGTCG

TCAGCTCGTGTTGTGAAATGTTGGGTTAAGTCCCGCAACGAGCGCAACCCTTATCCT

TTGTTGCCAGCACGTAATGGTGGGAACTCAAAGGAGACTGCCGGTGATAAACCGGA

GGAAGGTGGGGATGACGTCAAGTCATCATGGCCCTTACGAGTAGGGCTACACACGT

GCTACAATGGCATATACAAAGAGAAGCAAACTCGCGAGAGCAAGCGGACCTCATAA

AGTATGTCGTAGTCCGGATTGGAGTCTGCAACTCGACTCCATGAAGTCGGAATCGCT

AGTAATCGTAGATCAGAATGCTACGGTGAATACGTTCCCGGGNCTTGTACACACCGC

CCGTCACACCATGNNAGTGGGTTGCAAAAGAAGTNNNAGCTTAACCTTCGGGAGGG

CGCTTANNACTTTGTGATTCATGACTGGGNGAGTCNNNNNNNNNNNNNNNNNNNN

NNNNNNNNNNANNCGNGNNNNNNNNNNANNNGNNNNNNNNNNNNNNNNNN

*Pseudomonas fluorescens* (SEQ ID NO: 12):
NNNNNNNNCNNNNNNNNNNTNNNAGNNNNNNNNCCNGGNNCCCGNNAGNCCGNA

CNNNNNTANACCCGAANNCNNNCCNNNNNNANNNNNNNNNNNNNNNGCTCAGATT

GAACGCTGGCGGCAGGNNAACACATGCAAGTCGAGCGGTAGAGAGAAGCTTGCTTC

TCTTGAGAGCGGCGGACGGGTGAGTAATGCCTAGGAATCTGCCTGGTAGTGGGGGA

TAACGCTCGGAAACGGACGCTAATACCGCATACGTCCTACGGGAGAAAGCAGGGGA

CCTTCGGGCCTTGCGCTATCAGATGAGCCTAGGTCGGATTAGCTAGTGGTGAGGTA

ATGGCTCACCAAGGCGACGATCCGTAACTGGTCTGAGAGGATGATCAGTCACACTG

GAACTGAGACACGGTCCAGACTCCTACGGGAGGCAGCAGTGGGGAATATTGGACAA

TGGGCGAAAGCCTGATCCAGCCATGCCGCGTGTGTGAAGAAGGTCTTCGGATTGTA

AAGCACTTTAAGTTGGGAGGAAGGGCATTAACCTAATACGTTGGTGTCTTGACGTTA

CCGACAGAATAAGCACCGGCTAACTCTGTGCCAGCAGCCGCGGTAATACAGAGGGT

GCAAGCGTTAATCGGAATTACTGGGCGTAAAGCGCGCGTAGGTGGTTCGTTAAGTTG

GATGTGAAATCCCCGGGCTCAACCTGGGAACTGCATTCAAAACTGTCGAGCTAGAG

TATGGTAGAGGGTGGTGGAATTTCCTGTGTAGCGGTGAAATGCGTAGATATAGGAA

GGAACACCAGTGGCGAAGGCGACCACCTGGACTGATACTGACACTGAGGTGCGAAA

GCGTGGGGAGCAAACAGGATTAGATACCCTGGTAGTCCACGCCGTAAACGATGTCA

ACTAGCCGTTGGGAGCCTTGAGCTCTTAGTGGCGCAGCTAACGCATTAAGTTGACCG

CCTGGGGAGTACGGCCGCAAGGTTAAAACTCAAATGAATTGACGGGGGCCCGCACA

AGCGGTGGAGCATGTGGTTTAATTCGAAGCAACGCGAAGAACCTTACCAGGCCTTG

ACATCCAATGAACTTTCCAGAGATGGATTGGTGCCTTCGGGAACATTGAGACAGGTG

-continued

CTGCATGGCTGTCGTCAGCTCGTGTCGTGAGATGTTGGGTTAAGTCCCGTAACGAGC

GCAACCCTTGTCCTTAGTTACCAGCACGTCATGGTGGGCACTCTAAGGAGACTGCCG

GTGACAAACCGGAGGAAGGTGGGGATGACGTCAAGTCATCATGGCCCTTACCTGCCT

GGGCTACACACGTGCTACAATGGTCGGTACAAAGGGTTGCCAAGCCGCGAGGTGGA

GCTAATCCCATAAAANCCGATCGTAGTCCGGATCGCAGTUGCAACTCGACTGCGTG

AAGTCGGAATCGCTAGTAATCGCGAATCAGAATGTCGCGGTGAATACGTTCCCGGG

CCTTGTACACACCGCCCGTCACACCATGGGAGTGGGTTGCACCAGAAGTAGCTAGTC

TAACCTTCGGGAGGACGGTTACCACGGTGTGATTCATGACTGGGGTGANTCNNNNN

NNNNNNNNNNNNNNNNNNNNNNNGNNNNNNGNNNTNCNNTGNNGNNNNNNNAAA

ANNNNN

*Burkhoideria* sp. III (SEQ ID NO: 13):
NANNNNATCTANNNCGGGTANNNNNNGNTGNTNNTNNAGNAAAGCGTTACCNNAG

TNNNNNTAAATGGTANNANGGTAANNNNNNGAGCNCNGACTCCNNNNAATNCTTA

ANCNAAGGGNAACCCGNAAGTCGNNNCCNNNNNNNNNNNNTTNTNNNNNNNNNNN

CTCAGATTGAACGCTGGCGGCATGCCTTACACATGCAAGTCGAACGGCAGCACGGG

TGCTTGCACCTGGTGGCGAGTGGCGAACGGGTGAGTAATACATCGGAACATGTCCT

GTAGTGGGGGATAGCCCGGCGAAAGCCGGATTAATACCGCATACGATCTACGGATG

AAAGCGGGGGACCTTCGGGCCTCGCGCTATAGGGTTGGCCGATGGCTGATTAGCTA

GTTGGTGGGGTAAAGGCCTACCAAGGCGACGATCAGTAGCTGGTCTGAGAGGACGA

CCAGCCACACTGGGACTGAGACACGGCCCAGACTCCTACGGGAGGCAGCAGTGGGG

AATTTTGGACAATGGGCGAAAGCCTGATCCAGCAATGCCGCGTGTGTGAAGAAGGC

CTTCGGGTTGTAAAGCACTTTTGTCCGGAAAGAAATCCTTGACCCTAATACGGTCGG

GGGATGACGGTACCGGAAGAATAAGCACCGGCTAACTACGTGCCAGCAGCCGCGGT

AATACGTAGGGTGCGAGCGTTAATCGGAATTACTGGGCGTAAAGCGTGCGCAGGCG

GTTTGCTAAGACCGATGTGAAATCCCCGGGCTCAACCTGGGAACTGCATTGGTGACT

GGCAGGCTAGAGTATGGCAGAGGGGGGTAGAATTCCACGTGTAGCAGTGAAATGCG

TAGAGATGTGGAGGAATACCGATGGCGAAGGCAGCCCCCTGGGCCAATACTGACGC

TCATGCACGAAAGCGTGGGGAGCAAACAGGATTAGATACCCTGGTAGTCCACGCCC

TAAACGATGTCAACTAGTTGTTGGGGATTCATTTCCTTAGTAACGTAGCTAACGCGT

GAAGTTGACCGCCTGGGGAGTACCTGTCGCAAGATTAAAACTCAAAGGAATTGACGG

GGACCCGCACAAGCGGTGGATGATGTGGATTAATTCGATGCAACGCGAAAAACCTT

ACCTACCCTTGACATGGTCGGAATCCCGCTGAGAGGTGGGGGTGCTCGAAAGAGAA

CCGATACACAGGTGCTGCATGGCTGTCGTCAGCTCGTGTCGTGAGATGTTGGGTTAA

GTCCCGCAACGAGCGCAACCCTTGTCCTTAGTTGCTACGCAAGAGCACTCTAAGGAG

ACTGCCGGTGACAAACCGGAGGAAGGTGGGGATGACGTCAAGTCCTCATGGCCCTT

ATGGGTAGGGCTTCACACGTCATACAATGGTCGGAACAGAGGGTTGCCAACCCGCG

AGGGGGAGCTAATCCCAGAAAACCGATCGTAGTCCGGATTGCACTCTGCAACTCGA

GTGCATGAAGCTGGAATCGCTAGTAATCGCGGATCAGCATGCCGCGGTGAATACGT

TCCCGGGTVTTGTACACACCGCCCGTCACACCATGGGAGTGGGTTTTACCAGAAGTG

-continued

```
GCTAGTCTAACCGCAAGGAGGACGGTCACCACGGTANATTCATGACTGGGGTGANT

CGTANNNNNGGNNNNNCNNCNNNANANNNNNNCNGGNTNGNGNTNTNTTCTTNNN

NNNNNANNNCCTCANNCNCNNNNNNCNNNNNNNNNNANANNTGTNN
```

*Averyella dalhousiensis* (SEQ ID NO: 14):

```
NNNNNNNNNNNNNNANNCNNNNNNNCCTCANNCCGNTNNAANNNGATNNNGGCNNC

CGTANNTCGTAACNCANGNAACCNNAANNNCNNNCNNNNTNNNNTTTTTTTTNTCT

GCTCAGATTGAACGCTGGCGGCAGGCCTAACACATGCAAGTCGAACGGTAACAGGA

AGCAGCTTGCTGCTTTGCTGACGAGTGGCGGACGGGTGAGTAATGTCTGGGAAACT

GCCCGATGGAGGGGGATAACTACTGGAAACGGTAGCTAATACCGCATAACGTCTTC

GGACCAAAGAGGGGGACCTTCGGGCCTCTTGCCATCGGATGTGCCCAGATGGGATT

AGCTAGTAGGTGGGGTAACGGCTCACCTAGGCGACGATCCCTAGCTGGTCTGAGAG

GATGACCAGCCACACTGGAACTGAGACACGGTCCAGACTCCTACGGGAGGCAGCAG

TGGGGAATATTGCACAATGGGCGCAAGCCTGATGCAGCCATGCCGCGTGTATGAAG

AAGGCCTTCGGGTTGTAAAGTACTTTCAGCGAGGAGGAAGGCATTGTGGTTAATAA

CCACAGTGATTGACGTTACTCGCAGAAGAAGCACCGGCTAACTCCGTGCCAGCAGC

CGCGGTAATACGGAGGGTGCAAGCGTTAATCGGAATTACTGGGCGTAAAGCGCACG

CAGGCGGTCTGTCAAGTCGGATGTGAAATCCCCGGGCTCAACCTGGGAACTGCATTC

GAAACTGGCAGACTAGAGTCTTGTAGACTGGGGGTAGAATTCCAGGTGTAGCGGTGA

AATGCGTAGAGATCTGGAGGAATACCGGTGGCGAAGGCGGCCCCCTGGACAAAGAC

TGACGCTCAGGTGCGAAAGCGTGGGGAGCAAACAGGATTAGATACCCTGGTAGTCC

ACGCCGTAAACGATGTCGACTTGGAGGTTGTGCCCTTGAGGCGTGGCTTCCGGAGCT

AACGCGTTAAGTCGACCGCCTGGGGAGTACGGCCGCAAGGTTAAAACTCAAATGAA

TTGACGGGGGCCCGCACAAGCGGTGGAGCATGTGGTTTAATTCGATGCAACGCGAA

GAACCTTACCTACTCTTGACATCCAGAGAACTTAGCAGAGATGCTTTGGTGCCTTCG

GGAACTCTGAGACAGGTGCTGCATGGCTGTCGTCAGCTCGTGTTGTGAAATGTTGGG

TTAAGTCCCGCAACGAGCGCAACCCTTATCCTTTGTTGCCAGCGGTTCGGCCGGGAA

CTCAAAGGAGACTGCCAGTGATAAACTGGAGGAAGGTGGGGATGACGTCAAGTCAT

CATGGCCCTTACGAGTAGGGCTACACACGTGCTACAATGGCGCATACAAAGAGAAG

CGACCTCGCGAGAGCAAGCGGACCTCATAAAGTGCGTCGTAGTCCGGATTGGAGTC

TGCAACTCGACTCCATGAAGTCGGAATCGCTAGTAATCGTAGATCANAATGCTACGG

TGAATACGTTCCCGGGCCTTGTACACACCGCCCGTCACACCATGGGAGTGGGTTGCA

AAAGAAGTAGGTAGCTTAACCTTCGGGAGGGCGCTTA
```

Microbial Culture Input Preparation

All bacterial cultures underwent an initial "starter phase", whereby glycerol stocks of non-fluorescent environmental isolates ("Environmental microbe isolation" section below) and fluorescently labeled strains ("Fluorescently labeled microbe assay in droplets" section below) were inoculated into 525 μL (2-mL-deep 96-well plate) and 4 mL (15-mL culture Falcon tube) of Lysogeny broth (LB) medium, respectively (30° C., 220 RPM, 16 hr). Inoculations from glycerol stocks were conducted via pin replicator (sterilized via 70% v/v ethanol bath and heat treatment between inoculations).

A subsequent "preculture phase" (30° C., 220 RPM, 24 hr) began with washing all cultures in a custom minimal medium (MM) two times. Cultures were then normalized to a starting optical density (OD600) of 0.01 in MM+0.5% w/v glucose.

Figure 28A:
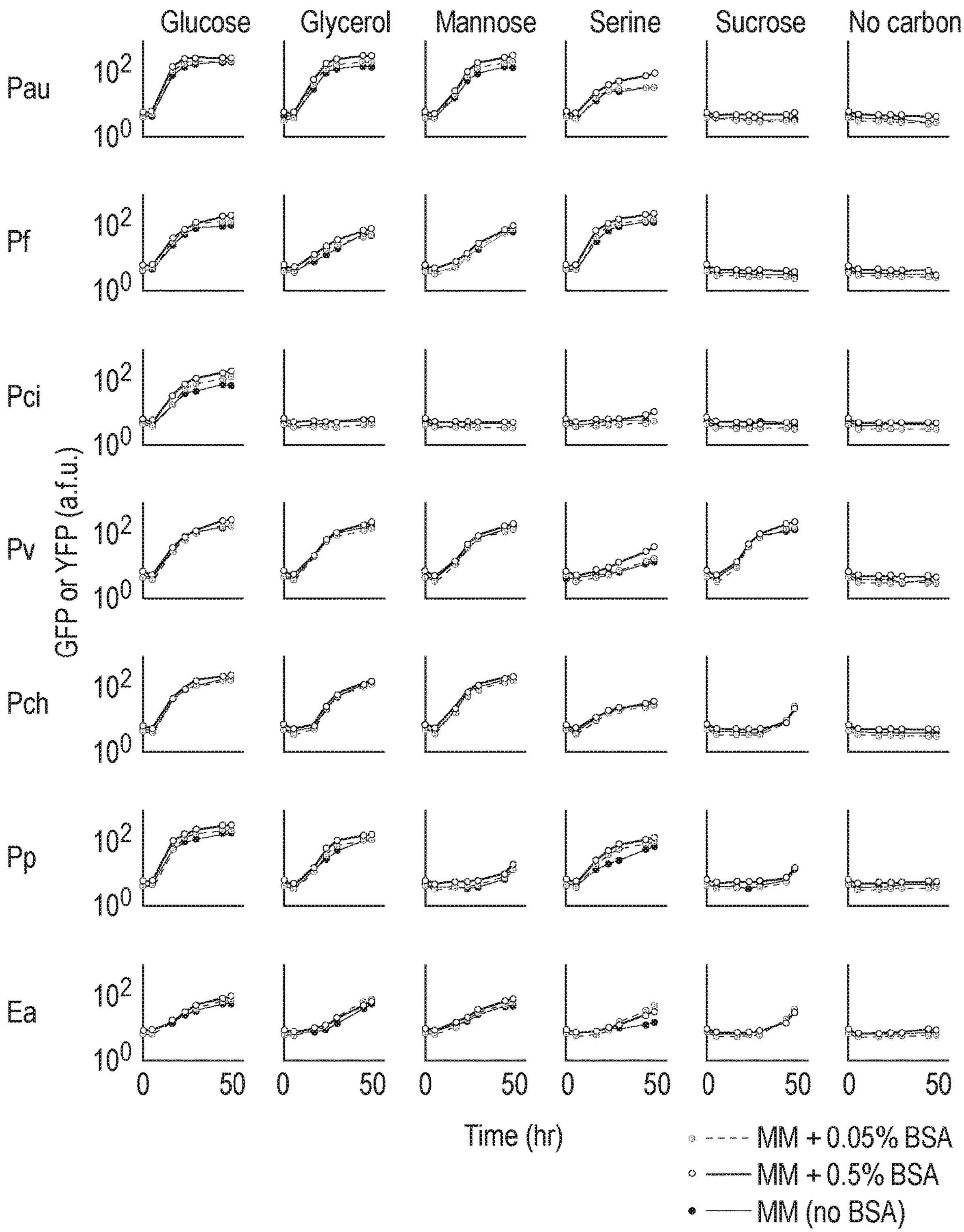
FIGS. 28A-28C show that BSA did not impact microbial growth but affected droplet size.
Figure 28B:
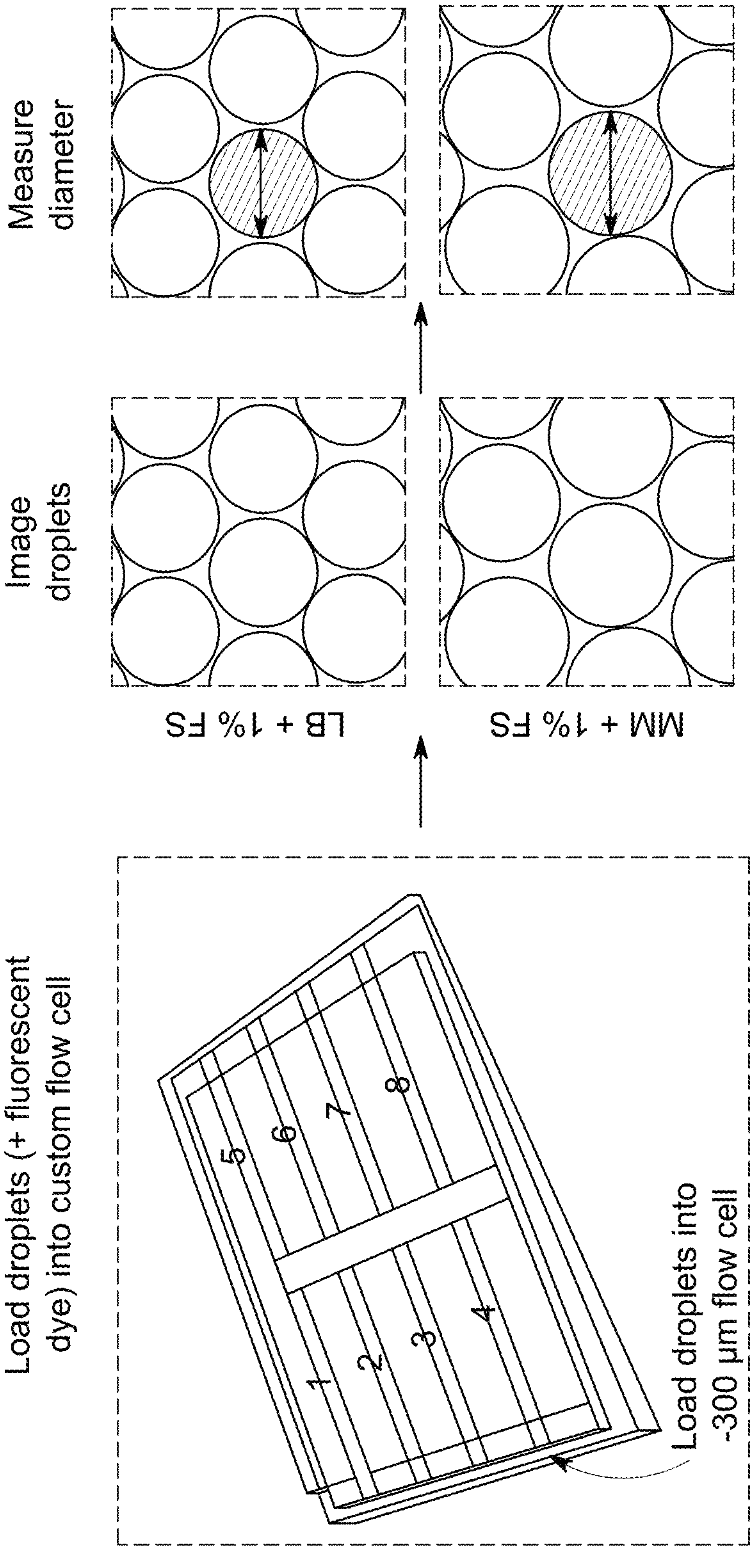
Figure 28C:
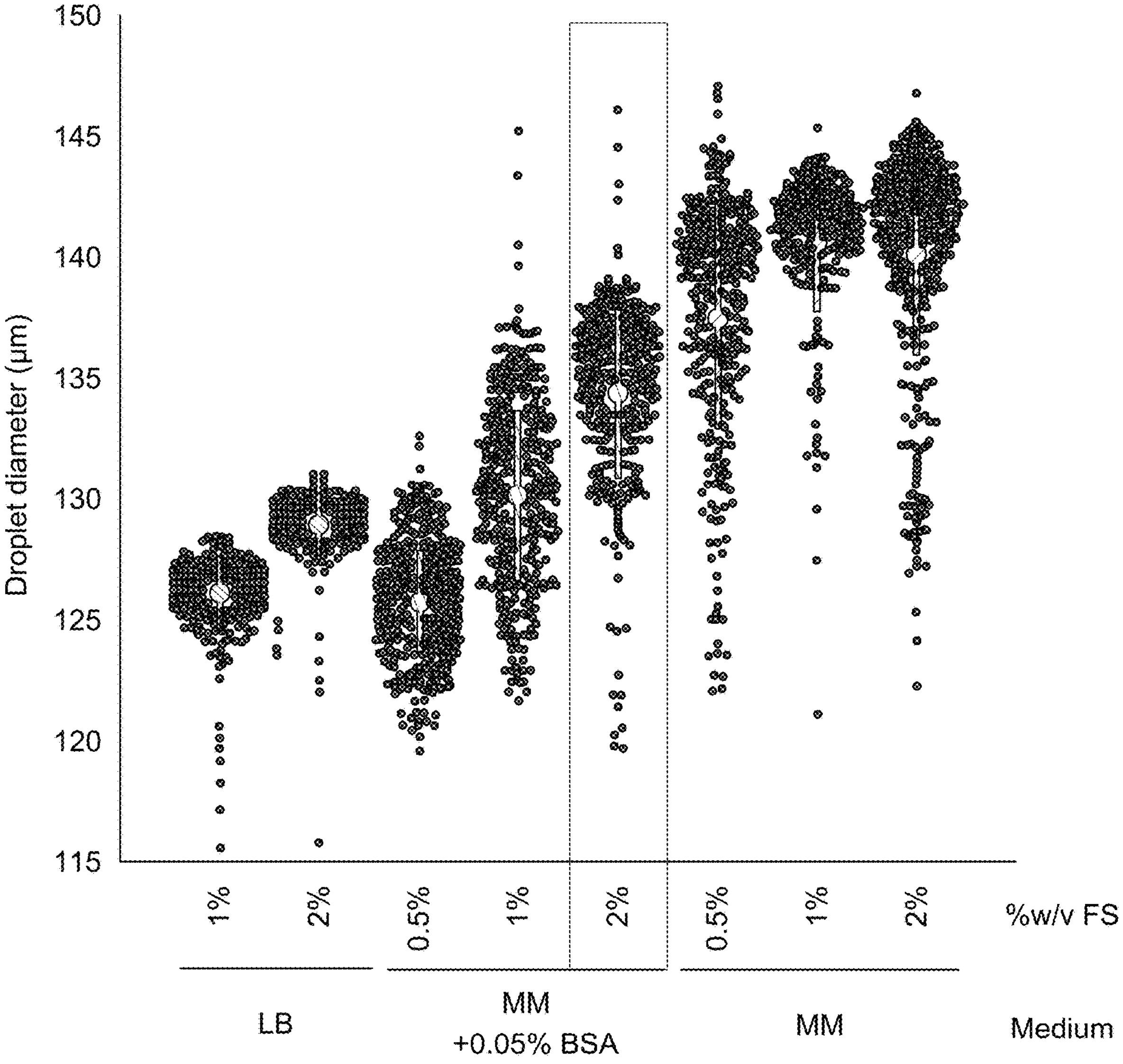

MM consisted of 1×M9 salts (Teknova®), 1× trace metals (Teknova®), 0.1 mM calcium chloride, and 2 mM magnesium sulfate. 0.05% w/v bovine serum albumin (BSA) was additionally added to MM to improve the retention of fluorescent dyes used in color codes and, presumably, other small molecules (49) ("kChip input preprocessing" section below). This is necessary because droplets are not solid compartments, and the fluorosurfactant at the interface forms reverse-micelles in the oil phase. It is a well-known phenomenon that hydrophobic small molecules, such as the fluorescent dyes used for color coding, can partition into these reverse-micelles such that they are depleted from the droplets (50, 51). It was herein identified that the quality of color code signals was improved in MM droplets when 0.05% w/v BSA was added (with no apparent improvements using 1% w/v BSA). The growth of a panel of seven fluorescent strains was additionally measured on a panel of five carbon sources, with and without BSA. Growth curves appeared highly similar when 0.05% w/v BSA or 0.5% w/v BSA was added (FIG. 28A). Notably, instances in which a culture was unable to grow on a given carbon source were maintained despite the addition of BSA (i.e. BSA caused no false positives by serving as an alternative carbon source). 0.05% w/v BSA was therefore included when making MM droplets. In addition, it was identified herein that BSA affected the size of droplets produced (Bio-Rad QX200 cartridges). A custom flow cell apparatus with small flow channels was therefore generated, to enable simultaneous assessment of droplet sizes produced from various media and fluorosurfactant concentrations (FIGS. 28B and 28C). Droplets were labeled with Alexa Fluor 647 to enable detection. The following was identified: (1) increasing fluorosurfactant from 0.5% w/w to 2% w/w increased droplet size across both LB and MM; (2) MM droplets were inherently more polydisperse than LB droplets; and (3) the incorporation of 0.05% w/v BSA decreases droplet size. These results informed kChip microwell dimensions ("kChip design and fabrication" section above), with geometries chosen to accommodate droplets with 135-μm diameter (FIG. 6A), i.e. the size of MM droplets made with 0.05% w/v BSA and 2% w/w fluorosurfactant.

The "experimental phase" began by washing cells three times in MM to remove residual glucose and normalizing, typically, to a starting OD600 of 0.02 (or ~20 cells/droplet depending on the strain) in MM+0.05% BSA. After adding the color codes ("kChip input preprocessing" section below), droplets of the normalized cultures were produced, pooled, and loaded onto the kChip ("Droplet making and kChip loading" section below).

Figure 7C:
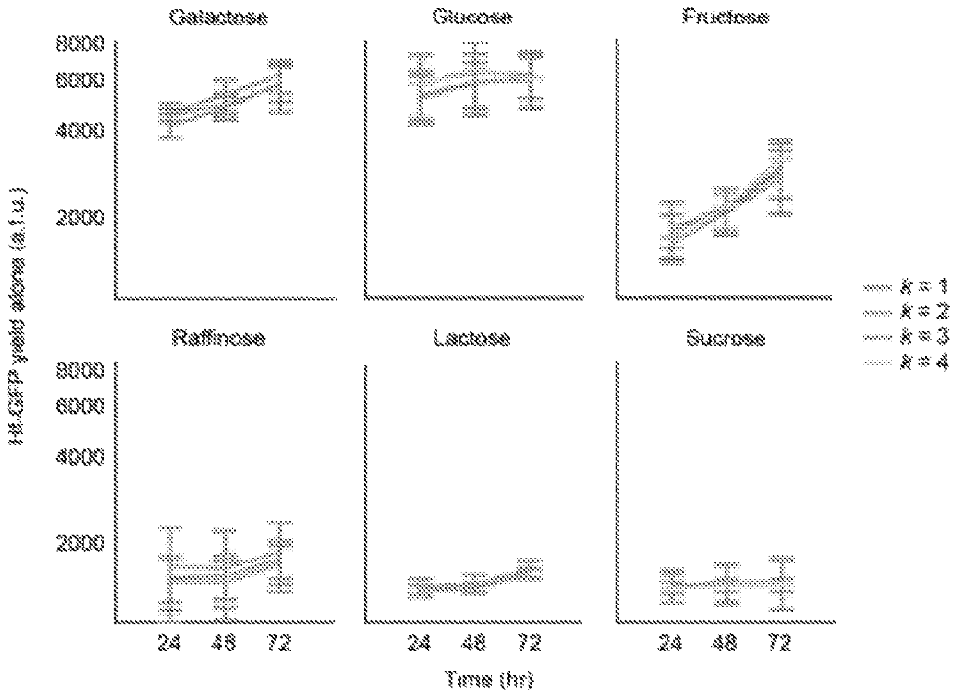
Figure 7D:
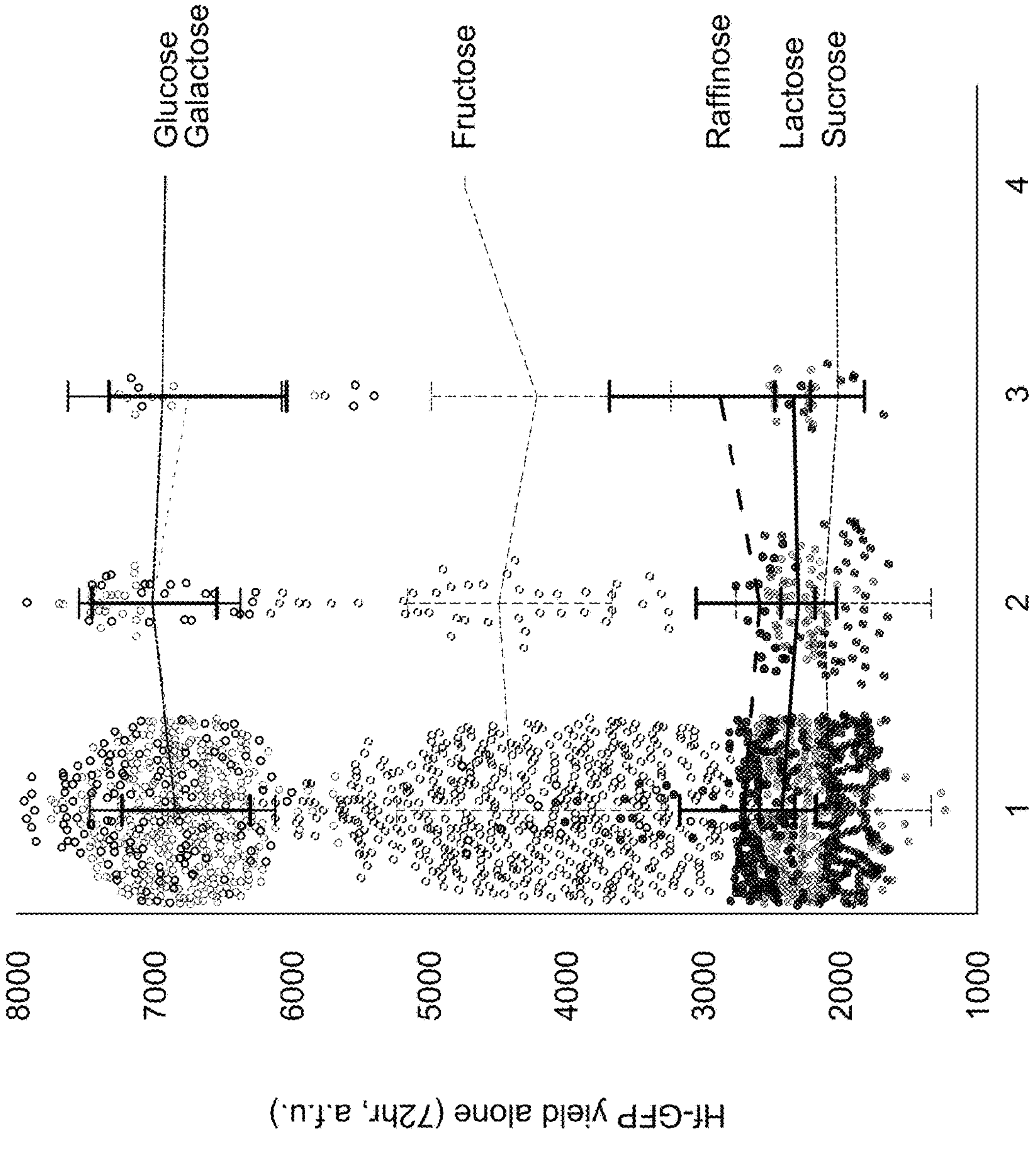

It was observed that increases in the microwell size and the number internal posts as k increased produced no gross effects on the growth rate (FIG. 7C) or final yield (FIG. 7D) of the model organism *H. frisingense* used in the instant screen ("*H. frinsingense* facilitation screen" section below). Minimal evaporation was detected comparing droplets at 24 and 72 hrs (FIGS. 29A and 29B), and it is likely that this exerted little effect on microbe growth given the observation herein that different microbes reach saturation in droplets and 96-well plate cultures on similar timescales (FIGS. 9A-9C, 10A and 10B).

For propagation of fungal cells (e.g., filamentous fungi including *aspergillus, penicillium*, and *mucor*) flasks containing an appropriate liquid medium (e.g., Y M Agar, Sabouraud's Agar, Potato Dextrose Agar, Yeast Extract Peptone Dextrose, Malt Extract Agar, Cornmeal Agar, V8 Juice Agar, and Czapek's Agar) were inoculated with a loopful of cells from stock cultures and incubated overnight in an orbital shaker (150-180 rpm) at 30° C. For some fungal cultures, conidia can be harvested from cultures on agar plates by flooding the surface of the plates with 5 ml of PBS containing 0.025% (v/v) Tween-20 and rocking gently. The conidial suspension is then recovered and dispensed into a 15 ml sterile tube.

Cells were harvested from overnight-grown liquid cultures or from conidial suspension by centrifugation (approximately 3,000 g for 5 min at 4° C.), and supernatant was removed, with pellets washed twice in sterile PBS (by resuspending the pellet in approximately 20 ml of ice-cold buffer, vortexing vigorously, followed by centrifugation as above). Because fungal cells tend to settle and/or aggregate, cell suspensions were vortexed vigorously after washings and before pipetting for the different manipulations used.

The final pellet of cells was resuspended in approximately 20 ml of appropriate medium prewarmed to an appropriate temperature. From the resulting cell suspension, 1:100 and/or 1:1,000-fold dilutions were prepared in the same respective medium and the cells were counted using a hemocytometer and a bright field microscope with a 40× objective. After counting, the volumes needed to prepare a suspension of cells were calculated. The cell suspensions were emulsified and then added to the kChip for each isolate under investigation.

Carbon Source Input Preparation

A bank of kChip-deployable growth substrates was developed from which libraries could be drawn for use in screening (FIG. 33). Carbon compounds in this bank met the following criteria: (1) the compounds were soluble at 2% w/v in water; (2) the solutions were emulsifiable using Bio-Rad QX200 cartridges; (3) the integrity of the color code signals were maintained despite the presence of the carbon compound (or impacts could be mitigated by careful selection of the fluorescent dye concentrations).

kChip Input Preprocessing

If droplets containing microbial cultures were to be generated, cell cultures were first normalized to the desired starting density in MM+0.5% w/v BSA ("Microbial culture input preparation" section above). If droplets containing carbon sources were to be generated, 2% w/v carbon source in water was prepared and sterilized 24-48 hrs in advance ("Carbon source input preparation" section above). Droplets could also be generated containing both a microbial culture and carbon source prepared in this manner (as in the Hf-GFP facilitation screen outlined in FIG. 3A).

To identify the contents of a given droplet, every unique input (e.g. a strain or environmental condition) received a "color code", or unique ratio of three fluorescent dyes (standardized to a total final dye concentration of 1 μM or 10 μM) —prior to generating droplets (FIG. 8). Each set of three dyes collectively labeled each specific input. These three dyes were chosen among Alexa Fluor 488, Alexa Fluor 555, Alexa Fluor 594, and Alexa Fluor 647, all of which have distinct excitation and emission spectra ("Fluorescence microscopy" section below). The selection of fluorescent dyes ensured that interference with any fluorescence-based assay signals (such as GFP, YFP, or resorufin) was avoided ("Fluorescently labeled microbe assay in droplets" and "Resazurin assay in droplets" sections below). The broad agreement in substrate-specific growth between droplets (which included color codes) and 200-μL cultures in 96-well plates (which had no color codes) (FIGS. 2C, 10A and 10B) indicated that inclusion of the encoding dyes did not confer any gross growth defects on the 10 strains tested.

Droplet Making and kChip Loading

After microbial inputs were normalized ("Microbial culture input preparation" section above) and/or carbon sources prepared ("Carbon source input preparation" section above), all inputs were preprocessed, i.e. color codes and BSA were added as necessary ("kChip input preprocessing" section above). Droplets were then produced on a Bio-Rad QX200 Droplet Generator (which generated roughly 20,000~1-nL emulsifications prepared per 20 μL input for eight inputs at a time, three minutes per 8-input cartridge). The continuous phase was a fluorocarbon oil (3M Novec 7500). For droplet making, 2% w/w fluorosurfactant (RAN Biotech 008 FluoroSurfactant) was added to stabilize droplets.

Droplets were pooled in equal proportions to prepare a total of 200 μL of droplet suspension, or ~200,000 droplets (e.g. for a set of 16 inputs, 200/16=12.5 μL of droplet suspension of each input would be pooled and mixed via micropipette), which was then injected into a custom built kChip loading apparatus in a single dispensing step (FIG. 5C). The loading apparatus consisted of two acrylic pieces. The bottom piece held in place a piece of custom-cut glass (Brain Research Laboratories; 1.2 mm thickness) made hydrophobic via pretreatment with Aquapel. The top side of the kChip, which was not coated with parylene ("kChip design and fabrication" section above), spontaneously formed a seal with the top piece of acrylic. Four neodymium magnet pairs were oriented such that the two acrylic pieces repelled each other. Working against this repulsive force, the top piece was lowered toward the bottom piece via tightening nuts until the desired standoff between the glass and kChip was attained (~500-700 μm) to create a space for flow under the microwells (FIG. 5C). Via a slot in the top acrylic piece and kChip, the flow space was pre-wetted with an injection of oil (~3 mL to fill the entirety of the flow space) followed by the pooled droplets. Buoyant in the surrounding oil, the droplets were distributed around the flow space via tilting the loading apparatus. Droplet entry into microwells above was a random process whereby each microwell sampled a set of k droplets ("kChip loading statistics" section above). After the droplets had passed through the flow space and entered microwells, additional oil (no fluorosurfactant) was flushed through the device to wash away excess droplets and fluorosurfactant. The wingnuts were tightened further to bring the kChip into contact with the glass and limit inter-microwell crosstalk (32).

Figure 31A:
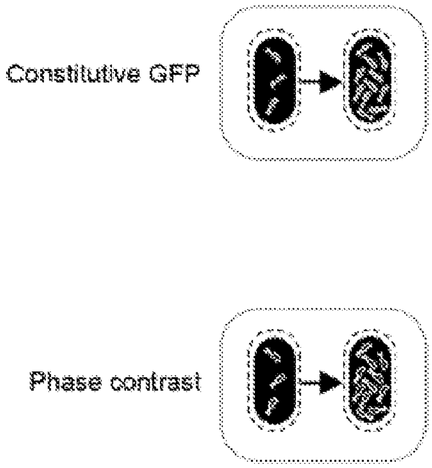
FIGS. 31A-31C show that phase contrast microscopy enabled a label-less and reagent-free growth readout for unlabeled microbes.
Figure 31B:
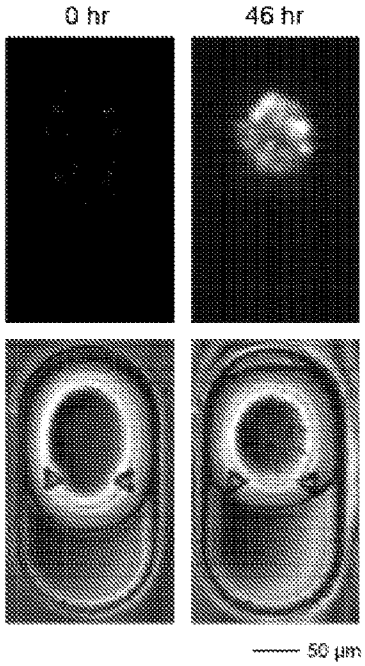
Figure 31C:
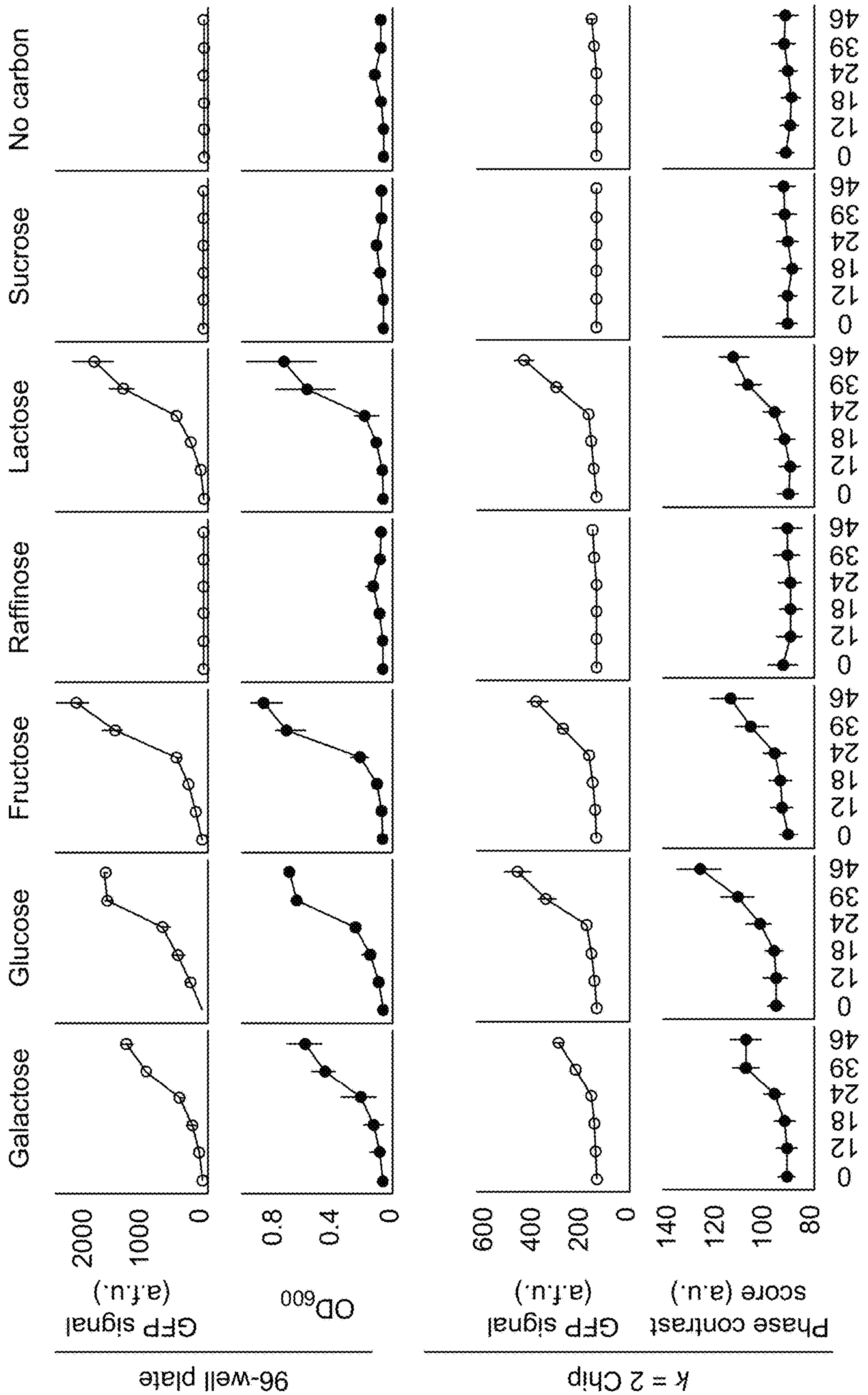

The kChip was scanned initially at 2× magnification to identify the droplets in each microwell from their color codes (FIG. 8 and "Fluorescence microscopy" section below). Droplets were then merged within their microwells via exposure to an alternating current (AC) electric field (4.5 MHz, 10,000-45,000-volts) underneath the glass. The field was generated by corona treater (Electro-Technic Products), the tip of which was moved around the glass for ~10 seconds. Without application of the electric field, spontaneous merging of droplets was rare (detected as incorrectly loaded microwells in FIGS. 7A-7D). The kChip was imaged subsequently in accordance with the relevant optical or fluorescent assay. Growth assays tested on the kChip included monitoring constitutive fluorescent protein expression ("Fluorescently labeled microbe assay in droplets" section below), reduction of resazurin to fluorescent resorufin ("Resazurin assay in droplets" section below), and phase contrast microscopy (FIGS. 31A-31C).

Setting up the kChip loading apparatus in preparation to receive droplets took 5-10 minutes and was completed ahead of time. The remaining setup time was ~30 minutes: Droplet making took ~3 minutes per eight inputs on the Bio-Rad QX200, droplet pooling and mixing took ~5 minutes, loading the kChip took ~5-10 minutes, and scanning the kChip took ~12-15 minutes.

kChip Loading Statistics

The appropriate number of distinct inputs n can be calculated prior to loading a kChip to ensure the desired number of replicates of a distinct composition of s droplets is attained (with a full breakdown of the realized screen size and degree of replication outlined in FIG. 35). The number of replicates is determined by the following factors: (1) the total number of distinct inputs, n; (2) the number of droplets per microwell, k; (3) the desired number of inputs per composition, s (where s is ≤k); and (4) Nk, the total number of observed microwells filling with k droplets (FIG. 18A). In some cases it is desirable that s be lesser than k. For example, to measure the robustness of a pairwise effect for the composition [A+B] (s=2) to additional inputs in the library, all instances where the set [A+B] appears with any given additional input(s) for the communities [(A+B)+X+Y+ . . . ] (k≥3) can be measured.

A formula for the probability p that all k droplets in a given microwell were unique and that a given desirable composition of size s was present among those k was derived (FIG. 18B). The case where s=k, i.e. the desirable subset composition is the same as the number of droplets loaded per microwell, for which p reduces to $n!/n^k$ was also considered. From here, the total expected number of replicates was determined by multiplying p by the number of observed microwells Nk.

Figure 17:
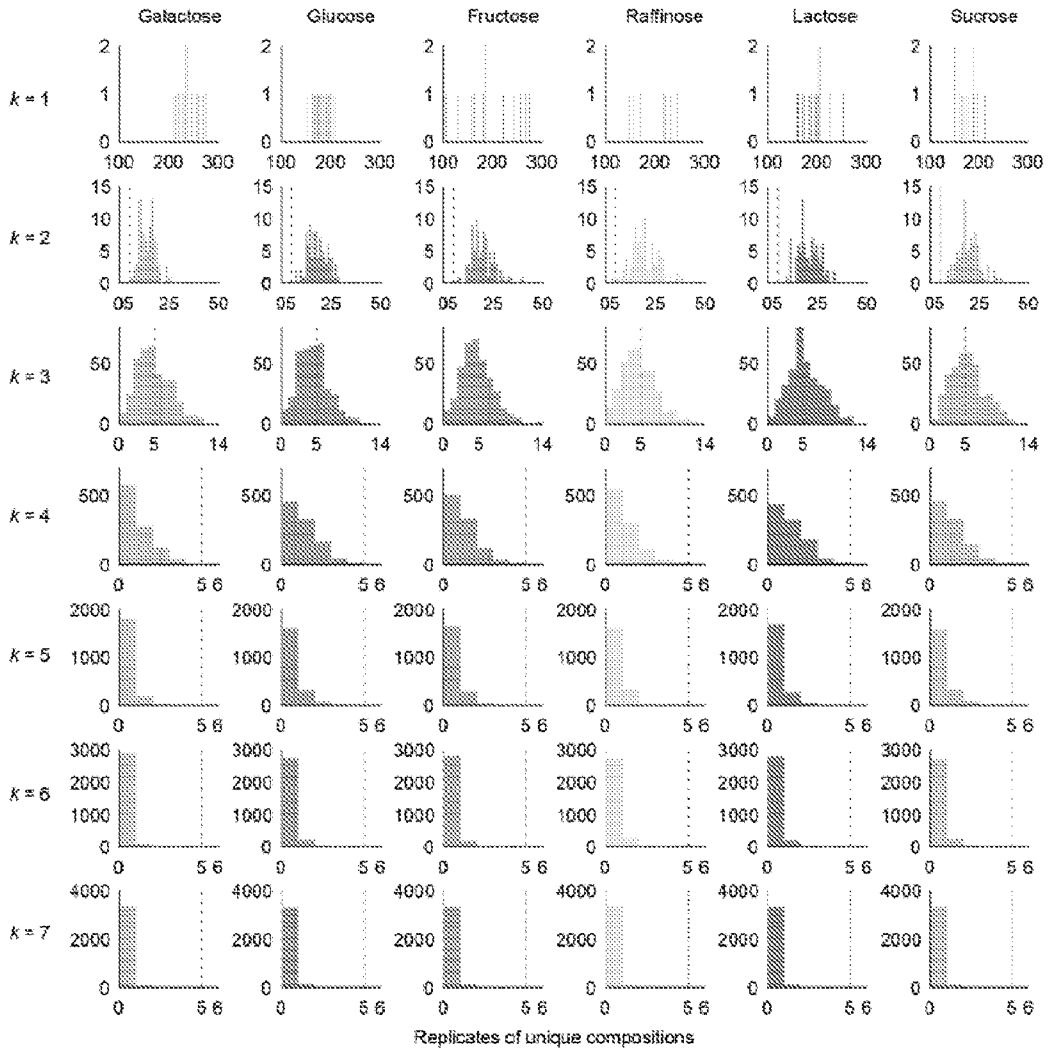
FIG. 17 depicts graphs of replicates of unique compositions. Compositions that were replicated ≥5 times in this screen occurred at k=1, 2, and 3. The number of replicates at each k was determined by the sampling (number of microwells per kChip) and library size. For the Hf-GFP facilitation screen, all k=1, almost all k=2, and ~half of k=3 compositions were represented ≥5 times (see FIG. 35 below). Almost no compositions for k≥4 were represented ≥5 times. Dotted gray line=5 replicates, the expected (see FIGS. 18A-18D below) and actualized mean representation of unique compositions in k=3 microwells. The cutoff for inclusion in FIG. 3E above was that a composition was replicated ≥30 times across the six kChips in the screen (though they did not need to be represented ≥5 times/kChip).

For library sizes n=8, 16, 25, and 50, the sampling probability and mean number of replicates obtained were plotted for one of the instant k=(1:7;19) Chips for desired subset compositions s=1, 2, 3, and k (FIG. 18B). Notably, for the Hf-GFP facilitation screen conducted presently (n=16), we predicted and confirmed (FIG. 17 and FIG. 35) that a given composition of three strains s=3 would be represented ~5 times on average in k=3 microwells and increasingly among all communities at the higher values of k. This greater representation allowed for the inspection of the robustness of three-input compositions to the presence of additional inputs in k≥4 microwells.

Figure 18C:
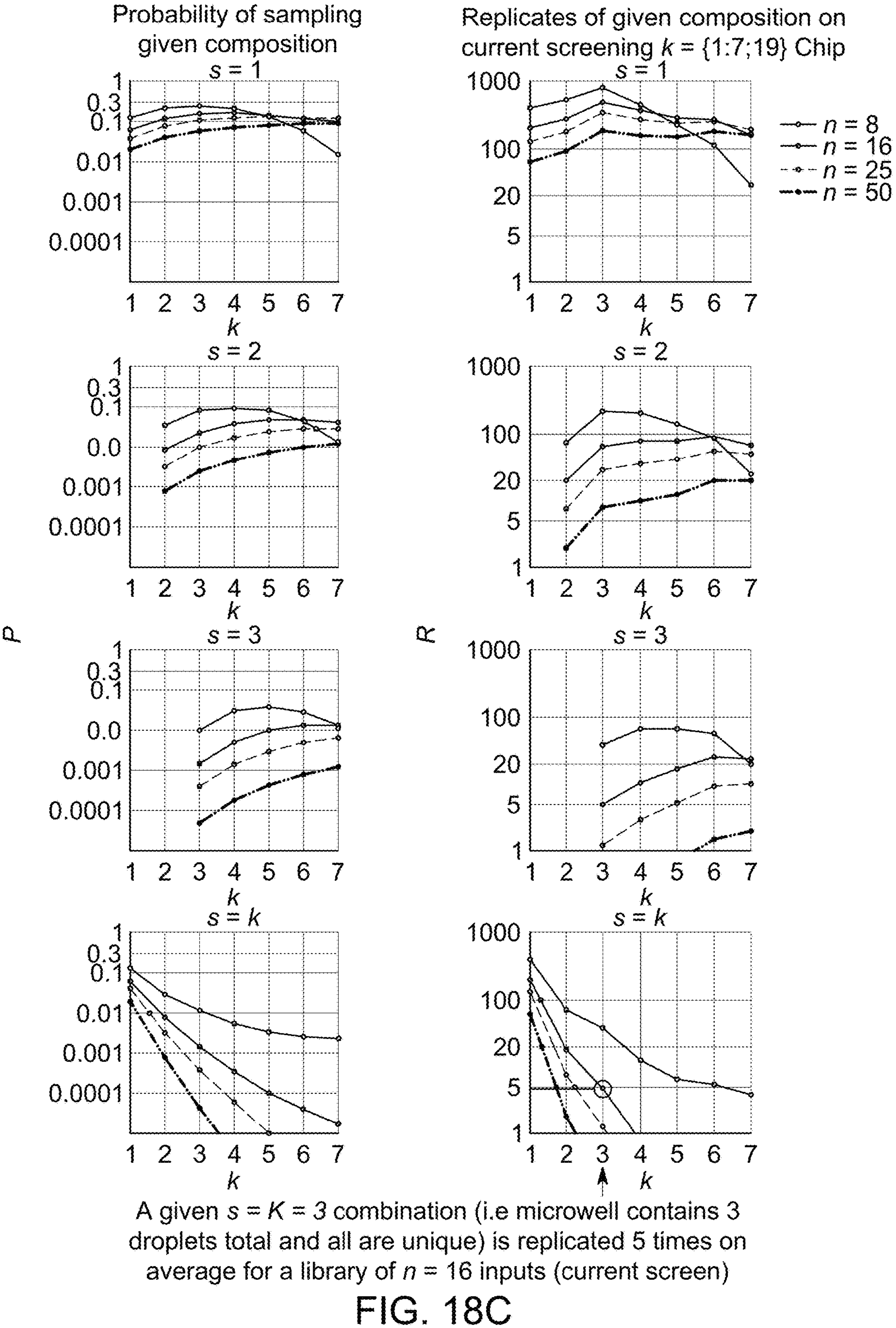
Figure 18D:
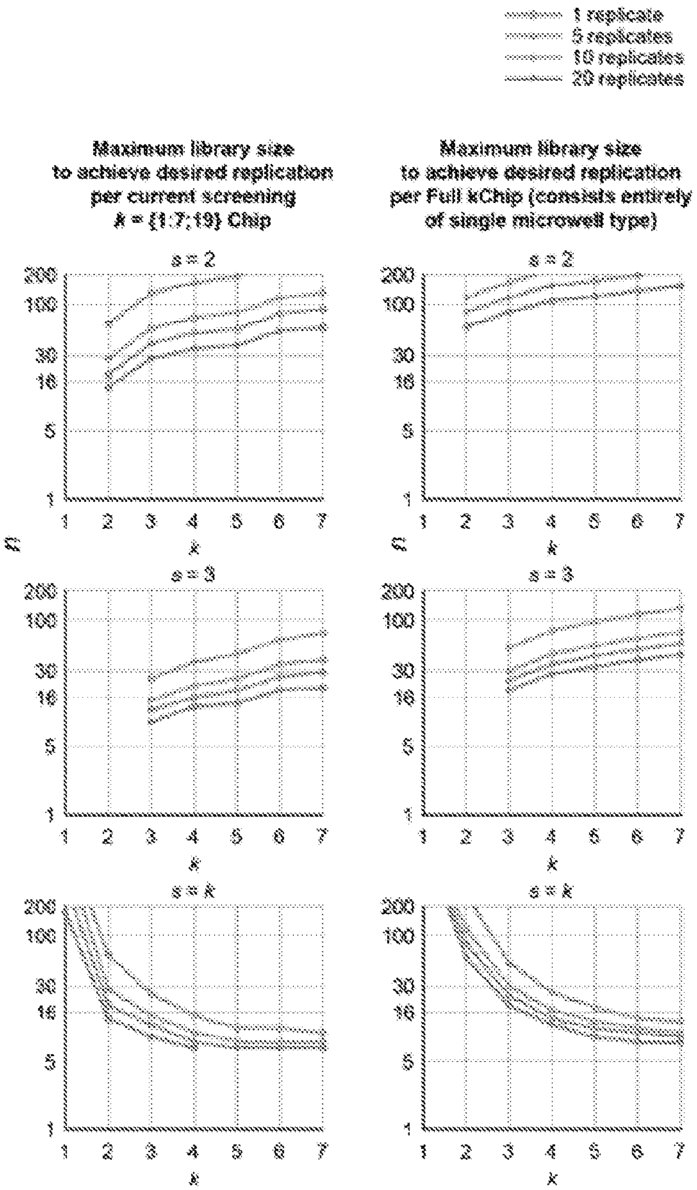

From FIG. 18C (bottom-most plot), it is apparent that the probability of sampling a given composition at high k decreases quickly, especially for large input libraries (e.g. for a given k=7 combination and a library size of 25 inputs, there are ~2.6e6 possible configurations, and the probability of sampling a given combination of all unique inputs approaches 0.00001). This small probability is further exacerbated by the relatively larger footprint of a k=7 microwell that results in fewer microwells per kChip compared to smaller values of k (e.g. ~13,000 k=7 microwells takes up the same amount of space as ~60,000 k=1 microwells). While one way to overcome the sampling issue is to use more kChips to generate more combinations (see below), the primary reason undersampling occurs at higher k is due to the exponential increase in combinatorial space (which has little to do with the sub-linear decrease in microwell density with k). FIG. 18D (right panel) plots the expected number of replicates per Full kChip. From these plots, it's clear that to achieve >1 replicate on average per combination on a single k=7 Chip, a library of 25 inputs is far too large. However, sampling among composition subsets s<k remains high for relatively small s, even for large library sizes. To achieve 20 replicates on average per s=3 combination among k=7 microwells, for example, a library of ~40 inputs could be used. To achieve 1 replicate on average, a library of >100 inputs could be used. This sort of experimental set up is useful for identifying combinations, e.g. facilitative communities consisting of 2 or 3 isolates, when the experimenter wishes to test the robustness of the facilitative effect to the presence of additional, randomly sampled microbes from the library (the analysis described in FIGS. 3D-3E).

In practice, it may be advantageous to work with kChips with an assortment of different microwell types, as exemplified herein, or kChips composed entirely of single microwell type. For each of these cases, we calculated the maximum allowable library size to attain the desirable mean number of replicates per kChip (FIG. 18D).

Fluorescence Microscopy

All fluorescence microscopy was performed using a Nikon Ti-E inverted fluorescence microscope with fluorescence excitation by a Lumencor Sola light emitting diode illuminator (100% power setting). Images were taken across up to four fluorescence channels-three for the color codes ("kChip input preprocessing" section above) and one additional channel for fluorescence-based assays ("Fluorescently labeled microbe assay in droplets" and "Resazurin assay in droplets" sections below). Each dye (or assay signal) was detected with a different excitation wavelength generated by a collection of excitation filters (FIG. 8): Alexa Fluor 488 dye (or GFP or YFP expression, FIG. 2A) by Semrock GFP-1828A (blue excitation); Alexa Fluor 555 dye (or resazurin/resorufin, FIG. 2B) by Semrock SpGold-B (green excitation); Alexa Fluor 594 dye by Semrock FF03-575/25-25 [excitation filter]+FF01-615/24-25 [emission filter] (yellow excitation); and Alexa Fluor 647 dye (or *C. reinhardtii* autofluorescence, FIGS. 30A-30E) by Semrock LF635-B (red excitation). At the image analysis stage ("kChip image analysis" section below), the emission signals corresponding to each dye channel were used to identify the contents of a given droplet within each droplet grouping prior to droplet merging (FIG. 8). The final channel was used post-merge and at subsequent time points to quantify the assay signal.

Images were collected by a Hamamatsu ORCA-Flash 4.0 CMOS camera (exposure times range 50 ms-500 ms) and 2× optical magnification (with 2× pixel binning resulting in 6.5 μm/pixel resolution). The total scanning time for a single kChip was 12-15 minutes.

Fluorescently Labeled Microbe Assay in Droplets

Figure 2A:
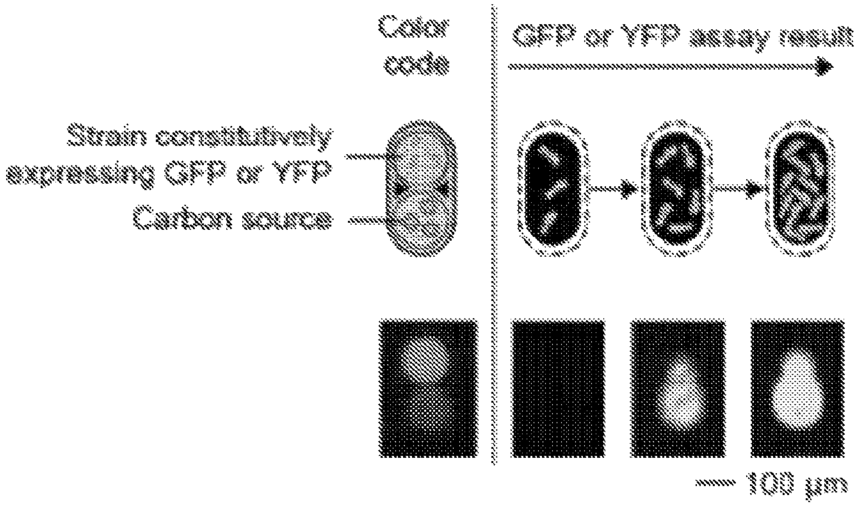
FIGS. 2A-2F show how carbon utilization profiles of labeled and unlabeled strains were measured on k=2 chips.
Figure 2B:
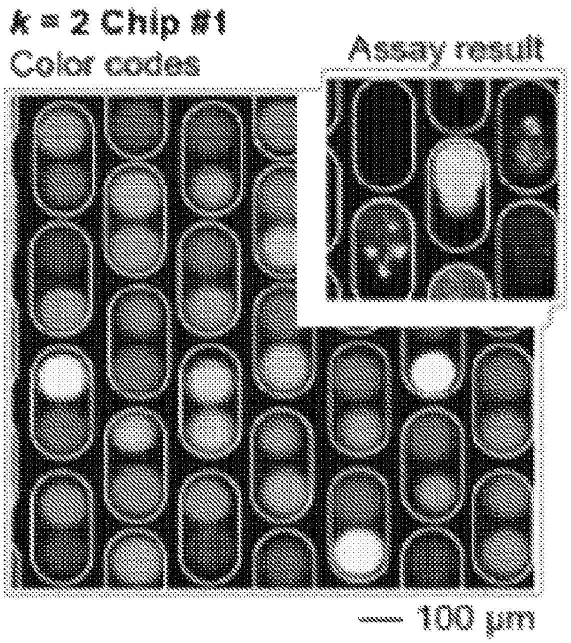
Figure 2C:
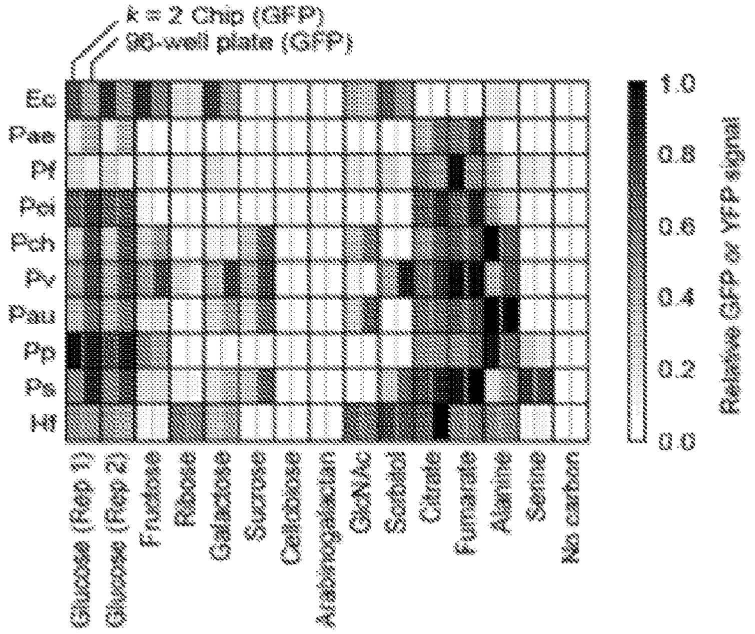
Figure 2D:
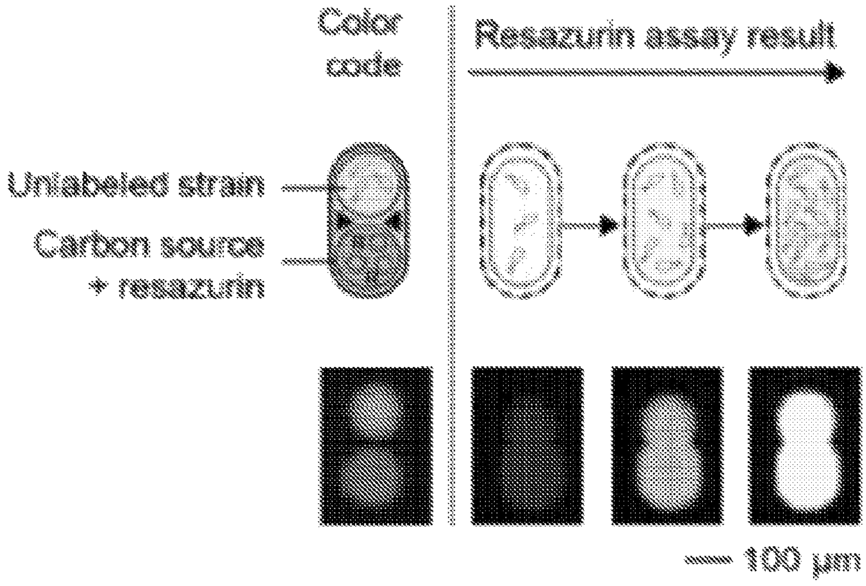
Figure 2E:
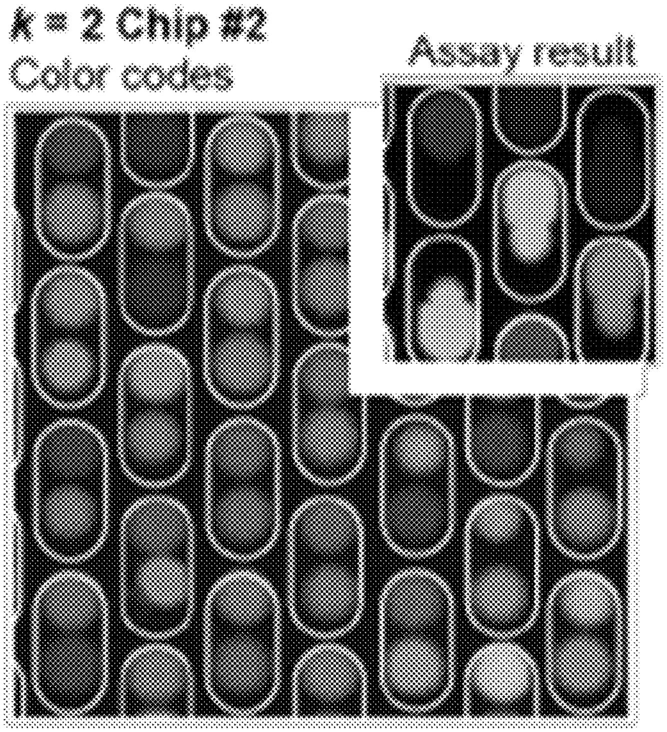
Figure 10A:
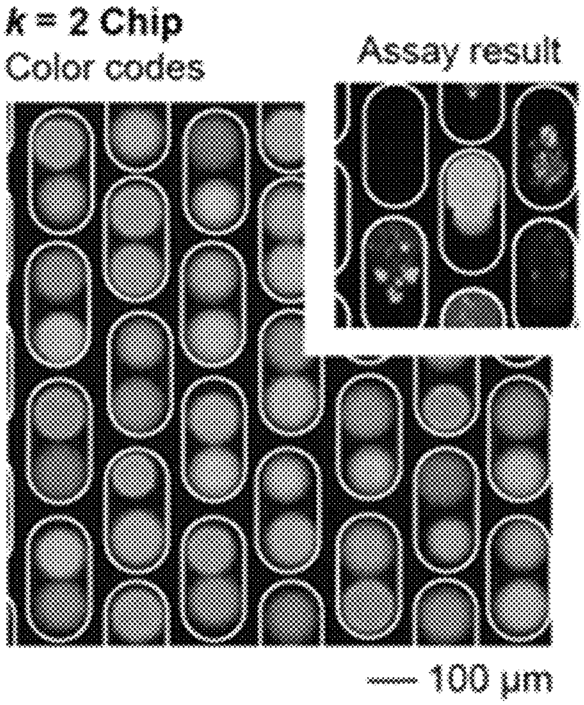
FIGS. 10A and 10B show carbon utilization profiles that were obtained on k=2 Chips via constitutive fluorescent protein expression and match standard culture techniques.
Figure 10B:
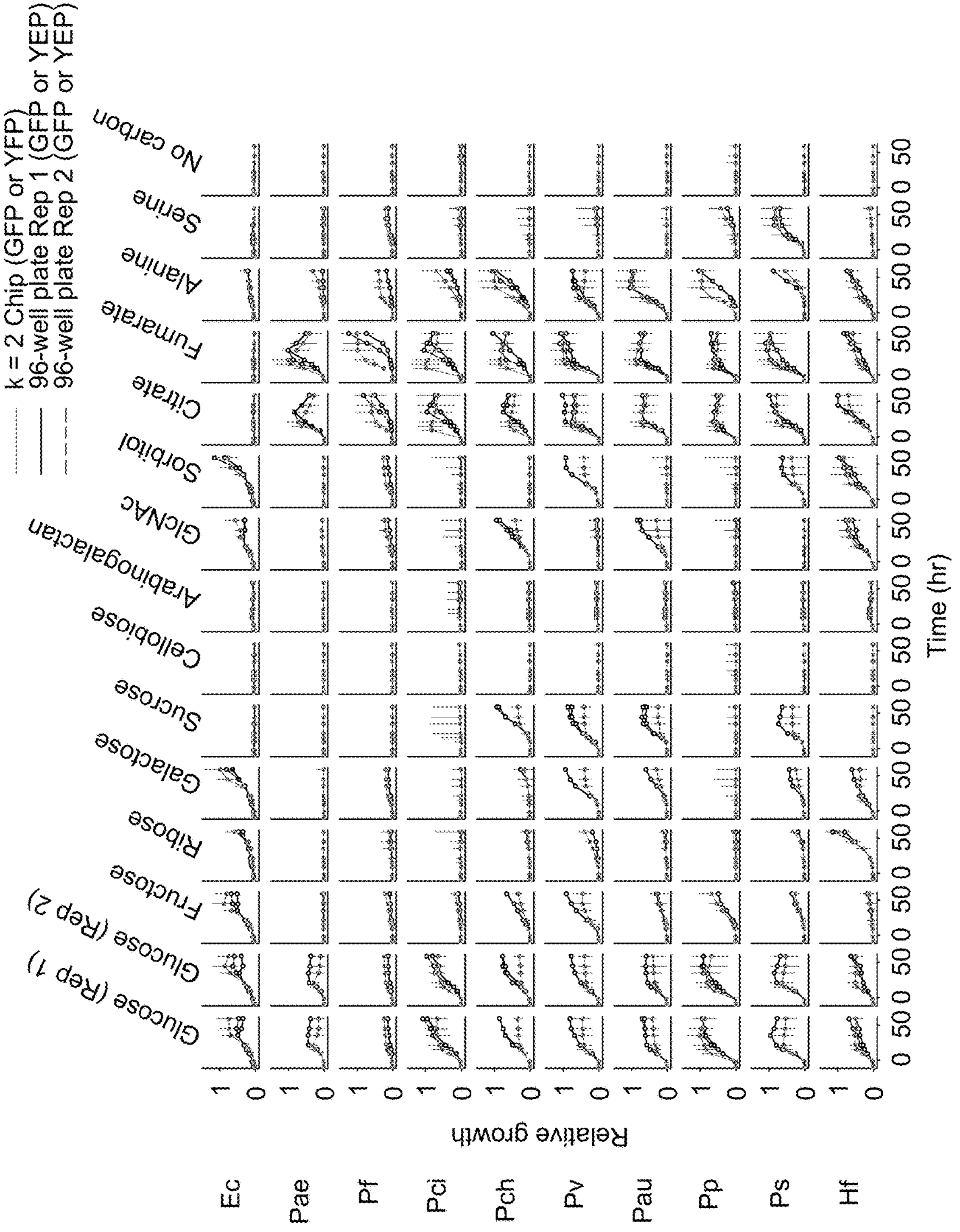
Figure 30A:
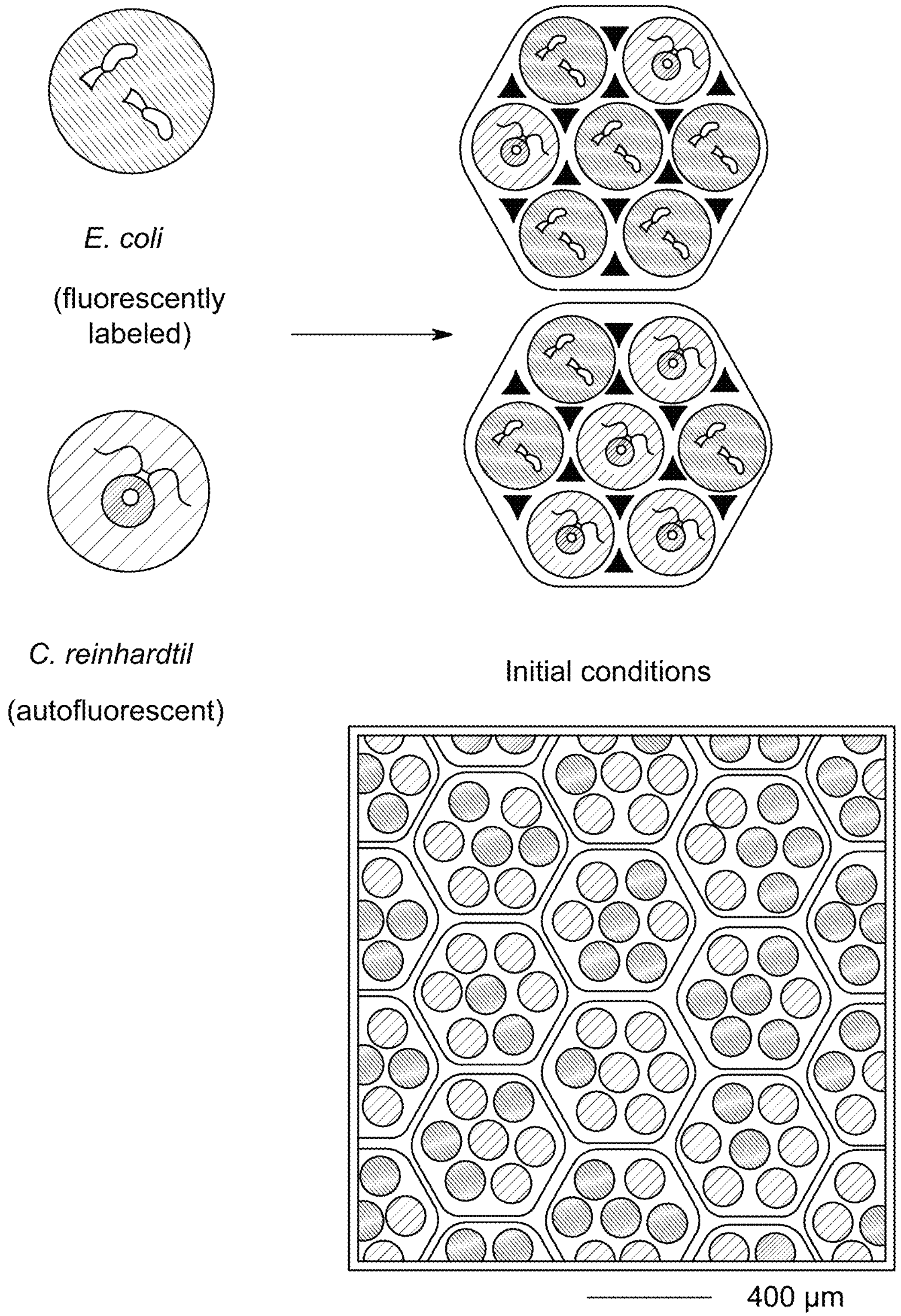
FIGS. 30A-30E show additional kChip screening functionalities, including co-culture monitoring and control of physical abiotic environment conditions.

A panel of strains constitutively expressing a fluorescent protein (GFP or YFP; either plasmid-mediated or genome integrated) was obtained (FIG. 32). An autofluorescent (naturally fluorescing) eukaryotic alga (*Chlamydomonas reinhardtii* CC-503) was also acquired (FIG. 30A). Agreement between carbon utilization profiles was demonstrated for cultures in droplets and standard 96-well plate bulk cultures (SpectraMax plate reader) (FIGS. 2C, 10A and 10B). The fluorescent dyes Alexa Fluor 555, 594, and 647 were used to avoid overlap with the GFP or YFP excitation channel (i.e. Alexa Fluor 488 was excluded from the encoding set) ("Fluorescence microscopy" section above). For experiments involving the *C. reinhardtii* CC-503, which was autofluorescent for red excitation, the fluorescent dyes Alexa Fluor 488, 555, and 594 were used (i.e. Alexa Fluor 647 was excluded from the encoding set). Multiple fluorescent organisms can be monitored simultaneously. For example, *C. reinhardtii* was monitored in co-culture with GFP-labeled *E. coli* (FIG. 30A) (for which both Alexa Fluor 488 and Alexa Flour 647 were excluded from the encoding set).

Any kChip screen could be designed whereby the growth of a fluorescent strain or set of fluorescent strains is screened against biotic backgrounds (i.e. microbial communities) ("Microbial culture input preparation" section above), abiotic backgrounds (e.g. drug combinations, carbon source combinations) ("Carbon source input preparation" section above), or a combination thereof.

Resazurin Assay in Droplets

Figure 24:
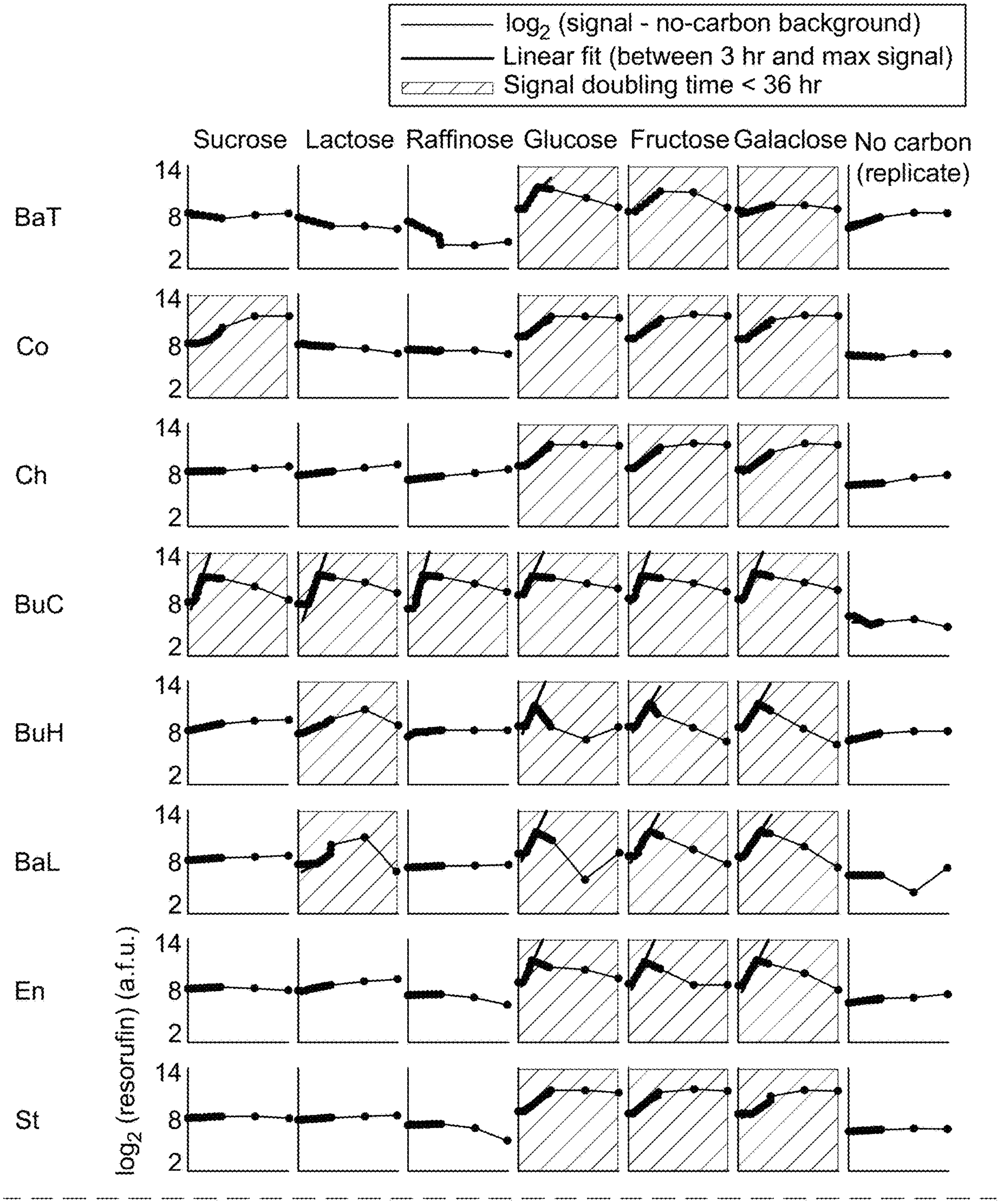
FIG. 24 shows the results of the resazurin assay, which was used to measure growth rate of the isolates on each carbon source. The fluorescence of resorufin was measured every 30 minutes for 24 hours and again at 48 and 72 hrs. The $\log_2$ (background-subtracted resorufin) signal was calculated (signal used for subtraction was a no-carbon control, not shown here) and a linear fit was performed between the 3-hr time point and the maximum signal (see FIG. 4C above). Gray plots=at least one doubling has been detected by 36 hr (midpoint of the screen). A replicate no-carbon control set of droplets (shown) was also included and produced no false positives by this metric.
Figure 24:
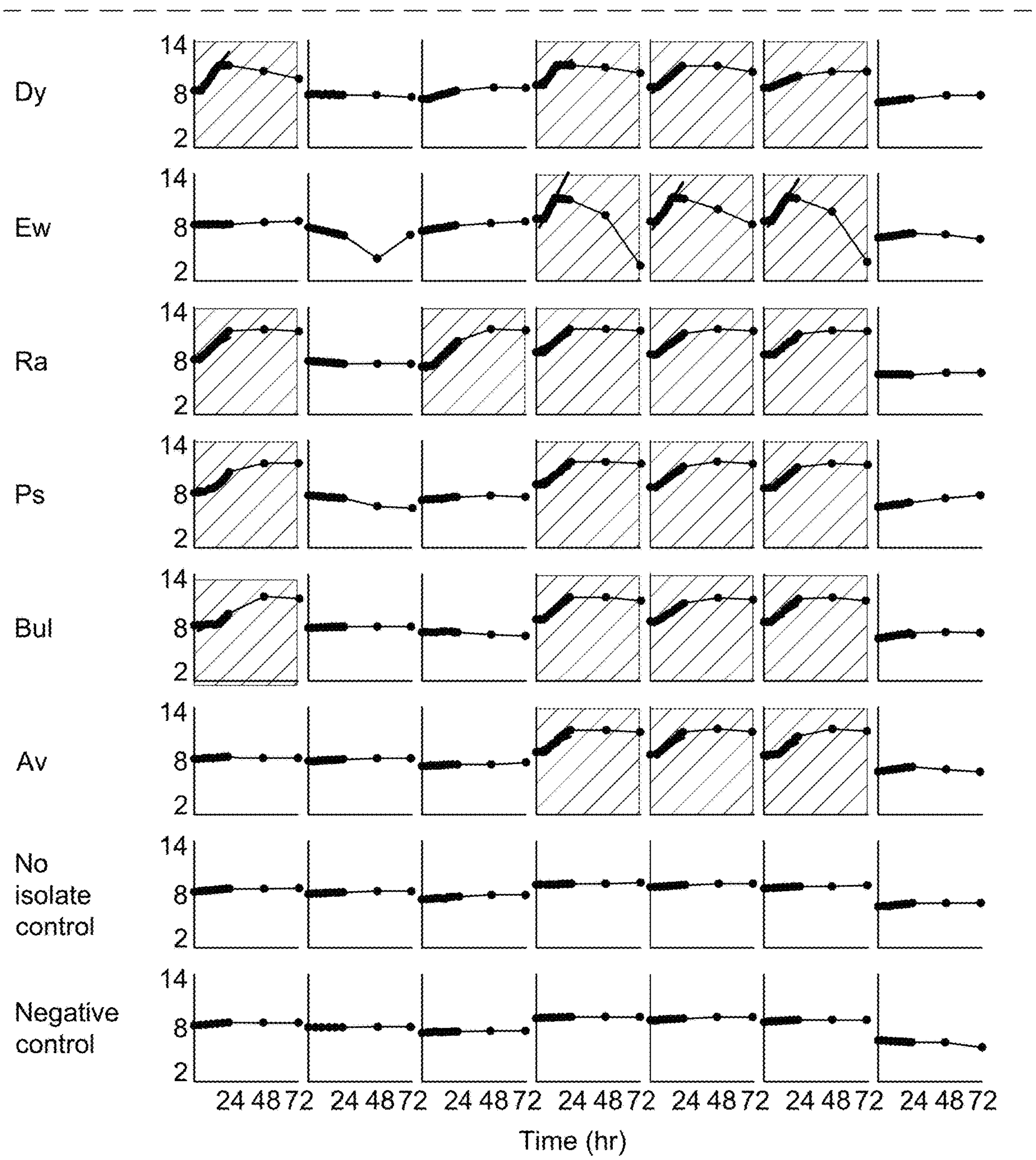

In the presence of respiring microbes, the blue indicator dye resazurin is reduced to the pink, fluorescent dye resorufin (52), and therefore constitutes a colorimetric and fluorescent indicator of cell metabolic activity. Here, levels of resorufin were measured dynamically as an assay for cell growth, to characterize the growth of a given strain across an assortment of carbon sources (FIGS. 2B and 24). In some cases, resorufin further reacts to yield non-fluorescent products, which results in a drop in resorufin fluorescence at later times.

To assess how well the resazurin assay in droplets recapitulated 96-well plate growth as assayed with the conventional $OD_{600}$ readout (FIG. 58), two sets of droplets were created. The first set of droplets (three types in total) contained microbial monocultures with no carbon source (normalized to $OD_{600}$=0.01, such that, upon merging within k=2 microwells, starting $OD_{600}$=0.005 in MM+0.05% w/v BSA). The second set of droplets (four types in total) was generated that contained single carbon sources (1% w/v) with 80 μM resazurin (such that, upon merging within k=2 microwells, the final carbon source concentration was 0.5% w/v and the final resazurin concentration was 40 μM). The fluorescent dyes Alexa Fluor 488, Alexa Fluor 594, and Alexa Fluor 647 were used to minimize interference with the excitation spectrum of resorufin ("Fluorescence microscopy" section above). These dyes were added at 10 μM, rather than 1 μM, to mitigate interference from the absorbance of the fluorescent dye signals by resazurin (at 80 μM). Upon merging of droplets in k=2 microwells, strains were thereby contacted with both a carbon source and the resazurin. If the carbon source enabled growth, a fluorescent signal corresponding to the accumulation of resorufin was detected.

Cultures were kept at 21° C., their yield was measured up to 50 hr. For each strain, measurements were normalized by first subtracting the background fluorescence of each carbon source (in a merged droplet containing only the carbon source and no strain), and then subtracting background resorufin fluorescence of each strain (in a merged droplet containing only the strain but no carbon source; this might be attributable to metabolic activity that is unrelated to utilization of the carbon source added to the media, e.g. carbon stored intracellularly). Resorufin signals were then normalized for each strain by the maximum across all carbon sources and time points.

Environmental Microbe Isolation

Soil samples (two ~10 cm columns of topsoil, ~1 cm in diameter) were collected from Middlesex Fells Reservation in Somerville, MA (2:20 μm, Nov. 12, 2017, 2:20 μm, 5.6° C.). These samples were diluted in PBS within a few hours of collection (5 g soil of each vortexed in 40 mL PBS). Single strains were first isolated from streaking 70 μL of dilutions of this mixture ($10^{-1}$, $10^{-2}$, $10^{-3}$, and $10^{-4}$) on 20 different solid (agar) media (Tryptic Soy Broth (TSB) (Bacto), 1% v/v TSB, Lysogeny Broth (LB) (Bacto), 1% v/v LB, Nutrient Broth (NB) (Bacto), 1% v/v NB, M9 salts (Sigma-Aldrich)+0.5% w/v glucose, M9 salts+0.005% w/v glucose, M9 salts+0.005% w/v glucose+0.2% w/v casamino acids, M9 salts+0.005% w/v glucose+0.002% w/v casamino acids, M9 salts+0.5% w/v glucose+0.2% w/v casamino acids at pH=4 and 5, M9 salts+0.005% w/v glucose+0.002% w/v casamino acids at pH=4 and 5, Actinomycete Isolation Agar (Teknova), *Brucella* Agar (Teknova), *Streptomyces* Medium (Teknova), *Campylobacter* Medium (Teknova), Bordatella Medium (Teknova), and ATCC Medium 1111 (Teknova)). Strains were selected based on the following criteria: growth in LB liquid medium of transferred colony (25° C.), frozen glycerol stock revival in LB ($OD_{600}$>0.1) (30° C.), and subsequent growth on M9+0.5% w/v glucose (OD600>0.1) (30° C.). A 96-well working plate of isolates (LB, 25% v/v glycerol) was stored at −80° C.

Figure 13:
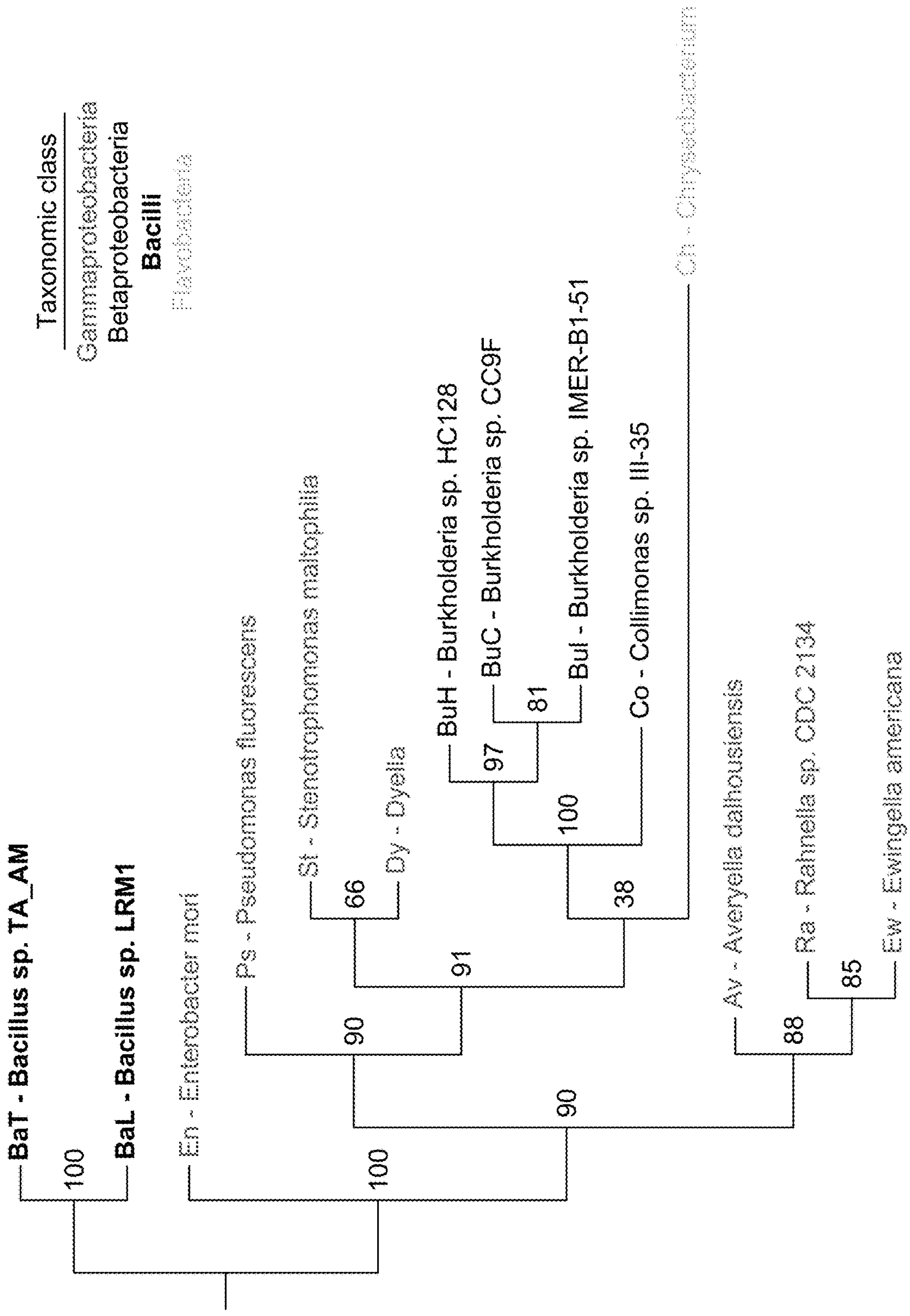
FIG. 13 shows a phylogenetic tree of 14 soil isolates used in a *H. frisingense* facilitation screen. Sequences of the V1 to V9 region of the 16S rRNA gene were obtained via Sanger sequencing (FIG. 34). Clustal X, with penalizations for gap opening and gap extension of 12 and 6, was used to align the sequences. PhyML-SMS with default parameters was used to select GTR as the best model of nucleotide substitution, to infer the tree, and to get bootstrap support values. Taxonomy classification and labels in the tree were obtained by selecting the sequence match with highest S_ab score from Seqmatch. *Sulfolobus solfataricus*, a thermophilic archaeon, was used as an outgroup species to root the tree.

Isolates included in the Hf-GFP facilitation screen (FIG. 13) were selected based on robust revival from glycerol stocks and subsequent culturing steps (as outlined in "Microbial culture input preparation" section above) with prioritization of more phylogenetically distant strains ("16S sequencing and phylogenetic assignment" section below).

16S Sequencing and Phylogenetic Assignment

Sequences of the 16S rRNA gene were obtained by Sanger sequencing. Clustal X with penalizations for gap opening and gap extension of 12 and 6 was used to align the sequences (53). PhyML-SMS with default parameters was used to select GTR as the best model of nucleotide substitution, to infer the tree, and to get bootstrap support values (54). Taxonomic classifications and labels used in the phylogenetic tree (FIG. 13) were obtained by selecting the hit with highest S_ab score obtained from Seqmatch (55). *Sulfolobus solfataricus*, a thermophilic archaea, was used as an outgroup species to root the tree.

*H. frinsingense* Facilitation Screen

Microbial cultures were prepared as described in the "Microbial culture input preparation" section above. The culture medium for *H. frisingense* revival from a glycerol stock also included the selection antibiotic kanamycin (30 μg/mL). Six carbon sources (galactose, glucose, fructose, raffinose, lactose, sucrose) were prepared as described in the "Carbon source input preparation" section above to a concentration of 2% w/v, which were added 1:1 with MM+0.05% w/v BSA to produce 1×MM+1% w/v carbon source (six unique MM each with one carbon source). A plate of 16 color codes were also prepared in advance at 50 μM total concentration ("kChip input preprocessing" section above).

At the onset of the screen, all cultures were washed three times and resuspended in MM+0.05% w/v BSA (no carbon source) and normalized to an initial $OD_{600}$=0.08. A "droplet plate" (96-well plate) was prepared whereby each of 16 wells, corresponding to the 16 input conditions of the screen, received the following four elements: (1) 50 μL MM+1% w/v carbon source; (2) 25 μL unique soil isolate at $OD_{600}$=0.08 (or a no-isolate control or a negative control); (3) 25 μL Hf-GFP at $OD_{600}$=0.08; and (4) 2 μL 50 μM color code. The two controls, a negative control and a no-isolate control, were in principle the same (just different color codes), with the negative control used to measure Hf-GFP monocultures and the no-isolate used to calculate isolate-mediated differences. The carbon source and color code were mixed in advance, though the cultures were added just before making droplets to load on a kChip.

After emulsification, each 1-nL droplet contained the following: (1) 0.5% w/v carbon source; (2) soil isolate at $OD_{600}$=0.02 (~20 cells) (or no-isolate control or negative control); (3) Hf-GFP at $OD_{600}$=0.02 (~20 cells); and (4) a set of color code (total concentration of all three fluorescent dyes at 1 μM). Droplets were prepared for each carbon source at a time and loaded onto a k={1:7;19} Chip, i.e. first all sucrose-containing droplets were prepared and loaded onto the first kChip in the screen, then all lactose-containing droplets were prepared and loaded onto the second kChip, and so forth. Because there were only 16 inputs in total, there were no instances where all inputs were unique in k=19 microwells. The instant analysis was focused upon the k=1-7 microwells, and specifically on instances where all droplets within a given microwell were unique. Throughput tradeoffs associated with this number of inputs and k values are discussed below.

Figure 3A:
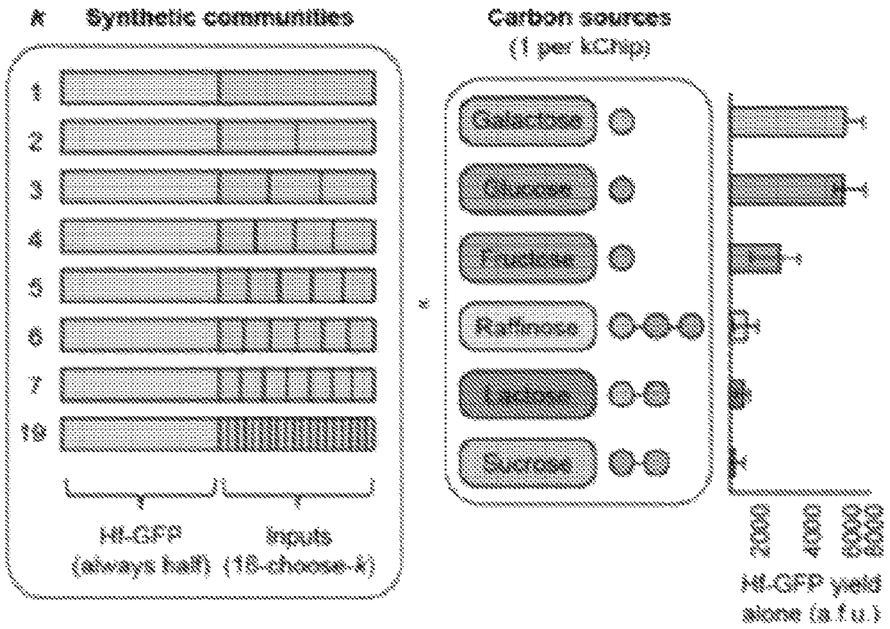

After loading droplets, the kChip was imaged to read the color-code of each droplet ("pre-merge" scan) and droplet sets were merged within their corresponding microwells ("Droplet making and kChip loading" section above). The post-merge communities contained the following: (1) 0.5% w/v carbon source; (2) k=1, 2, 3, 4, 5, 6, 7, or 19 soil isolates collectively at $OD_{600}$=0.02 (or no-isolate control or negative control); (3) Hf-GFP at $OD_{600}$=0.02; and (4) 1 μM mixed color codes (no longer serving a purpose). (All analyses in FIGS. 3A-3G and 4A-4D were conducted only considering microwells filled with isolate-containing droplets and no control droplets, as summarized in FIG. 35, such that the initial isolate $OD_{600}$ was always 0.02. That is, the final relative density of [Hf-GFP]:[total isolate] was 1:1, i.e. Hf-GFP made up about half of the initial biomass in the community and the total isolate content made up the remainder (FIG. 3A). The kChips were kept at 21° C. and imaged ("post-merge" scans) at 24 hr, 48, and 72 hr ("Fluorescently labeled microbe assay in droplets" section above). A breakdown of the total number of data points is shown in FIG. 35.

Figure 22:
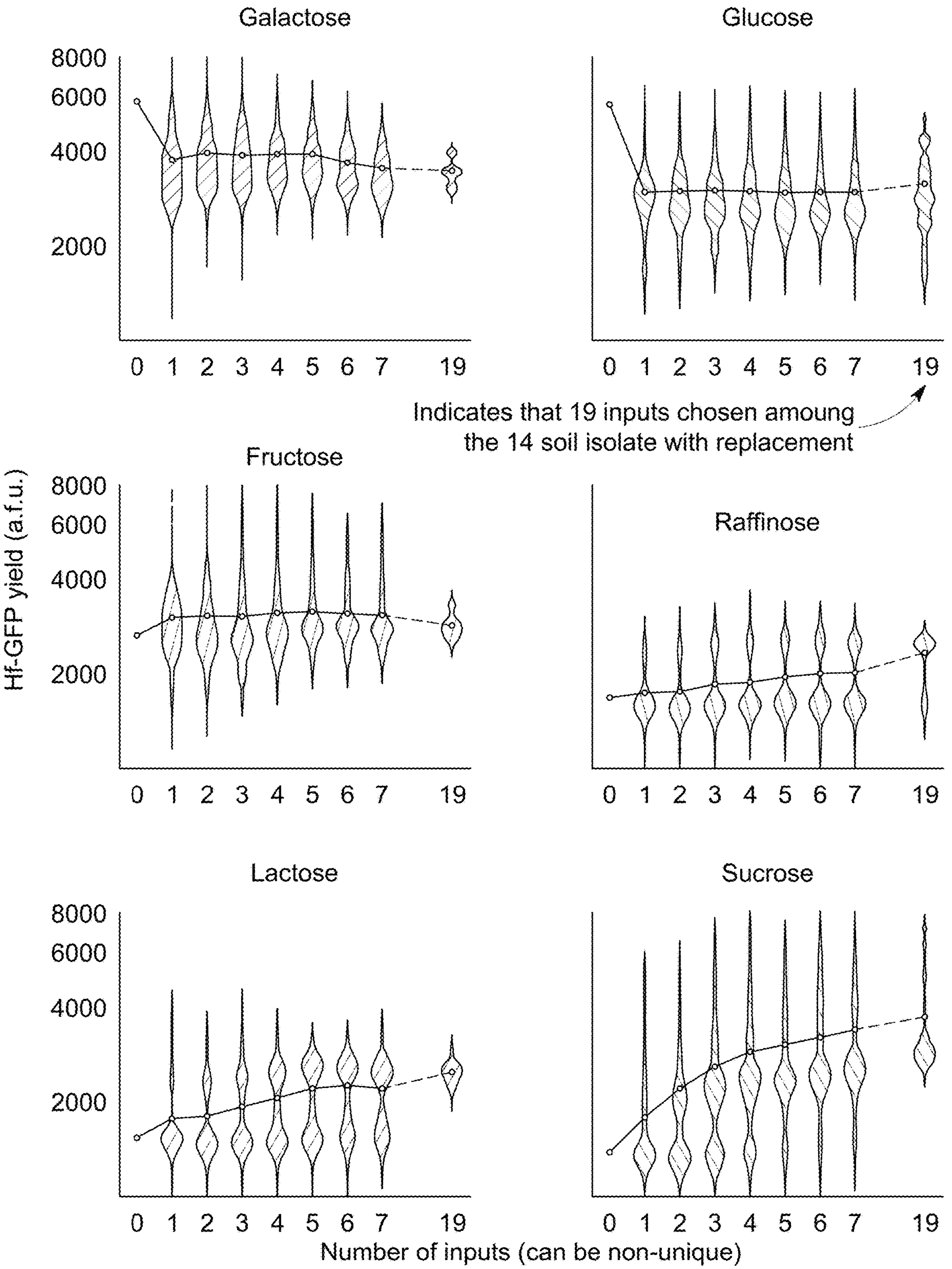
FIG. 22 shows graphs of Hf-GFP yield, which was measured across 1-7 and 19 combinations of inputs. If Hf-GFP yield is measured across all input combinations, even when the inputs within a microwell are non-unique (e.g. an instance of 3 inputs could include isolates [A+B+C], [A+B+B], or [A+A+A]), the qualitative trends observed when uniqueness is required (FIG. 4A and FIG. 21 above) are preserved for each carbon source. Hf-GFP yield did not differ substantially for 7 and 19 inputs, suggesting an agnosticism to increases in community richness in the regime of relatively high richness values. Black data points=means of distributions.
Figure 23:
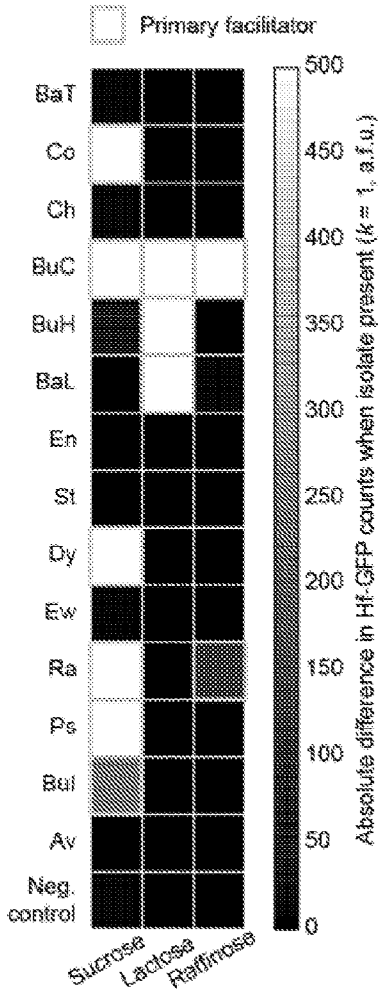
FIG. 23 shows that primary facilitators individually increased growth of Hf-GFP. Primary facilitators (outlined in orange) were classified as the isolates increasing median Hf-GFP yield by an absolute difference of >100 GFP counts (a.f.u.) over Hf-GFP monoculture yield. These are the isolates left out from the gray distributions in FIG. 4B above and highlighted for their ability to facilitate Hf-GFP in FIG. 4C above.

Following the loading of each kChip in the screen, a k=2 Chip was subsequently loaded with isolate-only droplets and carbon source-only droplets with resazurin (pre-merge concentration 1% w/v carbon and 80 μM resazurin; post-merge concentration 0.5% w/v carbon and 40 μM resazurin) ("Resazurin assay in droplets" section above). This kChip was imaged every 30 minutes for 24 hours and again at 48 and 72 hrs, enabling estimates of each isolate's growth rate on each carbon source (FIG. 22). The present resazurin assay was employed for both bacteria and fungi applications.

Identification of Highly Facilitative and Robust Compositions

Figure 3B:
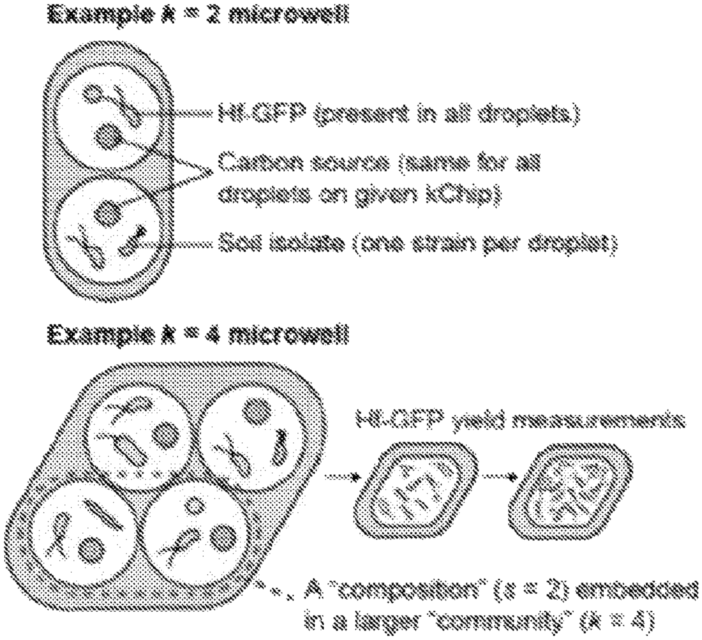
Figure 3D:
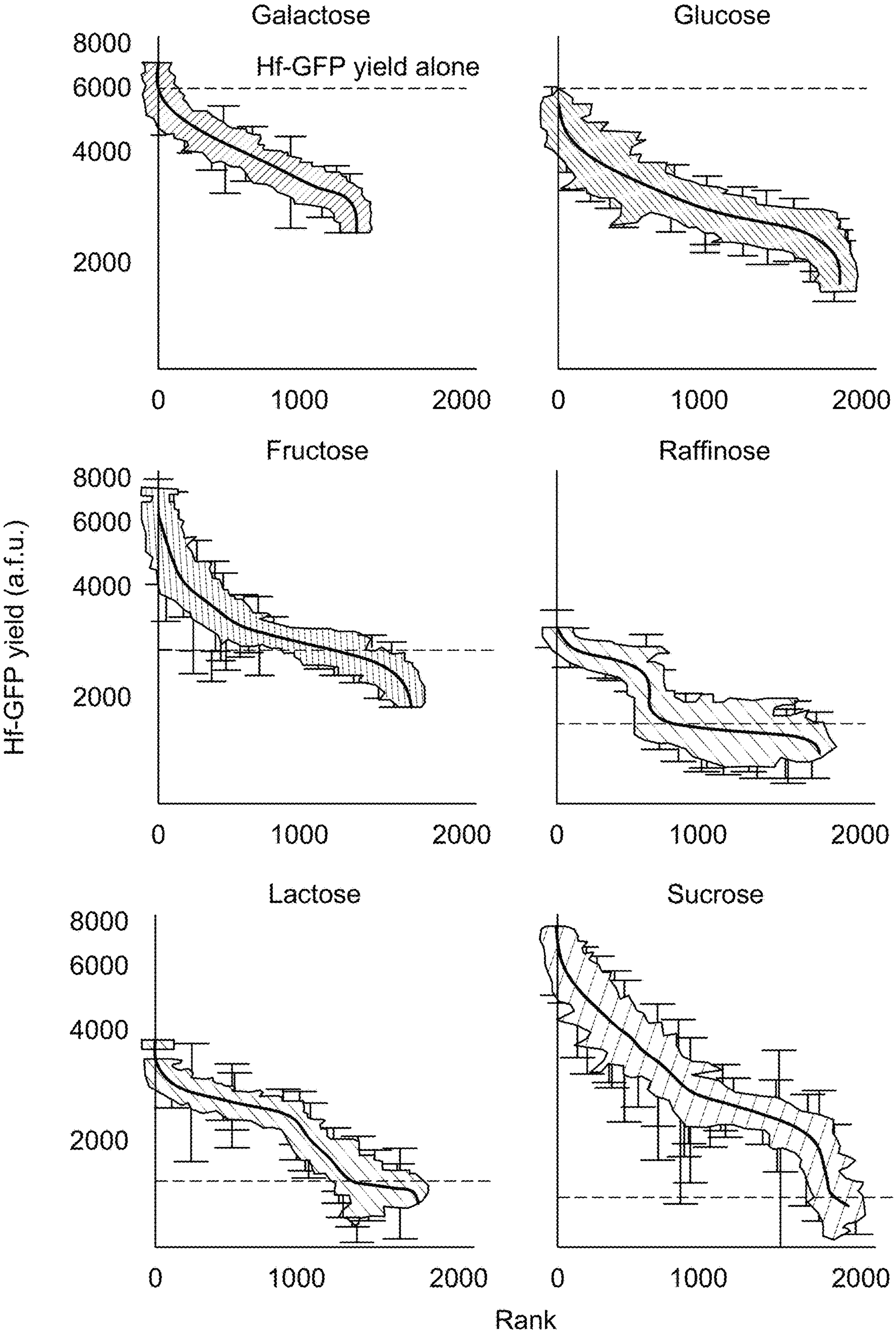
Figure 3E:
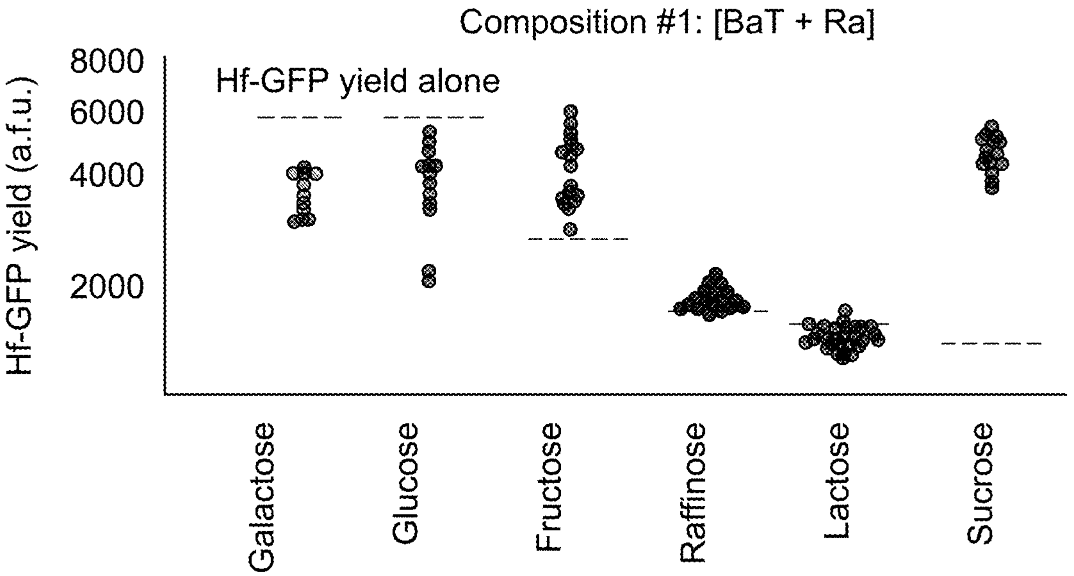
Figure 16:
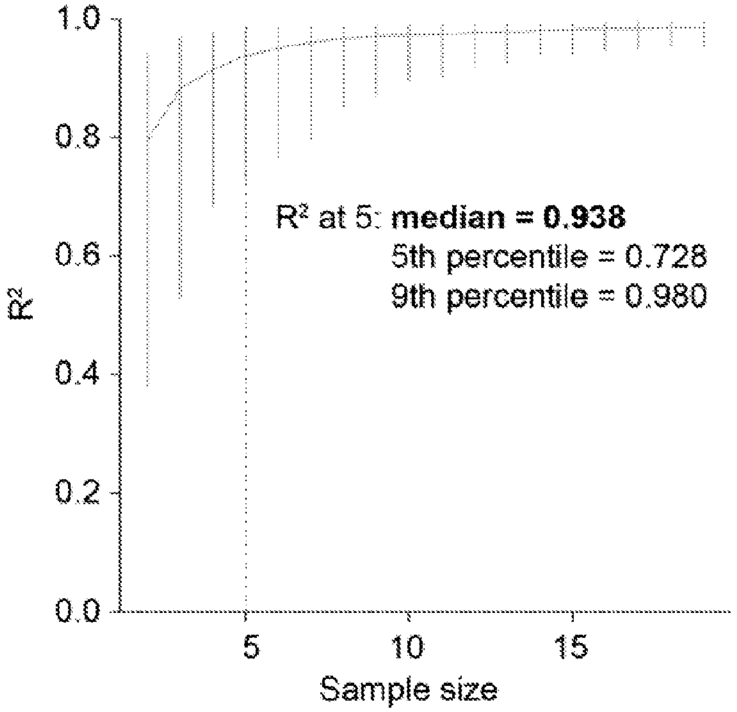
FIG. 16 shows a graph which represents an analysis of the tradeoff between microwell-replication and technical noise for Hf-GFP growth assays. The expected number of microwell-replicates for a given input library size are shown in FIG. 18C below. To determine the input library size for the Hf-GFP facilitation screen in FIGS. 3A-3G above, the number of microwell-replicates desired was determined by estimating technical noise in Hf-GFP (FIG. 12B above) for given expected microwell-replication sample sizes. Data were resampled with replacement and median growth measurements were calculated for each carbon source at t=63 hours (assay endpoint). These estimates were compared with the growth values measured using all data (FIG. 10B above, t=63 hours), and an $R^2$ value was computed for each bootstrap sample (500 iterations). The curve shows the median $R^2$ value, and error bars show the 5th to 95th percentile of $R^2$ measurements from bootstrapped samples over the 500 iterations. A microwell-replication level of 5 microwells is shown as a dotted line, where the median $R^2$ value was found to be 0.938 (5th percentile: 0.728, 95th percentile: 0.980, worst case: 0.414).

Two scores were used to calculate the effect size of a composition on Hf-GFP yield ("Hf-GFP median yield") and the robustness of a composition's effect to the presence of additional isolates ("Hf-GFP robustness"), respectively (FIGS. 3D and 3E). To calculate "Hf-GFP median yield," all instances of a composition appearing ≥30 times across all carbon sources were identified. This cutoff was based on the confidence with which Hf-GFP yield could be measured at different degrees of replication (where the analysis was conducted using the data collected for the experiment in FIG. 2C). To study the effect of different levels of replication on the reliability of the instant results, data were downsampled from FIG. 2C, and measurements of Hf-GFP yield were compared in downsampled bootstrapped samples at different levels of replication against estimates using the entire dataset. It was observed that at 5 replicates (or, the average number of measurements per kChip when a composition appeared 30 times in the entire screen), the measurement of Hf-GFP yield corresponded strongly with that of the all replicates ($R^2$=0.938, FIGS. 16 and 17). In total, 191 compositions appeared ≥30 times and were composed of k=1 (14/14 possible combinations=100%), k=2 (91/91 possible combinations=100%), or k=3 isolates (86/384 possible combinations=23.6%). With 4.5 replicates on average per unique k=3 composition (FIG. 35), it was expected that 27 replicates on average would occur per k=3 community across the six chips and 111/374=30.6% of these would be represented >5 times (assuming a Poisson model centered at 27), just slightly more than what was achieved The median Hf-GFP yield at 72 hrs in the presence of each of these 191 compositions (across all carbon sources) was calculated (FIG. 3E, "Hf-GFP median yield"). These values were compared to a baseline "minimal viable yield" value of 1500 counts (one standard deviation above Hf-GFP yield in sucrose), the point at which yield was considered detectable.

To calculate "Hf-GFP robustness", all communities where each composition appeared along with additional isolates were identified across all carbon sources. Here, differentiation was made between "composition" as the exclusive subset of isolates under consideration and "communities" as all combinations including this composition and 21 isolate. For example, a given 3-isolate composition [A+B+C] (s=3) appeared as part of larger communities [A+B+C+X+ . . . +Z] (k≥4) (FIG. 3D) with a predictably high number of instances (FIG. 18C). The tenth percentile of Hf-GFP yield at 72 hr across communities containing each given composition was calculated (FIG. 3E, "Hf-GFP robustness").

Figure 27A:
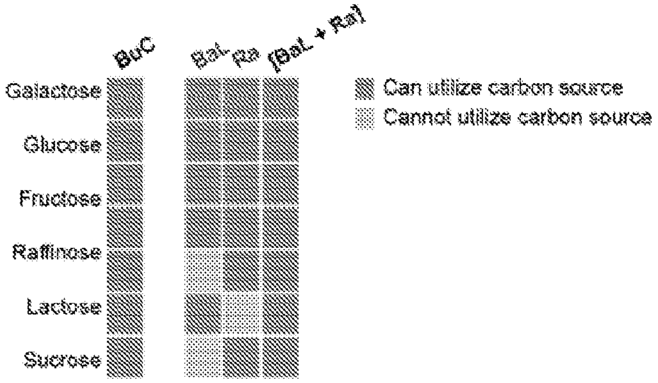
FIGS. 27A-27C show that the two most robust compositions consisted of "core" groups of primary facilitators among which all carbon sources could be utilized.
Figure 27B:
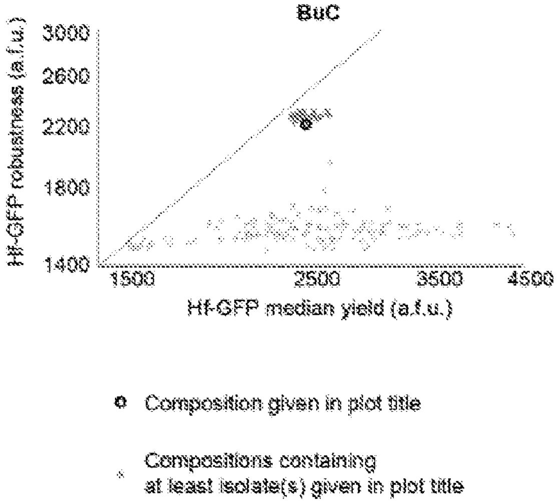

Compositions were uncovered that produced a wide range of facilitative effects (FIGS. 3B and 3E), but few performed highly by the Hf-GFP robustness score. The single isolate BuC imparted both a high facilitative effect and high robustness (FIG. 3E). Notably, BuC was the only isolate in the instant library able to grow on all six carbon sources tested (FIGS. 24 and 27A). Among compositions that included BuC, e.g. [BuC+Ch+Dy], small improvements to robustness were further observed (FIGS. 3E and 27B). The composition BuC alone was the least robust of BuC-containing compositions.

Figure 27C:
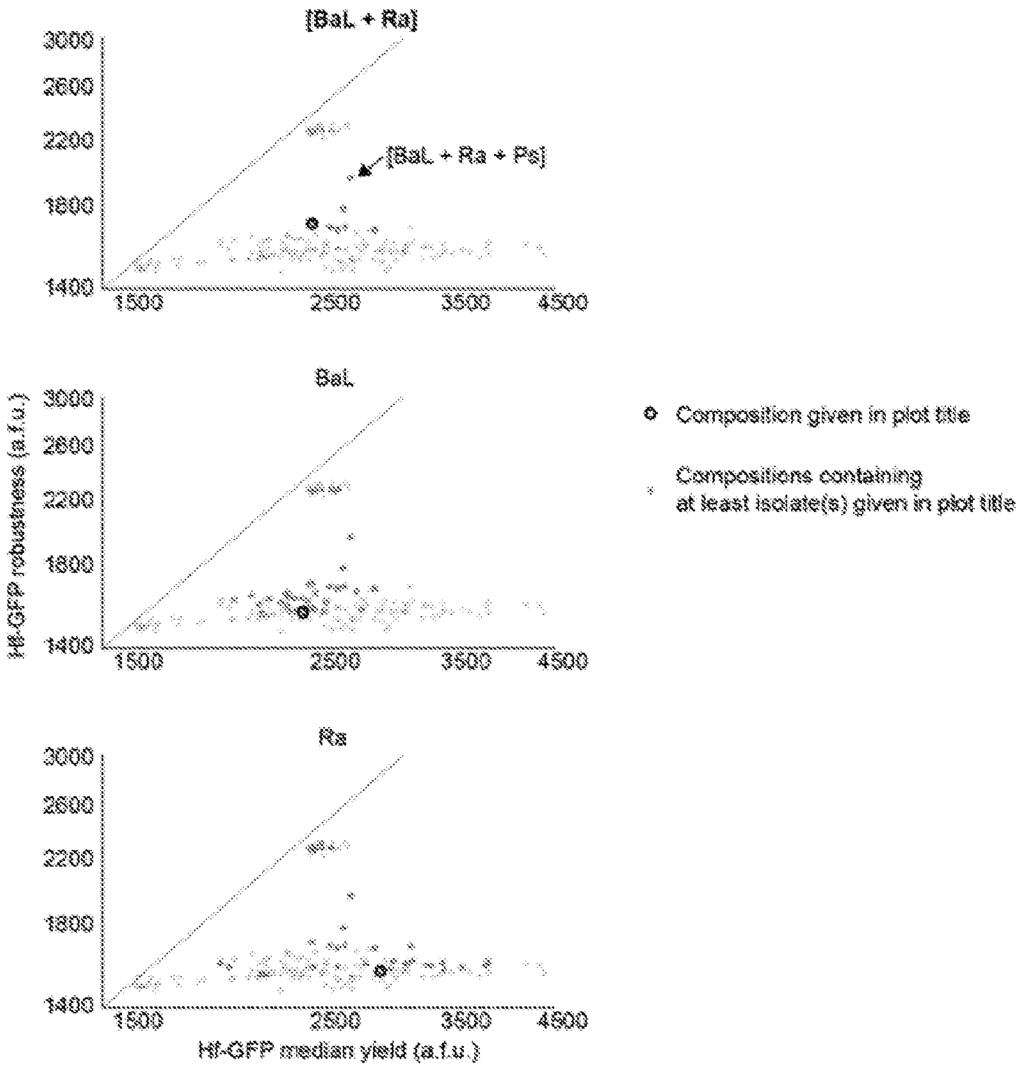

The pair of isolates [BaL+Ra] also appeared among compositions where Hf-GFP yield was high and robust (FIGS. 3E and 27C). Each carbon source provided a growth substrate for at least one of these two isolates (FIG. 27A). It was observed that the compositions BaL alone and Ra alone were both less robust than the composition [BaL+Ra] (FIG. 27C). Instances were identified where the incorporation of a third isolate, e.g in the composition [BaL+Ra+Ps], improved the magnitude and robustness of Hf-GFP facilitation (FIGS. 3E and 27C).

It was posited that robust compositions would obey the property that each carbon source can be consumed by at least one isolate in the composition, e.g. the composition BuC alone and the composition [BaL+Ra] (FIG. 27A). This may be a necessary but insufficient criterion, as compositions obeying this property may not impart high robustness. It was further posited that specific isolates incorporated beyond such "core" groups, e.g. the composition [(BuC)+Ch+Dy] and the composition [(BaL+Ra)+Ps], could bolster the effect size and/or robustness further. These properties point to a design strategy for operating in very large combinatorial spaces whereby robust compositions are first identified from a set rationally selected hypothetical core groups, and then [(core group)+additional isolate(s)] could be screened for further improvements.

Validation of Facilitative Effects

To validate results from the screen in larger-scale culture, cultures of Hf-GFP, BuC, BaL, and Ra were generated as described in the "Microbial culture input preparation" section above (except only 4-mL culture volumes were used in the "starter phase" and "preculture phase"). The compositions Hf-GFP, Hf-GFP+BuC, Hf-GFP+BaL, Hf-GFP+Ra, and Hf-GFP+[BaL+Ra] were constructed in duplicate in 200 μL MM containing one of each of the six carbon sources used in the screen (0.5% w/v) (as well as an even mix of all carbon sources (total 0.5% w/v) and a no-carbon control) in 96-well plates (21° C., 220 RPM). Hf-GFP and the isolates were normalized to standard starting densities [Hf-GFP $OD_{600}$=0.02]:[total isolate $OD_{600}$=0.02]. The GFP signal was monitored over five days (SpectraMax plate reader) and displayed a strong correspondence with the screening results in terms of carbon source specificity and relative size of the facilitative effect (FIGS. 20A-20F) for all compositions and carbon sources tested.

*H. frinsingense* Yield Vs. Number of Isolates Analysis

Figure 4A:
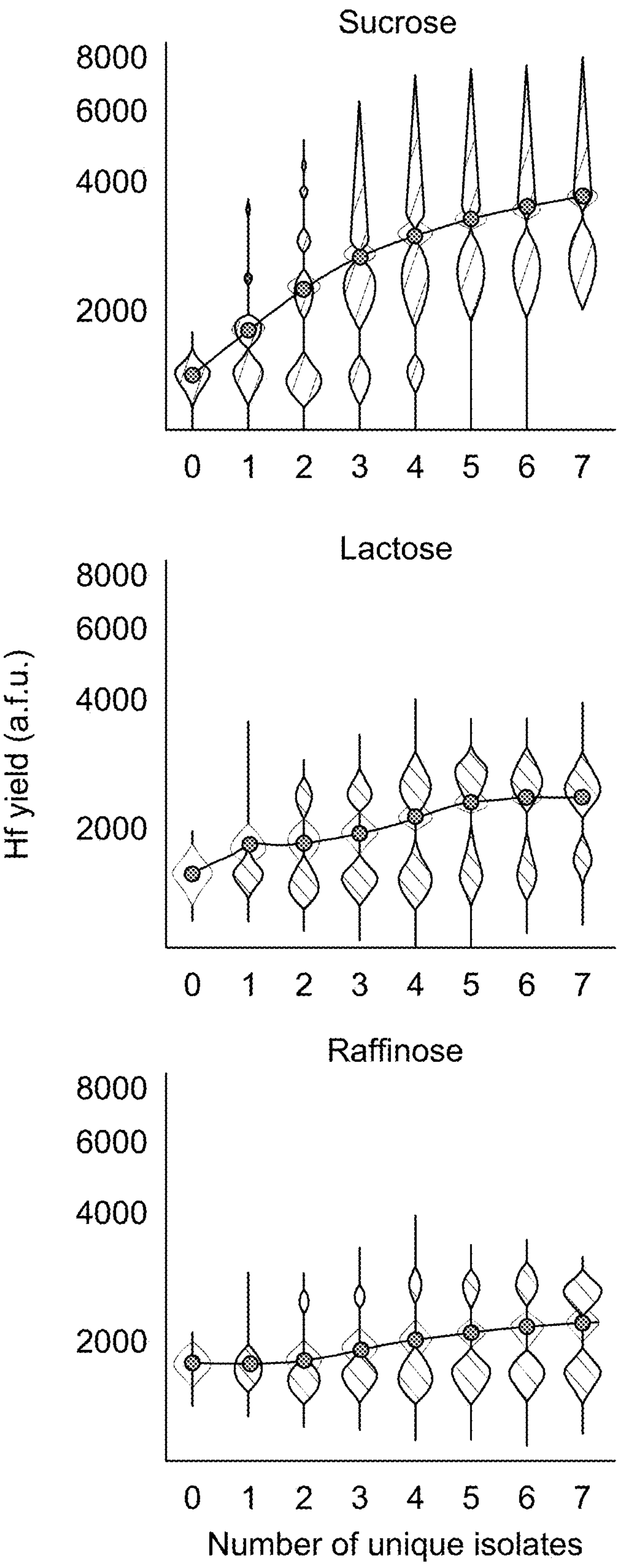
FIGS. 4A-4D show how facilitation increased with community richness and was driven by a few strains.
Figure 21:
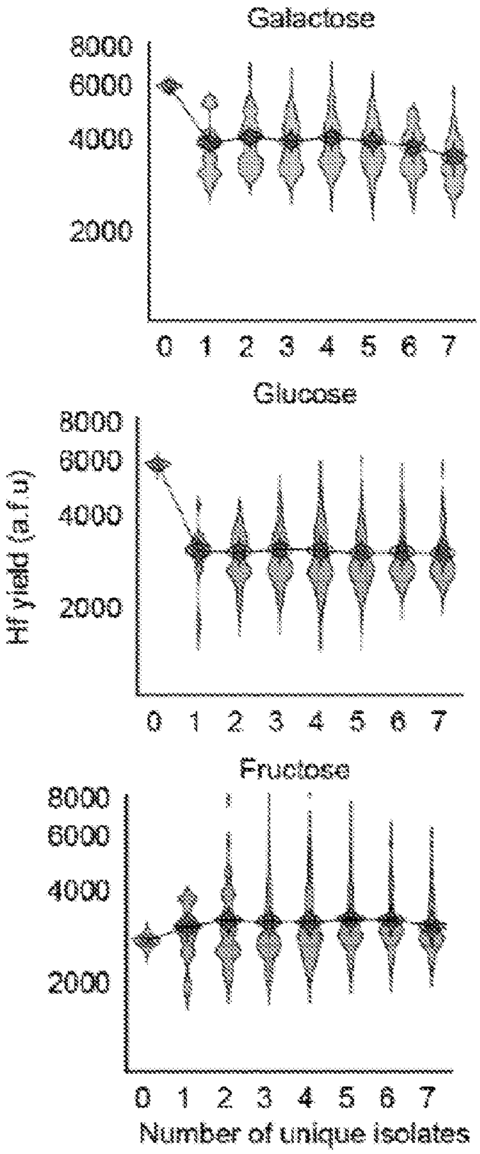
FIG. 21 shows that the Hf-GFP yield depended on community richness and carbon source. Hf-GFP yield was measured across different numbers of unique isolates in different carbon source media (lactose, raffinose, and sucrose, the carbon sources in which it grew most poorly in monoculture, shown in FIG. 4A above). In galactose and glucose, carbon sources in which Hf-GFP monocultures grew well, a suppressive effect was observed for ≥1 isolate that generally appeared agnostic to the number of unique isolates. With fructose, a carbon source for which Hf-GFP yield was greater than its yield in lactose, raffinose, and sucrose, but lesser than its yield in galactose and glucose, an initial increase in yield was observed as the number of isolates increased from 1 to 3 isolates. Beyond this point, yield appeared to plateau.

The effect of the number of unique isolates in co-culture with Hf-GFP was estimated (FIGS. 4A and 21). For a given carbon source, the distributions of Hf-GFP yield (a.f.u.) across k values were first generated by considering all unique compositions at each value of k (i.e. at k=3, composition [A+B+C] was considered, but both [A+B+B] and [A+B+C+C] were not). Medians were calculated in instances when compositions appeared >1 time (and a mean was calculated if the composition was represented only 2 times). At k=1, this amounted to 14 unique compositions (Hf-GFP in co-culture with one isolate) in the distribution, at k=2, this amounted to 14-choose-2=91 compositions; and so forth. As k increased, the fraction of compositions represented in the data decreased relative to the total number of possible combinations, e.g. ~300 compositions at the k=7 level were generated for each carbon source, even though 14-choose-7=3,432 were possible. The number of data points generated in screen as it relates to the total number of possible combinations is shown in FIG. 35.

To estimate Hf-GFP yield values, the distribution of yields for each k was resampled with replacement (with resampling count equal to the actual sampling count), and a median of the resampled data was calculated. This exercise was performed 100 times in each instance and the distribution the medians calculated was reported (FIGS. 4A and 21).

Hf-GFP yield was also measured without the constraint of uniqueness of the isolates at each k (i.e. at k=3, the composition [A+A+B] was included in the analysis) (FIG. 22). As a result, the communities with 19 inputs were included, even though there were only 14 unique isolates in the library. From this analysis, it is predicted that Hf-GFP yield would not change drastically with community richness beyond 7 strains (relative to the change observed between 1 and 7 strains), although this was not assessed directly.

Physical Abiotic Considerations

Figure 30B:
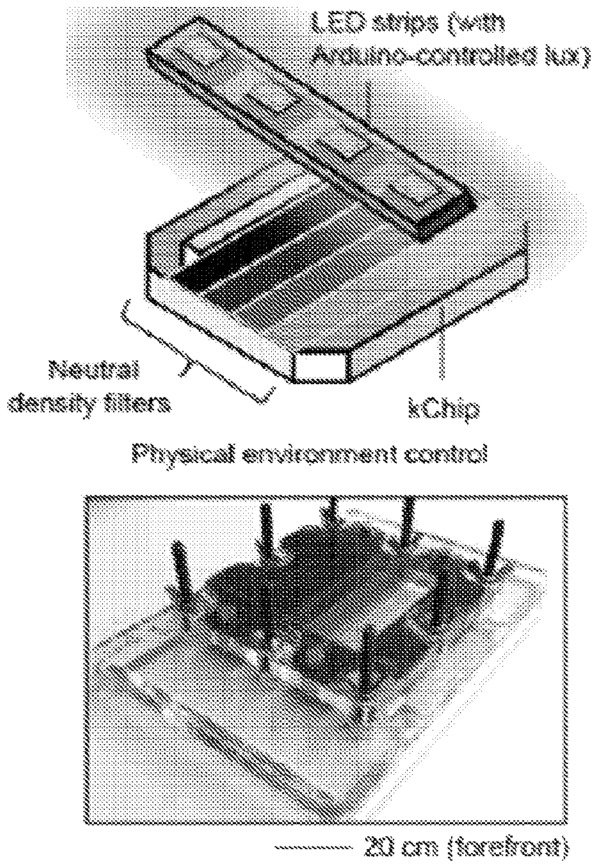
Figure 30C:
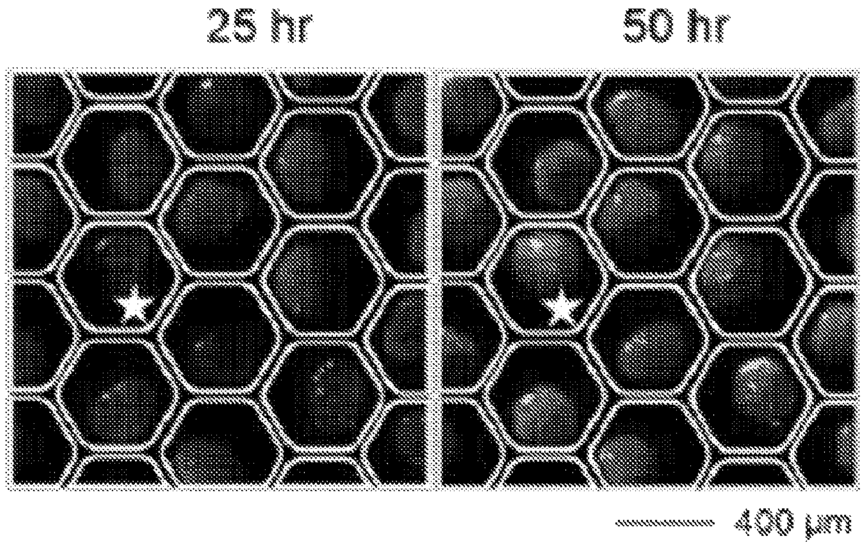

Control of physical environmental factors like temperature and illuminance can be incorporated into a kChip screen. To demonstrate how illuminance can be incorporated into these experiments, the growth of the photoautotroph (*Chlamydomonas reinhardtii* CC-503, a naturally fluorescent alga) and a heterotroph (*Escherichia coli* constitutively expressing GFP) in co-culture were screened on a kChip under an array of neutral density filters (Lee Filters Gel Sheet 209 and 210) (FIGS. 30A and 30B). Each filter attenuated light to a different extent. The yield of the two organisms in co-cultures was measured at 50 hr (FIGS. 30C and 30D), and showed the impact of initial density and light intensity on the abundance of the two organisms (FIG. 30E). kChip screening can be conducted across a broad range of experimental temperatures.

Figure 29A:
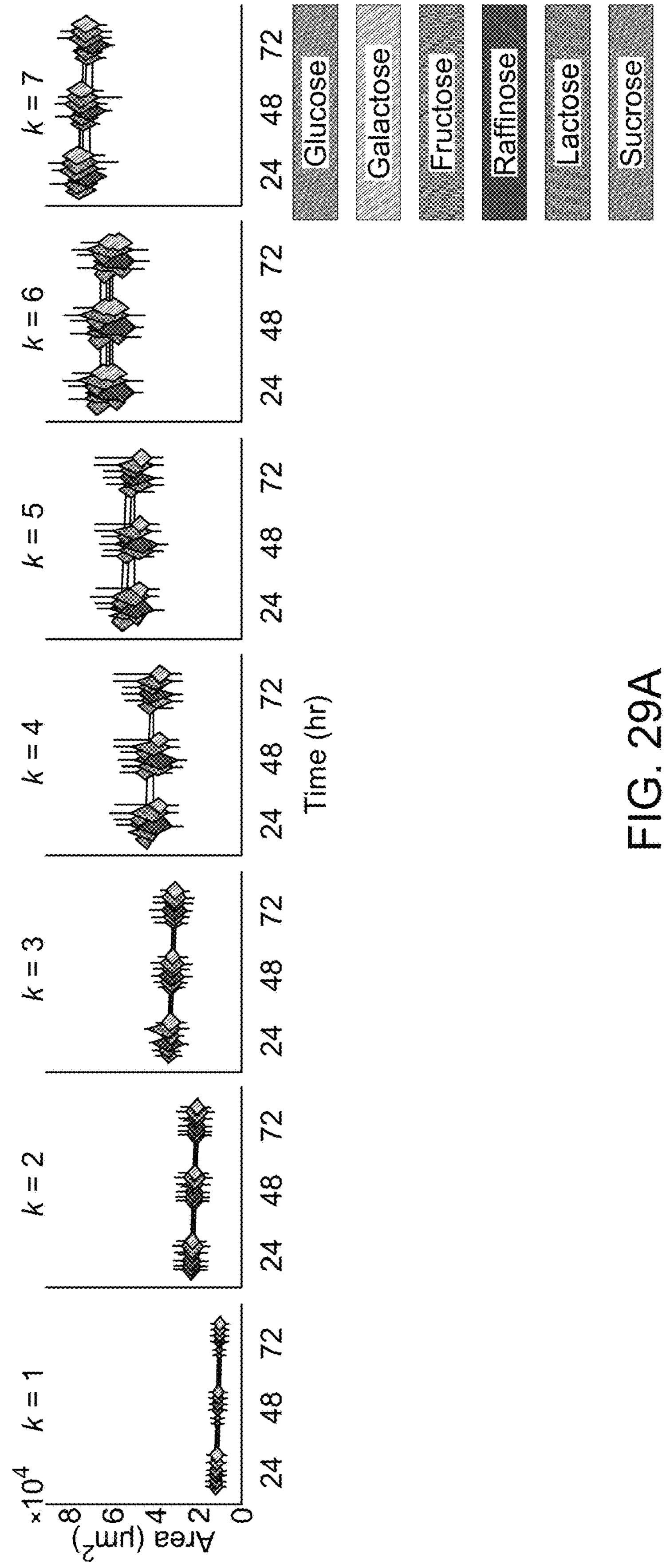
FIGS. 29A and 29B show that droplet evaporation was typically <10% between 24 and 74 hours.
Figure 29B:
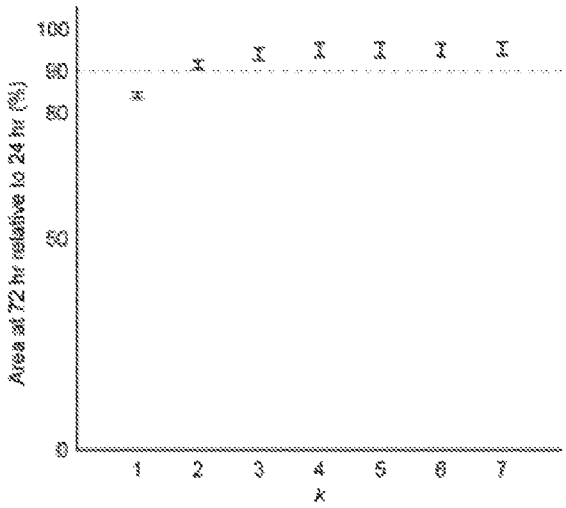

Droplet evaporation within the kChip, which occurs to greater extents as temperature and time increase, may limit the maximum assay duration. In the Hf-GFP facilitation screen, kChips were incubated at 21° C., and only minor droplet evaporation was observed by 72 hr (FIGS. 29A and 29B). The *C. reinhardtii*/*E. coli* co-culture experiment was conducted at 30° C.

kChip Image Analysis

An image analysis pipeline was developed to: (1) identify droplets as circular objects within the image; (2) decode the contents of each droplet based on the color code; (3) assign each droplet to a microwell; and (4) measure the average fluorescence of the merged droplets in each microwell.

To detect each droplet in the image, all fluorescence channels are averaged and a circular Hough transform (scikit-image) is applied to detect circular objects with a diameter of 100-140 μm. To decode each droplet's color code, the average fluorescence intensity of each dye (a 3-dimensional vector for each droplet) is measured. These vectors are then projected onto a two-dimensional plane, eliminating systematic effects from differences in illumination intensity across the images. The DBSCAN algorithm (scikit-learn) identifies the clusters of droplets corresponding to each input condition. Optionally, a user can correct clustering errors, such as cluster collisions caused by optical activity of reagents in the input library. A quality score for each droplet can be computed based on the distance to the assigned cluster centroid. The Hungarian algorithm (scikit-learn) then maps each cluster to the predetermined centroids of each dye mixture. Pre-determined centroids can typically be set by a priori dye ratios.

Once identified and decoded, the optimal alignment between [the centroid positions of all droplets] and [the photomask design used to construct a given kChip] is computed. After alignment, it is inferred that droplets share a microwell if their centroids aligned to the same microwell in the photomask. Once droplet sets are assigned to microwells, microwells with merged droplet areas exceeding ±30% of the mean merged area for a given k are filtered out, as an additional data quality control to account for instances where there was incomplete merging of all droplets within the microwell. For each microwell that passes this filter, the average fluorescence (e.g. fluorescent protein or resorfun reporter) across the merged droplet area is then measured at each timepoint.

Images obtained from the kChip can be processed in a number of ways. For example, kChip images can be processed using computer image analyses to objectively and quantitatively characterize the images at macroscopic and microscopic levels (i.e., the level of bacteria, fungi, yeast, etc.). The morphology and life cycle changes of the microbes (e.g., germination of hyphae in *Aspergillus*) can be visualized and quantified in the kChip using readily available software systems (e.g., IncuCyte and ImageJ). Image analysis techniques, including but not limited to, morphological segmentation, single cell morphometry, live tracking of structural components (e.g., hyphae of *Aspergillus*), and detection of protein tags (e.g., detection of fluorescence intensity, e.g., GFP protein tag intensity) can be used for quantification and qualification of image data.

Example 2: The kChip Rapidly Constructs Massively Parallel Community Sets of Controlled Size To generate parallel synthetic communities from a library of n input strains, each kChip contains tens of thousands of microwells, where each microwell produces a random grouping of k inputs. Multiple kChips and/or values of k can be used in accordance with the desired size, number, and replication of combinatorial groupings. The setup for kChip screening (~30 minutes) as presently exemplified involves three steps: (1) droplet generation and pooling (10 min), (2) droplet loading and grouping (20 min), and (3) droplet merging (10 seconds) (FIG. 1A). Prior to droplet generation, a “color code”, or unique ratio of three fluorescent dyes, is mixed with each input. Each color code is therefore packaged with its input when droplets are initially generated (Bio-Rad QX200 Droplet Generator, which produces 20,000 1-nL droplets per 20-μL input) and can be used to identify droplet contents (32). Color-coded droplet sets are then pooled together to form a droplet library. The droplet library is loaded onto the kChip in a single pipetting step (via a custom kChip-loading apparatus, FIGS. 5A-5I). Droplets spontaneously self-assemble into random groupings of k droplets determined by the size, shape, and internal design features of the microwell (FIGS. 1B, 6A, 6B, 7A and 7B). The kChip is imaged (2× magnification) to identify contents of each microwell from the droplet color codes (FIG. 1B and FIG. 8). The droplets in each microwell are subsequently merged to combine their contents via exposure to an alternating current (AC) electric field (corona treater, Electro-Technic Products) (FIGS. 1A and 1B), generating parallel n-multichoose-k synthetic communities.

Figures 1C, 1D:
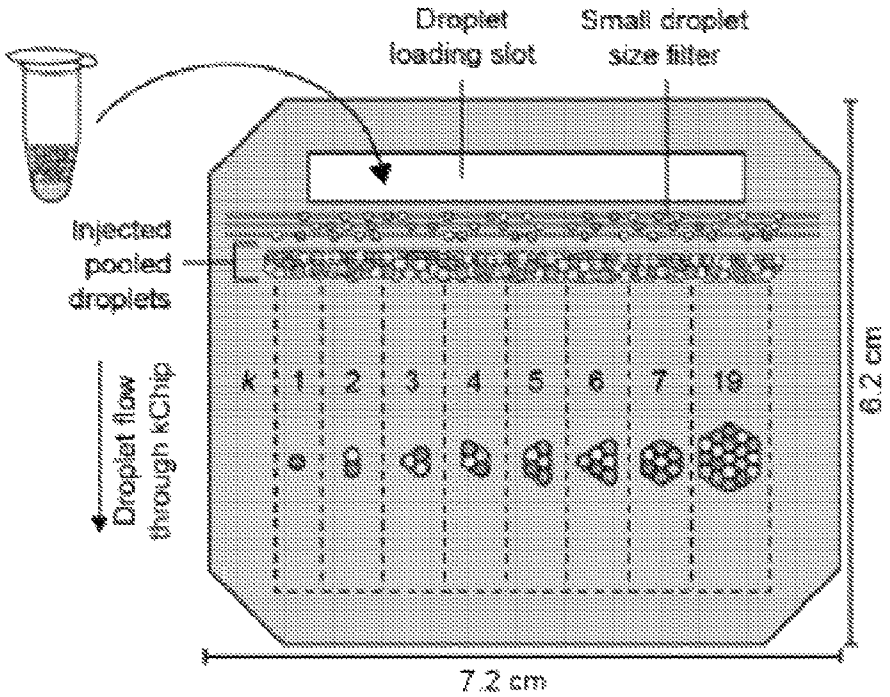

Microwells that group different numbers of inputs can be combined on a kChip in any organizational pattern chosen by the user (FIG. 1C). Owing to the increase in microwell size as k increases, microwell density on a kChip decreases as k increases (FIG. 1D), so the total number of assay points on a given kChip depends on the microwell layout (~13,000 if all microwells are k=7; ~60,000 if all microwells are k=1). The presently exemplified kChip, used for screening applications described below, has microwells that accept up to 7 or 19 droplets (“k={1:7;19}”) with roughly even representation of each microwell type to enable simultaneous construction and assessment of communities of different richnesses (FIG. 1D).

Example 3: Growth of Labeled and Unlabeled Strains Profiled Across Environmental Conditions kChip screening allows for rapid functional profiling of both fluorescently labeled and unlabeled strains across libraries of environmental conditions, e.g. antibiotics, natural products, and carbon sources, with desired temporal resolution (limited only by kChip scan time, <15 minutes at 2× magnification). Carbon utilization profiles, i.e. growth curves for each strain across different single carbon sources in a minimal medium (see Example 1 above), were obtained for a panel of droplet monocultures as well as conventional 96-well plate monocultures for comparison (SpectraMax plate reader). Library of microbe-containing droplets were pooled with a library of carbon source-containing droplets and loaded the droplets onto a k=2 Chip (i.e. all microwells on the kChip grouped 2 droplets). From microwells that received one droplet from each library (~½ the total microwells on the k=2 Chip, ~17,000), growth of each strain was profiled on each carbon source. To track growth on each carbon source, one of two assays were used: (1) measurement of a constitutively expressed fluorescent protein (GFP or YFP) (FIGS. 2A-2C); or (2) reduction of resazurin dye to its fluorescent product resorufin by cellular metabolism (proportional to cell density), a label-less assay that can be used with unlabeled or genetically-intractable strains (FIGS. 2E-2G). 10 fluorescently labeled strains were selected (FIG. 32), and first confirmed that glucose utilization was recapitulated on a k=1 Chip (FIG. 9).

Figure 2F:
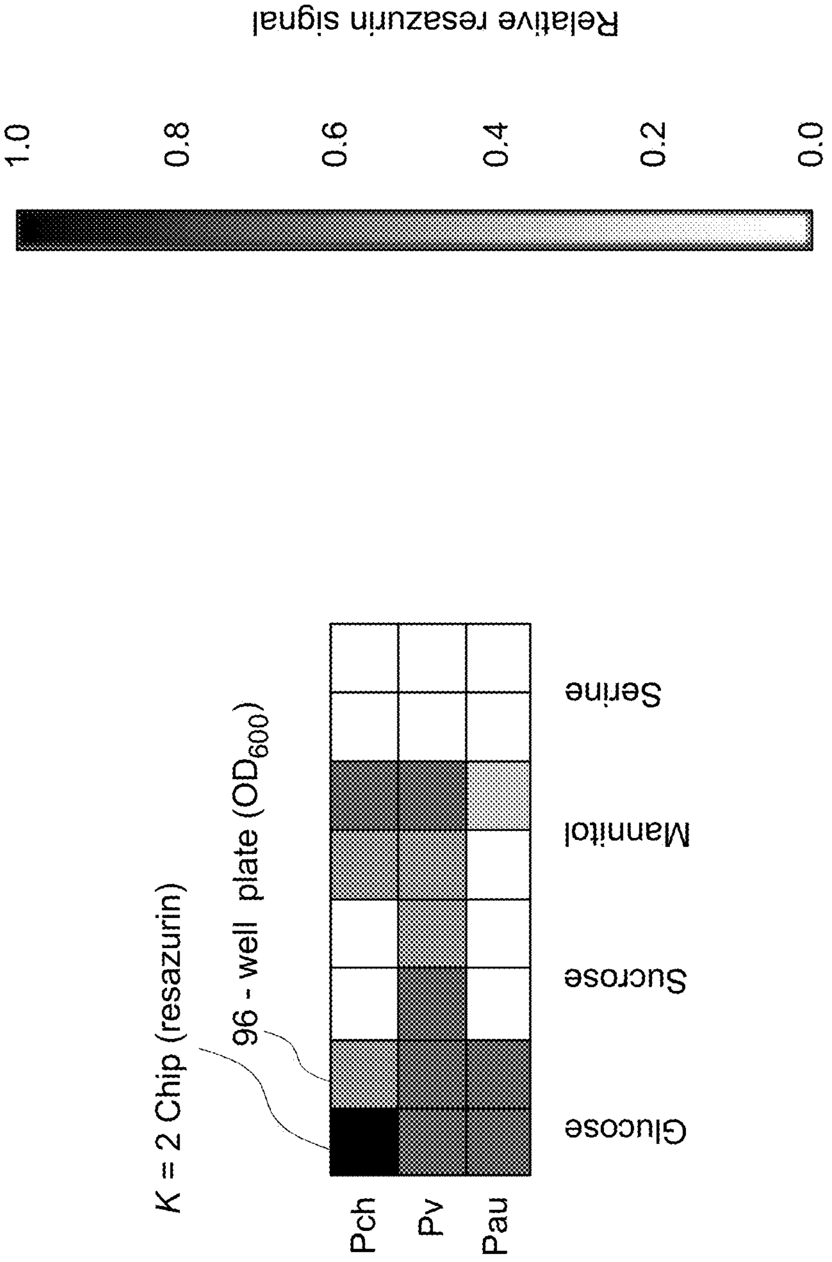
Figure 11:
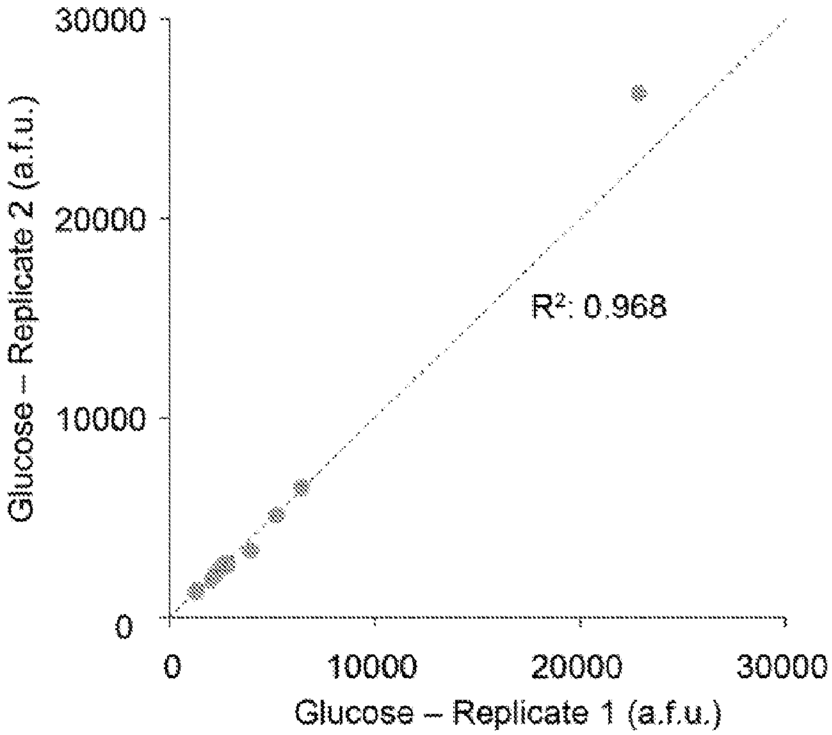
FIG. 11 presents correlation data that demonstrate the technical replicability of kChip bacterial growth assays. To measure the technical replicability, the carbon source utilization experiment (FIGS. 2C and 10B above) contained two technical replicates of glucose for each strain. A scatterplot compared the median signal obtained for each strain for each replicate of glucose at t=50 hours. Gray diagonal line=x=y line.
Figure 12A:
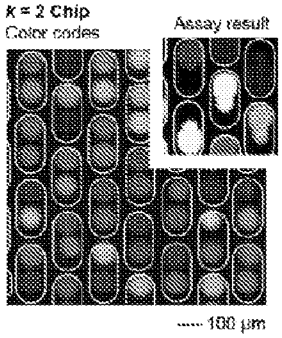
FIGS. 12A and 12B show carbon utilization profiles attained on k=2 Chips via the resazurin assay and match standard culture techniques.
Figure 12B:
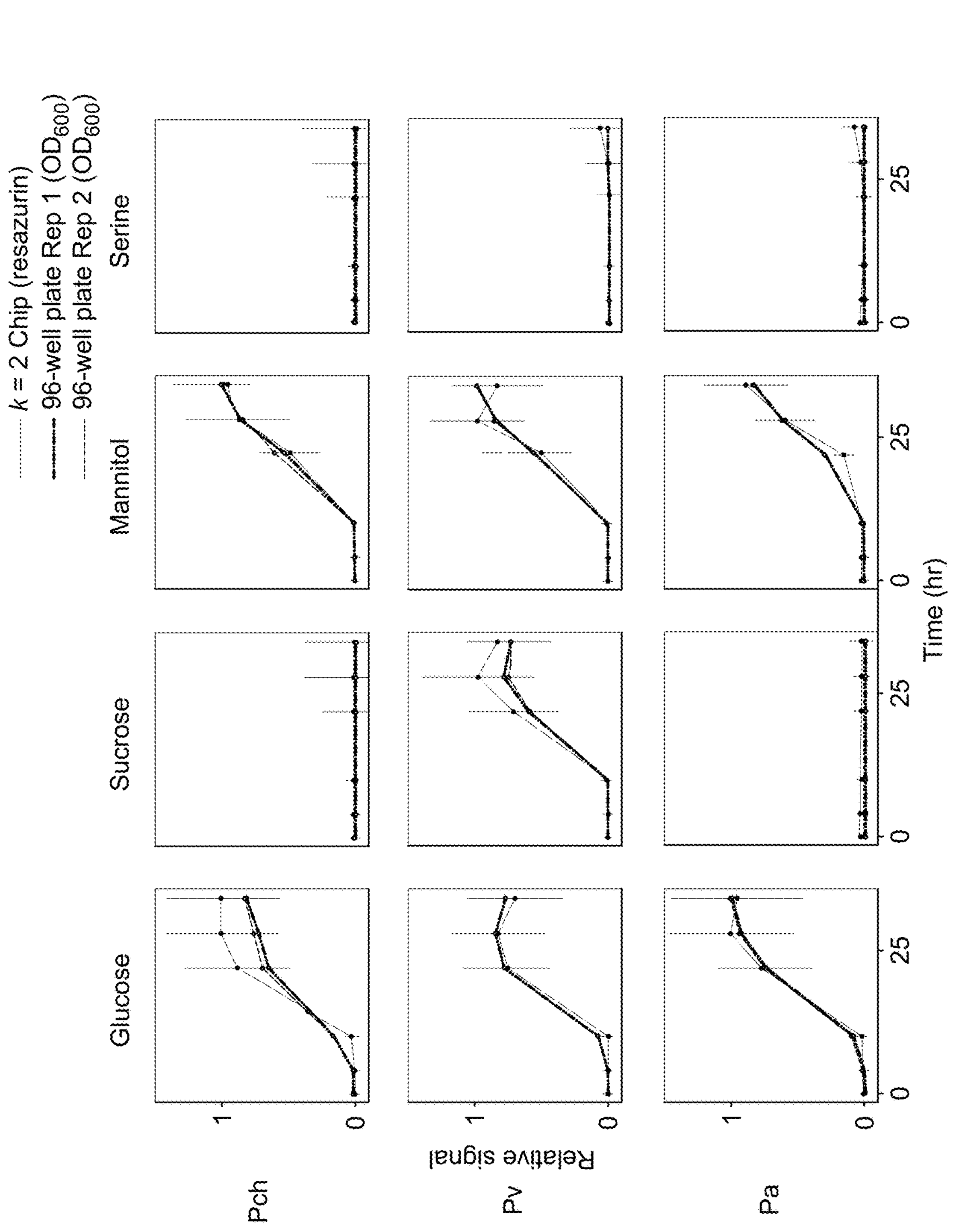

This panel was then crossed with 13 carbon sources (FIG. 33). Carbon utilization profiles produced from GFP or YFP signal on a k=2 Chip and 96-well plates agreed strongly (Pearson r=0.868) (FIGS. 2C, 10A and 10B) with on-chip consistency between technical replicates ($R^2$=0.968, FIG. 11). To assay growth of unlabeled bacteria, the resazurin assay, which has previously been used to quantify cell viability in droplets (34), was used by incorporating resazurin in all carbon source-containing droplets. For a panel of three strains profiled across four carbon sources, growth curves produced via resorufin fluorescence measurements on a k=2 Chip and $OD_{600}$ measurements on a 96-well plate agreed strongly (Pearson r=0.969) (FIGS. 2F, 12A and 12B).

Example 4: kChip Screening Identifies Compositions that Robustly Promote Growth of *H. frinsingense*

One application of kChip synthetic community screening is the discovery of compositions that promote or suppress the growth of a strain of interest. Moreover, the robustness of the effects of these compositions across abiotic environments and the presence of additional environmental strains ("isolates") can be simultaneously assessed. Discovering such compositions can inform the formulation of synthetic microbial cocktails for use in probiotic-based interventions that are effective across a diversity of native settings. For the current screen, the yield of a GFP-expressing strain of *Herbaspirillum frisingense* was measured (Hf-GFP) (35), a model plant symbiont whose growth is likely impacted by variable biotic and abiotic environments in agricultural settings. A diverse set of soil bacterial isolates were collected (FIG. 13 and FIG. 34) and Hf-GFP yield across isolate combinations were measured. These combinations were constructed across a media library that included carbohydrate oligomers (sucrose, lactose, and raffinose) and their monomeric constituents (glucose, galactose, and fructose). Hf-GFP grew in monoculture to various extents on each of these carbon sources, with growth on sucrose being indistinguishable from background (FIG. 3A). Droplets that each contained the following were generated: (1) Hf-GFP (starting $OD_{600}$=0.02); (2) one isolate (starting $OD_{600}$=0.02, chosen among 14 isolates+1 no-isolate control+1 negative control) such that the synthetic communities contained the same initial [Hf-GFP]: [total isolate] ratio if no control droplets were present; and (3) one carbon source. All droplets that received the same carbon source were loaded onto the same kChip such that droplet grouping produced combinations of k=1, 2, . . . , 7, or 19 inputs with the carbon source type and concentration held constant (FIG. 3B).

It was differentiated between "composition" as a given isolate subset of size s, e.g. the pair [A+B] (s=2), and a "community" as a larger set of size k that contains the given composition and ≥1 additional isolates, e.g. all communities [A+B+X+ . . . +Y] (k≥3). Overall, ~100,000 assay points were produced (which were evenly divided among the carbon sources) (FIG. 3C, FIG. 35).

Figure 3F:
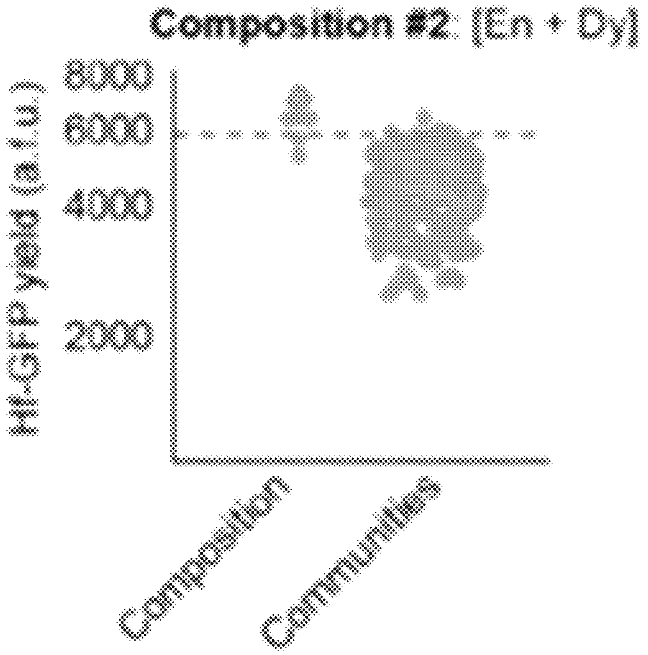
Figure 14:
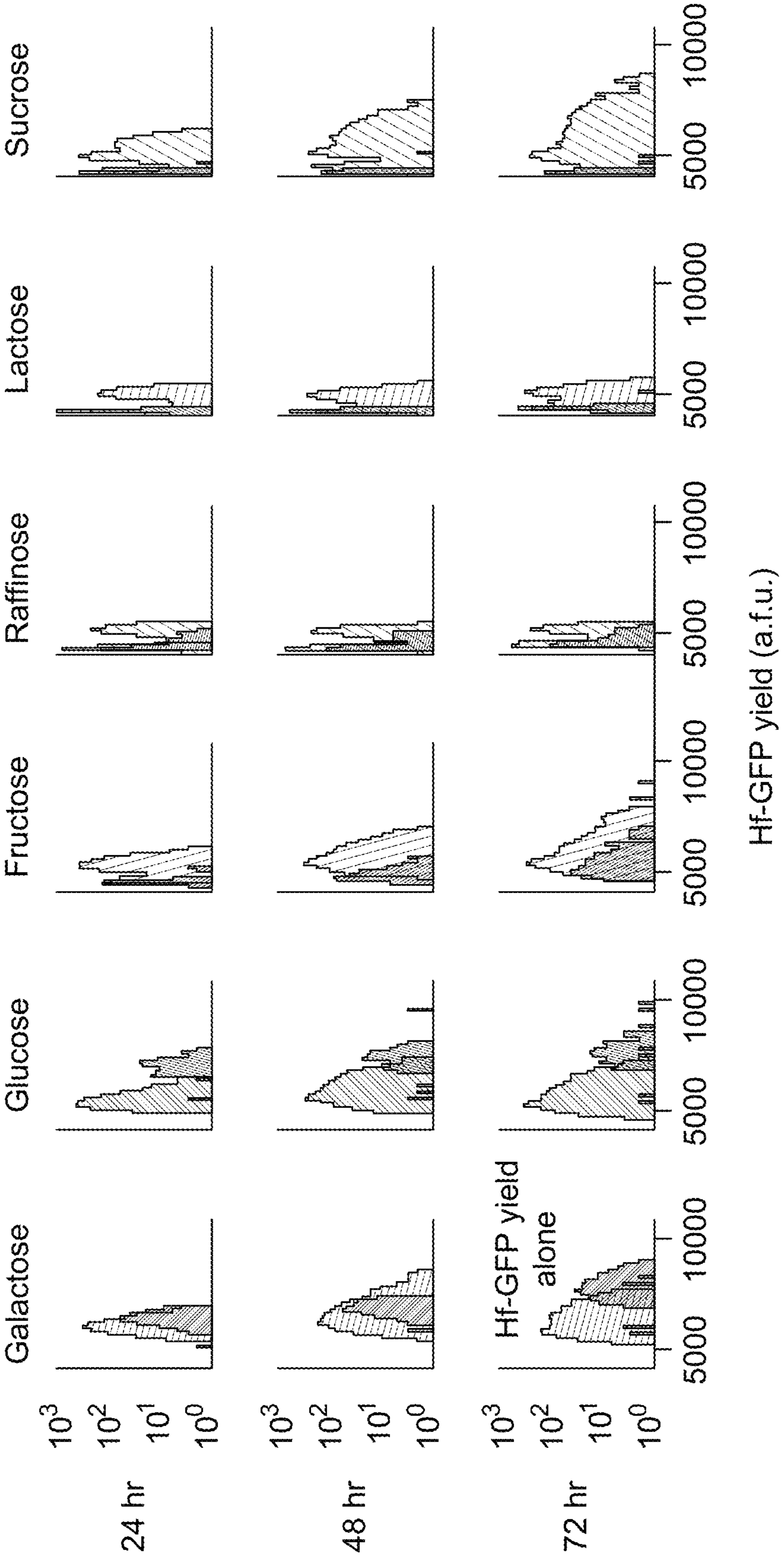
FIG. 14 shows graphs of Hf-GFP yield across compositions, while varying indicated carbon sources and at indicated time points. Hf-GFP yield was measured within each composition and carbon source at 24, 48, and 72 hr after droplet merging. The 72-hr data is also represented in FIG. 3C above. Colored distributions=yield of Hf-GFP+≥1 isolate; Gray distributions=yield of Hf-GFP alone (k=1 microwells where droplet received no isolate). While the focus of the present analysis was yield at 72 hrs (FIGS. 3A-3G and 4A-4D above), time-dependent effects were evident, particularly in fructose, where ubiquitous facilitation of Hf-GFP yield appeared by 24 hrs.
Figure 15A:
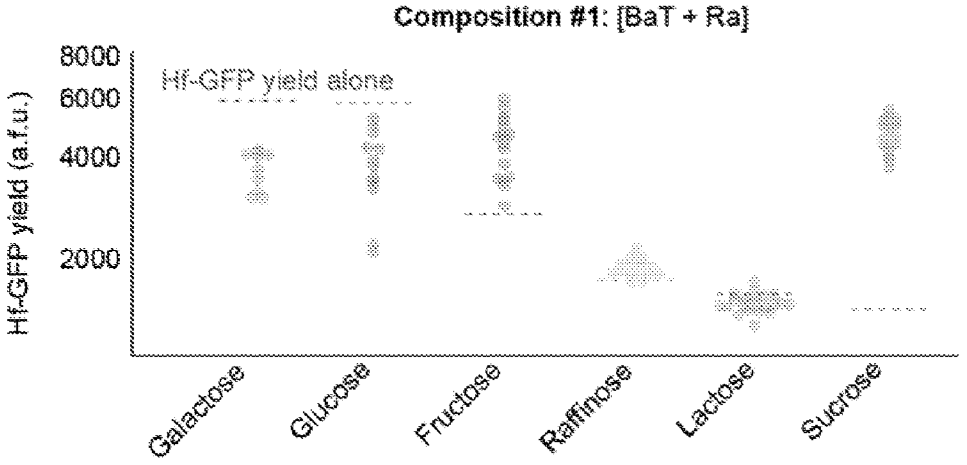
FIGS. 15A and 15B show that a facilitative composition may not be robust to carbon source or community context.
Figure 15B:
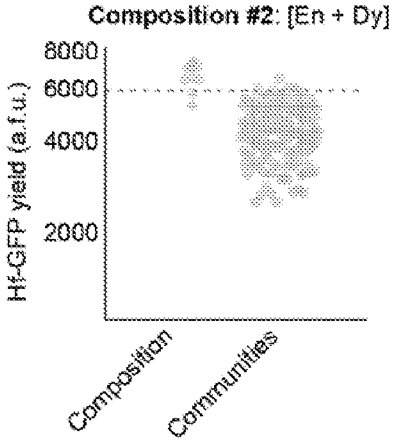

Most communities had a significant effect on Hf-GFP yield, showing both suppressive (decrease in yield) and facilitative (increase in yield) effects. Hf-GFP yield was measured at 24, 48, and 72 hrs and yield at 72 hr, the time point when yields were highest, was rank-ordered (FIGS. 3D, 14). On carbon sources where Hf-GFP monocultures achieved high yield by 72 hours (glucose, galactose), the addition of other isolates almost always attenuated its growth. By contrast, facilitative compositions were common on carbon sources where Hf-GFP growth was low (fructose, raffinose, lactose) and ubiquitous when undetectably low (sucrose). For the majority of compositions, however, the facilitative effect did not persist across different carbon sources or community contexts. For example, the composition [*Bacillus* sp. I+*Rahnella* sp.] ([BaT+Ra]) (measured at k=2 on each kChip) facilitated HF-GFP growth on fructose, sucrose, and raffinose, but suppressed its growth on the other carbon sources (FIG. 3E). Similarly, the facilitation imparted by the composition [*Enterobacter mori*+*Dyella* sp.] ([En+Dy]) (measured at k=2) in a medium containing galactose was not robust to community context [En+Dy+≥1 additional unique isolates] (an s=2 composition among all k≥3 communities on the same kChip) (FIG. 3F).

Figure 3G:
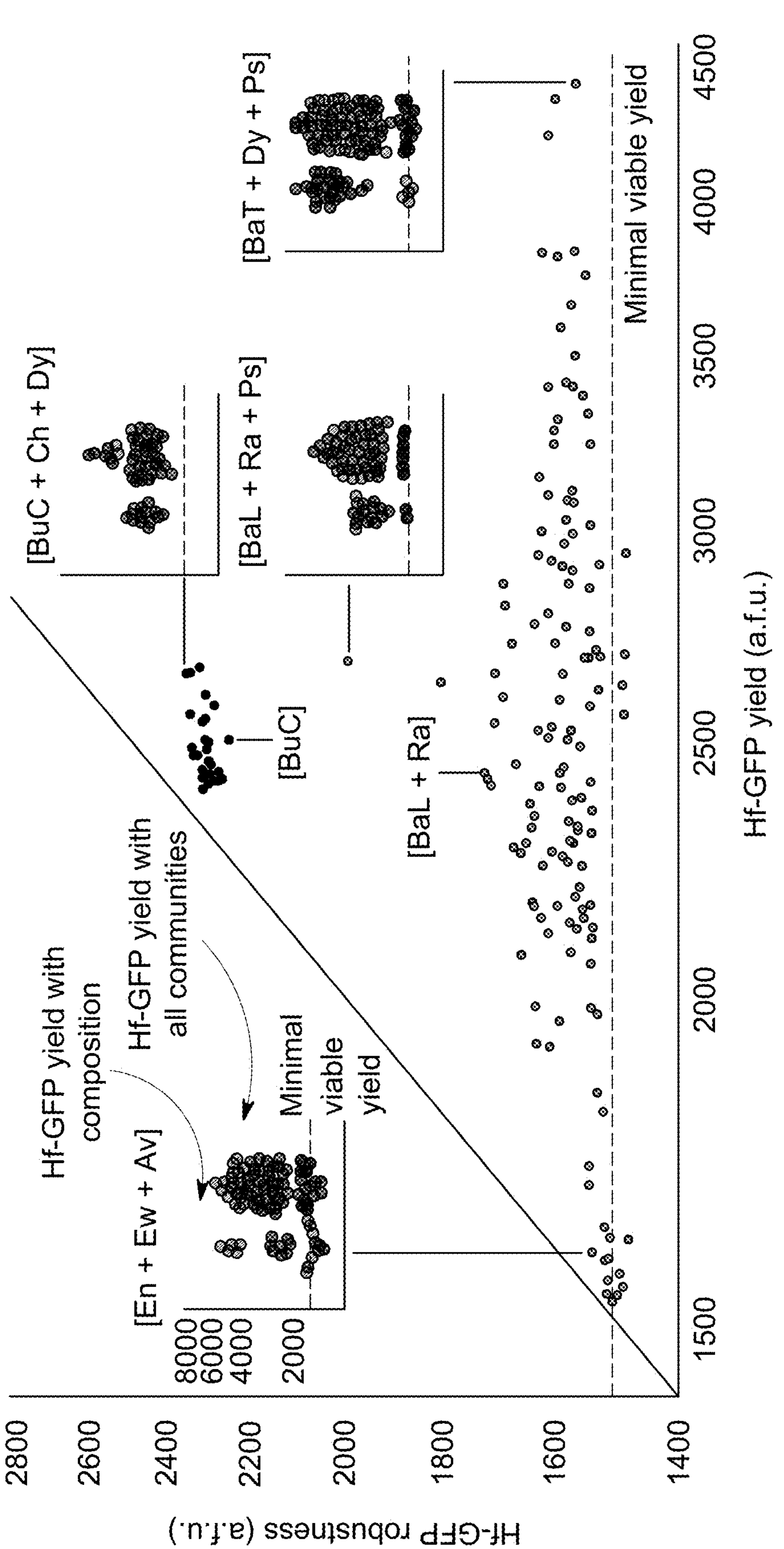
Figure 19:
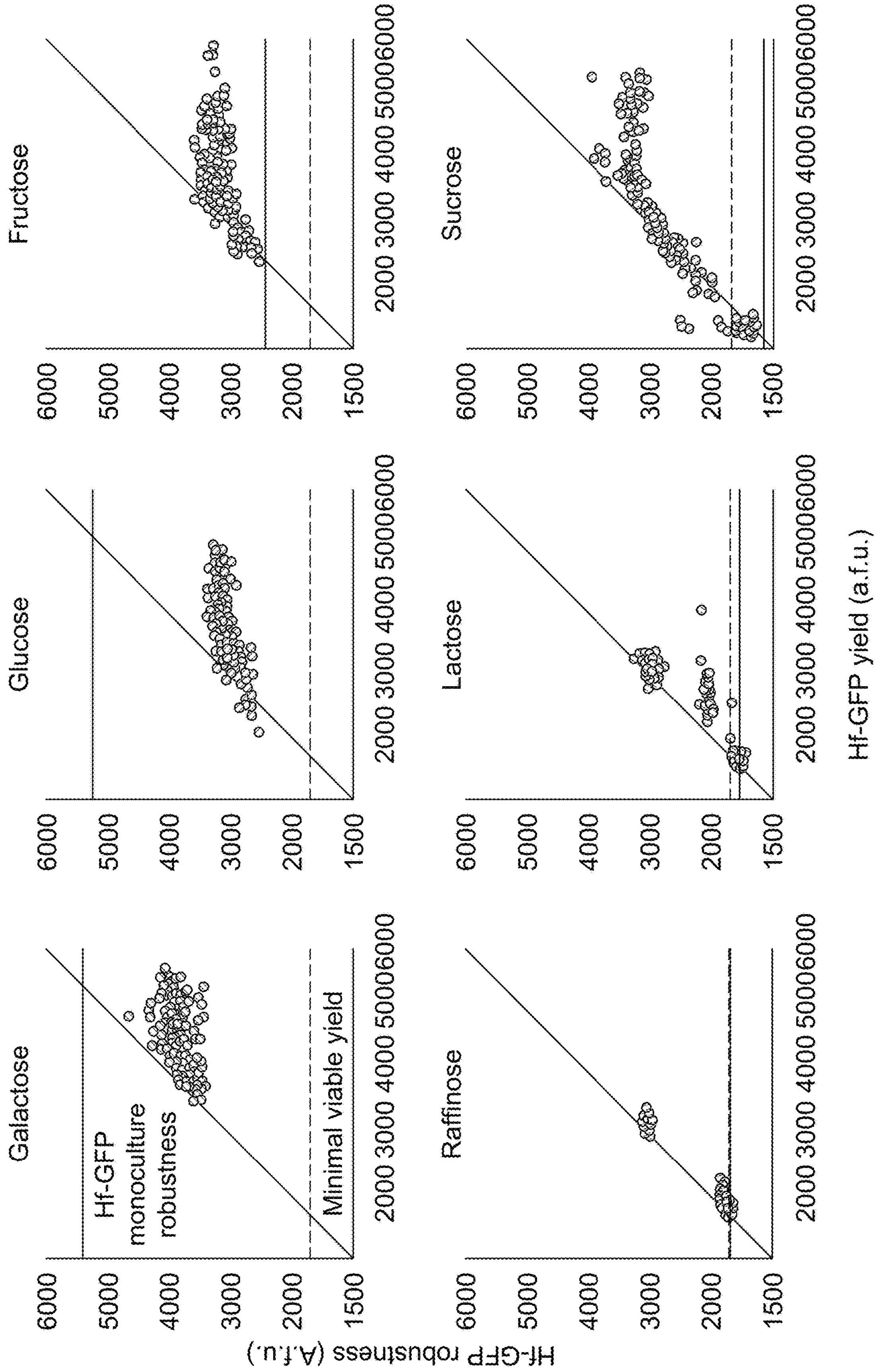
FIG. 19 shows that the effect of facilitative composition is typically robust to additional isolates. All data here represent compositions replicated ≥5 times (see FIG. 17 above) separated by carbon source (with no separation by carbon source shown in FIG. 3E above). "Hf-GFP yield" is the median Hf-GFP yield at 72 hr for a given composition represented ≥5 times for the given carbon source. "Hf-GFP robustness" is the 10th percentile of Hf-GFP yield for all communities containing the given composition with ≥1 additional isolates. Consistently, the facilitative effects of compositions enabling high growth of Hf-GFP were robust to the presence of additional isolates for each given carbon source. Gray dotted lines="minimal viable growth" of Hf-GFP (1500 GFP counts, or ~one standard deviation above mean Hf-GFP yield alone in sucrose at which GFP signal was indistinguishable from background). Solid horizontal lines=Hf-GFP monoculture 10th percentile ("robustness"). Black diagonal line=x=y line for reference.
Figure 20A:
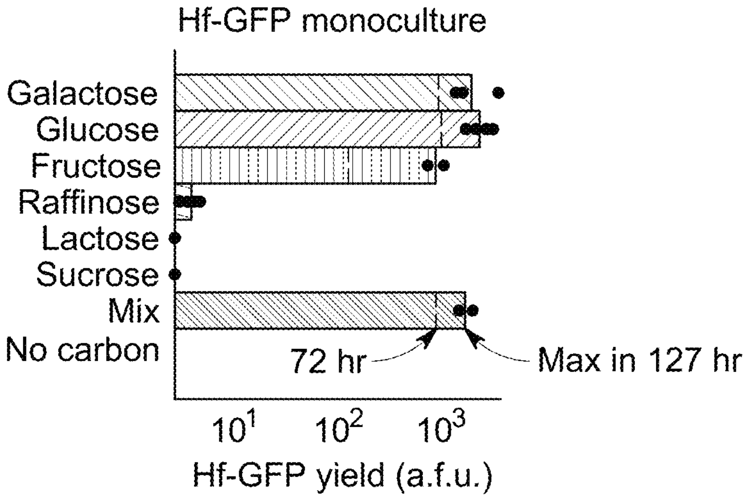
FIGS. 20A-20F show that the most robust compositions enabled facilitation across all carbon sources in 96-well plates in bulk cultures, validating results obtained from the kChip screen.
Figure 20B:
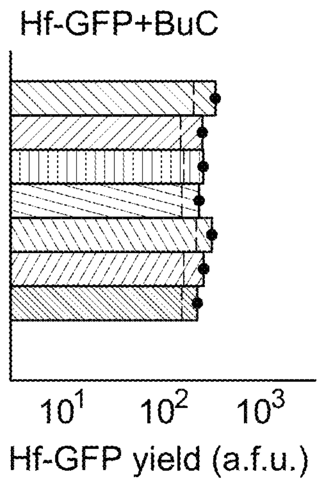
Figure 20C:
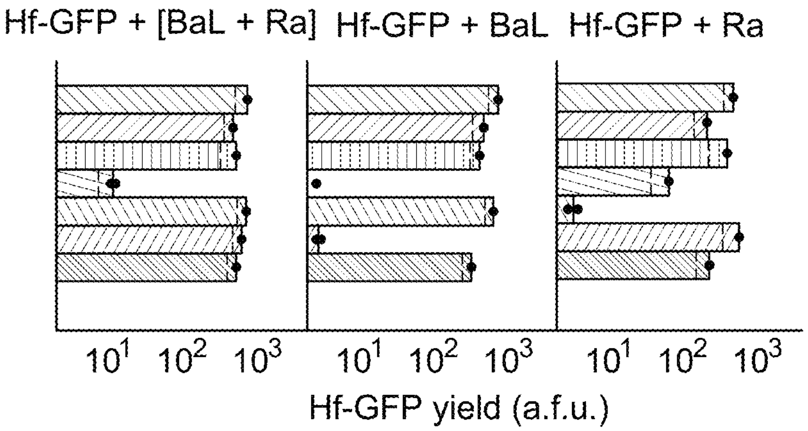
Figure 20D:
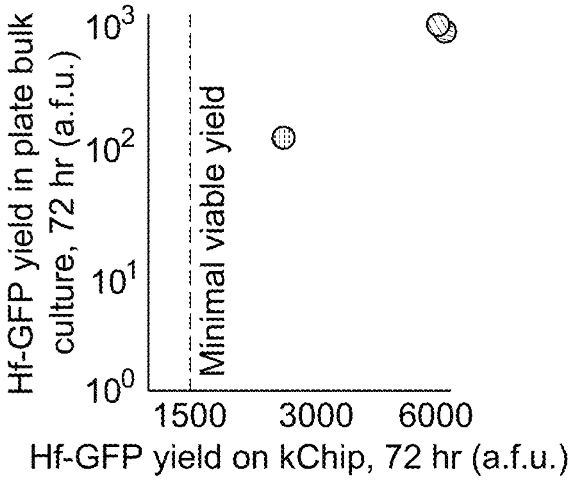
Figure 20E:
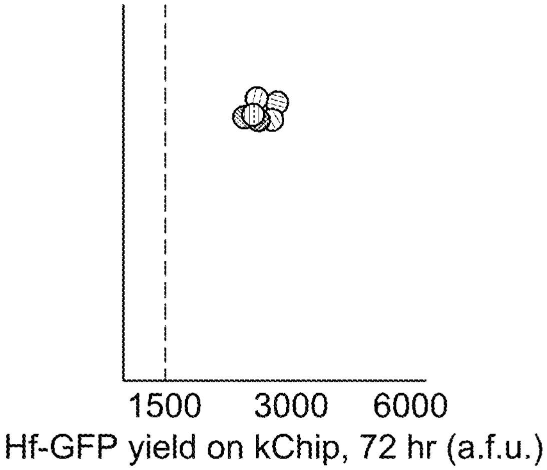
Figure 20F:
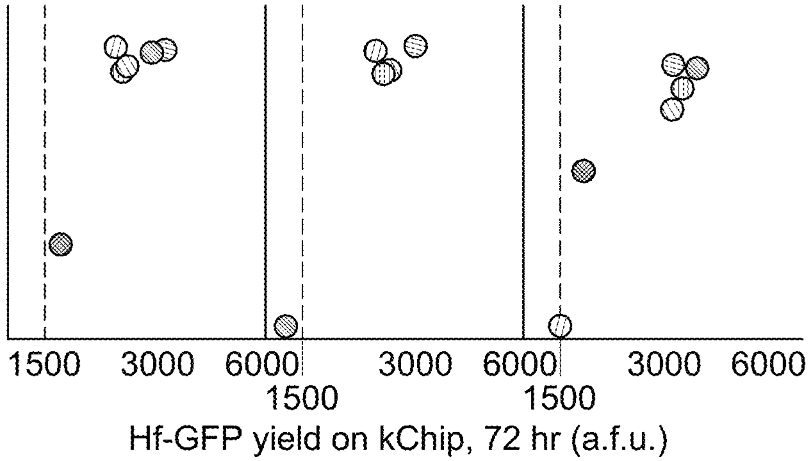

It was then sought to determine the facilitative compositions that were most robust to both carbon source and community context. Each composition was scored in two ways (see Example 1 above). First, median Hf-GFP yield at 72 hr was computed in co-culture with just the composition across all carbon sources ("Hf-GFP yield"). As a second score, the 10th percentile of Hf-GFP yield was computed in co-culture with all communities containing the given composition to detect whether the composition's effect on Hf-GFP was appreciably diminished by additional isolates across all carbon sources ("Hf-GFP robustness"). Based on noise estimates of Hf-GFP growth data, the analysis was restricted to instances where a given composition was represented 5 times on average on a kChip (or ≥30 times in total) (FIG. 16), which occurred for about half of s=k=3 compositions (FIG. 17), a value consistent with a probabilistic model of combinatorial space sampling (FIGS. 18A-18D). Two isolate compositions that were strongly facilitative and robust to both carbon source and community context were also uncovered (FIG. 3G). While most facilitative compositions showed robustness to community context for a given carbon source (FIG. 19), few showed robustness to both carbon source and community context. Interestingly, a particular isolate, *Burkholderia* sp. I (BuC), was identified as consistently present among compositions where Hf-GFP yield was high across carbon source and community context. Further, the isolate composition [*Bacillus* sp. II+*Rahnella* sp.] ([BaL+Ra]) was also identified to have enabled strong Hf-GFP yield across carbon source and community context. These two compositions' facilitative effects on Hf-GFP with the different carbon sources in 96-well plate bulk co-culture experiments were validated (FIGS. 20A-20F).

Figure 4B:
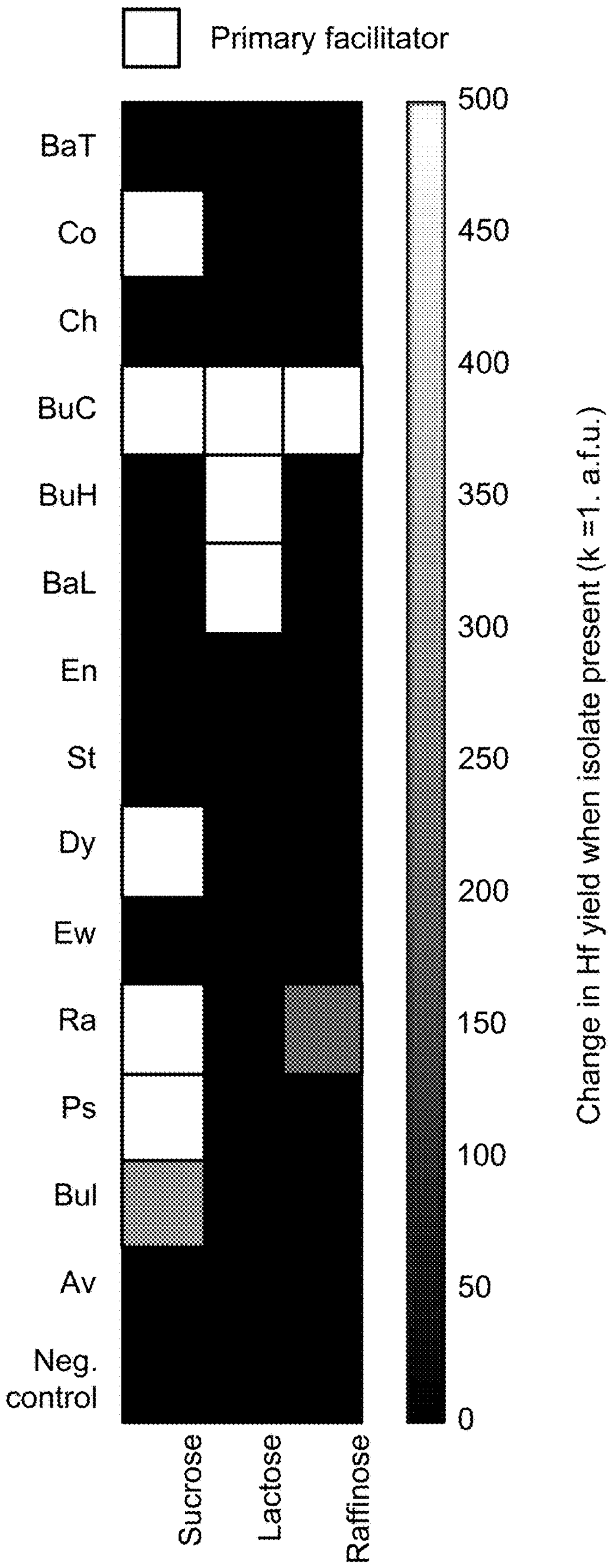
Figure 4C:
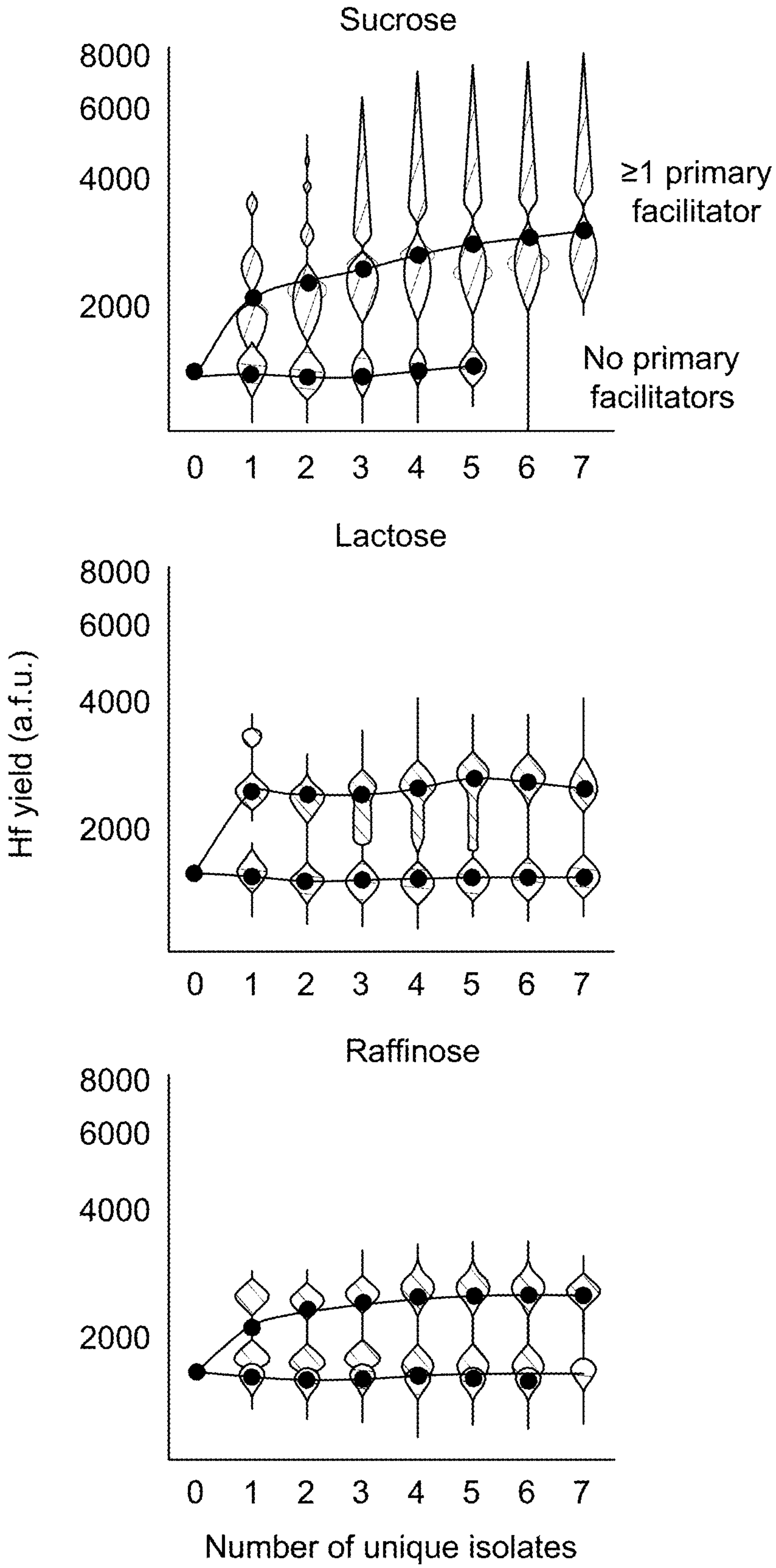
Figure 4D:
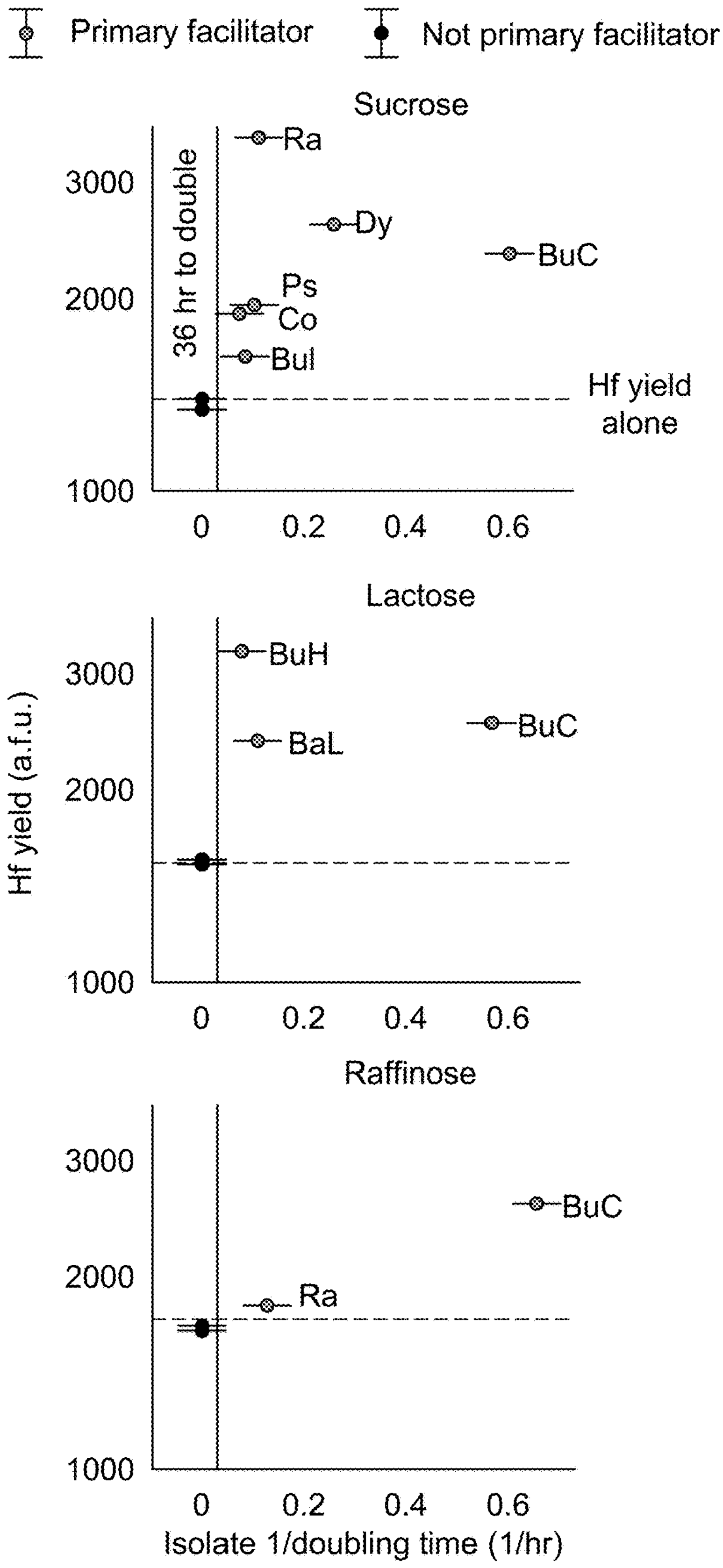

Example 5: Facilitation Increases with Community Richness and is Driven by a Small Number of Strains The datasets that kChip screening generates can be used to detect the ecological trends that underpin particularly facilitative or robust compositions like BuC or [BaL+Ra]. Broadly, it was found that Hf-GFP yield either increased or declined with community richness depending on its baseline growth on each carbon source in monoculture. In raffinose, lactose, and sucrose, the three carbon sources where it grew most poorly, Hf-GFP yield increased and then plateaued with community richness (FIG. 4A). A similar but weaker trend was observed in fructose, where Hf-GFP grew to a limited extent alone, and an isolate-agnostic suppressive effect in glucose and galactose where Hf-GFP grew well in monoculture (FIG. 21). Without restricting the analysis to communities consisting of all unique isolates, the same trend was observed for k=1-7 inputs and a roughly equivalent yield of Hf-GFP for 7 and 19 inputs (FIG. 22). In co-culture with a single isolate (k=1 microwells), "primary facilitator" strains that facilitated Hf-GFP growth in a given carbon source was identified (FIG. 4B). It was also found that the inclusion of 1 primary facilitator strains was necessary and almost always sufficient to facilitate Hf-GFP growth regardless of the number of other strains present (calculated from k>1 microwells) (FIG. 4C). In conjunction with the screen, growth rates of the isolates on the different carbon sources were assayed via the resazurin assay on a k=2 Chip (FIG. 24). For the raffinose, lactose, and sucrose conditions, it was found that the subset of isolates that could grow (≥1 doubling by 36 hr) matched the subset of primary facilitators (FIG. 4D). It was concluded that, for these conditions, isolate growth was sufficient for Hf-GFP facilitation.

Figure 25:
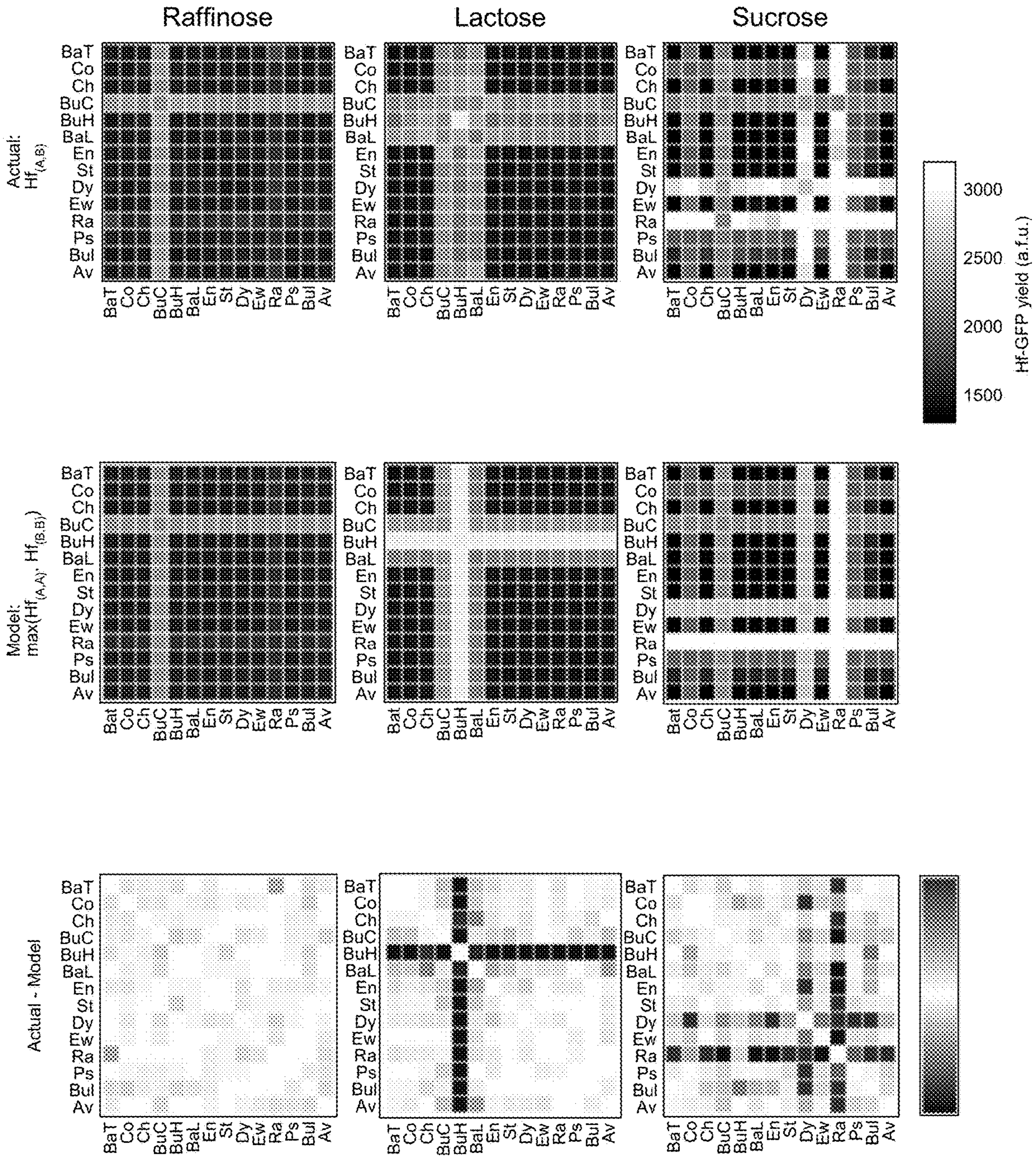
FIG. 25 shows that the Hf-GFP yield observed in the presence of two isolates could exceed its growth with each isolate individually. In the top panel $Hf_{(A,B)}$, the Hf-GFP yield at 72 hr in co-culture with the k=2 composition [A+B] in a given carbon source is shown. The middle panel presents a simple model where Hf-GFP yield in the presence of [A+B] is determined from k=2 data as $\max(Hf_{(A,A)}, Hf_{(B,B)})$. The bottom panel presents the difference between the top and middle panels. Red and blue indicate the degree to which $Hf_{(A,B)}$ is greater than or less than $\max(Hf_{(A,A)}, Hf_{(B,B)})$, respectively. Hf-GFP often exceeded the model's expectation in sucrose.

To investigate why facilitation increased with community richness beyond the presence of one primary facilitator, the k=2 level was first considered. Many instances were identified where Hf-GFP yield in the presence of two isolates was greater than its yield with either isolate individually, particularly when the carbon source was sucrose (FIG. 25).

Figure 26:
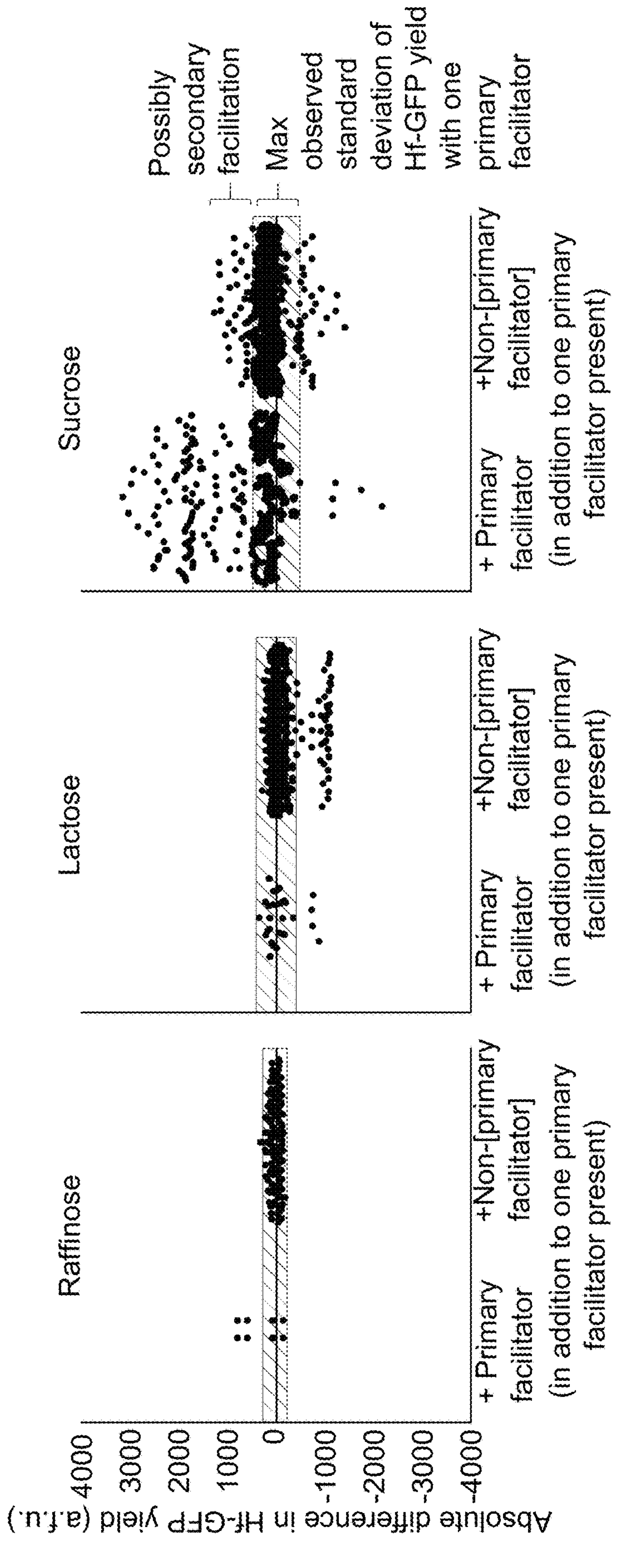
FIG. 26 shows that with one primary facilitator already present, Hf-GFP yield could further improve with additional primary facilitators and non-[primary facilitators] in a sucrose medium. Hf-GFP yield was enabled by the presence of a single primary facilitator in a composition (see FIG. 4C above). With one primary facilitator present, the addition of a second primary facilitator (left distributions) or non-[primary facilitator] (right distributions) could mediate this size of the facilitation. This effect was often positive in a sucrose medium, especially when the second isolate was a primary facilitator. Isolates were therefore identified, tentatively, as "secondary facilitators" if they were non-[primary facilitators] but appeared to exert a positive effect on Hf-GFP yield in the presence of a primary facilitator. The compositions analyzed here consist of all single isolate and pairwise isolate subsets of the 3-isolate compositions represented ≥5 times on each given carbon source. Black horizontal line=no effect. Gray shading=the maximum standard deviation among Hf-GFP yield in the presence of a single primary facilitator in the given carbon source, as an approximation for noise.

With a single primary facilitator present, it was observed that the largest Hf-GFP yield increases were imparted by the addition of a second primary facilitator (FIG. 26). It was also observed that modest increases could be imparted by the addition of a non-[primary facilitator] when a primary facilitator was present. These data pointed to general design principles useful in constructing facilitative consortia. Based on carbon source utilization as a criterion for primary facilitation (FIG. 4D), it could be expected that certain "core" compositions of isolates facilitate Hf-GFP across all carbon sources if at least one isolate within the core composition is able to grow on each carbon source. Further, based on the increase in Hf-GFP yield seen with community richness (FIGS. 4A, 25 and 26), improvements to the facilitative effect size or its robustness with the incorporation of specific isolates to the composition could be expected. Indeed, the two top-scoring compositions, BuC and [BaL+Ra], abide by these principles (FIGS. 27A-27C and Example 1 above).

Droplet microfluidics have recently been applied across a diverse range of assay types, including in single-cell transcriptomics, drug discovery, and microbiology (30, 36). The kChip platform of the instant disclosure expands upon these technologies to enable the rapid construction and high-throughput screening of beyond-pairwise species combinations. It has been demonstrated herein that the currently disclosed kChip screening paradigm is compatible with fluorescently labeled species (10 were tested herein, FIG. 32), diverse environmental isolates (14 were specifically tested herein, FIG. 34), and environmental conditions (16 were tested herein, FIG. 33). The kChip platform has been demonstrated herein to enable phenotypic screening of fluorescently labeled species across combinations of biotic (isolate) and abiotic (carbon source) settings, as well as growth profiling of unlabeled isolate libraries via the resazurin assay. Further demonstrating the utility of kChip screening as instantly disclosed, compositions that facilitate the model plant symbiont *Herbaspirillum frisingense* in a manner robust to carbon source and community context were identified herein. The ecological trends in the data were extrapolated, hypotheses about consortia design principles were generated, and consistency with these principles for top-scoring compositions identified in the screen were demonstrated.

Data generated through kChip screening is a valuable resource to explore the underlying ecology of cellular interactions among microorganisms (bacterial, algal, and/or fungal) and their environmental dependencies. Taking the carbon sources glucose and galactose, for which conserved glycolytic pathways are used ubiquitously by the bacterial kingdom, pervasive competition (FIG. 21), attributable to nutrient competition, was observed. Taking the more complex oligomers (sucrose, lactose, and raffinose) on which Hf-GFP monocultures grew poorly in monoculture, a possible explanation for the common facilitation that was observed (FIG. 4A) is the secretion of enzymes that increase carbon availability to Hf-GFP (37). In the case of sucrose, for example, it can be speculated that extracellular enzymes produced by facilitating strains cleave sucrose into glucose and fructose, monomers that are then utilized by Hf-GFP. It was identified herein that these facilitative effects were typically robust to community context (FIGS. 18A-18D), which indicated that this facilitation is driven by key interactions and is agnostic to the presence of additional strains. Improvement to the median yield of Hf-GFP with community richness (FIG. 4A) could be explained by the probability of sampling primary facilitator strains that individually facilitate Hf-GFP. In the case of sucrose, it was additionally observed that the effect of a primary facilitator could be bolstered by additional strains, which indicated additive and/or higher-order effects as well (FIG. 25 and FIG. 26). Finally, the rarity of robustness to both carbon source and community context (FIG. 3G) indicated that facilitative mechanisms depend highly on the environment and further indicated a need for testing under many conditions to identify mechanisms and interactions robust to carbon source variation.

Example 6: kChip Efficiently Assessed Fungal Strains

Figure 36B:
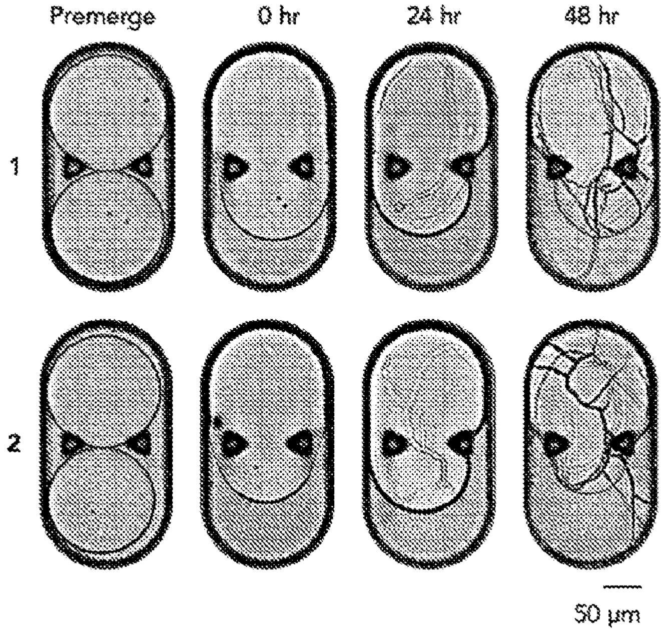

Having demonstrated the efficacy of kChip for screening of bacterial communities, application of kChip to fungi was also examined. In particular, kChip was demonstrated herein to be capable of assessing filamentous fungi. As shown in FIGS. 36A and 36B, when the filamentous fungi *Aspergillus, Penicillium*, and *Mucor* were applied to kChip, bright field microscopy enabled detection of label-less and reagent-free growth readout images for kChip droplets harboring these unlabeled forms of filamentous fungi. When zoomed-in (see FIG. 36B) images of wells harboring fungi were examined over a period of 48 hours, some merged droplets were identified to harbor fungi that formed filamentous structures (e.g., hyphae). Filamentous fungi such as those assayed are characterized by life cycles that include a "germination" phase (forming of the filamentous structures observed, e.g., in FIG. 36B). Notably, it is specifically contemplated herein that the ability to identify fungi that form filamentous structures as demonstrated on the instant kChip enables use of the kChip for fungal biology/activity monitoring across a range of fungal growth and lifecycle metrics, including but not limited to various aspects of fungal growth cycle and behavior (e.g., sporulation, germination, formation of mycelium) and gene expression. Examples of fungal screening performed using the kChip can therefore include assessment of fungal growth cycle and behavior under combinatorial challenge with chemical compounds or mixtures and/or bacteria (e.g., combinations of chemical compounds or mixtures, bacteria and/or both) and/or optionally other forms of fungi. In one specific example, which is not intended to be limiting, fungi in wells and/or droplets on the kChip can be contacted with combinations of bacteria and/or chemical compounds or mixtures in adjacent wells and/or droplets, while monitoring for the formation of filamentous structures within merged droplets and/or monitoring for one or more genes relevant to germination within such merged droplets, thereby identifying such bacteria and/or chemical compounds or mixtures as capable of, e.g., suppressing germination and/or expression of a gene relevant to germination. In addition to the example of germination, such specifically contemplated fungal screening approach can also be performed, for example, to assess chemical compound or mixture, bacterial and/or the effect of other fungi in modulating fungal sporulation, modulating mycelium formation, etc.

The above-described demonstration of kChip's efficacy for assessing fungi—particularly for assessing filamentous fungi as exemplified—additionally shows that the instant kChip is uniquely and advantageously suited to image fungal phenotypes in high-throughput (e.g., the otherwise difficult-to-image filamentous structures observed in FIG. 36B form in a small, enclosed space on the kChip and can therefore be readily imaged with standard microscopy techniques). As such, it is specifically contemplated that image analysis techniques can be readily deployed with the kChip described herein to quantify aspects of the shape/morphology of fungal spores, filaments, etc.

While the filamentous fungi assessed in the instant example were unlabeled, it is additionally contemplated that assessment of labeled and/or engineered strains of fungi can also be advantageously performed on the instant kChip. In one such application, among many others, GFP markers are used to track fungal growth and/or gene expression of fungi, optionally including growth and/or gene expression of fungi that have been engineered to express particular genes, gene products and/or compounds.

Further, it is expressly contemplated that the instant kChip can be employed to assess merged combinations of; (a) one or more fungi+one or more bacteria; (b) one or more fungi+one or more other fungi; (c) one or more chemical compounds or mixtures and one or more fungi; (d) one or more fungi+one or more bacteria+one or more chemical compounds or mixtures; etc.

It is also explicitly contemplated that the kChip of the instant disclosure has numerous applications to elucidating microbial community ecology, namely the phenotypic characterization of a given species or cell type across an array of biotic and/or abiotic settings. Datasets can be used to parameterize or assess mathematical models of growth or interactions as well as to determine how biotic metrics (e.g. the genetic and metabolic diversity of co-cultured species) and abiotic factors (e.g. the complexity, concentration, or ratio of carbon substrates provided) drive metabolic decision making and interactions. The kChip also enables performance of screens to detect when higher-order interactions emerge that are unpredictable from measured pairwise interactions (16, 38, 39) and to produce hypotheses about community design principles (40) and the environments that induce desirable interactions (41,42). Beyond basic ecology, kChip screens can now be used to identify promising compositions for development into probiotics. Inspired by the diversity of microbes residing in hosts (43) and the success of microbiota transplantation to counter ecological dysbiosis (44, 45), standardized interventions remain difficult to develop for a variety of reasons including a lack of mechanistic understanding and the explosion of possible strain combinations. Analogous to in vitro compound screening to generate therapeutic candidates, kChip screens can generate short lists of "hit" microbial cocktails that are also robust to relevant biotic and abiotic perturbations and constitute attractive candidates for validation and follow-up studies. For example, combinations of soil species can be identified that robustly facilitate plant growth-promoting rhizobacteria (PGPR), which have been shown to improve crop yields substantially (46) by providing the plant with nutrients and resisting pathogen colonization (47). On the other hand, it is contemplated herein that screens to identify combinations that robustly suppress the growth of pathogens may be particularly useful in the context of dysbiotic human microbiomes. Indeed, defined probiotics are under development to address infections like vancomycin-resistant enterococci (10), *Clostridium difficile* (11), and *Salmonella* (12). Screening combinations of species from healthy, pathogen-resistant microbiomes is expected to expedite probiotic discovery or identify higher-performing formulations. More broadly, any optically detectable community-wide phenotype can be screened, e.g. the degradation of a fluorescently labeled recalcitrant organic compound (or the growth of a fluorescently labeled species that consumes one of its byproducts); community-induced changes in gene expression (via promoter-GFP reporter fusions); and the production of cryptic, interaction-mediated metabolites that impact growth, such as antimicrobials (48).

Without wishing to be bound by theory, the random combinatorial construction and optical readout of kChip assays disclosed herein involve several design tradeoffs.

First, the construction of all the combinations happens spontaneously in a single step, but the random nature of the approach causes dispersion in the number of replicates for each assay condition, necessitating a statistical approach to covering the desired assay at a given level of replication. The resulting throughput/replication tradeoff becomes limiting for larger combinations, e.g. for $k \geq 4$ in the Hf-GFP facilitation screen, given the number of microwells available on the instantly disclosed kChip devices (FIGS. 3A-3G and 17). This effect is due to the super-geometric increase in the number of possible combinations as k increases (for $k \ll n$). The "kChip loading statistics" section above discusses how to calculate the expected replication.

To aid in experimental design, FIGS. 18A-18D plot the expected replication for many different scenarios based on the size of the input library (values of n), the number of microwells, and the microwell size(s) (values of k) for a given screen. For example, in the case of the Hf-GFP facilitation screen, a library of 16 inputs (n=16) and kChips designed with arrays of k=1, 2, . . . , 7, or 19 inputs per microwell were used (with the number of microwells per kChip given in FIG. 1B). Based on these numbers, the number of expected replicates for each k was calculated (red plots in right column in FIG. 18C). For s=k=1, 2, 3, and 4, the average number of expected replicates per combination (where all inputs were unique) are >100, ~20, ~5, and <1, respectively. A library of >16 inputs generates fewer s=k replicates at each k (orange and purple plots in FIG. 18C), placing an upper bound on the library size to achieve a given number of replicates per combination given a fixed number of available microwells.

While a smaller library size increases the number of replicates per combination (e.g. for a library of 8 inputs, blue plots in FIG. 18C), the screening efficiency is reduced if certain combinations are considered undesirable. For example, in the Hf-GFP facilitation screen, there was a primary interest in instances in which all inputs within a given combination were different (e.g. a given combination A:B:C:D:E=1:1:1:1:1 in a k=5 microwell was always considered in the instant analyses, but the combination A:B:C=2:2:1 in a k=5 microwell was typically excluded). In this case, a smaller library size might actually decrease the number of desirable combinations. For example, consider a small library size of 8 inputs (blue plots in FIG. 18C). At k=7, there are only 8 possible unique combinations (where each input is represented up to one time), but 3,432 possible non-unique combinations (where at least one input is represented greater than one time). Indeed, as k increases for a small library size, the efficiency of sampling desirable (no multi-choice) combinations decreases. In the Hf-GFP facilitation screen, a library size of 16 was therefore chosen to balance this reduction in efficiency associated with small libraries while still generating a sufficiently high number of replicates for s=k=1, 2, and 3 where all inputs were different.

In addition to the aforementioned considerations of the input library size, the number of microwells, and the microwell sizes, the overall throughput of a screen is also determined by the total number of microwells/kChips available to a screen. In the Hf-GFP facilitation screen, for example, six kChips were run in series with a single imaging system with ~half a day of hands-on set up time (~30 minutes required to set up each kChip). Depending on the desired time resolution for multiple timepoint studies (e.g. a 2× imaging scan currently takes ~12-15 minutes per kChip), one may wish to load greater or fewer kChips in the course of a given screen. The upper limit on the throughput of kChip screening is dictated by the number of microwells. For screens consisting of ~100 chips (a scale practiced in the past (32)), ~$10^6$-$10^7$ communities could be constructed. Use of larger numbers of chips (and optionally additional personnel) is explicitly contemplated to enable even higher levels of throughput.

Figure 30D:
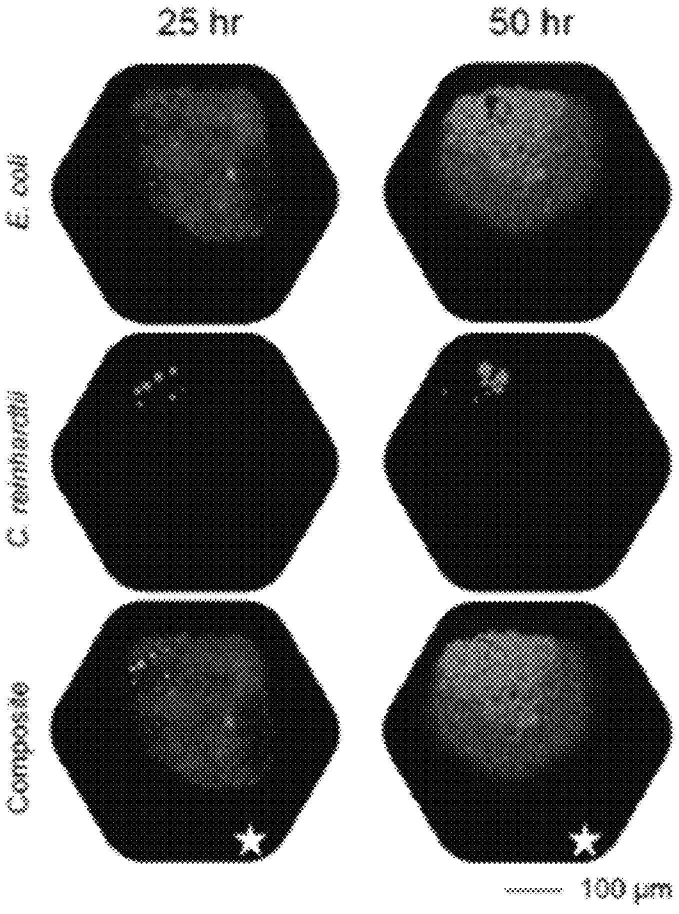
Figure 30E:
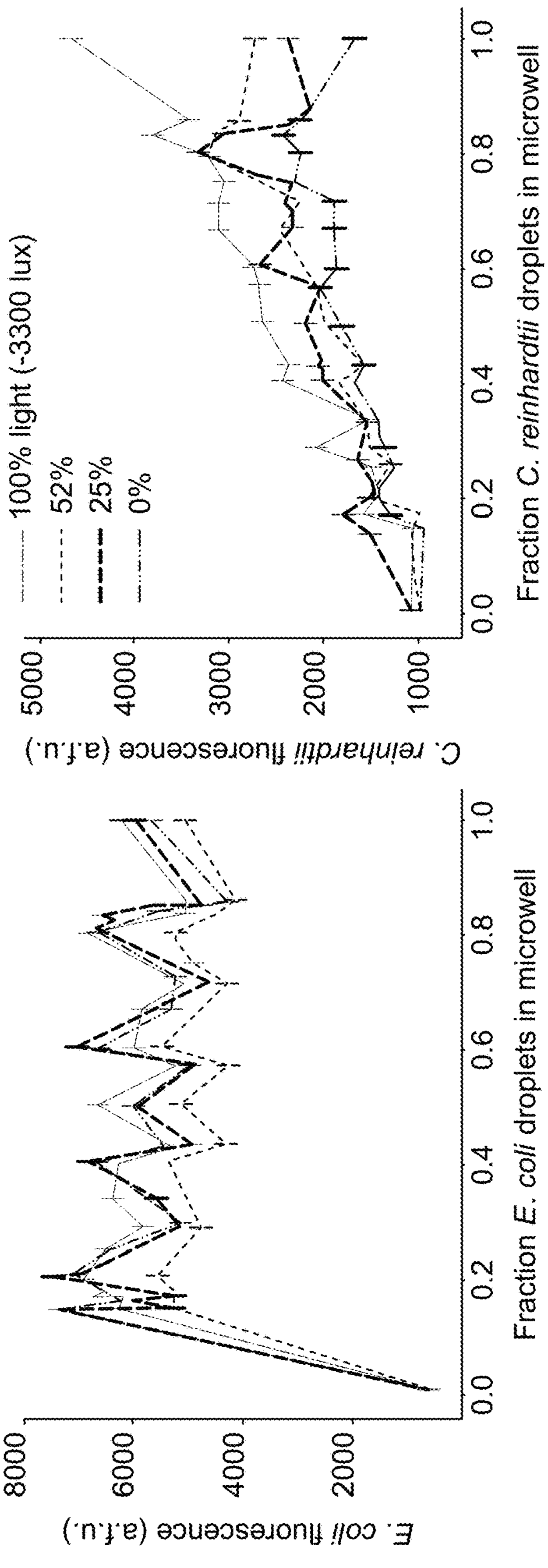

Second, while the kChip platform has been demonstrated for optical assays in the instant disclosure, such as the fluorescence imaging used herein, biochemical assays such as nucleic acid sequencing or mass spectrometry are contemplated as highly useful applications of the compositions and methods of the instant disclosure, and can likely be achieved by retrieving droplets from the array for further analysis. In addition, adding reagents after the initial loading of the array, e.g. to add stains at the assay endpoint or to feed cells over the course of an assay, is also contemplated. It is contemplated that some organisms could interfere with the optical assay, for example by secreting a fluorescent compound that interferes with the desired signal. To date, growth has been assessed as a phenotype, but "high content" morphological phenotypes such as filamentation, microcolony formation, and aggregation are also contemplated as feasible, especially with the aid of higher magnification. For example, consider the spatial organization of cultures observed under 10× magnification images (FIG. 30D).

Beyond fluorescence-based assays, the potential for bright field and/or phase contrast microscopy as a generalized readout that can be used to monitor microbial growth on the kChip without labeling (e.g. GFP expression) or addition of assay reagents (e.g. resazurin) is explicitly noted. Herein, the use of a phase contrast metric was demonstrated to measure *E. coli* growth on six single carbon sources (FIGS. 31A-31C). The instant phase contrast readout produced similar growth curves to those taken with other on-chip assays (GFP) and off-chip assays (GFP and $OD_{600}$ on 96-well plate taken via SpectraMax plate reader).

While only the growth of aerobic microbes has been expressly exemplified herein, there are no inherent limitations associated with the cultivation of any particular class or microbes that are small enough to fit inside the droplets, e.g. anaerobes (provided that the droplets and loaded chips can be prepared and stored under anaerobic conditions).

As will be recognized by the skilled artisan, while not essential, a high-performance microscope (high numerical-aperture optics, wide field of view, and low camera dark current and read noise) is useful to the extent that throughput is not rate-limited by optics and camera quality. Additionally, off-chip droplet production may be expedited by a dedicated droplet generating instrument (e.g. the Bio-Rad QX200 used for these experiments) or a custom pressure manifold (32). Finally, basic proficiency with scientific image analysis (e.g. Matlab, Python) and data analysis for identifying and classifying droplet signals is also useful.

Ecological Interpretation of Results

Data generated through kChip screening provides a valuable resource to explore the underlying ecology of cellular interactions among microorganisms (bacterial, algal, and/or fungal) and their environmental dependencies.

Taking the carbon sources glucose and galactose, for which conserved glycolytic pathways are used ubiquitously across the bacterial domain, pervasive competition was observed herein (FIG. 21). In contrast, the instant results with the more complex oligomers (sucrose, lactose, and raffinose), on which Hf-GFP monocultures grew poorly in monoculture), are consistent with cross-feeding (FIG. 4A) that increases the availability of carbon accessible to Hf-GFP (56). In the case of sucrose, for example, without wishing to be bound by theory, it is speculated that enzymes produced by facilitating strains cleave sucrose into glucose and fructose, monomers that are then utilized by Hf-GFP.

It was identified herein that such facilitative effects were typically robust to community context (FIGS. 18A-18D), which indicated that this facilitation is driven by key interactions and agnostic to the presence of additional strains. Improvement to the median yield of Hf-GFP with community richness (FIG. 4A) could likely be explained by the probability of sampling primary facilitator strains that individually facilitate Hf-GFP. In the case of sucrose, it was additionally observed that the effect of a primary facilitator could be bolstered by additional strains, which indicated additive and/or higher-order (e.g., synergistic and/or multiplicative) effects as well (FIGS. 25 and 26). Due to this increased probability of sampling primary facilitators and these additive and/or higher-order effects, it was observed that Hf-GFP yield converges across carbon sources as community size increases (FIGS. 4A, 21 and 22). Finally, the rarity of high robustness to both carbon source and community context (FIG. 3E) indicated that facilitative mechanisms depend highly on the environment and further indicated a need for testing under many conditions to identify mechanisms and interactions robust to diverse biotic and chemical contexts.

kChip Use for Probiotic Discovery

Inspired by the diversity of microbes residing in hosts (57) and the success of microbiota transplantation to counter ecological dysbiosis (58, 59), standardized interventions remain difficult to develop for a variety of reasons including a lack of mechanistic understanding and the explosion of possible strain combinations. Analogous to in vitro compound screening to generate therapeutic candidates, kChip screens can generate short lists of "hit" microbial cocktails that are also robust to relevant biotic and abiotic perturbations and constitute attractive candidates for validation and follow-up studies. For example, combinations of soil species can be identified that robustly facilitate plant growth-promoting rhizobacteria (PGPR), which have been shown to improve crop yields substantially (60) by providing the plant with nutrients and resisting pathogen colonization (61).

Screens to identify combinations that possess certain therapeutic functions may be particularly useful in the context of dysbiotic human microbiomes. Defined probiotics are already under development to address infections like vancomycin-resistant enterococci (62), *Clostridium difficile* (63), and *Salmonella* (64). Using the kChip, direct screens can be performed for strain combinations that suppress the growth of pathogens, assess the robustness of hit combinations to the presence of microbiome-like communities (as a proxy for the diversity of native microbiota among which delivered microbes may need to persist), and identify strains that inhibit suppressive capabilities of hit combinations (as an exclusionary diagnostic for use of a hit combination as a microbial therapeutic). Other potentially desirable functions of therapeutic cocktails, e.g. interactions with immune cells, can be hypothetically screened on the kChip platform, as it has been shown that mammalian cells can be cultivated in droplets as well (65). Finally, toward the development of prebiotics, the kChip can be used to screen environmental conditions, e.g. carbon sources that specifically support the growth of commensal strains rather than pathogenic strains, or elicit desirable bacterial functions or immune interactions.

REFERENCES

1. Hemingway J D, et al. (2018) Microbial oxidation of lithospheric organic carbon in rapidly eroding tropical mountain soils. *Science* 360(6385): 209-212.
2. Bardgett R D, Freeman C, Ostle N J (2008) Microbial contributions to climate change through carbon cycle feedbacks. *ISME J* 2(8): 805-814.
3. Firestone M (2015) Plant stimulation of soil microbial community succession: how sequential expression mediates soil carbon stabilization and turnover doi: 10.2172/1177136.
4. Buffie C G, et al. (2015) Precision microbiome reconstitution restores bile acid mediated resistance to *Clostridium difficile. Nature* 517(7533): 205-208.
5. Berendsen R L, Pieterse C M J, Peter A H (2012) The rhizosphere microbiome and plant health. *Trends Plant Sci* 17(8): 478-486.
6. Hays S G, Patrick W G, Ziesack M, Oxman N, Silver P A (2015) Better together: engineering and application of microbial symbioses. *Curr Opin Biotechnol* 36: 40-49.
7. Zhou K, Qiao K, Edgar S, Stephanopoulos G (2015) Distributing a metabolic pathway among a microbial consortium enhances production of natural products. *Nat Biotechnol* 33(4): 377-383.
8. Li L, et al. (2008) Removal of methyl parathion from artificial off-gas using a bioreactor containing a constructed microbial consortium. *Environ Sci Technol* 42(6): 2136-2141.
9. Mendes R, et al. (2011) Deciphering the rhizosphere microbiome for disease-suppressive bacteria. *Science* 332 (6033): 1097-1100.
10. Caballero S, et al. (2017) Cooperating Commensals Restore Colonization Resistance to Vancomycin-Resistant *Enterococcus faecium. Cell Host Microbe* 21(5): 592-602.e4.
11. Lawley T D, et al. (2012) Targeted restoration of the intestinal microbiota with a simple, defined bacteriotherapy resolves relapsing *Clostridium difficile* disease in mice. *PLoS Pathog* 8(10): e1002995.
12. Brugiroux S, et al. (2016) Genome-guided design of a defined mouse microbiota that confers colonization resistance against *Salmonella enterica* serovar Typhimurium. *Nat Microbiol* 2: 16215.
13. Mitri S, Foster K R (2013) The genotypic view of social interactions in microbial communities. *Annu Rev Genet* 47: 247-273.
14. Ghoul M, Mitri S (2016) The Ecology and Evolution of Microbial Competition. *Trends Microbiol* 24(10): 833-845.
15. Momeni B, Xie L, Shou W (2017) Lotka-Volterra pairwise modeling fails to capture diverse pairwise microbial interactions. *Elife* 6. doi: 10.7554/eLife.25051.
16. Sanchez-Gorostiaga A, Bajić D, Osborne M L, Poyatos J F, Sanchez A (2018) High-order interactions dominate the functional landscape of microbial consortia. doi: 10.1101/333534.
17. Tsai K-N, Lin S-H, Liu W-C, Wang D (2015) Inferring microbial interaction network from microbiome data using RMN algorithm. *BMC Syst Biol* 9: 54.
18. Harcombe W R, et al. (2014) Metabolic resource allocation in individual microbes determines ecosystem interactions and spatial dynamics. *Cell Rep* 7(4): 1104-1115.
19. Magnúsdóttir S, et al. (2017) Generation of genome-scale metabolic reconstructions for 773 members of the human gut microbiota. *Nat Biotechnol* 35(1): 81-89.
20. Friedman J, Higgins L M, Gore J (2017) Community structure follows simple assembly rules in microbial microcosms. *Nat Ecol Evol* 1(5): 109.
21. de Vos M G J, Zagorski M, McNally A, Bollenbach T (2017) Interaction networks, ecological stability, and collective antibiotic tolerance in polymicrobial infections. *Proc Nat Acad Sci USA* 114(40): 10666-10671.
22. Bell T, Newman J A, Silverman B W, Turner S L, Lilley A K (2005) The contribution of species richness and composition to bacterial services. *Nature* 436(7054): 1157-1160.
23. Croston G E (2002) Functional cell-based uHTS in chemical genomic drug discovery. *Trends Biotechnol* 20(3): 110-115.
24. Sundberg S A (2000) High-throughput and ultra-high-throughput screening: solution- and cell-based approaches. *Curr Opin Biotechnol* 11(1): 47-53.
25. Nai C, Meyer V (2017) From Axenic to Mixed Cultures: Technological Advances Accelerating a Paradigm Shift in Microbiology. *Trends Microbiol.* doi: 10.1016/j.tim.2017.11.004.
26. Foster K R, Bell T (2012) Competition, Not Cooperation, Dominates Interactions among Culturable Microbial Species. *Curr Biol* 22(19): 1845-1850.
27. Mee M T, Collins J J, Church G M, Wang H H (2014) Syntrophic exchange in synthetic microbial communities. *Proc Natl Acad Sci USA* 111(20): E2149-E2156.
28. Venturelli O S, et al. (2018) Deciphering microbial interactions in synthetic human gut microbiome communities. *Mol Syst Biol* 14(6): e8157.
29. Cordero O X, et al. (2012) Ecological populations of bacteria act as socially cohesive units of antibiotic production and resistance. *Science* 337(6099): 1228-1231.
30. Kaminski T S, Scheler O, Garstecki P (2016) Droplet microfluidics for microbiology: techniques, applications and challenges. *Lab Chip* 16(12): 2168-2187.
31. Cira N J, Ho J Y, Dueck M E, Weibel D B (2012) A self-loading microfluidic device for determining the minimum inhibitory concentration of antibiotics. *Lab Chip* 12(6): 1052-1059.
32. Kulesa A, Kehe J, Hurtado J E, Tawde P, Blainey P C (2018) Combinatorial drug discovery in nanoliter droplets. *Proc Natl Acad Sci USA* 115(26): 6685-6690.
33. Datta M S, Sliwerska E, Gore J, Polz M F, Cordero O X (2016) Microbial interactions lead to rapid micro-scale successions on model marine particles. *Nat Commun* 7: 11965.
34. Boedicker J Q, Li L, Kline T R, Ismagilov R F (2008) Detecting bacteria and determining their susceptibility to antibiotics by stochastic confinement in nanoliter droplets using plug-based microfluidics. *Lab Chip* 8(8): 1265-1272.
35. Straub D, Rothballer M, Hartmann A, Ludewig U (2013) The genome of the endophytic bacterium *H. frisingense* GSF30T identifies diverse strategies in the *Herbaspirillum* genus to interact with plants. *Front Microbiol* 4. doi: 10.3389/fmicb.2013.00168.
36. Terekhov S S, et al. (2018) Ultrahigh-throughput functional profiling of microbiota communities. *Proc Natl Acad Sci USA* 115(38): 9551-9556.
37. Celiker H, Gore J (2013) Cellular cooperation: insights from microbes. *Trends Cell Biol.* 23(1): 9-15.

38. Guo X, Boedicker J (2016) High-Order Interactions between Species Strongly Influence the Activity of Microbial Communities. *Biophys J* 110(3): 143a.
39. Gould A L, et al. (2017) High-dimensional microbiome interactions shape host fitness. doi: 10.1101/232959.
40. Johns N I, Blazejewski T, Gomes A L, Wang H H (2016) Principles for designing synthetic microbial communities. *Curr Opin Microbiol* 31: 146-153.
41. Hom E F Y, Murray A W (2014) Plant-fungal ecology. Niche engineering demonstrates a latent capacity for fungal-algal mutualism. *Science* 345(6192): 94-98.
42. Zhou W, Chow K-H, Fleming E, Oh J (2018) Selective colonization ability of human fecal microbes in different mouse gut environments. *ISME J.* doi: 10.1038/s41396-018-0312-9.
43. Kowarsky M A, et al. (2017) Humans are colonized by many uncharacterized and highly divergent microbes. doi: 10.1101/113746.
44. Borody T J, Khoruts A (2011) Fecal microbiota transplantation and emerging applications. *Nat Rev Gastroenterol Hepatol* 9(2): 88-96.
45. Hu J, et al. (2016) Probiotic Diversity Enhances Rhizosphere Microbiome Function and Plant Disease Suppression. *MBio* 7(6). doi: 10.1128/mBio.01790-16.
46. Bhattacharyya P N, Jha D K (2012) Plant growth-promoting rhizobacteria (PGPR): emergence in agriculture. *World J Microbiol Biotechnol* 28(4): 1327-1350.
47. Benizri E, Baudoin E, Guckert A (2001) Root Colonization by Inoculated Plant Growth Promoting Rhizobacteria. *Biocontrol Sci Technol* 11(5): 557-574.
48. Seyedsayamdost M R, Traxler M F, Clardy J, Kolter R (2012) Old meets new: using interspecies interactions to detect secondary metabolite production in actinomycetes. *Methods Enzymol* 517: 89-109.
49. Skhiri Y, et al. (2012) Dynamics of molecular transport by surfactants in emulsions. *Soft Matter* 8(41): 10618.
50. Pan M, Lyu F, Tang S K Y (2015) Fluorinated Pickering Emulsions with Nonadsorbing Interfaces for Droplet-based Enzymatic Assays. Anal Chem 87(15): 7938-7943.
51. Gruner P, et al. (2016) Controlling molecular transport in minimal emulsions. Nat Commun 7: 10392.
52. Gonzalez-Pinzon R, Haggerty R, Myrold D D (2012) Measuring aerobic respiration in stream ecosystems using the resazurin-resorufin system. Journal of Geophysical Research: Biogeosciences 117(G3). doi: 10.1029/2012jg001965.
53. Larkin M A, et al. (2007) Clustal W and Clustal X version 2.0. Bioinformatics 23(21): 2947-2948.
54. Lefort V, Longueville J-E, Gascuel O (2017) SMS: Smart Model Selection in PhyML. Mol Biol Evol 34(9): 2422-2424.
55. Cole J R, et al. (2014) Ribosomal Database Project: data and tools for high throughput rRNA analysis. Nucleic Acids Res 42(Database issue): D633-42.
56. Celiker H, Gore J (2013) Cellular cooperation: insights from microbes. Trends Cell Biol 23(1):9-15.
57. Kowarsky M A, et al. (2017) Humans are colonized by many uncharacterized and highly divergent microbes. doi:10.1101/113746.
58. Hu J, et al. (2016) Probiotic Diversity Enhances Rhizosphere Microbiome Function and Plant Disease Suppression. MBio 7(6). doi:10.1128/mBio.01790-16.
59. Borody T J, Khoruts A (2011) Fecal microbiota transplantation and emerging applications. Nat Rev Gastroenterol Hepatol 9(2):88-96.
60. Bhattacharyya P N, Jha D K (2012) Plant growth-promoting rhizobacteria (PGPR): emergence in agriculture. World J Microbiol Biotechnol 28(4):1327-1350.
61. Benizri E, Baudoin E, Guckert A (2001) Root Colonization by Inoculated Plant Growth-Promoting Rhizobacteria. Biocontrol Sci Technol 11(5):557-574.
62. Caballero S, et al. (2017) Cooperating Commensals Restore Colonization Resistance to Vancomycin-Resistant *Enterococcus faecium*. Cell Host Microbe 21(5):592-602.e4.
63. Lawley T D, et al. (2012) Targeted restoration of the intestinal microbiota with a simple, defined bacteriotherapy resolves relapsing *Clostridium difficile* disease in mice. PLoS Pathog 8(10):e1002995.
64. Brugiroux S, et al. (2016) Genome-guided design of a defined mouse microbiota that confers colonization resistance against *Salmonella enterica* serovar Typhimurium. Nat Microbiol 2:16215.
65. Clausell-Tormos J, et al. (2008) Droplet-based microfluidic platforms for the encapsulation and screening of Mammalian cells and multicellular organisms. Chem Biol 15(5):427-4

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A microfluidic screening platform comprising:

at least one droplet input for receiving one or more sets of droplets, each set of droplets comprising individual droplets each individual droplet comprising a single type of microbe and/or chemical compound or mixture; and an array of microwells, wherein each microwell is capable of receiving an individual droplet and wherein three or more posts encircle each microwell of the array.

2. The microfluidic screening platform of claim 1, wherein a plurality of the microwells of the array of microwells comprises one and only one droplet.

3. The microfluidic screening platform of claim 1, wherein individual droplets of the array of microwells are optically screened.

4. The microfluidic screening platform of claim 3, wherein the optical screening comprises measurement of luminescence and/or fluorescence.

5. The microfluidic screening platform of claim 1, wherein individual droplets in user-selected adjacent microwells are merged into a single merged assay.

6. The microfluidic screening platform of claim 1, wherein, across the array:

(a) individual droplets in two adjoining microwells are merged into single merged assays;

(b) individual droplets in three adjoining microwells are merged into single merged assays;

(c) individual droplets in four adjoining microwells are merged into single merged assays;

(d) individual droplets in five adjoining microwells are merged into single merged assays;

(e) individual droplets in six adjoining microwells are merged into single merged assays;

(f) individual droplets in seven adjoining microwells are merged into single merged assays;

(g) individual droplets in eight to eighteen adjoining microwells are merged into single merged assays;

(h) individual droplets in nineteen adjoining microwells are merged into single merged assays; or (i) individual droplets in twenty to fifty adjoining microwells are merged into single merged assays.

7. The microfluidic screening platform of claim 5, wherein one or more attributes of the microbes and/or chemical compounds or mixtures present in each merged assay are measured via optical screening.

8. The microfluidic screening platform of claim 7, wherein the optical screening comprises measurement of luminescence and/or fluorescence.

9. The microfluidic screening platform of claim 1, wherein the droplets comprising microbes and/or chemical compounds or mixtures self-assemble randomly into microwells.

10. The microfluidic screening platform of claim 7, wherein the one or more attributes of the microbes present in each merged assay measured via optical screening comprise growth of the microbes.

11. The microfluidic screening platform of claim 6, wherein each single merged assay comprises two or more types of microbes.

12. The microfluidic screening platform of claim 6, wherein each single merged assay comprises two or more types of microbes and/or chemical compounds or mixtures, wherein at least one of the two or more types of microbes and/or chemical compounds or mixtures is a microbe.

13. The microfluidic screening platform of claim 12, wherein:

at least one of the two or more types of microbes and/or chemical compounds or mixtures is a chemical compound; and/or at least one of the two or more types of microbes and/or chemical compounds or mixtures is a bacterium.

14. The microfluidic screening platform of claim 6, wherein:

each single merged assay comprises two or more types of fungi;

at least one of the single merged assays comprises a combination of at least one fungus and at least one bacterium;

at least one of the single merged assays comprises a combination of at least one fungus and at least one chemical compound or mixture;

at least one of the single merged assays comprises a combination of at least one bacterium and at least one chemical compound or mixture; and/or at least one of the single merged assays comprises a combination of at least one bacterium, at least one fungus and at least one chemical compound or mixture.

15. The microfluidic screening platform of claim 1, wherein:

the array of microwells comprises droplets constituting at least four different types of microbe;

each microwell of the array of microwells is approximately 80 μm to approximately 180 μm or more in diameter, approximately 80 μm to approximately 170 μm or more in diameter, approximately 125 μm to 165 μm in diameter, approximately 130 μm to 160 μm in diameter, approximately 135 μm to 155 μm in diameter, approximately 140 μm to 150 μm in diameter, approximately 145 μm to 150 μm in diameter, approximately 148 μm in diameter, or precisely 148.2 μm in diameter;

each microwell of the array of microwells is approximately 110 μm to 120 μm deep; and/or a majority of the individual droplets are of size approximately 120 μm to 150 μm in diameter, 125 μm to 145 μm in diameter, or 130 μm to 140 μm in diameter.

16. A microfluidic screening platform comprising:

at least one droplet input for receiving one or more sets of droplets, wherein said one or more sets of droplets are administered to a high-pass size filter comprising a series of channels designed to trap droplets of less than a predefined diameter; and an array of microwells for receiving the droplets, wherein three or more posts encircle each microwell of the array.

17. The microfluidic screening platform of claim 16, wherein said series of channels designed to trap droplets of less than a predefined diameter comprises a series of 10 or more channels of approximately 80 μm to 134 μm in width.

18. A method of comparing pairwise or higher order complexes of droplet-encapsulated fluids in parallel, the method comprising:

administering a variety of droplet-encapsulated fluidic compositions to the microfluidic screening platform of claim 1;

applying electrocoalescence, thermal coalescence or acoustic coalescence to merge droplets in user-selected adjacent microwells into a single merged assay, across the array of microwells, thereby forming an array of at least 500 independent merged assays; and comparing merged assays selected from among the at least 500 independent merged assays with one another to identify attributes of the merged assays, thereby comparing pairwise or higher order complexes of droplet-encapsulated fluidic compositions in parallel.

19. The method of claim 18, wherein:

the droplet-encapsulated fluids comprise microbes and/or chemical compounds or mixtures;

a plurality of the microwells of the array of microwells comprises one and only one droplet;

individual droplets of the array of microwells are optically screened;

across the array:

(a) individual droplets in two adjoining microwells are merged into single merged assays;

(b) individual droplets in three adjoining microwells are merged into single merged assays;

(c) individual droplets in four adjoining microwells are merged into single merged assays;

(d) individual droplets in five adjoining microwells are merged into single merged assays;

(e) individual droplets in six adjoining microwells are merged into single merged assays;

(f) individual droplets in seven adjoining microwells are merged into single merged assays;

(g) individual droplets in eight to eighteen adjoining microwells are merged into single merged assays;

(h) individual droplets in nineteen adjoining microwells are merged into single merged assays; or (i) individual droplets in twenty to fifty adjoining microwells are merged into single merged assays;

the droplets comprise microbes, wherein one or more attributes of the microbes present in each merged assay are measured via optical screening;

the array of microwells comprises droplets constituting at least five different types of microbe;

each microwell of the array of microwells is approximately 125 μm to 165 μm in diameter;

each microwell of the array of microwells is approximately 110 μm to 120 μm deep;

a majority of the individual droplets are of size approximately 120 μm to 150 μm in diameter;

a fungal biology/activity is evaluated; and/or image analysis is performed to quantify aspects of the shape, morphology and/or growth of microbes.

20. A microfluidic screening platform, comprising:

a top plate having an upper portion including a plurality of top plate through holes, a lower portion, wherein the lower portion comprises a lower surface comprising an array of microwells and wherein each microwell is capable of receiving an individual droplet and wherein three or more posts encircle each microwell of the array, and an inlet, wherein the inlet extends through both the upper portion and the lower portion;

a bottom plate having an upper portion including a plurality of bottom plate through holes and a lower portion, wherein the lower portion includes an internal cut out;

a glass substrate configured to seat on the upper portion of the bottom plate and cover the internal cut out; and a plurality of shafts corresponding to the plurality of top plate through holes and bottom plate through holes configured to mate the top plate to the bottom plate, wherein a droplet flow channel is defined by an upper surface of the glass substrate and a lower surface of the lower portion of the top plate when the top plate is mated to the bottom plate.

21. The microfluidic screening platform of claim 1, wherein:

a majority of the microwells of the array of microwells comprises one and only one droplet;

optical screening of individual droplets identifies the single type of microbe and/or chemical compound or mixture present in the individual droplet;

individual droplets in user-selected adjacent microwells are merged into a single merged assay by electrocoalescence, thermal coalescence, or acoustic coalescence;

the array of microwells comprises droplets constituting at least five, at least six, at least seven, at least eight, at least nine, at least ten, at least eleven, at least twelve, at least thirteen, at least fourteen, at least fifteen, at least sixteen, at least seventeen, at least eighteen, or at least nineteen different types of microbe;

six posts encircle each microwell of the array;

the three or more posts are triangular, square, round, oval or rectangular; and/or each post is approximately 10 μm to 100 μm wide, approximately 10 μm to 50 μm wide, or approximately 40 μm wide.

22. The microfluidic screening platform of claim 4, wherein:

the measurement of luminescence and/or fluorescence comprises measuring one or more agents selected from the group consisting of Alexa Fluor 488, Alexa Fluor 555, Alexa Fluor 594, Alexa Fluor 647, GFP, YFP and resorufin;

the measurement of luminescence and/or fluorescence comprises measuring a ratio or ratios of Alexa Fluor 488, Alexa Fluor 555, Alexa Fluor 594 and/or Alexa Fluor 647, thereby identifying the single type of microbe present in the individual droplet;

the measurement of luminescence and/or fluorescence comprises measuring autofluorescence; and/or the optical screening is a label free optical assay.

23. The microfluidic screening platform of claim 6, wherein each single merged assay comprises two or more types of microbes selected from the group consisting of *Achromobacter* spp. (e.g., *Achromobacter denitrificans, Achromobacter xylosoxidans, Achromobacter ruhlandii*); *Actinomadura* spp. (e.g., *Actinomadura luteofluorescens, Actinomadura madurae, Actinomadura pelletieri, Actinomadura viridis*); *Agrobacterium* spp. (e.g., *Agrobacterium radiobacter, Agrobacterium luteum, Agrobacterium agile, Agrobacterium rubi*); *Arthrobacter* spp. (e.g., *Arthrobacter arilaitensis, Arthrobacter chlorophenolicus, Arthrobacter aurescens*); *Bacillus* spp. (e.g., *Bacillus cereus, Bacillus subtilis, Bacillus coagulans, Bacillus psychrosaccharolyticus, Bacillus amyloliquefaciens, Bacillus lentus, Bacillus circulans, Bacillus firmus*); *Burkholderia* spp. (e.g., *Burkholderia gladioli, Burkholderia plantarii, Burkholderia cepacia*); *Clostridium* spp. (e.g., *Clostridium orbiscindens, Clostridium formicaceticum*); *Escherichia coli; Ewingella* spp. (e.g., *Ewingella americana*); *Flavobacterium* spp. (e.g., *Flavobacterium flevense, Flavobacterium aquatile, Flavobacterium saccharophilum, Flavobacterium hydatis, Flavobacterium johnsoniae*); *Flexibacter* spp. (e.g., *Flexibacter flexilis, Flexibacter columnare*); *Herbaspirillum frisingense; Hyphomicrobium* spp. (e.g., *Hyphomicrobium aestuarii*); *Micromonospora* spp. (e.g., *Micromonospora rosaria, Micromonospora facile, Micromonospora zavarzinii, Micromonospora denitrificans*); *Mycobacterium* spp. (e.g., *Mycobacterium neoaurum*); *Nocardia* spp. (e.g., *Nocardia jiangxiensis, Nocardia miyunensis*); *Paenibacillus* spp. (e.g., *Paenibacillus macquariensis, Paenibacillus macerans, Paenibacillus alvei, Paenibacillus polymyxa, Paenibacillus chibensis*); *Pseudomonas* spp. (e.g., *Pseudomonas aeruginosa, Pseudomonas putida, Pseudomonas fluorescens, Pseudomonas citronellolis, Pseudomonas chlororaphis, Pseudomonas aurantiaca, Pseudomonas pseudopalustris, Pseudomonas palustris, Pseudomonas syringae, Pseudomonas veronii, Pseudomonas aurantiaca*); *Ralstonia* spp. (e.g., *Ralstonia solanacearum, Ralstonia pickettii, Ralstonia syzygii*); *Rhodococcus* spp. (e.g., *Rhodococcus erythropolis, Rhodococcus rhodochrous*); *Serratia* spp. (e.g., *Serratia marcescens, Serratia liquefaciens*); *Sphingomonas* spp. (e.g., *Sphingomonas echinoides, Sphingomonas leidyi, Sphingomonas wittichii*); *Streptomyces* spp. (e.g., *Streptomyces lividans, Streptomyces coelicolor, Streptomyces tanashiensis, Streptomyces clavuligerus, Streptomyces griseus*); *Venturia, Aspergillus, Podosphaera, Erysiphe, Monilinia, Uncinula, Aureobasidium, Sclerophoma, Acremonium, Actinoplanes, Agaricus, Chrysosporium, Colletotrichum, Coprinus, Cryptococcus, Filibasidum, Humicola, Magnaporthe, Myceliophthora, Neocallimastix, Neurospora, Paecilomyces, Phytophthora, Piromyces, Panerochaete, Pleurotus, Pythium, Schizophyllum, Talaromyces, Thermoascus, Thielavia, Tolypocladium, Trichoderma, Hemileia, Rhizoctonia, Puccinia, Coniophora, Serpula, Poria, Uromyces, Gloeophyllum, Lentinus, Coriolus, Irpex, Mucor, Botrytis, Helminthosporium, Rhynchosporium, Fusarium, Septoria, Cercospora, Alternaria, Pyricularia, Penicillium, Geotrichum*, and Zymoseptoria.

* * * * *